United States Patent
Brooks et al.

(10) Patent No.: US 6,500,924 B1
(45) Date of Patent: Dec. 31, 2002

(54) METHODS AND COMPOSITIONS USEFUL FOR INHIBITION OF ANGIOGENESIS

(75) Inventors: Peter C. Brooks, Hollywood, CA (US); David A. Cheresh, Encinitas, CA (US); Steven A. Silletti, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 09/194,468

(22) PCT Filed: May 30, 1997

(86) PCT No.: PCT/US97/09158

§ 371 (c)(1),
(2), (4) Date: Mar. 23, 1999

(87) PCT Pub. No.: WO97/45137

PCT Pub. Date: Dec. 4, 1997

Related U.S. Application Data

(60) Provisional application No. 60/018,773, filed on May 31, 1996, and provisional application No. 60/015,869, filed on May 31, 1996.

(51) Int. Cl.[7] .......................... C07K 1/00; A61K 38/00; A01N 37/18; G01N 33/53

(52) U.S. Cl. ...................... 530/350; 530/300; 530/382; 514/2; 435/975

(58) Field of Search ............................... 530/300, 350, 530/382; 435/975; 514/2

(56) References Cited

U.S. PATENT DOCUMENTS

| | | |
|---|---|---|
| 5,092,885 A | 3/1992 | Yamada et al. |
| 5,112,946 A | 5/1992 | Maione |
| 5,135,919 A | 8/1992 | Folkman et al. |
| 5,192,744 A | 3/1993 | Bouck et al. |
| 5,202,352 A | 4/1993 | Okada et al. |
| 5,575,815 A | 11/1996 | Slepian et al. |
| 5,849,692 A | 12/1998 | Jonczyk et al. |
| 5,866,540 A | 2/1999 | Jonczyk et al. |
| 5,968,902 A | 10/1999 | Scarborough et al. |
| 5,981,478 A | 11/1999 | Ruoslahti et al. |

FOREIGN PATENT DOCUMENTS

| | | |
|---|---|---|
| EP | 0 576 898 A2 | 6/1993 |
| EP | 0 578 083 A2 | 6/1993 |
| EP | 0 770 622 A | 5/1997 |
| WO | 8905155 | 6/1989 |
| WO | 8906356 | 7/1989 |
| WO | 89/06536 | 7/1989 |
| WO | 9320229 | 10/1993 |
| WO | 95/14714 | 6/1995 |
| WO | 95/28426 | 10/1995 |
| WO | 97/14716 | 4/1997 |

OTHER PUBLICATIONS

Aimes et al., Biochem J. vol. 300, pp. 729–736, 1994, and sequence comparisons.*
Eisen et al., (ID No. P91139) Genbank Sequence Database, National Center for Biotechnology Information, National Library of Medicine, Bethesda, Maryland, publicly available May 17, 1989.*
Friedlander et al., (Science, vol. 270, Dec. 1, 1995.*
Pfaff et al., Cell Adhes. Commun. vol. 2, No. 6, 1994, abstract.*
Davis, et al., "Identification of a Role of the Vitronectin Receptor and Protein Kinase C in the Induction of Endothelial Cell Vascular Formation", *J. of Cell. Biochem. 51*: 206–218 (1993).
Folkman, et al., "Angiogenic Factors", *Science 235*: 442–447 (1987).
Moses, et al., "Identification of an Inhibitor of Neovascularization from Cartilage", *Science 248*: 1408–1410 (1990).
Folkman, et al., "Inhibition of Angiogenesis", *Cancer Bio. 3*: 89–96 (1992).
Blood, et al., "Tumor Interactions with the Vasculature: Angiogenesis and Tumor Metastasis", *Biochim. et Biophy. Acta 1032*: 89–118 (1990).
Ingber, et al., "Inhibition of Angiogenesis through Modulation of Collagen Metabolism", *Lab. Invest. 59(1)*: 44–51 (1988).
Aumailley, et al., "Arg–Gly–Asp Constrained within Cyclic Pentapeptides: Strong and Selective Inhibitors of Cell Adhesion to Vitronectin and Laminin—Fragment P1", *Fed. of Euro. Biochem. Soc. 291(1)*: 50–54 (1991).
Choi, et al., "Inhibition of Neointimal Hyperplasia by Blocking $\alpha_v\beta_3$ Integrin with a Small Peptide Antagonist GpenGRGDSPCA", *J. of Vasc. Surg. 19*: 125–134 (1994).
Nicosia, et al., "Inhibition of Angiogenesis in vitro by Arg–Gly–Asp–Containing Synthetic Peptide", *Amer. Jour. of Patho. 138(4)*: 829–833 (1991).
Cheresh, et al., "Biosynthetic and Functional Properties of an Arg–Gly–Asp–directed Receptor Involved in Human Melanoma Cell Attachment to Vitronectin, Fibrinogen, and von Willebrand Factor", *J. of Bio. Chem.262(36)*: 17703–17711 (1987).
Leavesley, et al., "Integrin $\beta 1–$ and $\beta 3–$mediated Endothelial Cell Migration is Triggered through Distinct Signaling Mechanisms", *J. of Cell Biol. 121*: 163–170 (1993).
Swerlick, et al., "Expression and Modulation of the Vitronectin Receptor on Human Dermal Microvascular Endothelial Cells", *J. of Inves. Derm. 99(6)*: 715–722 (1992).

(List continued on next page.)

*Primary Examiner*—Anthony C. Caputa
*Assistant Examiner*—Gary B. Nickol
(74) *Attorney, Agent, or Firm*—Emily Holmes; Thomas Fitting

(57) ABSTRACT

The present invention describes methods for inhibition of angiogenesis in tissues using vitronectin $\alpha_v\beta_3$ antagonists, and particularly for inhibiting angiogenesis in inflamed tissues and in tumor tissues and metastases using therapeutic compositions containing $\alpha_v\beta_3$ antagonists.

6 Claims, 46 Drawing Sheets

OTHER PUBLICATIONS

Brooks, et al., "Subtractive Immunization Yields Monoclonal Antibodies that Specifically Inhibit Metastasis", *J. of Cell biol.* 122(6): 1351–1359 (1993).

Nip, et al., "Human Melonoma Cells Derived from Lymphatic Metastases Use Integrin $\alpha_v\beta_3$ to Adhere to Lymph Node Vitronectin", *J. Clin. Invest.* 90: 1406–1413 (1992).

Jackson, et al., "Isolation and Propagation of Endothelial Cells Derived from Rheumatoid Synovial Microvasculature", *Ann. of the Rheu. Dis.* 48: 733–736 (1989).

Waldman, Thomas A., "Monoclonal Antibodies in Diagnosis and Therapy", *Science* 252: 1657–1662 (1991).

Brooks, et al., "Requirement of Vascular Integrin $\alpha_v\beta_3$ for Angiogenesis", *Science* 264: 569–570 (1994).

Chuntharapai, et al., "Blocking Monoclonal Antibodies to $\alpha V\beta 3$ Integrin: A Unique Epitope of $\alpha V\beta 3$ Integrin is Present on Human Osteoclasts", *Exper. Cell Res.* 205: 345–352 (1993).

Osband, et al., "Problems in the Investigational Study and Clinical Use of Cancer Immunotherapy", *Imm. Today 11 (6)*: 193–195 (1990).

Ausprunk, et al., "Vascularization of Normal and Neoplastic Tissues Grafted to the Chick Chorioallantois", *Amer. J. of Path.* 79(3): 597–610 (1975).

Cheresh, et al., "Recognition of Distinct Adhesive Sites on Fibrinogen by Related Integrins on Platelets and Endothelial Cells", *Cell* 58: 945–953 (1989).

D'Amato, et al., "Thalidomide is an Inhibitor of Angiogenesis", *Proc. Natl. Acad. Sci. USA* 91: 4082–4085 (1994).

Leibovich, et al., "Macrophage–induced Angiogenesis is Mediated by Tumour Necrosis Factor–$\alpha$", *Nature* 329: 630–632 (1987).

Pfaff, et al., "Selective Recognition of Cyclic RGD Peptides of NMR Defined Conformation by $\alpha IIb\beta 3$, and $\alpha 5\beta 1$ Integrins", *J. of Biol. Chem.* 269(32): 20233–20238 (1994).

Yan, et al., "Human/Severe Combined Immunodeficient Mouse Chimeras: An Experimental in Vivo Model System to Study the Regulation of Human Endothelial Cell–Leukocyte Adhesion Molecules", *J. Clin. Invest.* 91: 986–996 (1993).

Gurrath, et al., "Conformation/Activity Studies of Rationally Designed Potent Anti–Adhesive RGD Peptides", *Eur. J. Biochem* 210: 911–921 (1992).

Leven, et al., "Extracellular Matrix Stimulation of Guinea Pig Megakaryocyte Proplatelet Formation in vitro Is Mediated Through the Vitronectin Receptor", *Exp. Hematol.* 20: 1316–1322 (1992).

Matsuno, et al., Inhibition of integrin function by a cyclic RGD–containing peptide prevents neointima formation, 1994, *Circulation*, 90(5):2203–2205.

Timar, et al., The antimetabolite tiazofurin (TR) inhibits glycoconjugate biosynthesis and invasiveness of tumour cells, 1996, *Eur. J. Cancer*, 32A(1):152–159.

Smith, et al., Interaction of integrins $\alpha v\beta 3$ and glycoprotein IIb–IIIa with fibrinogen, 1990, *J. Biol. Chem.*, 265:12267–12271.

Mueller, et al., Pre–clinical therapy of human melanoma with morpholino–doxorubicin conjugated to a monoclonal antibody directed against an integrin on melanoma cells, *Antibody, Immunoconjugates, and Radiopharmaceuticals*, 1991, 4(2):99–106.

Ossowski, et al., Experimental model for quantitative study of metastasis, 1980, *Cancer Res.*, 40:2300–2309.

Hammes, et al., Subcutaneous injection of a cyclic peptide antagonist of vitronectin receptor–type integrins inhibits retinal neovascularization, 1996, *Nature Med.*, 2(5):529–533.

Brooks, et al., Integrin $\alpha v\beta 3$ antagonists promote tumor regression by inducing apoptosis of angiogenic blood vessels, 1994, *Cell*, 79:1157–1164.

Clark, et al, Transient functional expression of $\alpha v\beta 3$ on vascular cells during wound repair, 1996, *Am. J Pathol.*, 148:1407–1421.

Bauer, et al., In vitro model of angiogenesis using a human endothelium–derived permanent cell line: contributions of induced gene expression, G–proteins and integrins, 1992, *J. Cell. Physiol.*, 153:437–449.

Ingber, Extracellular matrix as a solid state regulator of angiogenesis: identification of new targets for anti–cancer therapy, 1992, *Seminars in Cancer Biology*, 3:57–63.

Hardan, et al., Inhibition of metastatic cell colonization in murine lungs and tumor–induced morbidity by non–peptidic Arg–Gly–Asp mimetics, 1993, *Intl. J. Cancer*, 55:1023–1028.

Hynes, Integrins: versatility, modulation, and signaling in cell adhesion, 1992, *Cell*, 69:11–25.

Lehmann, et al., A monoclonal antibody inhibits adhesion to fibronectin and vitronectin of a colon carcinoma cell line and recognizes the integrins $\alpha v\beta 3$, $\alpha v\beta 5$ and $\alpha v\beta 6$, 1994, *Cancer Res.*, 54:2102–2107.

Pierschbacher, et al., Influence of stereochemistry of the sequence Arg–Gly–Asp–Xaa on binding specificity in cell adhesion, 1987, *J. Biol. Chem.*, 262:17294–17296.

Folkman, et al., Angiogenesis, 1992, *J. Biol. Chem.*, 267:10931–10934.

Teicher, et al., Potentiation of cytotoxic cancer therapies by TNP–470 alone and with other anti–angiogenic agents, 1994, *Intl. J. Cancer*, 57:920–925.

Drake, et al., A antago nist of integrin $\alpha v\beta 3$ prevent maturation of blood vessels during embryonic neovascularization, 1995, *J. Cell Sci.*, 108:2655–2661.

\* cited by examiner

Normal Skin

Granulation Tissue

Normal Skin

Granulation Tissue

Normal Skin

Anti-vWF

Granulation Tissue

Anti-vWF

Normal Skin

Anti-laminin

Granulation Tissue

Anti-laminin

Bladder Cancer

Colon Cancer

Breast Cancer

Lung Cancer

Untreated
Anti-$\beta_1$

Untreated
Anti-$\alpha v \beta_3$ bFGF Treated
Anti-$\alpha v \beta_3$

FIG. 8A
Control
bFGF
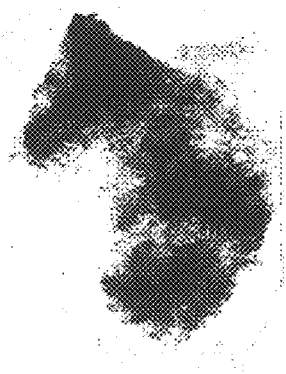
FIG. 8B
FIG. 8C
Anti-$\beta_1$
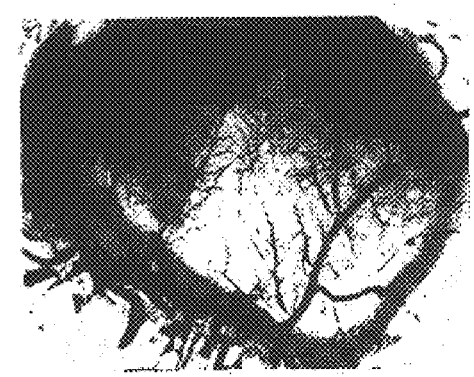
FIG. 8D
Anti-$\alpha_v\beta_5$
FIG. 8E
Anti-$\alpha_v\beta_3$

  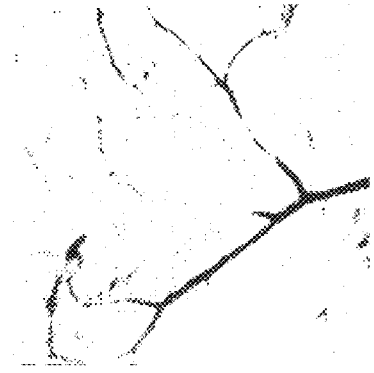
FIG. 9A Control Peptide Tumor
FIG. 9B Cyclic RGD Tumor
FIG. 9C Cyclic RGD Adjacent CAM Control Anti-αVβ5 (P3G2)

Anti-αVβ3 (LM609)

Anti-β1

Anti-αvβ5

Anti-αvβ3

Anti-αVβ5
(P3G2)

Anti-αVβ3
(LM609)

FIG. 15A FIG. 15B FIG. 15C
  
Control Peptide Tumor  Cyclic RGD Tumor  Cyclic RGD Adjacent CAM
FIG. 15D FIG. 15E
Control Peptide  Cyclic RGD Peptide P1F6
(Anti-$\alpha_v\beta_5$)

LM609
(Anti-$\alpha_v\beta_3$)

```
TCAATTACTGGACCAGTCAGGTACTGGCACCCAAACATTAAGTACTACTGGTACACATCTGATAATTTAAAAGTGTTTGCCTCCTCAACATACAAAAG    +2091
ATGTTTACGTATCTATTCTGGTACAATTTTTCAGTTCAGTAGCAGAACACGTAAGTTCTTTATTCCCTGGTGCTTG                         +2191
AAGAAAGCATTGAAATCATTGGAGACTGGACCAGACCCCTGTGTTAAATAGCCCTCAAATAGCCCTCAAATAGCCCTTGATCATTACTGCCATTTATTACA +2291
TTTTAATTTTTTATACAACTCTTGTTATAAATAGAATGGTTTGTGCCACGGGATTTGATTTGCTTGATGATGAATCATGGCAAGATCATGGAATCATGATCATCCTATACAGTGTATTAAGTGATATGTT +2391
TAATGATAACAAAAGACTGTCCAAAGGCACAGTTCAACCTTAGTAGAAACCTTAGTAGAACACAGAAGTCAAGTATTTCAACTTGTCTATAACTGTCTATAACAGCAGATATAATATAATATATGAGTTTTGTTTGTTAGG +2491
TAAAGTACTTTCTATTTTAAATCAATGTATTTATACAGAAGTGTTCCTTTCACATATGATATGATGCAATTCACACTAGTGTTTTCCACATATGATGAATGGAATGTTTCACATATGATATGATGCATATGATGGAATGTTTCACATATGATGCATATGATGGAATGTTTCCTTCTATTATTATTAATTATATATGAAAGGTTAAAAAAAAATCCAGAAACAAT +2591
GATGTTTTAAATCAATGTATTGGGCAACATGCATTGGCAACAGAAGGTGTTCCTTTCACATATGATGAAATGTCAAAAAAAAAAAAAAAACGGTTAAC
CTTTTCGCTTAGGCAATGATGAAAT
GTCCCAAACATGAAAT
```

FIG. 22D

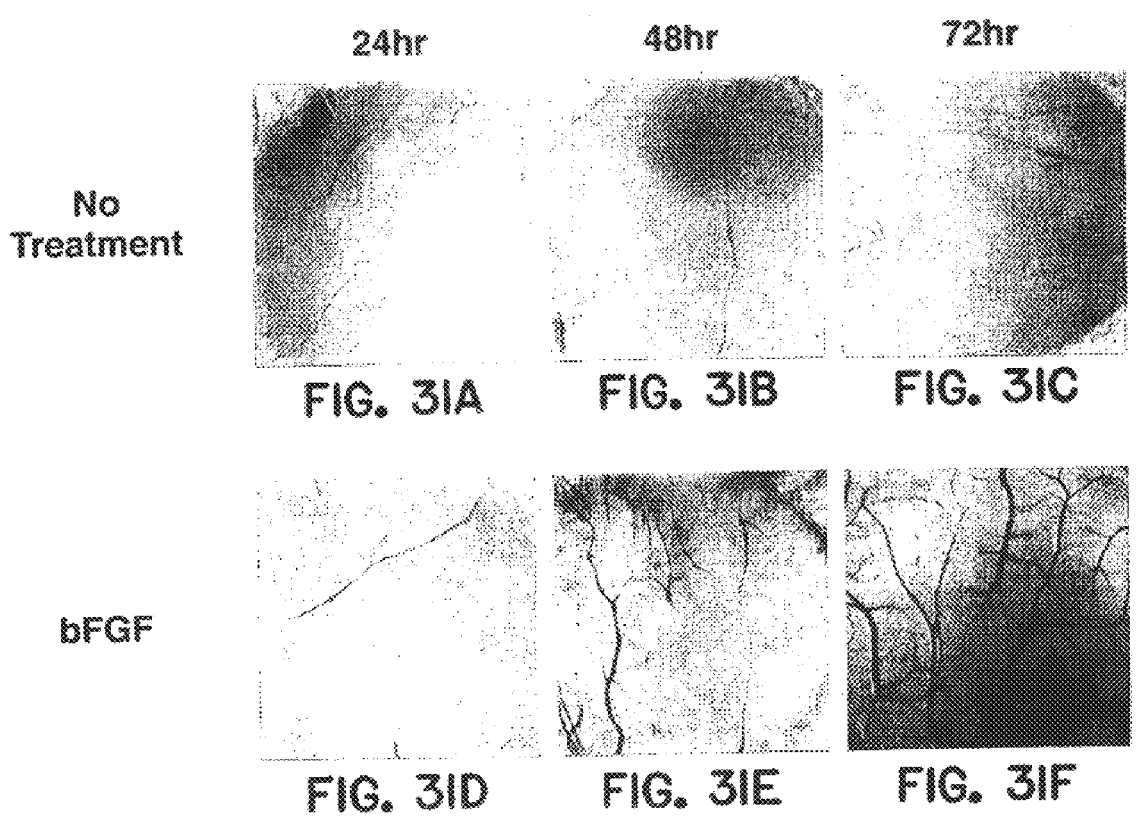

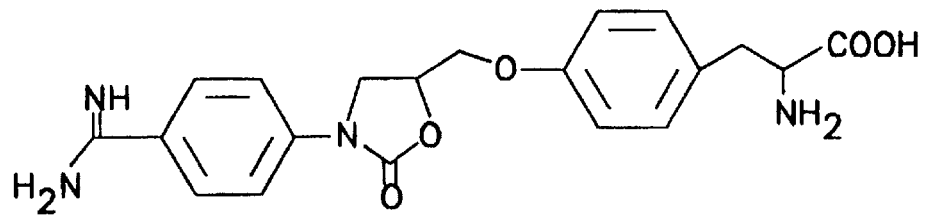
COMPOUND 15
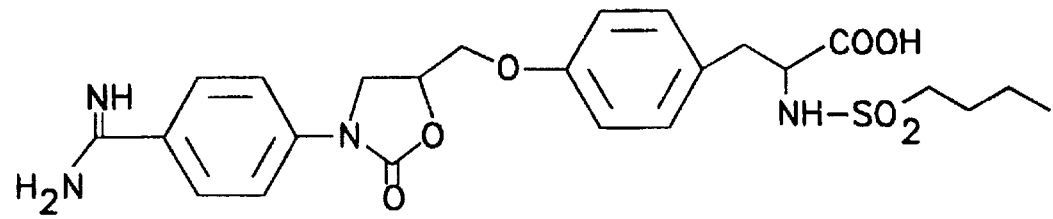
COMPOUND 16
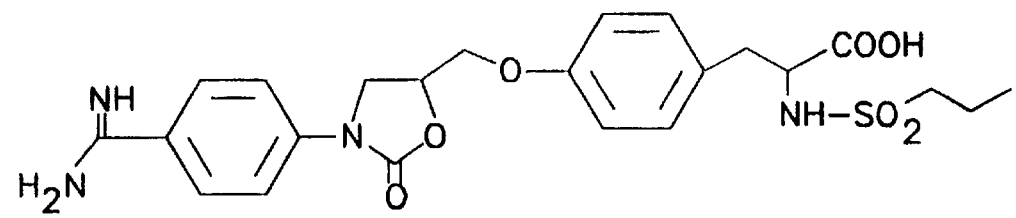
COMPOUND 17
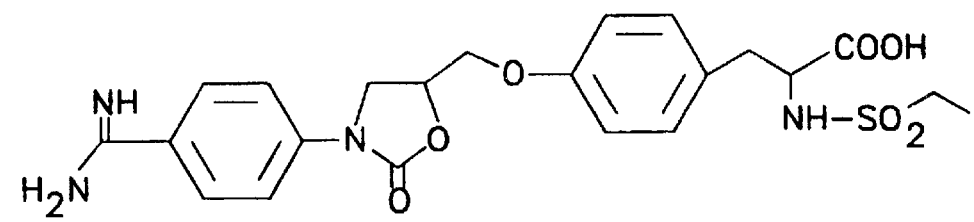
COMPOUND 18
FIG. 42

```
                            SEQUENCE LISTING

<160> NUMBER OF SEQ ID NOS:  45

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence:  peptide
<221> NAME/KEY: PEPTIDE
<222> LOCATION: (1)..(6)
<223> OTHER INFORMATION: BOC signifies the N-terminal protecting group
      butyloxycarbonyl; OMe signifies a C-terminal
      methyl ester; arginine in the second position.
<221> NAME/KEY: PEPTIDE
<222> LOCATION: (1)..(6)
<223> OTHER INFORMATION: OMe signifies the C-terminal protecting group
      methyl ester.
<221> NAME/KEY: PEPTIDE
<222> LOCATION: (1)..(6)
<223> OTHER INFORMATION: A prefix "D" in D-arg signifies that the
      arginine in position 2 is a D-amino acid.

<400> SEQUENCE: 1

Gly Arg Gly Asp Phe Val
  1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence:  peptide
<221> NAME/KEY: PEPTIDE
<222> LOCATION: (1)..(6)
<223> OTHER INFORMATION: BOC signifies the N-terminal blocking group
      tertbutyloxycarbonyl.
<221> NAME/KEY: PEPTIDE
<222> LOCATION: (1)..(6)
<223> OTHER INFORMATION: OH signifies a free C-terminal carboxylic acid.
<221> NAME/KEY: PEPTIDE
<222> LOCATION: (1)..(6)
<223> OTHER INFORMATION: A prefix "D" in D-arg signifies that the
      arginine in position 2 is a D-amino acid.

<400> SEQUENCE: 2

Gly Arg Gly Asp Phe Val
  1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence:  peptide
<221> NAME/KEY: PEPTIDE
<222> LOCATION: (1)..(6)
<223> OTHER INFORMATION: H signifies a free N-terminal amine.
<221> NAME/KEY: PEPTIDE
<222> LOCATION: (1)..(6)
<223> OTHER INFORMATION: OH signifies a free C-terminal carboxylic acid.
<221> NAME/KEY: PEPTIDE
<222> LOCATION: (1)..(6)
<223> OTHER INFORMATION: A prefix "D" in D-Arg at position 2, signifies
      that the arginine is a D-amino acid.
```

```
<400> SEQUENCE: 3

Gly Arg Gly Asp Phe Val
 1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (2)
<223> OTHER INFORMATION: Arg is a D-amino acid.

<400> SEQUENCE: 4

Gly Arg Gly Asp Phe Val
 1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (4)
<223> OTHER INFORMATION: Phe is a D-amino acid.

<400> SEQUENCE: 5

Arg Gly Asp Phe Val
 1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (4)
<223> OTHER INFORMATION: Phe is a D-amino acid.

<400> SEQUENCE: 6

Arg Ala Asp Phe Val
 1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (5)
<223> OTHER INFORMATION: Val is a D-amino acid.

<400> SEQUENCE: 7

Arg Gly Asp Phe Val
 1               5

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: peptide

<400> SEQUENCE: 8
```

```
Tyr Thr Ala Glu Cys Lys Pro Gln Val Thr Arg Gly Asp Val Phe
 1               5                  10                  15

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (2)
<223> OTHER INFORMATION: Ala is a D-amino acid.

<400> SEQUENCE: 9

Arg Ala Asp Phe Val
 1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (5)
<223> OTHER INFORMATION: Phe is a D-amino acid.

<400> SEQUENCE: 10

Ala Arg Gly Asp Phe Leu
 1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (5)
<223> OTHER INFORMATION: Phe is a D-amino acid.

<400> SEQUENCE: 11

Gly Arg Gly Asp Phe Leu
 1               5

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: peptide

<400> SEQUENCE: 12

Thr Arg Gln Val Val Cys Asp Leu Gly Asn Pro Met
 1               5                  10

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: peptide

<400> SEQUENCE: 13

Gly Val Val Arg Asn Asn Glu Ala Leu Ala Arg Leu Ser
 1               5                  10

<210> SEQ ID NO 14
```

```
<211> LENGTH: 11
<212> TYPE: PRT
<213> ORGANISM: Artificial Sequence
<220> FEATURE:
<223> OTHER INFORMATION: Description of Artificial Sequence: peptide

<400> SEQUENCE: 14

Thr Asp Val Asn Gly Asp Gly Arg His Asp Leu
  1               5                  10

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (5)
<223> OTHER INFORMATION: Methylation is at the amino (NH2) terminus of
      the valine residue.

<400> SEQUENCE: 15

Arg Gly Asp Phe Val
  1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (5)
<223> OTHER INFORMATION: Methylation is at the amino (NH2) terminus of
      the valine residue.

<400> SEQUENCE: 16

Arg Gly Glu Phe Val
  1               5

<210> SEQ ID NO 17
<211> LENGTH: 222
<212> TYPE: PRT
<213> ORGANISM: Homo sapiens

<400> SEQUENCE: 17

Lys Gly Ile Gln Glu Leu Tyr Gly Ala Ser Pro Asp Ile Asp Leu Gly
  1               5                  10                  15

Thr Gly Pro Thr Pro Thr Leu Gly Pro Val Thr Pro Glu Ile Cys Lys
             20                  25                  30

Gln Asp Ile Val Phe Asp Gly Ile Ala Gln Ile Arg Gly Glu Ile Phe
         35                  40                  45

Phe Phe Lys Asp Arg Phe Ile Trp Arg Thr Val Thr Pro Arg Asp Lys
     50                  55                  60

Pro Met Gly Pro Leu Leu Val Ala Thr Phe Trp Pro Glu Leu Pro Glu
 65                  70                  75                  80

Lys Ile Asp Ala Val Tyr Glu Ala Pro Gln Glu Glu Lys Ala Val Phe
                 85                  90                  95

Phe Ala Gly Asn Glu Tyr Trp Ile Tyr Ser Ala Ser Thr Leu Glu Arg
            100                 105                 110

Gly Tyr Pro Lys Pro Leu Thr Ser Leu Gly Leu Pro Pro Asp Val Gln
        115                 120                 125

Arg Val Asp Ala Ala Phe Asn Trp Ser Lys Asn Lys Lys Thr Tyr Ile
    130                 135                 140
```

```
Phe Ala Gly Asp Lys Phe Trp Arg Tyr Asn Glu Val Lys Lys Met
145                 150                 155                 160

Asp Pro Gly Phe Pro Lys Leu Ile Ala Asp Ala Trp Asn Ala Ile Pro
                165                 170                 175

Asp Asn Leu Asp Ala Val Val Asp Leu Gln Gly Gly His Ser Tyr
        180                 185                 190

Phe Phe Lys Gly Ala Tyr Tyr Leu Lys Leu Glu Asn Gln Ser Leu Lys
        195                 200                 205

Ser Val Lys Phe Gly Ser Ile Lys Ser Asp Trp Leu Gly Cys
        210                 215                 220

<210> SEQ ID NO 18
<211> LENGTH: 193
<212> TYPE: PRT
<213> ORGANISM: Homo sapiens

<400> SEQUENCE: 18

Ile Cys Lys Gln Asp Ile Val Phe Asp Gly Ile Ala Gln Ile Arg Gly
 1               5                  10                  15

Glu Ile Phe Phe Phe Lys Asp Arg Phe Ile Trp Arg Thr Val Thr Pro
                20                  25                  30

Arg Asp Lys Pro Met Gly Pro Leu Leu Val Ala Thr Phe Trp Pro Glu
            35                  40                  45

Leu Pro Glu Lys Ile Asp Ala Val Tyr Glu Ala Pro Gln Glu Glu Lys
    50                  55                  60

Ala Val Phe Phe Ala Gly Asn Glu Tyr Trp Ile Tyr Ser Ala Ser Thr
65                  70                  75                  80

Leu Glu Arg Gly Tyr Pro Lys Pro Leu Thr Ser Leu Gly Leu Pro Pro
                85                  90                  95

Asp Val Gln Arg Val Asp Ala Ala Phe Asn Trp Ser Lys Asn Lys Lys
            100                 105                 110

Thr Tyr Ile Phe Ala Gly Asp Lys Phe Trp Arg Tyr Asn Glu Val Lys
        115                 120                 125

Lys Lys Met Asp Pro Gly Phe Pro Lys Leu Ile Ala Asp Ala Trp Asn
    130                 135                 140

Ala Ile Pro Asp Asn Leu Asp Ala Val Val Asp Leu Gln Gly Gly Gly
145                 150                 155                 160

His Ser Tyr Phe Phe Lys Gly Ala Tyr Tyr Leu Lys Leu Glu Asn Gln
                165                 170                 175

Ser Leu Lys Ser Val Lys Phe Gly Ser Ile Lys Ser Asp Trp Leu Gly
            180                 185                 190

Cys

<210> SEQ ID NO 19
<211> LENGTH: 74
<212> TYPE: PRT
<213> ORGANISM: Homo sapiens

<400> SEQUENCE: 19

Ile Cys Lys Gln Asp Ile Val Phe Asp Gly Ile Ala Gln Ile Arg Gly
 1               5                  10                  15

Glu Ile Phe Phe Phe Lys Asp Arg Phe Ile Trp Arg Thr Val Thr Pro
                20                  25                  30

Arg Asp Lys Pro Met Gly Pro Leu Leu Val Ala Thr Phe Trp Pro Glu
            35                  40                  45
```

```
Leu Pro Glu Lys Ile Asp Ala Val Tyr Glu Ala Pro Gln Glu Glu Lys
 50                  55                  60

Ala Val Phe Phe Ala Gly Asn Glu Tyr Trp
 65                  70
```

<210> SEQ ID NO 20
<211> LENGTH: 108
<212> TYPE: PRT
<213> ORGANISM: Homo sapiens

<400> SEQUENCE: 20

```
Ile Cys Lys Gln Asp Ile Val Phe Asp Gly Ile Ala Gln Ile Arg Gly
 1               5                  10                  15

Glu Ile Phe Phe Phe Lys Asp Arg Phe Ile Trp Arg Thr Val Thr Pro
                 20                  25                  30

Arg Asp Lys Pro Met Gly Pro Leu Leu Val Ala Thr Phe Trp Pro Glu
                 35                  40                  45

Leu Pro Glu Lys Ile Asp Ala Val Tyr Glu Ala Pro Gln Glu Glu Lys
 50                  55                  60

Ala Val Phe Phe Ala Gly Asn Glu Tyr Trp Ile Tyr Ser Ala Ser Thr
 65                  70                  75                  80

Leu Glu Arg Gly Tyr Pro Lys Pro Leu Thr Ser Leu Gly Leu Pro Pro
                 85                  90                  95

Asp Val Gln Arg Val Asp Ala Ala Phe Asn Trp Ser
                100                 105
```

<210> SEQ ID NO 21
<211> LENGTH: 122
<212> TYPE: PRT
<213> ORGANISM: Homo sapiens

<400> SEQUENCE: 21

```
Glu Tyr Trp Ile Tyr Ser Ala Ser Thr Leu Glu Arg Gly Tyr Pro Lys
 1               5                  10                  15

Pro Leu Thr Ser Leu Gly Leu Pro Pro Asp Val Gln Arg Val Asp Ala
                 20                  25                  30

Ala Phe Asn Trp Ser Lys Asn Lys Lys Thr Tyr Ile Phe Ala Gly Asp
                 35                  40                  45

Lys Phe Trp Arg Tyr Asn Glu Val Lys Lys Met Asp Pro Gly Phe
 50                  55                  60

Pro Lys Leu Ile Ala Asp Ala Trp Asn Ala Ile Pro Asp Asn Leu Asp
 65                  70                  75                  80

Ala Val Val Asp Leu Gln Gly Gly Gly His Ser Tyr Phe Phe Lys Gly
                 85                  90                  95

Ala Tyr Tyr Leu Lys Leu Glu Asn Gln Ser Leu Lys Ser Val Lys Phe
                100                 105                 110

Gly Ser Ile Lys Ser Asp Trp Leu Gly Cys
                115                 120
```

<210> SEQ ID NO 22
<211> LENGTH: 89
<212> TYPE: PRT
<213> ORGANISM: Homo sapiens

<400> SEQUENCE: 22

```
Phe Asn Trp Ser Lys Asn Lys Lys Thr Tyr Ile Phe Ala Gly Asp Lys
 1               5                  10                  15

Phe Trp Arg Tyr Asn Glu Val Lys Lys Lys Met Asp Pro Gly Phe Pro
```

```
                    20                  25                  30

Lys Leu Ile Ala Asp Ala Trp Asn Ala Ile Pro Asp Asn Leu Asp Ala
            35                  40                  45

Val Val Asp Leu Gln Gly Gly Gly His Ser Tyr Phe Phe Lys Gly Ala
50                      55                  60

Tyr Tyr Leu Lys Leu Glu Asn Gln Ser Leu Lys Ser Val Lys Phe Gly
65                  70                  75                  80

Ser Ile Lys Ser Asp Trp Leu Gly Cys
                85

<210> SEQ ID NO 23
<211> LENGTH: 228
<212> TYPE: PRT
<213> ORGANISM: Gallus gallus

<400> SEQUENCE: 23

Lys Gly Ile Gln Glu Leu Tyr Glu Val Ser Pro Asp Val Glu Pro Gly
1               5                   10                  15

Pro Gly Pro Gly Pro Gly Pro Gly Pro Arg Pro Thr Leu Gly Pro Val
                20                  25                  30

Thr Pro Glu Leu Cys Lys His Asp Ile Val Phe Asp Gly Val Ala Gln
            35                  40                  45

Ile Arg Gly Glu Ile Phe Phe Phe Lys Asp Arg Phe Met Trp Arg Thr
        50                  55                  60

Val Asn Pro Arg Gly Lys Pro Thr Gly Pro Leu Leu Val Ala Thr Phe
65                  70                  75                  80

Trp Pro Asp Leu Pro Glu Lys Ile Asp Ala Val Tyr Glu Ser Pro Gln
                85                  90                  95

Asp Glu Lys Ala Val Phe Phe Ala Gly Asn Glu Tyr Trp Val Tyr Thr
            100                 105                 110

Ala Ser Asn Leu Asp Arg Gly Tyr Pro Lys Lys Leu Thr Ser Leu Gly
        115                 120                 125

Leu Pro Pro Asp Val Gln Arg Ile Asp Ala Ala Phe Asn Trp Gly Arg
    130                 135                 140

Asn Lys Lys Thr Tyr Ile Phe Ser Gly Asp Arg Tyr Trp Lys Tyr Asn
145                 150                 155                 160

Glu Glu Lys Lys Lys Met Glu Leu Ala Thr Pro Lys Phe Ile Ala Asp
                165                 170                 175

Ser Trp Asn Gly Val Pro Asp Asn Leu Asp Ala Val Leu Gly Leu Thr
            180                 185                 190

Asp Ser Gly Tyr Thr Tyr Phe Phe Lys Asp Gln Tyr Tyr Leu Gln Met
        195                 200                 205

Glu Asp Lys Ser Leu Lys Ile Val Lys Ile Gly Lys Ile Ser Ser Asp
    210                 215                 220

Trp Leu Gly Cys
225

<210> SEQ ID NO 24
<211> LENGTH: 193
<212> TYPE: PRT
<213> ORGANISM: Gallus gallus

<400> SEQUENCE: 24

Leu Cys Lys His Asp Ile Val Phe Asp Gly Val Ala Gln Ile Arg Gly
1               5                   10                  15

Glu Ile Phe Phe Phe Lys Asp Arg Phe Met Trp Arg Thr Val Asn Pro
```

```
                    20                  25                  30
Arg Gly Lys Pro Thr Gly Pro Leu Leu Val Ala Thr Phe Trp Pro Asp
            35                  40                  45

Leu Pro Glu Lys Ile Asp Ala Val Tyr Glu Ser Pro Gln Asp Glu Lys
        50                  55                  60

Ala Val Phe Phe Ala Gly Asn Glu Tyr Trp Val Tyr Thr Ala Ser Asn
 65                  70                  75                  80

Leu Asp Arg Gly Tyr Pro Lys Lys Leu Thr Ser Leu Gly Leu Pro Pro
                85                  90                  95

Asp Val Gln Arg Ile Asp Ala Ala Phe Asn Trp Gly Arg Asn Lys Lys
                100                 105                 110

Thr Tyr Ile Phe Ser Gly Asp Arg Tyr Trp Lys Tyr Asn Glu Glu Lys
            115                 120                 125

Lys Lys Met Glu Leu Ala Thr Pro Lys Phe Ile Ala Asp Ser Trp Asn
130                 135                 140

Gly Val Pro Asp Asn Leu Asp Ala Val Leu Gly Leu Thr Asp Ser Gly
145                 150                 155                 160

Tyr Thr Tyr Phe Phe Lys Asp Gln Tyr Tyr Leu Gln Met Glu Asp Lys
                165                 170                 175

Ser Leu Lys Ile Val Lys Ile Gly Lys Ile Ser Ser Asp Trp Leu Gly
            180                 185                 190

Cys

<210> SEQ ID NO 25
<211> LENGTH: 74
<212> TYPE: PRT
<213> ORGANISM: Gallus gallus

<400> SEQUENCE: 25

Leu Cys Lys His Asp Ile Val Phe Asp Gly Val Ala Gln Ile Arg Gly
 1               5                  10                  15

Glu Ile Phe Phe Phe Lys Asp Arg Phe Met Trp Arg Thr Val Asn Pro
                20                  25                  30

Arg Gly Lys Pro Thr Gly Pro Leu Leu Val Ala Thr Phe Trp Pro Asp
            35                  40                  45

Leu Pro Glu Lys Ile Asp Ala Val Tyr Glu Ser Pro Gln Asp Glu Lys
        50                  55                  60

Ala Val Phe Phe Ala Gly Asn Glu Tyr Trp
 65                  70

<210> SEQ ID NO 26
<211> LENGTH: 108
<212> TYPE: PRT
<213> ORGANISM: Gallus gallus

<400> SEQUENCE: 26

Leu Cys Lys His Asp Ile Val Phe Asp Gly Val Ala Gln Ile Arg Gly
 1               5                  10                  15

Glu Ile Phe Phe Phe Lys Asp Arg Phe Met Trp Arg Thr Val Asn Pro
                20                  25                  30

Arg Gly Lys Pro Thr Gly Pro Leu Leu Val Ala Thr Phe Trp Pro Asp
            35                  40                  45

Leu Pro Glu Lys Ile Asp Ala Val Tyr Glu Ser Pro Gln Asp Glu Lys
        50                  55                  60

Ala Val Phe Phe Ala Gly Asn Glu Tyr Trp Val Tyr Thr Ala Ser Asn
 65                  70                  75                  80
```

Leu Asp Arg Gly Tyr Pro Lys Lys Leu Thr Ser Leu Gly Leu Pro Pro
            85                  90                  95

Asp Val Gln Arg Ile Asp Ala Ala Phe Asn Trp Gly
            100                 105

<210> SEQ ID NO 27
<211> LENGTH: 122
<212> TYPE: PRT
<213> ORGANISM: Gallus gallus

<400> SEQUENCE: 27

Glu Tyr Trp Val Tyr Thr Ala Ser Asn Leu Asp Arg Gly Tyr Pro Lys
 1               5                  10                  15

Lys Leu Thr Ser Leu Gly Leu Pro Pro Asp Val Gln Arg Ile Asp Ala
            20                  25                  30

Ala Phe Asn Trp Gly Arg Asn Lys Lys Thr Tyr Ile Phe Ser Gly Asp
        35                  40                  45

Arg Tyr Trp Lys Tyr Asn Glu Glu Lys Lys Lys Met Glu Leu Ala Thr
    50                  55                  60

Pro Lys Phe Ile Ala Asp Ser Trp Asn Gly Val Pro Asp Asn Leu Asp
65                  70                  75                  80

Ala Val Leu Gly Leu Thr Asp Ser Gly Tyr Thr Tyr Phe Phe Lys Asp
                85                  90                  95

Gln Tyr Tyr Leu Gln Met Glu Asp Lys Ser Leu Lys Ile Val Lys Ile
            100                 105                 110

Gly Lys Ile Ser Ser Asp Trp Leu Gly Cys
            115                 120

<210> SEQ ID NO 28
<211> LENGTH: 89
<212> TYPE: PRT
<213> ORGANISM: Gallus gallus

<400> SEQUENCE: 28

Phe Asn Trp Gly Arg Asn Lys Lys Thr Tyr Ile Phe Ser Gly Asp Arg
 1               5                  10                  15

Tyr Trp Lys Tyr Asn Glu Glu Lys Lys Lys Met Glu Leu Ala Thr Pro
            20                  25                  30

Lys Phe Ile Ala Asp Ser Trp Asn Gly Val Pro Asp Asn Leu Asp Ala
        35                  40                  45

Val Leu Gly Leu Thr Asp Ser Gly Tyr Thr Tyr Phe Phe Lys Asp Gln
    50                  55                  60

Tyr Tyr Leu Gln Met Glu Asp Lys Ser Leu Lys Ile Val Lys Ile Gly
65                  70                  75                  80

Lys Ile Ser Ser Asp Trp Leu Gly Cys
                85

<210> SEQ ID NO 29
<211> LENGTH: 2123
<212> TYPE: DNA
<213> ORGANISM: Gallus gallus
<220> FEATURE:
<221> NAME/KEY: CDS
<222> LOCATION: (132)..(2123)

<400> SEQUENCE: 29
aattccggca aaagagaaaa cggtgcagag agttaagatg tgcagataag caactagtgc     60
actgtgcagc caaagtaact gacagtcagt cagagaaatc ttttaaagag gattgcaaaa    120

-continued

```
atataggcag a atg aag act cac agt gtt ttt ggc ttc ttt ttt aaa gta         170
            Met Lys Thr His Ser Val Phe Gly Phe Phe Phe Lys Val
             1               5                  10 cta tta atc caa gtg tat ctt ttt aac aaa act tta gct gca ccg tca          218
Leu Leu Ile Gln Val Tyr Leu Phe Asn Lys Thr Leu Ala Ala Pro Ser
 15              20                  25 cca atc att aag ttc cct gga gac agc act cca aaa aca gac aaa gag          266
Pro Ile Ile Lys Phe Pro Gly Asp Ser Thr Pro Lys Thr Asp Lys Glu
 30              35                  40                  45 cta gca gtg caa tac ctg aat aaa tat tat gga tgc cca aaa gac aat          314
Leu Ala Val Gln Tyr Leu Asn Lys Tyr Tyr Gly Cys Pro Lys Asp Asn
                 50                  55                  60 tgc aac tta ttt gta ttg aaa gat act ttg aag aaa atg cag aaa ttt          362
Cys Asn Leu Phe Val Leu Lys Asp Thr Leu Lys Lys Met Gln Lys Phe
                 65                  70                  75 ttt ggg ctg cct gaa aca gga gat ttg gat caa aac aca att gag aca          410
Phe Gly Leu Pro Glu Thr Gly Asp Leu Asp Gln Asn Thr Ile Glu Thr
                 80                  85                  90 atg aag aaa ccc cgc tgt ggt aac ccc gat gtg gcc aat tac aac ttc          458
Met Lys Lys Pro Arg Cys Gly Asn Pro Asp Val Ala Asn Tyr Asn Phe
         95                 100                 105 ttt cca aga aag cca aaa tgg gaa aag aat cat ata aca tac agg att          506
Phe Pro Arg Lys Pro Lys Trp Glu Lys Asn His Ile Thr Tyr Arg Ile
110                 115                 120                 125 ata ggc tat acc ccg gat ttg gat cct gag aca gta gat gat gcc ttt          554
Ile Gly Tyr Thr Pro Asp Leu Asp Pro Glu Thr Val Asp Asp Ala Phe
                130                 135                 140 gcc cga gcc ttt aaa gtc tgg agt gat gtc acg cca ctg aga ttt aac          602
Ala Arg Ala Phe Lys Val Trp Ser Asp Val Thr Pro Leu Arg Phe Asn
                145                 150                 155 cga ata aat gat gga gag gca gac att atg att aat ttt ggc cga tgg          650
Arg Ile Asn Asp Gly Glu Ala Asp Ile Met Ile Asn Phe Gly Arg Trp
                160                 165                 170 gaa cat ggt gat ggc tat cca ttt gat ggc aaa gat ggt ctc ctg gct          698
Glu His Gly Asp Gly Tyr Pro Phe Asp Gly Lys Asp Gly Leu Leu Ala
                175                 180                 185 cac gcc ttt gca ccg ggg cca gga att gga gga gac tcc cat ttt gat          746
His Ala Phe Ala Pro Gly Pro Gly Ile Gly Gly Asp Ser His Phe Asp
190                 195                 200                 205 gat gat gaa ctg tgg act ctt gga gaa ggg caa gtg gtt aga gta aag          794
Asp Asp Glu Leu Trp Thr Leu Gly Glu Gly Gln Val Val Arg Val Lys
                210                 215                 220 tat gga aat gca gat ggt gaa tac tgc aaa ttt ccc ttc tgg ttc aat          842
Tyr Gly Asn Ala Asp Gly Glu Tyr Cys Lys Phe Pro Phe Trp Phe Asn
                225                 230                 235 ggt aag gaa tac aac agc tgc aca gat gca gga cgt aat gat gga ttc          890
Gly Lys Glu Tyr Asn Ser Cys Thr Asp Ala Gly Arg Asn Asp Gly Phe
                240                 245                 250 ctc tgg tgt tcc aca acc aaa gac ttt gat gca gat ggc aaa tat ggc          938
Leu Trp Cys Ser Thr Thr Lys Asp Phe Asp Ala Asp Gly Lys Tyr Gly
255                 260                 265 ttt tgt ccc cat gag tca ctt ttt aca atg ggt ggc aat ggt gat gga          986
Phe Cys Pro His Glu Ser Leu Phe Thr Met Gly Gly Asn Gly Asp Gly
270                 275                 280                 285 cag ccc tgc aag ttt ccc ttt aaa ttt caa ggc cag tcc tat gac cag         1034
Gln Pro Cys Lys Phe Pro Phe Lys Phe Gln Gly Gln Ser Tyr Asp Gln
                290                 295                 300 tgt aca aca gaa ggc agg aca gat gga tac aga tgg tgt gga acc act         1082
Cys Thr Thr Glu Gly Arg Thr Asp Gly Tyr Arg Trp Cys Gly Thr Thr
```

-continued

|     | 305 | | | | 310 | | | | 315 | | | | | |
|---|---|---|---|---|---|---|---|---|---|---|---|---|---|---|
| gaa | gac | tat | gat | aga | gat | aag | aaa | tac | gga | ttc | tgc | cca | gaa | act | gcc | 1130 |
| Glu | Asp | Tyr | Asp | Arg | Asp | Lys | Lys | Tyr | Gly | Phe | Cys | Pro | Glu | Thr | Ala |
|     |     |     | 320 |     |     |     | 325 |     |     |     | 330 |     |     |     |     |

| atg | tca | aca | gtt | ggt | gga | aat | tca | gaa | gga | gct | cct | tgt | gta | ttc | ccc | 1178 |
|---|---|---|---|---|---|---|---|---|---|---|---|---|---|---|---|---|
| Met | Ser | Thr | Val | Gly | Gly | Asn | Ser | Glu | Gly | Ala | Pro | Cys | Val | Phe | Pro |
| 335 |     |     |     |     | 340 |     |     |     |     | 345 |     |     |     |     |     |

| ttc | atc | ttc | ctt | ggg | aat | aaa | tac | gac | tcc | tgt | aca | agt | gca | ggt | cgc | 1226 |
|---|---|---|---|---|---|---|---|---|---|---|---|---|---|---|---|---|
| Phe | Ile | Phe | Leu | Gly | Asn | Lys | Tyr | Asp | Ser | Cys | Thr | Ser | Ala | Gly | Arg |
| 350 |     |     |     |     | 355 |     |     |     |     | 360 |     |     |     |     | 365 |

| aat | gat | ggc | aag | ctg | tgg | tgt | gct | tct | acc | agc | agc | tat | gat | gat | gac | 1274 |
|---|---|---|---|---|---|---|---|---|---|---|---|---|---|---|---|---|
| Asn | Asp | Gly | Lys | Leu | Trp | Cys | Ala | Ser | Thr | Ser | Ser | Tyr | Asp | Asp | Asp |
|     |     |     |     | 370 |     |     |     |     | 375 |     |     |     |     | 380 |     |

| cgc | aag | tgg | ggc | ttt | tgt | cca | gat | caa | gga | tac | agt | ctc | ttc | ttg | gtt | 1322 |
|---|---|---|---|---|---|---|---|---|---|---|---|---|---|---|---|---|
| Arg | Lys | Trp | Gly | Phe | Cys | Pro | Asp | Gln | Gly | Tyr | Ser | Leu | Phe | Leu | Val |
|     |     |     | 385 |     |     |     |     | 390 |     |     |     |     | 395 |     |     |

| gct | gcc | cac | gaa | ttt | ggc | cat | gcg | atg | gga | tta | gag | cac | tcc | gag | gac | 1370 |
|---|---|---|---|---|---|---|---|---|---|---|---|---|---|---|---|---|
| Ala | Ala | His | Glu | Phe | Gly | His | Ala | Met | Gly | Leu | Glu | His | Ser | Glu | Asp |
|     |     |     | 400 |     |     |     |     | 405 |     |     |     |     | 410 |     |     |

| cca | gga | gct | ctc | atg | gcc | ccg | atc | tac | acc | tac | acc | aag | aac | ttc | cgc | 1418 |
|---|---|---|---|---|---|---|---|---|---|---|---|---|---|---|---|---|
| Pro | Gly | Ala | Leu | Met | Ala | Pro | Ile | Tyr | Thr | Tyr | Thr | Lys | Asn | Phe | Arg |
|     | 415 |     |     |     |     | 420 |     |     |     |     | 425 |     |     |     |     |

| ctt | tct | cag | gat | gac | att | aag | ggg | att | cag | gag | cta | tat | gaa | gta | tca | 1466 |
|---|---|---|---|---|---|---|---|---|---|---|---|---|---|---|---|---|
| Leu | Ser | Gln | Asp | Asp | Ile | Lys | Gly | Ile | Gln | Glu | Leu | Tyr | Glu | Val | Ser |
| 430 |     |     |     |     | 435 |     |     |     |     | 440 |     |     |     |     | 445 |

| cct | gat | gtg | gaa | cct | gga | cca | ggg | cca | gga | cca | ggg | cca | gga | cca | cgt | 1514 |
|---|---|---|---|---|---|---|---|---|---|---|---|---|---|---|---|---|
| Pro | Asp | Val | Glu | Pro | Gly | Pro | Gly | Pro | Gly | Pro | Gly | Pro | Gly | Pro | Arg |
|     |     |     | 450 |     |     |     |     | 455 |     |     |     |     | 460 |     |     |

| cct | acc | ctt | gga | cct | gtc | act | cca | gag | ctc | tgc | aag | cac | gac | att | gta | 1562 |
|---|---|---|---|---|---|---|---|---|---|---|---|---|---|---|---|---|
| Pro | Thr | Leu | Gly | Pro | Val | Thr | Pro | Glu | Leu | Cys | Lys | His | Asp | Ile | Val |
|     |     |     | 465 |     |     |     |     | 470 |     |     |     |     | 475 |     |     |

| ttt | gat | gga | gtt | gca | caa | att | aga | gga | gaa | ata | ttt | ttc | ttc | aaa | gac | 1610 |
|---|---|---|---|---|---|---|---|---|---|---|---|---|---|---|---|---|
| Phe | Asp | Gly | Val | Ala | Gln | Ile | Arg | Gly | Glu | Ile | Phe | Phe | Phe | Lys | Asp |
|     |     |     | 480 |     |     |     |     | 485 |     |     |     |     | 490 |     |     |

| aga | ttc | atg | tgg | agg | act | gta | aac | cct | cga | gga | aaa | ccc | aca | ggt | cct | 1658 |
|---|---|---|---|---|---|---|---|---|---|---|---|---|---|---|---|---|
| Arg | Phe | Met | Trp | Arg | Thr | Val | Asn | Pro | Arg | Gly | Lys | Pro | Thr | Gly | Pro |
|     | 495 |     |     |     |     | 500 |     |     |     |     | 505 |     |     |     |     |

| ctt | ctc | gtt | gct | aca | ttc | tgg | cct | gat | ctg | cca | gag | aaa | atc | gat | gct | 1706 |
|---|---|---|---|---|---|---|---|---|---|---|---|---|---|---|---|---|
| Leu | Leu | Val | Ala | Thr | Phe | Trp | Pro | Asp | Leu | Pro | Glu | Lys | Ile | Asp | Ala |
| 510 |     |     |     |     | 515 |     |     |     |     | 520 |     |     |     |     | 525 |

| gtc | tac | gag | tcc | cct | cag | gat | gag | aag | gct | gta | ttt | ttt | gca | gga | aat | 1754 |
|---|---|---|---|---|---|---|---|---|---|---|---|---|---|---|---|---|
| Val | Tyr | Glu | Ser | Pro | Gln | Asp | Glu | Lys | Ala | Val | Phe | Phe | Ala | Gly | Asn |
|     |     |     |     | 530 |     |     |     |     | 535 |     |     |     |     | 540 |     |

| gag | tac | tgg | gtt | tat | aca | gcc | agc | aac | ctg | gat | agg | ggc | tat | cca | aag | 1802 |
|---|---|---|---|---|---|---|---|---|---|---|---|---|---|---|---|---|
| Glu | Tyr | Trp | Val | Tyr | Thr | Ala | Ser | Asn | Leu | Asp | Arg | Gly | Tyr | Pro | Lys |
|     |     |     | 545 |     |     |     |     | 550 |     |     |     |     | 555 |     |     |

| aaa | ctc | acc | agc | ctg | gga | cta | ccc | cct | gat | gtg | caa | cgc | att | gat | gca | 1850 |
|---|---|---|---|---|---|---|---|---|---|---|---|---|---|---|---|---|
| Lys | Leu | Thr | Ser | Leu | Gly | Leu | Pro | Pro | Asp | Val | Gln | Arg | Ile | Asp | Ala |
|     |     |     | 560 |     |     |     |     | 565 |     |     |     |     | 570 |     |     |

| gcc | ttc | aac | tgg | ggc | aga | aac | aag | aag | aca | tat | att | ttc | tct | gga | gac | 1898 |
|---|---|---|---|---|---|---|---|---|---|---|---|---|---|---|---|---|
| Ala | Phe | Asn | Trp | Gly | Arg | Asn | Lys | Lys | Thr | Tyr | Ile | Phe | Ser | Gly | Asp |
|     | 575 |     |     |     |     | 580 |     |     |     |     | 585 |     |     |     |     |

| aga | tac | tgg | aag | tac | aat | gaa | gaa | aag | aaa | aaa | atg | gag | ctt | gca | acc | 1946 |
|---|---|---|---|---|---|---|---|---|---|---|---|---|---|---|---|---|
| Arg | Tyr | Trp | Lys | Tyr | Asn | Glu | Glu | Lys | Lys | Lys | Met | Glu | Leu | Ala | Thr |
| 590 |     |     |     |     | 595 |     |     |     |     | 600 |     |     |     |     | 605 |

| cca | aaa | ttc | att | gcg | gat | tct | tgg | aat | gga | gtt | cca | gat | aac | ctc | gat | 1994 |
|---|---|---|---|---|---|---|---|---|---|---|---|---|---|---|---|---|
| Pro | Lys | Phe | Ile | Ala | Asp | Ser | Trp | Asn | Gly | Val | Pro | Asp | Asn | Leu | Asp |
|     |     |     | 610 |     |     |     |     | 615 |     |     |     |     | 620 |     |     |

| gct | gtc | ctg | ggt | ctt | act | gac | agc | ggg | tac | acc | tat | ttt | ttc | aaa | gac | 2042 |

```
Ala Val Leu Gly Leu Thr Asp Ser Gly Tyr Thr Tyr Phe Phe Lys Asp
            625                 630                 635 cag tac tat cta caa atg gaa gac aag agt ttg aag att gtt aaa att    2090
Gln Tyr Tyr Leu Gln Met Glu Asp Lys Ser Leu Lys Ile Val Lys Ile
            640                 645                 650 ggc aag ata agt tct gac tgg ttg ggt tgc tga                        2123
Gly Lys Ile Ser Ser Asp Trp Leu Gly Cys
            655                 660
```

<210> SEQ ID NO 30
<211> LENGTH: 663
<212> TYPE: PRT
<213> ORGANISM: Gallus gallus

<400> SEQUENCE: 30

```
Met Lys Thr His Ser Val Phe Gly Phe Phe Lys Val Leu Leu Ile
  1               5                  10                  15

Gln Val Tyr Leu Phe Asn Lys Thr Leu Ala Ala Pro Ser Pro Ile Ile
                 20                  25                  30

Lys Phe Pro Gly Asp Ser Thr Pro Lys Thr Asp Lys Glu Leu Ala Val
             35                  40                  45

Gln Tyr Leu Asn Lys Tyr Tyr Gly Cys Pro Lys Asp Asn Cys Asn Leu
         50                  55                  60

Phe Val Leu Lys Asp Thr Leu Lys Lys Met Gln Lys Phe Phe Gly Leu
 65                  70                  75                  80

Pro Glu Thr Gly Asp Leu Asp Gln Asn Thr Ile Glu Thr Met Lys Lys
                 85                  90                  95

Pro Arg Cys Gly Asn Pro Asp Val Ala Asn Tyr Asn Phe Phe Pro Arg
            100                 105                 110

Lys Pro Lys Trp Glu Lys Asn His Ile Thr Tyr Arg Ile Ile Gly Tyr
        115                 120                 125

Thr Pro Asp Leu Asp Pro Glu Thr Val Asp Asp Ala Phe Ala Arg Ala
    130                 135                 140

Phe Lys Val Trp Ser Asp Val Thr Pro Leu Arg Phe Asn Arg Ile Asn
145                 150                 155                 160

Asp Gly Glu Ala Asp Ile Met Ile Asn Phe Gly Arg Trp Glu His Gly
                165                 170                 175

Asp Gly Tyr Pro Phe Asp Gly Lys Asp Gly Leu Leu Ala His Ala Phe
            180                 185                 190

Ala Pro Gly Pro Gly Ile Gly Gly Asp Ser His Phe Asp Asp Asp Glu
        195                 200                 205

Leu Trp Thr Leu Gly Glu Gly Gln Val Val Arg Val Lys Tyr Gly Asn
    210                 215                 220

Ala Asp Gly Glu Tyr Cys Lys Phe Pro Phe Trp Phe Asn Gly Lys Glu
225                 230                 235                 240

Tyr Asn Ser Cys Thr Asp Ala Gly Arg Asn Asp Gly Phe Leu Trp Cys
                245                 250                 255

Ser Thr Thr Lys Asp Phe Asp Ala Asp Gly Lys Tyr Gly Phe Cys Pro
            260                 265                 270

His Glu Ser Leu Phe Thr Met Gly Gly Asn Gly Asp Gly Gln Pro Cys
        275                 280                 285

Lys Phe Pro Phe Lys Phe Gln Gly Gln Ser Tyr Asp Gln Cys Thr Thr
    290                 295                 300

Glu Gly Arg Thr Asp Gly Tyr Arg Trp Cys Gly Thr Thr Glu Asp Tyr
305                 310                 315                 320
```

```
Asp Arg Asp Lys Lys Tyr Gly Phe Cys Pro Glu Thr Ala Met Ser Thr
            325                 330                 335

Val Gly Gly Asn Ser Glu Gly Ala Pro Cys Val Phe Pro Phe Ile Phe
            340                 345                 350

Leu Gly Asn Lys Tyr Asp Ser Cys Thr Ser Ala Gly Arg Asn Asp Gly
            355                 360                 365

Lys Leu Trp Cys Ala Ser Thr Ser Ser Tyr Asp Asp Arg Lys Trp
            370                 375                 380

Gly Phe Cys Pro Asp Gln Gly Tyr Ser Leu Phe Leu Val Ala Ala His
385                 390                 395                 400

Glu Phe Gly His Ala Met Gly Leu Glu His Ser Glu Asp Pro Gly Ala
                405                 410                 415

Leu Met Ala Pro Ile Tyr Thr Tyr Thr Lys Asn Phe Arg Leu Ser Gln
            420                 425                 430

Asp Asp Ile Lys Gly Ile Gln Glu Leu Tyr Glu Val Ser Pro Asp Val
            435                 440                 445

Glu Pro Gly Pro Gly Pro Gly Pro Gly Pro Arg Pro Thr Leu
450                 455                 460

Gly Pro Val Thr Pro Glu Leu Cys Lys His Asp Ile Val Phe Asp Gly
465                 470                 475                 480

Val Ala Gln Ile Arg Gly Glu Ile Phe Phe Lys Asp Arg Phe Met
            485                 490                 495

Trp Arg Thr Val Asn Pro Arg Gly Lys Pro Thr Gly Pro Leu Leu Val
            500                 505                 510

Ala Thr Phe Trp Pro Asp Leu Pro Glu Lys Ile Asp Ala Val Tyr Glu
            515                 520                 525

Ser Pro Gln Asp Glu Lys Ala Val Phe Phe Ala Gly Asn Glu Tyr Trp
            530                 535                 540

Val Tyr Thr Ala Ser Asn Leu Asp Arg Gly Tyr Pro Lys Lys Leu Thr
545                 550                 555                 560

Ser Leu Gly Leu Pro Pro Asp Val Gln Arg Ile Asp Ala Ala Phe Asn
                565                 570                 575

Trp Gly Arg Asn Lys Lys Thr Tyr Ile Phe Ser Gly Asp Arg Tyr Trp
            580                 585                 590

Lys Tyr Asn Glu Glu Lys Lys Met Glu Leu Ala Thr Pro Lys Phe
            595                 600                 605

Ile Ala Asp Ser Trp Asn Gly Val Pro Asp Asn Leu Asp Ala Val Leu
            610                 615                 620

Gly Leu Thr Asp Ser Gly Tyr Thr Tyr Phe Phe Lys Asp Gln Tyr Tyr
625                 630                 635                 640

Leu Gln Met Glu Asp Lys Ser Leu Lys Ile Val Lys Ile Gly Lys Ile
                645                 650                 655

Ser Ser Asp Trp Leu Gly Cys
            660

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 31
attgaattct tctacagttc a                                          21
```

```
<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 32
atgggatcca ctgcaaattt c                                                  21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 33
gccggatcca tgaccagtgt a                                                  21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 34
gtgggatccc tgaagactat g                                                  21

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 35 agggatcct taagggatt c                                                    21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 36
ctcggatcct ctgcaagcac g                                                  21

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 37
ctcggatcct ctgcaagcac g                                                  21
```

<210> SEQ ID NO 38
<211> LENGTH: 26
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 38
gcaggatccg agtgctgggt ttatac                                            26

<210> SEQ ID NO 39
<211> LENGTH: 27
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 39
gcagaattca actgtggcag aaacaag                                           27

<210> SEQ ID NO 40
<211> LENGTH: 26
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 40
gtagaattcc agcactcatt tcctgc                                            26

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 41
tctgaattct gccacagttg aagg                                              24

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 42
attgaattct tctacagttc a                                                 21

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 43
gatgaattct actgcaagtt                                                   20

<210> SEQ ID NO 44

```
<211> LENGTH: 21
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 44
cactgaattc atctgcaaac a                                              21

<210> SEQ ID NO 45
<211> LENGTH: 429
<212> TYPE: PRT
<213> ORGANISM: Homo sapiens

<400> SEQUENCE: 45

Tyr Cys Lys Phe Pro Phe Leu Phe Asn Gly Lys Glu Tyr Asn Ser Cys
  1               5                  10                  15

Thr Asp Thr Gly Arg Ser Asp Gly Phe Leu Trp Cys Ser Thr Thr Tyr
                 20                  25                  30

Asn Phe Glu Lys Asp Gly Lys Tyr Gly Phe Cys Pro His Glu Ala Leu
             35                  40                  45

Phe Thr Met Gly Gly Asn Ala Glu Gly Gln Pro Cys Lys Phe Pro Phe
         50                  55                  60

Arg Phe Gln Gly Thr Ser Tyr Asp Ser Cys Thr Thr Glu Gly Arg Thr
 65                  70                  75                  80

Asp Gly Tyr Arg Trp Cys Gly Thr Thr Glu Asp Tyr Asp Arg Asp Lys
                 85                  90                  95

Lys Tyr Gly Phe Cys Pro Glu Thr Ala Met Ser Thr Val Gly Gly Asn
            100                 105                 110

Ser Glu Gly Ala Pro Cys Val Phe Pro Phe Thr Phe Leu Gly Asn Lys
        115                 120                 125

Tyr Glu Ser Cys Thr Ser Ala Gly Arg Ser Asp Gly Lys Met Trp Cys
    130                 135                 140

Ala Thr Thr Ala Asn Tyr Asp Asp Asp Arg Lys Trp Gly Phe Cys Pro
145                 150                 155                 160

Asp Gln Gly Tyr Ser Leu Phe Leu Val Ala Ala His Glu Phe Gly His
                165                 170                 175

Ala Met Gly Leu Glu His Ser Gln Asp Pro Gly Ala Leu Met Ala Pro
            180                 185                 190

Ile Tyr Thr Tyr Thr Lys Asn Phe Arg Leu Ser Gln Asp Asp Ile Lys
        195                 200                 205

Gly Ile Gln Glu Leu Tyr Gly Ala Ser Pro Asp Ile Asp Leu Gly Thr
    210                 215                 220

Gly Pro Thr Pro Thr Leu Gly Pro Val Thr Pro Glu Ile Cys Lys Gln
225                 230                 235                 240

Asp Ile Val Phe Asp Gly Ile Ala Gln Ile Arg Gly Glu Ile Phe Phe
                245                 250                 255

Phe Lys Asp Arg Phe Ile Trp Arg Thr Val Thr Pro Arg Asp Lys Pro
                260                 265                 270

Met Gly Pro Leu Leu Val Ala Thr Phe Trp Pro Glu Leu Pro Glu Lys
            275                 280                 285

Ile Asp Ala Val Tyr Glu Ala Pro Gln Glu Glu Lys Ala Val Phe Phe
        290                 295                 300

Ala Gly Asn Glu Tyr Trp Ile Tyr Ser Ala Ser Thr Leu Glu Arg Gly
305                 310                 315                 320
```

```
-continued

Tyr Pro Lys Pro Leu Thr Ser Leu Gly Leu Pro Pro Asp Val Gln Arg
            325                 330              335

Val Asp Ala Ala Phe Asn Trp Ser Lys Asn Lys Lys Thr Tyr Ile Phe
            340                 345              350

Ala Gly Asp Lys Phe Trp Arg Tyr Asn Glu Val Lys Lys Lys Met Asp
            355                 360              365

Pro Gly Phe Pro Lys Leu Ile Ala Asp Ala Trp Asn Ala Ile Pro Asp
        370                 375              380

Asn Leu Asp Ala Val Val Asp Leu Gln Gly Gly His Ser Tyr Phe
385             390                 395                  400

Phe Lys Gly Ala Tyr Tyr Leu Lys Leu Glu Asn Gln Ser Leu Lys Ser
                405                 410              415

Val Lys Phe Gly Ser Ile Lys Ser Asp Trp Leu Gly Cys
            420                 425
```

METHODS AND COMPOSITIONS USEFUL FOR INHIBITION OF ANGIOGENESIS

This application is a 371 of PCT US97/09158, this application claims the benefit of provisional application 60/018773 filed May 31, 1996 and 60/015869 filed May 31, 1996.

This invention was made with government support under Contract Nos. CA50826, CA45726, HL54444, T32 AI07244-11 and F32 CA72192 by the National Institutes of Health. The government has certain rights in the invention.

TECHNICAL FIELD

The present invention relates generally to the field of medicine, and relates specifically to methods and compositions for inhibiting angiogenesis of tissues using antagonists of the vitronectin receptor $\alpha_v\beta_3$.

BACKGROUND

Integrins are a class of cellular receptors known to bind extracellular matrix proteins, and therefore mediate cell-cell and cell-extracellular matrix interactions, referred generally to as cell adhesion events. However, although many integrins and the ligands that bind an integrin are described in the literature, the biological function of many of the integrins remains elusive. The integrin receptors constitute a family of proteins with shared structural characteristics of noncovalent heterodimeric glycoprotein complexes formed of $\alpha$ and $\beta$ subunits.

The vitronectin receptor, named for its original characteristic of preferential binding to vitronectin, is now known to refer to three different integrins, designated $\alpha_v\beta_1$, $\alpha_v\beta_3$ and $\alpha_v\beta_5$. Horton, *Int. J. Exp. Pathol.*, 71:741–759 (1990). $\alpha_v\beta_1$ binds fibronectin and vitronectin. $\alpha_v\beta_3$ binds a large variety of ligands, including fibrin, fibrinogen, laminin, thrombospondin, vitronectin, von Willebrand's factor, osteospontin and bone sialoprotein I. $\alpha_v\beta_5$ binds vitronectin. The specific cell adhesion roles these three integrins play in the many cellular interactions in tissues are still under investigation, but it is clear that there are different integrins with different biological functions.

One important recognition site in the ligand for many integrins is the arginine-glycine-aspartic acid (RGD) tripeptide sequence. RGD is found in all of the ligands identified above for the vitronectin receptor integrins. This RGD recognition site can be mimicked by polypeptides ("peptides") that contain the RGD sequence, and such RGD peptides are known inhibitors of integrin function. It is important to note, however, that depending upon the sequence and structure of the RGD peptide, the specificity of the inhibition can be altered to target specific integrins.

For discussions of the RGD recognition site, see Pierschbacher et al., *Nature*, 309:30–33 (1984), and Pierschbacher et al., *Proc. Natl. Acad. Sci., USA*, 81:5985–5988 (1984). Various RGD polypeptides of varying integrin specificity have also been described by Grant et al., *Cell*, 58:933–943 (1989), Cheresh et al., *Cell*, 58:945–953 (1989), Aumailley et al., *FEBS Letts.*, 291:50–54 (1991), and Pfaff et al., *J. Biol. Chem.*, 269:20233–20238 (1994), and in U.S. Pat. Nos. 4,517,686, 4,578,079, 4,589,881, 4,614,517, 4,661,111, 4,792,525, 4,683,291, 4,879,237, 4,988,621, 5,041,380 and 5,061,693.

Angiogenesis is a process of tissue vascularization that involves the growth of new developing blood vessels into a tissue, and is also referred to as neo-vascularization. The process is mediated by the infiltration of endothelial cells and smooth muscle cells. The process is believed to proceed in any one of three ways: the vessels can sprout from pre-existing vessels, de-novo development of vessels can arise from precursor cells (vasculogenesis), or existing small vessels can enlarge in diameter. Blood et al., *Bioch. Biophys. Acta*, 1032:89–118 (1990). Vascular endothelial cells are known to contain at least five RGD-dependent integrins, including the vitronectin receptor ($\alpha_v\beta_3$ or $\alpha_v\beta_5$), the collagen Types I and IV receptor ($\alpha_1\beta_1$), the laminin receptor ($\alpha_2\beta_1$), the fibronectin/laminin/collagen receptor ($\alpha_1\beta_1$) and the fibronectin receptor ($\alpha_5\beta_1$). Davis et al., *J. Cell. Biochem.*, 51:206–218 (1993). The smooth muscle cell is known to contain at least six RGD-dependent integrins, including $\alpha_5\beta_1$, $\alpha_v\beta_3$ and $\alpha_v\beta_5$.

Angiogenesis is an important process in neonatal growth, but is also important in wound healing and in the pathogenesis of a large variety of clinical diseases including tissue inflammation, arthritis, tumor growth, diabetic retinopathy, macular degeneration by neovascularization of retina and the like conditions. These clinical manifestations associated with angiogenesis are referred to as angiogenic diseases. Folkman et al., *Science*, 235:442–447 (1987). Angiogenesis is generally absent in adult or mature tissues, although it does occur in wound healing and in the corpeus leuteum growth cycle. See, for example, Moses et al., *Science*, 248:1408–1410 (1990).

It has been proposed that inhibition of angiogenesis would be a useful therapy for restricting tumor growth. Inhibition of angiogenesis has been proposed by (1) inhibition of release of "angiogenic molecules" such as bFGF (basic fibroblast growth factor), (2) neutralization of angiogenic molecules, such as by use of anti-βbFGF antibodies, and (3) inhibition of endothelial cell response to angiogenic stimuli. This latter strategy has received attention, and Folkman et al., *Cancer Biology*, 3:89–96 (1992), have described several endothelial cell response inhibitors, including collagenase inhibitor, basement membrane turnover inhibitors, angiostatic steroids, fungal-derived angiogenesis inhibitors, platelet factor 4, thrombospondin, arthritis drugs such as D-penicillamine and gold thiomalate, vitamin $D_3$ analogs, alpha-interferon, and the like that might be used to inhibit angiogenesis. For additional proposed inhibitors of angiogenesis, see Blood et al., *Bioch. Biophys. Acta.*, 1032:89–118 (1990), Moses et al., *Science*, 248:1408–1410 (1990), Ingber et al., *Lab. Invest.*, 59:44–51 (1988), and U.S. Pat. Nos. 5,092,885, 5,112,946, 5,192,744, and 5,202,352. None of the inhibitors of angiogenesis described in the foregoing references are targeted at inhibition of $\alpha_v\beta_3$.

RGD-containing peptides that inhibit vitronectin receptor $\alpha_v\beta_3$ have also been described. Aumailley et al., *FEBS Letts.*, 291:50–54 (1991), Choi et al., *J. Vasc. Surg.*, 19:125–134 (1994), Smith et al., *J. Biol. Chem.*, 265:12267–12271 (1990), and Pfaff et al., *J. Biol. Chem.*, 269:20233–20238 (1994). However, the role of the integrin $\alpha_v\beta_3$ in angiogenesis has never been suggested nor identified until the present invention.

For example, Hammes et al., *Nature Med.*, 2:529–53 (1996) confirmed the findings of the present invention. Specifically, the paper shows that cyclic peptides including cyclic RGDfV, the structure and function of the latter of which has been previously described in the priority applications on which the present application is based, inhibited retinal neovascularization in a mouse model of hypoxia-induced retinal neovascularization. In a separate study that also supports the present invention as well as the priority applications, Luna et al., *Lab. Invest.*, 75:563–573 (1996) described two particular cyclic methylated RGD-containing peptides that were partially effective at inhibiting retinal neovascularization in the mouse model of oxygen-induced ischemic retinopathy. In contrast, the peptides of the present invention exhibit almost complete inhibition of neovascularization in the model systems described herein.

Inhibition of cell adhesion in vitro using monoclonal antibodies immunospecific for various integrin α or β subunits have implicated $\alpha_v\beta_3$ in cell adhesion of a variety of cell types including microvascular endothelial cells. Davis et al., *J. Cell. Biol.*, 51:206–218 (1993). In addition, Nicosia et al., *Am. J. Pathol.*, 138:829–833 (1991), described the use of the RGD peptide GRGDS to in vitro inhibit the formation of "microvessels" from rat aorta cultured in collagen gel. However, the inhibition of formation of "microvessels" in vitro in collagen gel cultures is not a model for inhibition of angiogenesis in a tissue because it is not shown that the microvessel structures are the same as capillary sprouts or that the formation of the microvessel in collagen gel culture is the same as neovascular growth into an intact tissue, such as arthritic tissue, tumor tissue or disease tissue where inhibition of angiogenesis is desirable.

For angiogenesis to occur, endothelial cells must first degrade and cross the blood vessel basement membrane in a similar manner used by tumor cells during invasion and metastasis formation.

The inventors have previously reported that angiogenesis depends on the interaction between vascular integrins and extracellular matrix proteins. Brooks et al., *Science*, 264:569–571 (1994). Furthermore, it was reported that programmed cell death (apoptosis) of angiogenic vascular cells is initiated by the interaction, which would be inhibited by certain antagonists of the vascular integrin $\alpha_v\beta_3$. Brooks et al., *Cell*, 79:1157–1164 (1994). More recently, the inventors have reported that the binding of matrix metalloproteinase-2 (MMP-2) to vitronectin receptor ( can be inhibited using $\alpha_v\beta_5$ antagonists, and thereby inhibit the enzymatic function of the proteinase. Brooks et al., *Cell*, 85:683–693 (1996).

Other than the studies reported here, Applicants are unaware of any other demonstration that angiogenesis could be inhibited in a tissue using inhibitors of cell adhesion. In particular, it has never been previously demonstrated by others that $\alpha_v\beta_3$ function is required for angiogenesis in a tissue or that $\alpha_v\beta_3$ antagonists can inhibit angiogenesis in a tissue.

BRIEF DESCRIPTION OF THE INVENTION

The present invention disclosure demonstrates that angiogenesis in tissues requires integrin $\alpha_v\beta_3$, and that inhibitors of $\alpha_v\beta_3$ can inhibit angiogenesis. The disclosure also demonstrates that antagonists of other integrins, such as $\alpha_{IIb}\beta_3$, or $\alpha_v\beta_1$, do not inhibit angiogenesis, presumably because these other integrins are not essential for angiogenesis to occur.

The invention therefore describes methods for inhibiting angiogenesis in a tissue comprising administering to the tissue a composition comprising an angiogenesis-inhibiting amount of an $\alpha_v\beta_3$ antagonist.

The tissue to be treated can be any tissue in which inhibition of angiogenesis is desirable, such as diseased tissue where neo-vascularization is occurring. Exemplary tissues include inflamed tissue, solid tumors, metastases, tissues undergoing restenosis, and the like tissues.

An $\alpha_v\beta_3$ antagonist for use in the present methods is capable of binding to $\alpha_v\beta_3$ and competitively inhibiting the ability of $\alpha_v\beta_3$ to bind to a natural ligand. Preferably, the antagonist exhibits specificity for $\alpha_v\beta_3$ over other integrins.

In a particularly preferred embodiment, the $\alpha_v\beta_3$ antagonist inhibits binding of fibrinogen or other RGD-containing ligands to $\alpha_v\beta_3$ but does not substantially inhibit binding of fibrinogen to $\alpha_{IIb}\beta_3$. A preferred $\alpha_v\beta_3$ antagonist can be a fusion polypeptied, a cyclic or linear polypeptide, a derivatized polypeptide, a monoclonal antibody that immunoreacts with $\alpha_v\beta_3$, an organic mimetic of $\alpha_v\beta_3$ or functional fragment thereof.

BRIEF DESCRIPTION OF THE DRAWINGS

In the drawings forming a portion of this disclosure:

FIGS. 1A and 1B respectively illustrate the immunoreactivity of anti-$\beta_3$ in normal skin and granulation tissue. FIGS. 1C and 1D respectively illustrate the immunoreactivity of anti-$\beta_1$ in normal skin and granulation tissue.

FIGS. 2A and 2B respectively illustrate the immunoreactivity of anti-vWF in normal skin and granulation tissue. FIGS. 2C and 2D respectively illustrate the immunoreactivity of anti-laminin in normal skin and granulation tissue.

FIG. 5A shows the distribution of the $\beta_1$ subunit in an untreated 10 day old CAM preparation as detected by immunofluorescence immunoreactivity with CSAT, an anti-$\beta_1$ antibody. FIG. 5B shows the distribution of the $\alpha_v\beta_3$ receptor in an untreated 10 day old CAM preparation as detected by immunofluorescence immunoreactivity with LM609, an anti-$\alpha_v\beta_3$ antibody. FIG. 5C shows the distribution of the $\alpha_v\beta_3$ receptor in an bFGF treated 10 day old CAM preparation as detected by immunofluorescence immunoreactivity with LM609, an anti-$\alpha_v\beta_3$ antibody. The treatments and results are described in Example 5C.

FIGS. 8A–8E illustrate the effect of topical antibody treatment on bFGF-induced angiogenesis in a day 10 CAM as described in Example 7A1). FIG. 8A shows an untreated CAM preparation that is devoid of blood vessels, FIG. 8B shows the infiltration of new vasculature into an area previously devoid of vasculature induced by bFGF treatment. FIGS. 8C, 8D and 8E respectively show the effects of antibodies against $\beta_1$ (anti-$\beta_1$; CSAT), $\alpha_v\beta_5$ (anti-$\alpha_v\beta_5$; P3G2) and $\alpha_v\beta_3$ (anti-$\alpha_v\beta_3$; LM609).

FIGS. 9A–9C illustrate the effect of intravenous injection of synthetic peptide 66203 on angiogenesis induced by tumors as described in Example 7E2). FIG. 9A shows the lack of inhibitory effect of intravenous treatment with a control peptide (control peptide tumor) on angiogenesis resulting from tumor induction. The inhibition of such angiogenesis by intravenous injection of peptide 66203 (cyclic RGD tumor) is shown in FIG. 9B. The lack of inhibitory effects or cytotoxicity on mature preexisting vessels following intravenous infusion of peptide 66203 in an area adjacent to the tumor-treated area is shown in FIG. 9C (cyclic RGD adjacent CAM).

FIG. 10A shows bFGF-induced angiogenesis not exposed to antibody treatment (control). No inhibition of angiogenesis resulted when a similar preparation was treated with anti-$\alpha_v\beta_5$ antibody P3G2 as shown in FIG. 10B. Inhibition of angiogenesis resulted with treatment of anti-$\alpha_v\beta_3$ antibody LM609 as shown in FIG. 10C.

As shown in FIG. 14A, tumors treated with control antibody (P3G2) showed numerous viable and actively dividing tumor cells as indicated by mitotic figures (arrowheads) as well as by multiple blood vessels (arrows) throughout the tumor stroma. In contrast, few if any viable tumor cells or blood vessels were detected in tumors treated with LM609 (anti-$\alpha_v\beta_3$) in FIG. 14B.

FIGS. 15A–15E correspond to M21L tumors treated with peptides as described in Example 9A2) and are as follows:

FIG. 15A, control cyclic RAD peptide (69601); FIG. 15B, cyclic RGD peptide (66203); FIG. 15C, adjacent CAM tissue taken from the same embryos treated with cyclic RGD peptide (66203) and high magnification (13×) of tumors treated with the control RAD (69601) in FIG. 15D or cyclic RGD peptide (66203) in FIG. 15E. FIG. 15D depicts normal vessels from the RAD control peptide (69601) treated tumor. FIG. 15E depicts examples of disrupted blood vessels from cyclic RGD peptide (66203) treated tumors (arrows).

FIGS. 16A and 16B depict angiogenesis of the rabbit eye in the presence of bFGF and mAb P1F6 (anti-$\alpha_v\beta_5$). FIGS. 16C, 16D and 16E depict inhibition of angiogenesis of the rabbit eye in the presence of bFGF and mAb LM609 (anti-$\alpha_v\beta_3$).

FIGS. 20A and 20D depict tissues stained with Apop Tag and visualized by fluorescence (FITC) superimposed on a D.I.C. image. FIGS. 20B and 20E depict the same tissues stained with mAb LM609 (anti-$\alpha_v\beta_3$) and visualized by fluorescence (rhodamine). FIGS. 20C and 20F represent merged images of the same tissues stained with both Apop Tag and LM609 where yellow staining represents colocalization. The bar represents 15 and 50 $\mu$m in the left and right panels, respectively.

FIGS. 22A and 22B show the consecutive cDNA sequence of chicken MMP-2 along with the deduced amino acid sequence shown on the second line. The third and fourth lines respectively show the deduced amino acid sequence of human and mouse MMP-2 as described in Example 4A. The chicken cDNA sequence is listed in SEQ ID NO 29 along with the encoded amino acid sequence that is also presented separately as SEQ ID NO 30. The numbering of the first nucleotide of the 5' untranslated region and the region encoding the proenzyme sequence shown in FIG. 22A as a negative number is actually presented as number 1 in Sequence Listing making the latter appear longer than the figure; however, the nucleotide sequence is the figure is identical in length and sequence to that as presented in the listing with the exception of the numbering. Accordingly, references to nucleotide position for chicken or human MMP-2 in the specification, such as in primers for use in amplifying MMP-2 fragments, are based on the nucleotide position as indicated in the figure and not as listed in the Sequence Listing.

FIG. 25 show the effect of chicken MMP-2(410–637) GST fusion protein on bFGF-induced angiogenesis as described in Example 7A3).

FIGS. 31A–L show the effect of various treatments against untreated CAM preparations over a time course beginning at 24 hours and ending at 72 hours as further described in Example 7B3). Photographs for the categories labeled untreated, bFGF, bFGF+MAID (bFGF treated followed with exposure to chicken MMP-2(2–4) GST fusion protein) and bFGF+control (bFGF treatment followed by chicken MMP-2(10–1) are respectively shown in FIGS. 31A–C, 31D–F, 31G–I, and 31J–L.

FIGS. 38 through 42 schematically illustrate the various chemical syntheses of organic molecule $\alpha_v\beta_3$ antagonists as further described in Example 13.

DETAILED DESCRIPTION OF THE INVENTION

A. Definitions

Figure 1A:
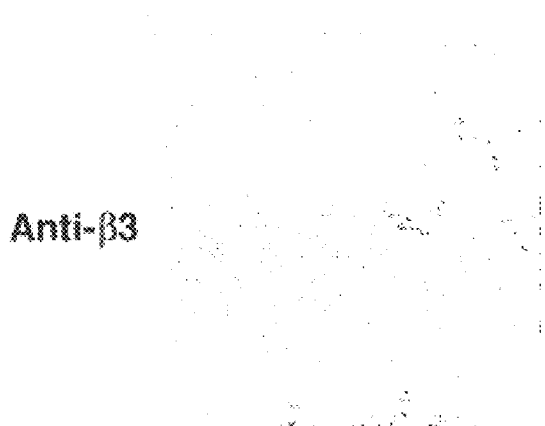
FIGS. 1A–1D illustrate the tissue distribution of the integrin subunits, $\beta_3$ and $\beta_1$, in normal skin and in skin undergoing wound healing designated as granulation tissue. Immunohistochemistry with antibodies to $\beta_3$ and $\beta_1$ was performed as described in Example 3A.
Figure 1B:
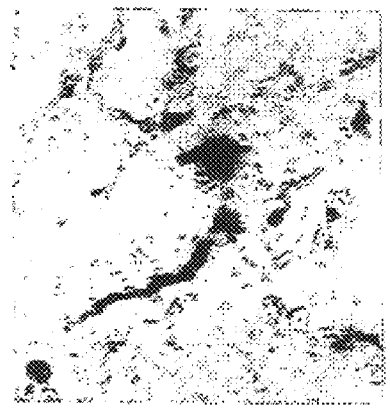
Figure 1C:
Figure 1D:
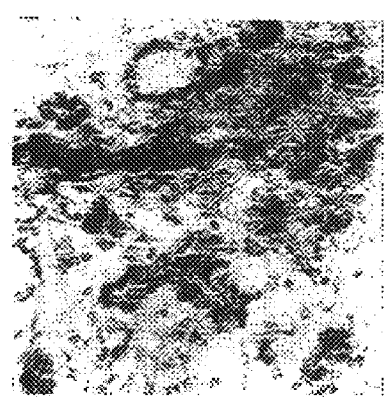

Amino Acid Residue: An amino acid formed upon chemical digestion (hydrolysis) of a polypeptide at its peptide linkages. The amino acid residues described herein are preferably in the "L" isomeric form. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature (described in *J. Biol. Chem.*, 243:3552–59 (1969) and adopted at 37 CFR §1.822 (b) (2)), abbreviations for amino acid residues are shown in the following Table of Correspondence:

TABLE OF CORRESPONDENCE

| SYMBOL | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| Z | Glx | Glu and/or Gln |
| W | Trp | tryptophan |
| R | Arg | arginine |
| D | Asp | aspartic acid |
| N | Asn | asparagine |
| B | Asx | Asn and/or Asp |
| C | Cys | cysteine |
| X | Xaa | unknown/other |

In addition the following have the meanings below:

| BOC | tert-butyloxycarbonyl |
|---|---|
| DCCI | dicylcohexylcarbodiimide |
| DMF | dimethylformamide |
| OMe | methoxy |
| HOBt | 1-hydroxybezotriazole |

It should be noted that all amino acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino acid residues.

Polypeptide: refers to a linear series of amino acid residues connected to one another by peptide bonds between the alpha-amino group and carboxy group of contiguous amino acid residues.

Peptide: as used herein refers to a linear series of no more than about 50 amino acid residues connected one to the other as in a polypeptide.

Cyclic peptide: refers to a compound having a heteroatom ring structure that includes several amide bonds as in a typical peptide. The cyclic peptide can be a "head to tail" cyclized linear polypeptide in which a linear peptide's n-terminus has formed an amide bond with the terminal carboxylate of the linear peptide, or it can contain a ring structure in which the polymer is homodetic or heterodetic and comprises amide bonds and/or other bonds to close the ring, such as disulfide bridges, thioesters, thioamides, guanidino, and the like linkages.

Protein: refers to a linear series of greater than 50 amino acid residues connected one to the other as in a polypeptide.

Fusion protein: refers to a polypeptide containing at least two different polypeptide domains operatively linked by a typical peptide bond ("fused"), where the two domains correspond to peptides no found fused in nature.

Synthetic peptide: refers to a chemically produced chain of amino acid residues linked together by peptide bonds that is free of naturally occurring proteins and fragments thereof.

B. General Considerations

The present invention relates generally to the discovery that angiogenesis is mediated by the specific vitronectin receptor $\alpha_v\beta_3$, and that inhibition of $\alpha_v\beta_3$ function inhibits angiogenesis. This discovery is important because of the role that angiogenesis plays in a variety of disease processes. By inhibiting angiogenesis, one can intervene in the disease, ameliorate the symptoms, and in some cases cure the disease.

Where the growth of new blood vessels is the cause of, or contributes to, the pathology associated with a disease, inhibition of angiogenesis will reduce the deleterious effects of the disease. Examples include rheumatoid arthritis, diabetic retinopathy, inflammatory diseases, restenosis, and the like. Where the growth of new blood vessels is required to support growth of a deleterious tissue, inhibition of angiogenesis will reduce the blood supply to the tissue and thereby contribute to reduction in tissue mass based on blood supply requirements. Examples include growth of tumors where neovascularization is a continual requirement in order that the tumor grow beyond a few millimeters in thickness, and for the establishment of solid tumor metastases.

The methods of the present invention are effective in part because the therapy is highly selective for angiogenesis and not other biological processes. As shown in the Examples, only new vessel growth contains substantial $\alpha_v\beta_3$, and therefore the therapeutic methods do not adversely effect mature vessels. Furthermore, $\alpha_v\beta_3$ is not widely distributed in normal tissues, but rather is found selectively on new vessels, thereby assuring that the therapy can be selectively targeted to new vessel growth.

The discovery that inhibition of $\alpha_v\beta_3$ alone will effectively inhibit angiogenesis allows for the development of therapeutic compositions with potentially high specificity, and therefore relatively low toxicity. Thus although the invention discloses the use of peptide-based reagents which have the ability to inhibit one or more integrins, one can design other reagents which more selectively inhibit $\alpha_v\beta_3$, and therefore do not have the side effect of inhibiting other biological processes other that those mediated by $\alpha_v\beta_3$.

For example, as shown by the present teachings, it is possible to prepare monoclonal antibodies highly selective for immunoreaction with $\alpha_v\beta_3$ that are similarly selective for inhibition of $\alpha_v\beta_3$ function. In addition, RGD-containing peptides can be designed to be selective for inhibition of $\alpha_v\beta_3$, as described further herein.

Prior to the discoveries of the present invention, it was not known that angiogenesis, and any of the processes dependent on angiogenesis, could be inhibited in vivo by the use of reagents that antagonize the biological function of $\alpha_v\beta_3$.

C. Methods for Inhibition of Angiogenesis

The invention provides for a method for the inhibition of angiogenesis in a tissue, and thereby inhibiting events in the tissue which depend upon angiogenesis. Generally, the method comprises administering to the tissue a composition comprising an angiogenesis-inhibiting amount of an 60 $_v\beta_3$ antagonist.

As described earlier, angiogenesis includes a variety of processes involving neovascularization of a tissue including "sprouting", vasculogenesis, or vessel enlargement, all of which angiogenesis processes are mediated by and dependent upon the expression of $\alpha_v\beta_3$. With the exception of traumatic wound healing, corpus leuteum formation and embryogenesis, it is believed that the majority of angiogenesis processes are associated with disease processes and therefore the use of the present therapeutic methods are selective for the disease and do not have deleterious side effects.

There are a variety of diseases in which angiogenesis is believed to be important, referred to as angiogenic diseases, including but not limited to, inflammatory disorders such as immune and non-immune inflammation, chronic articular rheumatism and psoriasis, disorders associated with inappropriate or inopportune invasion of vessels such as diabetic retinopathy, neovascular glaucoma, restenosis, capillary proliferation in atherosclerotic plaques and osteoporosis, and cancer associated disorders, such as solid tumors, solid tumor metastases, angiofibromas, retrolental fibroplasia, hemangiomas, Kaposi sarcoma and the like cancers which require neovascularization to support tumor growth.

Thus, methods which inhibit angiogenesis in a diseased tissue ameliorates symptoms of the disease and, depending upon the disease, can contribute to cure of the disease. In one embodiment, the invention contemplates inhibition of angiogenesis, per se, in a tissue. The extent of angiogenesis in a tissue, and therefore the extent of inhibition achieved by the present methods, can be evaluated by a variety of methods, such as are described in the Examples for detecting $\alpha_v\beta_3$-immunopositive immature and nascent vessel structures by immunohistochemistry.

As described herein, any of a variety of tissues, or organs comprised of organized tissues, can support angiogenesis in disease conditions including skin, muscle, gut, connective tissue, joints, bones and the like tissue in which blood vessels can invade upon angiogenic stimuli.

Thus, in one related embodiment, a tissue to be treated is an inflamed tissue and the angiogenesis to be inhibited is inflamed tissue angiogenesis where there is neovascularization of inflamed tissue. In this class the method contemplates inhibition of angiogenesis in arthritic tissues, such as in a patient with chronic articular rheumatism, in immune or non-immune inflamed tissues, in psoriatic tissue and the like.

The patient treated in the present invention in its many embodiments is desirably a human patient, although it is to be understood that the principles of the invention indicate that the invention is effective with respect to all mammals, which are intended to be included in the term "patient". In this context, a mammal is understood to include any mammalian species in which treatment of diseases associated with angiogenesis is desirable, particularly agricultural and domestic mammalian species.

In another related embodiment, a tissue to be treated is a retinal tissue of a patient with a retinal disease such as diabetic retinopathy, macular degeneration or neovascular glaucoma and the angiogenesis to be inhibited is retinal tissue angiogenesis where there is neovascularization of retinal tissue.

In an additional related embodiment, a tissue to be treated is a tumor tissue of a patient with a solid tumor, a metastases, a skin cancer, a breast cancer, a hemangioma or angiofibroma and the like cancer, and the angiogenesis to be inhibited is tumor tissue angiogenesis where there is neovascularization of a tumor tissue. Typical solid tumor tissues treatable by the present methods include lung, pancreas, breast, colon, laryngeal, ovarian, and the like tissues. Exemplary tumor tissue angiogenesis, and inhibition thereof, is described in the Examples.

Inhibition of tumor tissue angiogenesis is a particularly preferred embodiment because of the important role neovascularization plays in tumor growth. In the absence of neovascularization of tumor tissue, the tumor tissue does not obtain the required nutrients, slows in growth, ceases additional growth, regresses and ultimately becomes necrotic resulting in killing of the tumor.

Stated in other words, the present invention provides for a method of inhibiting tumor neovascularization by inhibiting tumor angiogenesis according to the present methods. Similarly, the invention provides a method of inhibiting tumor growth by practicing the angiogenesis-inhibiting methods.

The methods are also particularly effective against the formation of metastases because (1) their formation requires vascularization of a primary tumor so that the metastatic cancer cells can exit the primary tumor and (2) their establishment in a secondary site requires neovascularization to support growth of the metastases.

In a related embodiment, the invention contemplates the practice of the method in conjunction with other therapies such as conventional chemotherapy directed against solid tumors and for control of establishment of metastases. The administration of angiogenesis inhibitor is typically conducted during or after chemotherapy, although it is preferably to inhibit angiogenesis after a regimen of chemotherapy at times where the tumor tissue will be responding to the toxic assault by inducing angiogenesis to recover by the provision of a blood supply and nutrients to the tumor tissue. In addition, it is preferred to administer the angiogenesis inhibition methods after surgery where solid tumors have been removed as a prophylaxis against metastases.

Insofar as the present methods apply to inhibition of tumor neovascularization, the methods can also apply to inhibition of tumor tissue growth, to inhibition of tumor metastases formation, and to regression of established tumors. The Examples demonstrate regression of an established tumor following a single intravenous administration of an $\alpha_v\beta_3$ antagonist of this invention.

Restenosis is a process of smooth muscle cell (SMC) migration and proliferation at the site of percutaneous transluminal coronary angioplasty which hampers the success of angioplasty. The migration and proliferation of SMC's during restenosis can be considered a process of angiogenesis which is inhibited by the present methods. Therefore, the invention also contemplates inhibition of restenosis by inhibiting angiogenesis according to the present methods in a patient following angioplasty procedures. For inhibition of restenosis, the $\alpha_v\beta_3$ antagonist is typically administered after the angioplasty procedure for from about 2 to about 28 days, and more typically for about the first 14 days following the procedure.

The present method for inhibiting angiogenesis in a tissue, and therefore for also practicing the methods for treatment of angiogenesis-related diseases, comprises contacting a tissue in which angiogenesis is occurring, or is at risk for occurring, with a composition comprising a therapeutically effective amount of an $\alpha_v\beta_3$ antagonist capable of inhibiting $\alpha_v\beta_3$ binding to its natural ligand. Thus the method comprises administering to a patient a therapeutically effective amount of a physiologically tolerable composition containing an $\alpha_v\beta_3$ antagonist of the invention.

The dosage ranges for the administration of the $\alpha_v\beta_3$ antagonist depend upon the form of the antagonist, and its potency, as described further herein, and are amounts large enough to produce the desired effect in which angiogenesis and the disease symptoms mediated by angiogenesis are ameliorated. The dosage should not be so large as to cause adverse side effects, such as hyperviscosity syndromes, pulmonary edema, congestive heart failure, and the like. Generally, the dosage will vary with the age, condition, sex and extent of the disease in the patient and can be determined by one of skill in the art. The dosage can also be adjusted by the individual physician in the event of any complication.

A therapeutically effective amount is an amount of $\alpha_v\beta_3$ antagonist sufficient to produce a measurable inhibition of angiogenesis in the tissue being treated, ie., an angiogenesis-inhibiting amount. Inhibition of angiogenesis can be measured in situ by immunohistochemistry, as described herein, or by other methods known to one skilled in the art.

Insofar as an $\alpha_v\beta_3$ antagonist can take the form of a $\alpha_v\beta_3$ mimetic, an RGD-containing peptide, an anti-$\alpha_v\beta_3$ monoclonal antibody, or fragment thereof, it is to be appreciated that the potency, and therefore an expression of a "therapeutically effective" amount can vary. However, as shown by the present assay methods, one skilled in the art can readily assess the potency of a candidate $\alpha_v\beta_3$ antagonist of this invention.

Potency of an $\alpha_v\beta_3$ antagonist can be measured by a variety of means including inhibition of angiogenesis in the CAM assay, in the in vivo rabbit eye assay, in the in vivo chimeric mouse:human assay, and by measuring inhibition of binding of natural ligand to $\alpha_v\beta_3$, all as described herein, and the like assays.

A preferred $\alpha_v\beta_3$ antagonist has the ability to substantially inhibit binding of a natural ligand such as fibrinogen or vitronectin to $\alpha_v\beta_3$ in solution at antagonist concentrations of less than 0.5 micromolar (um), preferably less than 0.1 um, and more preferably less than 0.05 um. By "substantially" is meant that at least a 50 percent reduction in binding of fibrinogen is observed by inhibition in the presence of the $\alpha_v\beta_3$ antagonist, and at 50% inhibition is referred to herein as an $IC_{50}$ value.

A more preferred $\alpha_v\beta_3$ antagonist exhibits selectivity for $\alpha_v\beta_3$ over other integrins. Thus, a preferred $\alpha_v\beta_3$ antagonist substantially inhibits fibrinogen binding to $\alpha_v\beta_3$ but does not substantially inhibit binding of fibrinogen to another integrin, such as $\alpha_v\beta_1$, $\alpha_v\beta_5$ or $\alpha_{IIb}\beta_3$. Particularly preferred is an $\alpha_v\beta_3$ antagonist that exhibits a 10-fold to 100-fold lower $IC_{50}$ activity at inhibiting fibrinogen binding to $\alpha_v\beta_3$ compared to the $IC_{50}$ activity at inhibiting fibrinogen binding to another integrin. Exemplary assays for measuring $IC_{50}$ activity at inhibiting fibrinogen binding to an integrin are described in the Examples.

A therapeutically effective amount of an $\alpha_v\beta_3$ antagonist of this invention in the form of a monoclonal antibody is typically an amount such that when administered in a physiologically tolerable composition is sufficient to achieve a plasma concentration of from about 0.01 microgram (ug) per milliliter (ml) to about 100 ug/ml, preferably from about 1 ug/ml to about 5 ug/ml, and usually about 5 ug/ml. Stated differently, the dosage can vary from about 0.1 mg/kg to about 300 mg/kg, preferably from about 0.2 mg/kg to about 200 mg/kg, most preferably from about 0.5 mg/kg to about 20 mg/kg, in one or more dose administrations daily, for one or several days.

Where the antagonist is in the form of a fragment of a monoclonal antibody, the amount can readily be adjusted based on the mass of the fragment relative to the mass of the whole antibody. A preferred plasma concentration in molarity is from about 2 micromolar (uM) to about 5 millimolar (mM) and preferably about 100 uM to 1 mM antibody antagonist.

A therapeutically effective amount of an $\alpha_v\beta_3$ antagonist of this invention in the form of a polypeptide, or other similarly-sized small molecule $\alpha_v\beta_3$ mimetic, is typically an amount of polypeptide such that when administered in a physiologically tolerable composition is sufficient to achieve a plasma concentration of from about 0.1 microgram (ug) per milliliter (ml) to about 200 ug/ml, preferably from about 1 ug/ml to about 150 ug/ml. Based on a polypeptide having a mass of about 500 grams per mole, the preferred plasma concentration in molarity is from about 2 micromolar (uM) to about 5 millimolar (mM) and preferably about 100 uM to 1 mM polypeptide antagonist. Stated differently, the dosage per body weight can vary from about 0.1 mg/kg to about 300 mg/kg, and preferably from about 0.2 mg/kg to about 200 mg/kg, in one or more dose administrations daily, for one or several days.

The monoclonal antibodies or polypeptides of the invention can be administered parenterally by injection or by gradual infusion over time. Although the tissue to be treated can typically be accessed in the body by systemic administration and therefore most often treated by intravenous administration of therapeutic compositions, other tissues and delivery means are contemplated where there is a likelihood that the tissue targeted contains the target molecule. Thus, monoclonal antibodies or polypeptides of the invention can be administered intravenously, intraperitoneally, intramuscularly, subcutaneously, intracavity, transdermally, and can be delivered by peristaltic means.

The therapeutic compositions containing a monoclonal antibody or a polypeptide of this invention are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle.

In one preferred embodiment as shown in the Examples, the $\alpha_v\beta_3$ antagonist is administered in a single dosage intravenously.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired. Precise amounts of active ingredient required to be administered depend on the judgement of the practitioner and are peculiar to each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in viro therapies are contemplated.

As demonstrated by the present Examples, inhibition of angiogenesis and tumor regression occurs as early as 7 days after the initial contacting with antagonist. Additional or prolonged exposure to antagonist is preferable for 7 days to 6 weeks, preferably about 14 to 28 days.

In a related embodiment, the Examples demonstrate the relationship between inhibition of $\alpha_v\beta_3$ and induction of apoptosis in the neovasculature cells bearing $\alpha_v\beta_3$. Thus, the invention also contemplates methods for inhibition of apoptosis in neovasculature of a tissue. The method is practiced substantially as described herein for inhibition of angiogenesis in all tissues and conditions described therefor. The only noticeable difference is one of timing of effect, which is that apoptosis is manifest quickly, typically about 48 hours after contacting antagonist, whereas inhibition of angiogenesis and tumor regression is manifest more slowly, as described herein. This difference affects the therapeutic regimen in terms of time of administration, and effect desired. Typically, administration for apoptosis of neovasculature can be for 24 hours to about 4 weeks, although 48 hours to 7 days is preferred.

D. Therapeutic Compositions

The present invention contemplates therapeutic compositions useful for practicing the therapeutic methods described herein. Therapeutic compositions of the present invention contain a physiologically tolerable carrier together with an $\alpha_v\beta_3$ antagonist as described herein, dissolved or dispersed therein as an active ingredient. In a preferred embodiment, the therapeutic $\alpha_v\beta_3$ antagonist composition is not immunogenic when administered to a mammal or human patient for therapeutic purposes.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like.

The preparation of a pharmacological composition that contains active ingredients dissolved or dispersed therein is well understood in the art and need not be limited based on formulation. Typically such compositions are prepared as injectables either as liquid solutions or suspensions, however, solid forms suitable for solution, or suspensions, in liquid prior to use can also be prepared. The preparation can also be emulsified.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Particularly preferred are the salts of TFA and HCl, when used in the preparation of cyclic polypeptide $\alpha_v\beta_3$ antagonists. Representative salts of peptides are described in the Examples.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions can also contain liquid phases in addition to and to the exclusion of water. Exemplary of such additional liquid phases are glycerin, vegetable oils such as cottonseed oil, and water-oil emulsions.

A therapeutic composition contains an angiogenesis-inhibiting amount of an $\alpha_v\beta_3$ antagonist of the present invention, typically formulated to contain an amount of at least 0.1 weight percent of antagonist per weight of total therapeutic composition. A weight percent is a ratio by weight of inhibitor to total composition. Thus, for example, 0.1 weight percent is 0.1 grams of inhibitor per 100 grams of total composition.

E. Antagonists of Integrin $\alpha_v\beta_3$ $\alpha_v\beta_3$ antagonists are used in the present methods for inhibiting angiogenesis in tissues, and can take a variety of forms that include compounds which interact with $\alpha_v\beta_3$ in a manner such that functional interactions with natural $\alpha_v\beta_3$ ligands are interfered. Exemplary antagonists include analogs of $\alpha_v\beta_3$ derived from the ligand binding site on $\alpha_v\beta_3$, mimetics of either $\alpha_v\beta_3$ or a natural ligand of $\alpha_v\beta_3$ that mimic the structural region involved in $\alpha_v\beta_3$-ligand binding interactions, polypeptides having a sequence corresponding to a functional binding domain of the natural ligand specific for $\alpha_v\beta_3$, particularly corresponding to the RGD-containing domain of a natural ligand of $\alpha_v\beta_3$, and antibodies which immunoreact with either $\alpha_v\beta_3$ or the natural ligand, all of which exhibit antagonist activity as defined herein.

1. Polypeptides

In one embodiment, the invention contemplates $\alpha_v\beta_3$ antagonists in the form of polypeptides. A polypeptide (peptide) $\alpha_v\beta_3$ antagonist can have the sequence characteristics of either the natural ligand of $\alpha_v\beta_3$ or $\alpha_v\beta_3$ itself at the region involved in $\alpha_v\beta_3$-ligand interaction and exhibits $\alpha_v\beta_3$ antagonist activity as described herein. A preferred $\alpha_v\beta_3$ antagonist peptide contains the RGD tripeptide and corresponds in sequence to the natural ligand in the RGD-containing region.

Preferred RGD-containing polypeptides have a sequence corresponding to the amino acid residue sequence of the RGD-containing region of a natural ligand of $\alpha_v\beta_3$ such as fibrinogen, vitronectin, von Willebrand factor, laminin, thrombospondin, and the like ligands. The sequence of these $\alpha_v\beta_3$ ligands are well known. Thus, an $\alpha_v\beta_3$ antagonist peptide can be derived from any of the natural ligands, although fibrinogen and vitronectin are preferred.

A particularly preferred $\alpha_v\beta_3$ antagonist peptide preferentially inhibits $\alpha_v\beta_3$ binding to its natural ligand(s) when compared to other integrins, as described earlier. These $\alpha_v\beta_3$-specific peptides are particularly preferred at least because the specificity for $\alpha_v\beta_3$ reduces the incidence of undesirable side effects such as inhibition of other integrins. The identification of preferred $\alpha_v\beta_3$ antagonist peptides having selectivity for $\alpha_v\beta_3$ can readily be identified in a typical inhibition of binding assay, such as the ELISA assay described in the Examples.

A polypeptide of the present invention typically comprises no more than about 100 amino acid residues, preferably no more than about 60 residues, more preferably no more than about 30 residues. Peptides can be linear or cyclic, although particularly preferred peptides are cyclic.

Where the polypeptide is greater than about 100 residues, it is typically provided in the form of a fusion protein or protein fragment, as described herein.

Preferred cyclic and linear peptides and their designations are shown in Table 1 in the Examples.

It should be understood that a subject polypeptide need not be identical to the amino acid residue sequence of a $\alpha_v\beta_3$ natural ligand, so long as it includes the required sequence and is able to function as an $\alpha_v\beta_3$ antagonist in an assay such as those described herein.

A subject polypeptide includes any analog, fragment or chemical derivative of a polypeptide whose amino acid residue sequence is shown herein so long as the polypeptide is an $\alpha_v\beta_3$ antagonist. Therefore, a present polypeptide can be subject to various changes, substitutions, insertions, and deletions where such changes provide for certain advantages in its use. In this regard, $\alpha_v\beta_3$ antagonist polypeptide of this invention corresponds to, rather than is identical to, the sequence of a recited peptide where one or more changes are made and it retains the ability to function as an $\alpha_v\beta_3$ antagonist in one or more of the assays as defined herein.

Thus, a polypeptide can be in any of a variety of forms of peptide derivatives, that include amides, conjugates with proteins, cyclic peptides, polymerized peptides, analogs, fragments, chemically modified peptides, and the like derivatives.

The term "analog" includes any polypeptide having an amino acid residue sequence substantially identical to a sequence specifically shown herein in which one or more residues have been conservatively substituted with a functionally similar residue and which displays the $\alpha_v\beta_3$ antagonist activity as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that such polypeptide displays the requisite inhibition activity.

A "chemical derivative" refers to a subject polypeptide having one or more residues chemically derivatized by reaction of a functional side group. In addition to side group derivitations, a chemical derivative can have one or more backbone modifications including $\alpha$-amino substitutions such as N-methyl, N-ethyl, N-propyl and the like, and $\alpha$-carbonyl substitutions such as thioester, thioamide, guanidino and the like. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. For examples: 4-hydroxyproline may be substituted for praline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions or residues relative to the sequence of a polypeptide whose sequence is shown herein, so long as the requisite activity is maintained.

A particularly preferred derivative is a cyclic peptide according to the formula cyclo(Arg-Gly-Asp-D-Phe-NMeVal), abbreviated c(RGDf-NMeV), in which there is an N-methyl substituted $\alpha$-amino group on the valine residue of the peptide and cyclization has joined the primary amino and carboxy termini of the peptide.

The term "fragment" refers to any subject polypeptide having an amino acid residue sequence shorter than that of a polypeptide whose amino acid residue sequence is shown herein.

When a polypeptide of the present invention has a sequence that is not identical to the sequence of an $\alpha_v\beta_3$ natural ligand, it is typically because one or more conservative or non-conservative substitutions have been made, usually no more than about 30 number percent, and preferably no more than 10 number percent of the amino acid residues are substituted. Additional residues may also be added at either terminus of a polypeptide for the purpose of providing a "linker" by which the polypeptides of this invention can be conveniently affixed to a label or solid matrix, or carrier.

Labels, solid matrices and carriers that can be used with the polypeptides of this invention are described hereinbelow.

Amino acid residue linkers are usually at least one residue and can be 40 or more residues, more often 1 to 10 residues, but do not form $\alpha_v\beta_3$ ligand epitopes. Typical amino acid residues used for linking are tyrosine, cysteine, lysine, glutamic and aspartic acid, or the like. In addition, a subject polypeptide can differ, unless otherwise specified, from the natural sequence of an $\alpha_v\beta_3$ ligand by the sequence being modified by terminal-$NH_2$ acylation, e.g., acetylation, or thioglycolic acid amidation, by terminal-carboxylamidation, e.g., with ammonia, methylamine, and the like terminal modifications. Terminal modifications are useful, as is well known, to reduce susceptibility by proteinase digestion, and therefore serve to prolong half life of the polypeptides in solutions, particularly biological fluids where proteases may be present. In this regard, polypeptide cyclization is also a useful terminal modification, and is particularly preferred also because of the stable structures formed by cyclization and in view of the biological activities observed for such cyclic peptides as described herein.

Any peptide of the present invention may be used in the form of a pharmaceutically acceptable salt. Suitable acids which are capable of forming salts with the peptides of the present invention include inorganic acids such as trifluoroacetic acid (TFA) hydrochloric acid (HCl), hydrobromic acid, perchloric acid, nitric acid, thiocyanic acid, sulfuric acid, methane sulfonic acid, acetic acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like. HCl and TFA salts are particularly preferred.

Suitable bases capable of forming salts with the peptides of the present invention include inorganic bases such as sodium hydroxide, ammonium hydroxide, potassium hydroxide and the like; and organic bases such as mono-, di- and tri-alkyl and aryl amines (e.g. triethylamine, diisopropyl amine, methyl amine, dimethyl amine and the like) and optionally substituted ethanolamines (e.g. ethanolamine, diethanolamine and the like).

In addition, a peptide of this invention can be prepared as described in the Examples without including a free ionic salt in which the charged acid or base groups present in the amino acid residue side groups (e.g., Arg, Asp, and the like) associate and neutralize each other to form an "inner salt" compound.

A peptide of the. present invention also referred to herein as a subject polypeptide, can be synthesized by any of the techniques that are known to those skilled in the polypeptide art, including recombinant DNA techniques. Synthetic chemistry techniques, such as a solid-phase Merrifield-type synthesis, are preferred for reasons of purity, antigenic specificity, freedom from undesired side products, ease of production and the like. An excellent summary of the many techniques available can be found in Steward et al., "Solid Phase Peptide Synthesis", W. H. Freeman Co., San Francisco, 1969; Bodanszky, et al., "Peptide Synthesis", John Wiley & Sons, Second Edition, 1976; J. Meienhofer, "Hormonal Proteins and Peptides", Vol. 2, p. 46, Academic Press (New York), 1983; Merrifield, *Adv. Enzymol.,* 32:221–96, 1969; Fields et al., *Int. J. Peptide Protein Res.,* 35:161–214, 1990; and U.S. Pat. No. 4,244,946 for solid phase peptide synthesis, and Schroder et al., "The Peptides", Vol. 1, Academic Press (New York), 1965 for classical solution synthesis, each of which is incorporated herein by reference. Appropriate protective groups usable in such synthesis are described in the above texts and in J. F. W. McOmie, "Protective Groups in Organic Chemistry", Plenum Press, New York, 1973, which is incorporated herein by reference.

In general, the solid-phase synthesis methods contemplated comprise the sequential addition of one or more amino acid residues or suitably protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as exemplary, the protected or derivatized amino acid is attached to an inert solid support through its unprotected carboxyl or amino group. The protecting group of the amino or carboxyl group is then selectively removed and the next amino acid in the sequence having the complimentary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to afford the final linear polypeptide.

The resultant linear polypeptides prepared for example as described above may be reacted to form their corresponding cyclic peptides. An exemplary method for preparing a cyclic peptide is described by Zimmer et al., *Peptides* 1992, pp. 393–394, ESCOM Science Publishers, B.V., 1993. Typically, tertbutoxycarbonyl protected peptide methyl ester is dissolved in methanol and sodium hydroxide solution are added and the admixture is reacted at 20° C. (20 C.) to hydrolytically remove the methyl ester protecting group. After evaporating the solvent, the tertbutoxycarbonyl protected peptide is extracted with ethyl acetate from acidified aqueous solvent. The tertbutoxycarbonyl protecting group is then removed under mildly acidic conditions in dioxane cosolvent. The unprotected linear peptide with free amino and carboxy termini so obtained is converted to its corresponding cyclic peptide by reacting a dilute solution of the linear peptide, in a mixture of dichloromethane and dimethylformamide, with dicyclohexylcarbodiimide in the presence of 1-hydroxybenzotriazole and N-methylmorpholine. The resultant cyclic peptide is then purified by chromatography.

Alternative methods for cyclic peptide synthesis are described by Gurrath et al., *Eur. J. Biochem.,*210:911–921 (1992), and described in the Examples.

In addition, the $\alpha_v\beta_3$ antagonist can be provided in the form of a fusion protein. Fusion proteins are proteins produced by recombinant DNA methods as described herein in which the subject polypeptide is expressed as a fusion with a second carrier protein such as a glutathione sulfhydryl transferase (GST) or other well known carrier. Preferred fusion proteins comprise an MMP-2 polypeptide described herein. The preparation of a MMP-2 fusion protein is described in the Examples.

Particularly preferred peptides and derivative peptides for use in the present methods are c-(GrGDFV) (SEQ ID NO 4), c-(RGDfV) (SEQ ID NO 5), c-(RADfV) (SEQ ID NO 6), c-(RGDFv) (SEQ ID NO 7), c-(RGDf-NMeV)(SEQ ID NO 15) and linear peptide YTAECKPQVTRGDVF (SEQ ID NO 8), where "c-" indicates a cyclic peptide, the upper case letters are single letter code for an L-amino acid and the lower case letters are single letter code for D-amino acid. The amino acid residues sequence of these peptides are also shown in SEQ ID NOs 4, 5, 6, 7, 15 and 8, respectively.

Also preferred are polypeptides derived from MMP-2 described herein, having sequences shown in SEQ ID Nos 17–28 and 45.

2. Monoclonal Antibodies

The present invention describes, in one embodiment, $\alpha_v\beta_3$ antagonists in the form of monoclonal antibodies which immunoreact with $\alpha_v\beta_3$ and inhibit $\alpha_v\beta_3$ binding to its natural ligand as described herein. The invention also describes cell lines which produce the antibodies, methods for producing the cell lines, and methods for producing the monoclonal antibodies.

A monoclonal antibody of this invention comprises antibody molecules that 1) immunoreact with isolated $\alpha_v\beta_3$, and 2) inhibit fibrinogen binding to $\alpha_v\beta_3$ Preferred monoclonal antibodies which preferentially bind to $\alpha_v\beta_3$ include a monoclonal antibody having the immunoreaction characteristics of mAb LM609, secreted by hybridoma cell line ATCC HB 9537. The hybridoma cell line ATCC HB 9537 was deposited pursuant to Budapest Treaty requirements with the American Type Culture Collection (ATCC), 1301 Parklawn Drive, Rockville, Md., USA, on Sep. 15, 1987.

The term "antibody or antibody molecule" in the various grammatical forms is used herein as a collective noun that refers to a population of immunoglobulin molecules and/or immunologically active portions of immunoglobulin molecules, i.e., molecules that contain an antibody combining site or paratope.

An "antibody combining site" is that structural portion of an antibody molecule comprised of heavy and light chain variable and hypervariable regions that specifically binds antigen.

Exemplary antibodies for use in the present invention are intact immunoglobulin molecules, substantially intact immunoglobulin molecules and those portions of an immunoglobulin molecule that contain the paratope, including those portions known in the art as Fab, Fab', F(ab')$_2$ and F(v), and also referred to as antibody fragments.

In another preferred embodiment, the invention contemplates a truncated immunoglobulin molecule comprising a Fab fragment derived from a monoclonal antibody of this invention. The Fab fragment, lacking Fc receptor, is soluble, and affords therapeutic advantages in serum half life, and diagnostic advantages in modes of using the soluble Fab fragment. The preparation of a soluble Fab fragment is generally known in the immunological arts and can be accomplished by a variety of methods.

For example, Fab and F(ab')$_2$ portions (fragments) of antibodies are prepared by the proteolytic reaction of papain and pepsin, respectively, on substantially intact antibodies by methods that are well known. See for example, U.S. Pat. No. 4,342,566 to Theofilopolous and Dixon. Fab' antibody portions are also well known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact immunoglobulin molecules are preferred, and are utilized as illustrative herein.

The phrase "monoclonal antibody" in its various grammatical forms refers to a population of antibody molecules that contain only one species of antibody combining site capable of immunoreacting with a particular epitope. A monoclonal antibody thus typically displays a single binding affinity for any epitope with which it immunoreacts. A monoclonal antibody may therefore contain an antibody molecule having a plurality of antibody combining sites, each immunospecific for a different epitope, e.g., a bispecific monoclonal antibody.

A monoclonal antibody is typically composed of antibodies produced by clones of a single cell called a hybridoma that secretes (produces) only one kind of antibody molecule. The hybridoma cell is formed by fusing an antibody-producing cell and a myeloma or other self-perpetuating cell line. The preparation of such antibodies was first described by Kohler and Milstein, *Nature* 256:495–497 (1975), which description is incorporated by reference. Additional methods are described by Zola, *Monoclonal Antibodies: A Manual of Techniques*, CRC Press, Inc. (1987). The hybridoma supernates so prepared can be screened for the presence of antibody molecules that immunoreact with $\alpha_v\beta_3$ and for inhibition of $\alpha_v\beta_3$ binding to natural ligands.

Briefly, to form the hybridoma from which the monoclonal antibody composition is produced, a myeloma or other self-perpetuating cell line is fused with lymphocytes obtained from the spleen of a mammal hyperimmunized with a source of $\alpha_v\beta_3$, such as $\alpha_{v3}$ isolated from M21 human melanoma cells as described by Cheresh et al., *J. Biol. Chem.*, 262:17703–17711 (1987).

It is preferred that the myeloma cell line used to prepare a hybridoma be from the same species as the lymphocytes. Typically, a mouse of the strain 129 GlX$^+$ is the preferred mammal. Suitable mouse myelomas for use in the present invention include the hypoxanthine-aminopterin-thymidine-sensitive (HAT) cell lines P3X63-Ag8.653, and Sp2/0-Ag14 that are available from the American Type Culture Collection, Rockville, Md., under the designations CRL 1580 and CRL 1581, respectively.

Splenocytes are typically fused with myeloma cells using polyethylene glycol (PEG) 1500. Fused hybrids are selected by their sensitivity to HAT. Hybridomas producing a monoclonal antibody of this invention are identified using the enzyme linked immunosorbent assay (ELISA) described in the Examples.

A monoclonal antibody of the present invention can also be produced by initiating a monoclonal hybridoma culture comprising a nutrient medium containing a hybridoma that secretes antibody molecules of the appropriate specificity. The culture is maintained under conditions and for a time period sufficient for the hybridoma to secrete the antibody molecules into the medium. The antibody-containing medium is then collected. The antibody molecules can then be further isolated by well known techniques.

Media useful for the preparation of these compositions are both well known in the art and commercially available and include synthetic culture media, inbred mice and the like. An exemplary synthetic medium is Dulbeccots minimal essential medium (DMEM; Dulbecco et al., *Virol.* 8:396, 1959) supplemented with 4.5 gm/1 glucose, 20 mM glutamine, and 20% fetal calf serum. An exemplary inbred mouse strain is the Balb/c.

Other methods of producing a monoclonal antibody, a hybridoma cell, or a hybridoma cell culture are also well known. See, for example, the method of isolating monoclonal antibodies from an immunological repertoire as described by Sastry, et al., *Proc. Natl. Acad. Sci. USA*, 86:5728–5732 (1989); and Huse et al., *Science*, 246:1275–1281 (1989).

Also contemplated by this invention is the hybridoma cell, and cultures containing a hybridoma cell that produce a monoclonal antibody of this invention. Particularly preferred is the hybridoma cell line that secretes monoclonal antibody mAb LM609 designated ATCC HB 9537. mAb LM609 was prepared as described by Cheresh et al., *J. Biol. Chem.*, 262:17703–17711 (1987), and its preparation is also described in the Examples.

The invention contemplates, in one embodiment, a monoclonal antibody that has the immunoreaction characteristics of mAb LM609.

It is also possible to determine, without undue experimentation, if a monoclonal antibody has the same (i.e., equivalent) specificity (immunoreaction characteristics) as a monoclonal antibody of this invention by ascertaining whether the former prevents the latter from binding to a preselected target molecule. If the monoclonal antibody being tested competes with the monoclonal antibody of the invention, as shown by a decrease in binding by the monoclonal antibody of the invention in standard competition assays for binding to the target molecule when present in the solid phase, then it is likely that the two monoclonal antibodies bind to the same, or a closely related, epitope.

Still another way to determine whether a monoclonal antibody has the specificity of a monoclonal antibody of the invention is to pre-incubate the monoclonal antibody of the invention with the target molecule with which it is normally reactive, and then add the monoclonal antibody being tested to determine if the monoclonal antibody being tested is inhibited in its ability to bind the target molecule. If the monoclonal antibody being tested is inhibited then, in all likelihood, it has the same, or functionally equivalent, epitopic specificity as the monoclonal antibody of the invention.

An additional way to determine whether a monoclonal antibody has the specificity of a monoclonal antibody of the invention is to determine the amino acid residue sequence of the CDR regions of the antibodies in question. Antibody molecules having identical, or functionally equivalent, amino acid residue sequences in their CDR regions have the same binding specificity. Methods for sequencing polypeptides is well known in the art.

The immunospecificity of an antibody, its target molecule binding capacity, and the attendant affinity the antibody exhibits for the epitope, are defined by the epitope with which the antibody immunoreacts. The epitope specificity is defined at least in part by the amino acid residue sequence of the variable region of the heavy chain of the immunoglobulin the antibody, and in part by the light chain variable region amino acid residue sequence.

Use of the term "having the binding specificity of" indicates that equivalent monoclonal antibodies exhibit the same or similar immunoreaction (binding) characteristics and compete for binding to a preselected target molecule.

Humanized monoclonal antibodies offer particular advantages over murine monoclonal antibodies, particularly insofar as they can be used therapeutically in humans. Specifically, human antibodies are not cleared from the circulation as rapidly as "foreign" antigens, and do not activate the immune system in the same manner as foreign antigens and foreign antibodies. Methods of preparing "humanized" antibodies are generally well known in the art, and can readily be applied to the antibodies of the present invention.

Thus, the invention contemplates, in one embodiment, a monoclonal antibody of this invention that is humanized by grafting to introduce components of the human immune system without substantially interfering with the ability of the antibody to bind antigen.

3. $\alpha_v\beta_3$-Specific Mimetics

The present invention demonstrates that $\alpha_v\beta_3$ antagonists generally can be used in the present invention, which antagonists can include polypeptides, antibodies and other molecules, designated "mimetics", which have the capacity to interefere with avD3 function. Particularly preferred are antagonists which specifically interfere with $\alpha_v\beta_3$ function, and do not interfere with function of other integrins.

In this context it is appreciated that a variety of reagents may be suitable for use in the present methods, so long as these reagents posses the requisite biological activity. These reagents are generically referred to a mimetics because they possess the ability to "mimic" a binding domain on either $\alpha_v\beta_3$ or the $\alpha_v\beta_3$ ligand involved in the functional interaction of the receptor and ligand, and thereby interfere with (i.e., inhibit) normal function.

An $\alpha_v\beta_3$ mimetic is any molecule, other than an antibody or ligand-derived peptide, which exhibits the above-described properties. It can be a synthetic peptide, an analog or derivative of a peptide, a compound which is shaped like the binding pocket of the above-described binding domain such as an organic mimetic molecule, or other molecule.

A preferred mimetic of this invention is an organic-based molecule and thus is referred to as organic mimetic. Particularly preferred organic mimetic molecules that function as $\alpha_v\beta_3$ antagonists by being a mimetic to a ligand of $\alpha_v\beta_3$ are Compounds 7, 9, 10, 12, 14, 15, 16, 17 and 18 as described in Example 10.

The design of an $\alpha_v\beta_3$ mimetic can be conducted by any of a variety of structural analysis methods for drug-design known in the art, including molecular modelling, two-dimensional nuclear magnetic resonance (2-D NMR) analysis, x-ray crystallography, random screening of peptide, peptide analog or other chemical polymer or compound libraries, and the like drug design methodologies.

In view of the broad structural evidence presented in the present specification which shows that an $\alpha_v\beta_3$ antagonist can be a fusion polypeptide (e.g., an MMP-2 fusion protein), a small polypeptide, a cyclic peptide, a derivative peptide, an organic mimetic molecule, or a monoclonal antibody, that are diversely different chemical structures which share the functional property of selective inhibition of $\alpha_v\beta_3$, the structure of a subject $\alpha_v\beta_3$ antagonist useful in the present methods need not be so limited, but includes any $\alpha_v\beta_3$ mimetic, as defined herein.

F. Methods for Identifying Antagonists of $\alpha_v\beta_3$

The invention also described assay methods for identifying candidate $\alpha_v\beta_3$ antagonists for use according to the present methods. In these assay methods candidate molecules are evaluated for their potency in inhibiting $\alpha_v\beta_3$ binding to natural ligands, and furthermore are evaluated for their potency in inhibiting angiogenesis in a tissue.

The first assay measures inhibition of direct binding of natural ligand to $\alpha_v\beta_3$, and a preferred embodiment is described in detail in the Examples. The assay typically measures the degree of inhibition of binding of a natural ligand, such as fibrinogen, to isolated $\alpha_v\beta_3$ in the solid phase by ELISA.

The assay can also be used to identify compounds which exhibit specificity for $\alpha_v\beta_3$ and do not inhibit natural ligands from binding other integrins. The specificity assay is conducted by running parallel ELISA assays where both $\alpha_v\beta_3$ and other integrins are screened concurrently in separate assay chambers for their respective abilities to bind a natural ligand and for the candidate compound to inhibit the respective abilities of the integrins to bind a preselected ligand. Preferred screening assay formats are described in the Examples.

The second assay measures angiogenesis in the chick chorioallantoic membrane (CAM) and is referred to as the CAM assay. The CAM assay has been described in detail by others, and further has been used to measure both angiogenesis and neovascularization of tumor tissues. See Ausprunk et al., *Am. J. Pathol.,* 79:597–618 (1975) and Ossonski et al., *Cancer Res.,* 40:2300–2309 (1980).

The CAM assay is a well recognized assay model for in vivo angiogenesis because neovascularization of whole tissue is occurring, and actual chick embryo blood vessels are growing into the CAM or into the tissue grown on the CAM.

As demonstrated herein, the CAM assay illustrates inhibition of neovascularization based on both the amount and extent of new vessel growth. Furthermore, it is easy to monitor the growth of any tissue transplanted upon the CAM, such as a tumor tissue. Finally, the assay is particularly useful because there is an internal control for toxicity in the assay system. The chick embryo is exposed to any test reagent, and therefore the health of the embryo is an indication of toxicity.

The third assay that measures angiogenesis is the in vivo rabbit eye model and is referred to as the rabbit eye assay. The rabbit eye assay has been described in detail by others, and further has been used to measure both angiogenesis and neovascularization in the presence of angiogenic inhibitors such as thalidomide. See D'Amato, et al., *Proc. Natl, Acad. Sci. USA,* 91:4082–4085 (1994).

The rabbit eye assay is a well recognized assay model for in vivo angiogenesis because the neovascularization process, exemplified by rabbit blood vessels growing from the rim of the cornea into the cornea, is easily visualized through the naturally transparent cornea of the eye. Additionally, both the extent and the amount of stimulation or inhibition of neovascularization or regression of neovascularization can easily be monitored over time.

Finally, the rabbit is exposed to any test reagent, and therefore the health of the rabbit is an indication of toxicity of the test reagent.

The fourth assay measures angiogenesis in the chimeric mouse:human mouse model and is referred to as the chimeric mouse assay. The assay has been described in detail by others, and further has been described herein to measure angiogenesis, neovascularization, and regression of tumor tissues. See Yan, et al., *J. Clin. Invest.,* 91:986–996 (1993). The chimeric mouse assay is a useful assay model for in vivo angiogenesis because the transplanted skin grafts closely resemble normal human skin histologically and neovascularization of whole tissue is occurring wherein actual human blood vessels are growing from the grafted human skin into the human tumor tissue on the surface of the grafted human skin. The origin of the neovascularization into the human graft can be demonstrated by immunohistochemical staining of the neovasculature with human-specific endothelial cell markers.

As demonstrated herein, the chimeric mouse assay demonstrates regression of neovascularization based on both the amount and extent of regression of new vessel growth. Furthermore, it is easy to monitor effects on the growth of any tissue transplanted upon the grafted skin, such as a tumor tissue. Finally, the assay is useful because there is an internal control for toxicity in the assay system. The chimeric mouse is exposed to any test reagent, and therefore the health of the mouse is an indication of toxicity.

G. Article of Manufacture

The invention also contemplates an article of manufacture which is a labelled container for providing an $\alpha_v\beta_3$ antagonist of the invention. An article of manufacture comprises packaging material and a pharmaceutical agent contained within the packaging material.

The pharmaceutical agent in an article of manufacture is any of the $\alpha_v\beta_3$ antagonists of the present invention, formulated into a pharmaceutically acceptable form as described herein according the the disclosed indications. The article of manufacture contains an amount of pharmaceutical agent sufficient for use in treating a condition indicated herein, either in unit or multiple dosages.

The packaging material comprises a label which indicates the use of the pharmaceutical agent contained therein, e.g., for treating conditions assisted by the inhibition of angiogenesis, and the like conditions disclosed herein. The label can further include instructions for use and related information as may be required for marketing. The packaging material can include container(s) for storage of the pharmaceutical agent.

As used herein, the term packaging material refers to a material such as glass, plastic, paper, foil, and the like capable of holding within fixed means a pharmaceutical agent. Thus, for example, the packaging material can be plastic or glass vials, laminated envelopes and the like containers used to contain a pharamaceutical composition including the pharmaceutical agent.

In preferred embodiments, the packaging material includes a label that is a tangible expression describing the contents of the article of manufacture and the use of the pharmaceutical agent contained therein.

EXAMPLES

The following examples relating to this invention are illustrative and should not, of course, be construed as specifically limiting the invention. Moreover, such variations of the invention, now known or later developed, which would be within the purview of one skilled in the art are to be considered to fall within the scope of the present invention hereinafter claimed.

1. Preparation of Synthetic Peptides a. Synthesis Procedure

The linear and cyclic polypeptides listed in Table 1 were synthesized using standard solid-phase synthesis techniques as, for example, described by Merrifield, *Adv. Enzymol.*, 32:221–96, (1969), and Fields, G. B. and Noble, R. L., *Int. J. Peptide Protein Res.*, 35:161–214, (1990).

Two grams (g) of BOC-Gly-D-Arg-Gly-Asp-Phe-Val-OMe (SEQ ID NO 1) were first dissolved in 60 milliliters (ml) of methanol to which was added 1.5 ml of 2 N sodium hydroxide solution to form an admixture. The admixture was then stirred for 3 hours at 20 degrees C. (20 C.). After evaporation, the residue was taken up in water, acidified to pH 3 with diluted HCl and extracted with ethyl acetate. The extract was dried over $Na_2SO_4$, evaporated again and the resultant BOC-Gly-D-Arg-Gly-Asp-Phe-Val-OH (SEQ ID NO 2) was stirred at 20 C. for 2 hours with 20 ml of 2 N HCl in dioxane. The resultant admixture was evaporated to obtain H-Gly-D-Arg-Gly-Asp-Phe-Val-OH (SEQ ID NO 3) that was subsequently dissolved in a mixture of 1800 ml of dichloromethane and 200 ml of dimethylformamide (DMF) followed by cooling to 0 C. Thereafter, 0.5 g of dicyclohexylcarbodiimide (DCCI), 0.3 g of 1-hydroxybenzotriazole (HOBt) and 0.23 ml of N-methylmorpholine were added successively with stirring.

The resultant admixture was stirred for a further 24 hours at 0 C. and then at 20 C. for another 48 hours. The solution was concentrated and treated with a mixed bed ion exchanger to free it from salts. After the resulting resin was removed by filtration, the clarified solution was evaporated and the residue was purified by chromatography resulting in the recovery of cyclo(-Gly-D-Arg-Gly-Asp-Phe-Val) (SEQ ID NO 4). The following peptides, listed in Table 1 using single letter code amino acid residue abbreviations and identified by a peptide number designation, were obtained analogously: cyclo(Arg-Gly-Asp-D-Phe-Val) (SEQ ID NO 5); cyclo(Arg-Ala-Asp-D-Phe-Val) (SEQ ID NO 6); cyclo (Arg-D-Ala-Asp-Phe-Val) (SEQ ID NO 9); cyclo(Arg-Gly-Asp-Phe-D-Val) (SEQ ID NO 7); and cyclo (Arg-Gly-Asp-D-Phe-NMeVal) (methylation is at the alpha-amino nitrogen of the amide bond of the valine residue) (SEQ ID NO 15).

A peptide designated as 66203, having an identical sequence to that of peptide 62184, only differed from the latter by containing the salt HCl rather than the TFA salt present in 62184. The same is true for the peptides 69601 and 62185 and for 85189 and 121974.

b. Alternate Synthesis Procedure i. Synthesis of cyclo-(Arg-Gly-Asp-DPhe-NmeVal). TFA salt Fmoc-Arg(Mtr)-Gly-Asp(OBut)-DPhe-NMeVal-ONa is synthesized using solid-phase Merrifield-type procedures by sequentially adding NMeVal, DPhe, Asp(OBut), Gly and Fmoc-Arg(Mtr) in a step-wise manner to a 4-hydroxymethyl-phenoxymethyl-polystyrene resin (Wang type resin) (customary Merrifield-type methods of peptide synthesis are applied as described in Houben-Weyl, l.c., Volume 15/II, Pages 1 to 806 (1974). The polystyrene resin and amino acid residues precursors are commercially available from Aldrich, Sigma or Fluka chemical companies). After completion of sequential addition of the amino acid residues, the resin is then eliminated from the peptide chain using a 1:1 mixture of TFA/dichloromethane which provides the Fmoc-Arg(Mtr)-Gly-Asp(OBut)-DPhe-NMeVal-OH product. The Fmoc group is then removed with a 1:1 mixture of piperidine/DMF which provides the crude Arg(Mtr)-Gly-Asp(OBut)-DPhe-NMeVal-OH precursor which is then purified by HPLC in the customary manner.

For cyclization, a solution of 0.6 g of Arg(Mtr)-Gly-Asp (OBut)-DPhe-NMeVal-OH (synthesized above) in 15 ml of DMF (dimethylformamide; Aldrich) is diluted with 85 ml of dichloromethane (Aldrich), and 50 mg of $NaHCO_3$ are added. After cooling in a dry ice/acetone mixture, 40 µl of diphenylphosphoryl azide (Aldrich) are added. After standing at room temperature for 16 hours, the solution is concentrated. The concentrate is gel-filtered (Sephadex G10 column in isopropanol/water 8:2) and then purified by HPLC in the customary manner. Treatment with TFA (trifluoroacetic acid)/$H_2O$ (98:2) gives cyclo-(Arg-Gly-Asp-DPhe-NmeVal)×TFA which is then purified by HPLC in the customary manner; RT=19.5; FAB-MS (M+H): 589.

ii. Synthesis of "Inner Salt"

TFA salt is removed from the above-produced cyclic peptide by suspending the cyclo-(Arg-Gly-Asp-DPhe-NmeVal)×TFA in water followed by evaporation under vacuum to remove the TFA. The cyclic peptideformed is referred to as an "inner salt" and is designated cyclo-(Arg-Gly-Asp-DPhe-NMeVal). The term "inner salt" is used because the cyclic peptide contains two oppositely charged residues which intra-electronically counterbalance each other to form an overall noncharged molecule. One of the charged residues contains an acid moiety and the other charged residue contains an amino moiety. When the acid moiety and the amino moiety are in close proximity to one another, the acid moiety can be deprotonated by the amino moiety which forms a carboxylate/ammonium salt species with an overall neutral charge.

iii. HCl treatment to give cyclo-(Arg-Gly-Asp-DPhe-NMeVal)×HCl 80 mg of cyclo-(Arg-Gly-Asp-DPhe-NMeVal) are dissolved in 0.01 M HCl five to six times and freeze dried after each dissolving operation. Subsequent purification by HPLC give cyclo-(Arg-Gly-Asp-DPhe-NMeVal)×HCl; FAB-MS (M+H): 589.

iv. Methane sulfonic acid treatment to give cyclo-(Arg-Gly-Asp-DPhe-NMeVal)×MeSO$_3$H 80 mg of cyclo-(Arg-Gly-Asp-DPhe-NMeVal) are dissolved in 0.01 M MeSO$_3$H (methane sulfonic acid) five to six times and freeze dried after each dissolving operation. Subsequent purification by HPLC give cyclo-(Arg-Gly-Asp-DPhe-NMeVal)×MeSO$_3$H; RT=17.8 ; FAB-MS (M+H): 589.

Alternative methods of cyclization include derivatizing the side group chains of an acyclic peptide precursor with sulfhydryl moieties, and when exposed to slightly higher than normal physiological pH conditions (pH 7.5), intramolecularly forms disulfide bonds with other sulfhydryl groups present in the molecule to form a cyclic peptide. Additionally, the C-terminus carboxylate moiety of an acyclic peptide precurosor can be reacted with a free sulfhydryl moiety present within the molecule for producing thioester cyclized peptides.

In inhibition of angiogenesis assays as described in Example 7 where the synthetic peptides were used, the 66203 peptide in HCl was slightly more effective in inhibiting angiogenesis than the identical peptide in TFA.

TABLE 1

| Peptide Designation | Amino Acid Sequence | SEQ ID NO |
|---|---|---|
| 62181 | cyclo(GrGDFV) | 4 |
| 62184 (66203*) | cyclo(RGDfV) | 5 |
| 62185 (69601*) | cyclo(RADfV) | 6 |
| 62187 | cyclo(RGDFv) | 7 |
| 62880 | YTAECKPQVTRGDVF | 8 |
| 62186 | cyclo(RaDFV) | 9 |
| 62175 | cyclo(ARGDfL) | 10 |
| 62179 | cyclo(GRGDfL) | 11 |
| 62411 | TRQVVCDLGNPM | 12 |
| 62503 | GVVRNNEALARLS | 13 |
| 62502 | TDVNGDGRHDL | 14 |
| 121974 (85189*) | cyclo (RDGf-NH$_2$Me-V) | 15 |
| 112784 | cyclo (RGEf-NH$_2$Me-V) | 16 |
| huMMP-2 (410–631)** | | 17 |
| huMMP-2 (439–631)** | | 18 |
| huMMP-2 (439–512)** | | 19 |
| huMMP-2 (439–546)** | | 20 |
| huMMP-2 (510–631)** | | 21 |
| huMMP-2 (543–631)** | | 22 |
| chMMP-2 (410–637)*** | | 23 |

TABLE 1-continued

| Peptide Designation | Amino Acid Sequence | SEQ ID NO |
|---|---|---|
| chMMP-2 (445–637)*** | | 24 |
| chMMP-2 (445–518)*** | | 25 |
| chMMP-2 (445–552)*** | | 26 |
| chMMP-2 (516–637)*** | | 27 |
| chMMP-2 (549–637)*** | | 28 |

*The peptides designated with an asterisk are prepared in HCl and are identical in sequence to the peptide designated on the same line; the peptides without an asterisk are prepared in TFA. Lower case letters indicate a D-amino acid; capital letters indicate a L-amino acid.
**The human MMP-2 amino acid residue sequences for synthetic peptides are indicated by the corresponding residue positions shown in FIGS. 22A and 22B. (MMP-2 refers to a member of the family of matrix metalloproteinase enzymes). The human MMP-2 sequences are listed with the natural cysteine residues but are not listed with engineered cysteine residues as described for the fusion peptides. The non-natural cysteine residues were substituted for the natural amino acid residue at the indicated residue positions in order to facilitate solubility of the synthetic as well as expressed fusion proteins and to ensure proper folding for presentation of the binding site.
***The chicken MMP-2 amino acid residue sequences for synthetic peptides are indicated by the corresponding residue positions shown in FIGS. 22A and 22B. The chicken MMP-2 sequences are listed with the natural cysteine residues but not with the engineered cysteine residues as described for the fusion peptides as described above.

2. Monoclonal Antibodies

The monoclonal antibody LM609 secreted by hybridoma ATCC HB 9537 was produced using standard hybridoma methods by immunization with isolated $\alpha_v\beta_3$ adsorbed onto Sepharose-lentil lectin beads. The $\alpha_v\beta_3$ had been isolated from human melanoma cells designated M21, and antibody was produced as described by Cheresh et al., *J. Biol. Chem.*, 262:17703–17711 (1987). M21 cells were provided by Dr. D. L. Morton (University of California at Los Angeles, Calif.) and grown in suspension cultures in RPMI 1640 culture medium containing 2 mM L-glutamine, 50 mg/ml gentamicin sulfate and 10% fetal calf serum.

Monoclonal antibody LM609 has been shown to specifically immunoreact with $\alpha_v\beta_3$ complex, and not immunoreact with $\alpha_v$ subunit, with $\beta_3$ subunit, or with other integrins.

3. Characterization of the Tissue Distribution of $\alpha_v\beta_3$ Expression

A. Immunofluorescence with Anti-Integrin Receptor Antibodies

During wound healing, the basement membranes of blood vessels express several adhesive proteins, including von Willebrand factor, fibronectin, and fibrin. In addition, several members of the integrin family of adhesion receptors are expressed on the surface of cultured smooth muscle and endothelial cells. See, Cheresh, *Proc. Natl. Acad. Sci., USA*, 84:6471 (1987); Janat et al., *J. Cell Physiol.*, 151:588 (1992); and Cheng et al., *J. Cell Physiol.*, 139:275 (1989). Among these integrins is $\alpha_v\beta_3$, the endothelial cell receptor for von Willebrand factor, fibrinogen (fibrin), and fibronectin as described by Cheresh, *Proc. Natl. Acad. Sci., USA*, 84:6471 (1987). This integrin initiates a calcium-dependent signaling pathway leading to endothelial cell migration, and therefore appears to play a fundamental role in vascular cell biology as described by Leavelsey et al., *J. Cell Biol.*, 121:163 (1993).

To investigate the expression of $\alpha_v\beta_3$ during angiogenesis, human wound granulation tissue or adjacent normal skin was obtained from consenting patients, washed with 1 ml of phosphate buffered saline and embedded in O.T.C medium (Tissue Tek). The embedded tissues were snap frozen in liquid nitrogen for approximately 30 to 45 seconds. Six micron thick sections were cut from the frozen blocks on a cryostat microtome for subsequent immunoperoxidase staining with antibodies specific for either $\beta_3$ integrins ($\alpha_v\beta_3$ or $\alpha_{IIb}\beta_3$) or the $\beta_1$ subfamily of integrins.

The results of the staining of normal human skin and wound granulation tissue are shown in FIGS. 1A–1D. Monoclonal antibodies AP3 and LM534, directed to $\beta_3$ and $\beta_1$ integrins, respectively, were used for immunohistochemical analysis of frozen sections. Experiments with tissue from four different human donors yielded identical results. The photomicrographs are shown at magnification of 300×.

The $\alpha_v\beta_3$ integrin was abundantly expressed on blood vessels in granulation tissue (FIG. 1B) but was not detectable in the dermis and epithelium of normal skin from the same donor (FIG. 1A). In contrast, $\beta_1$ integrins were abundantly expressed on blood vessels and stromal cells in both normal skin (FIG. 1C) and granulation tissue (FIG. 1D) and, as previously shown as described by Adams et al., Cell, 63:425 (1991), on the basal cells within the epithelium.

B. Immunofluorescence with Anti-Lipand Antibodies

Figure 2A:
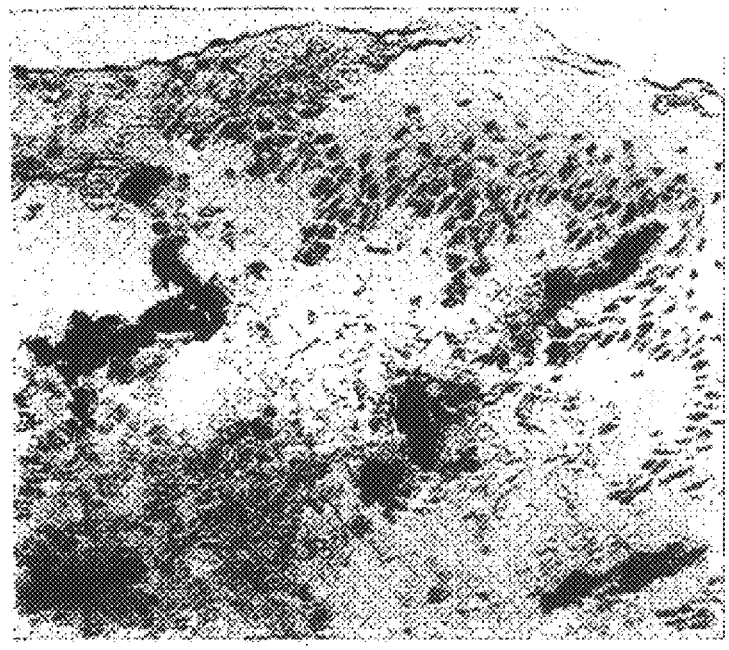
FIGS. 2A–2D illustrate the tissue distribution of the von Willebrand factor and laminin ligands that respectively bind the $\beta_3$ and $\beta_1$ integrin subunits in normal skin and in skin undergoing wound healing designated as granulation tissue. Immunohistochemistry with antibodies to von Willebrand factor (anti-vWF) and laminin (anti-laminin) was performed as described in Example 3B.
Figure 2B:
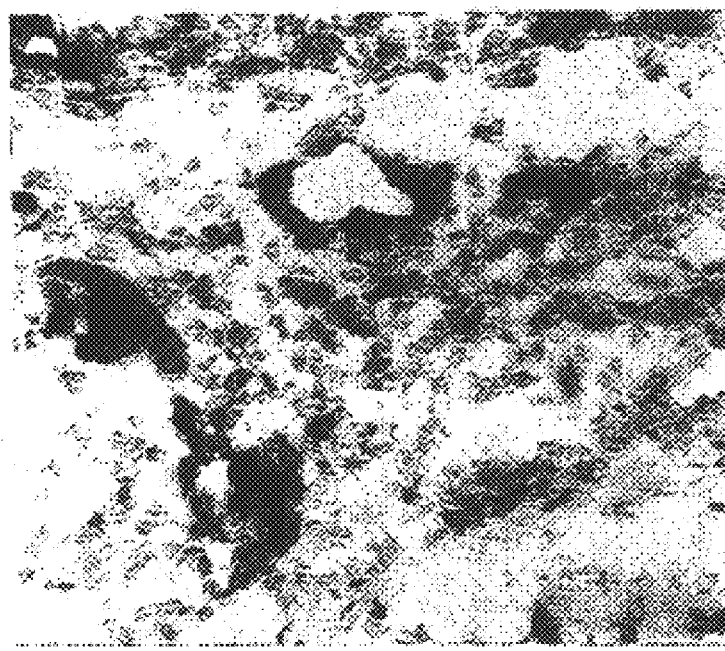
Figure 2C:
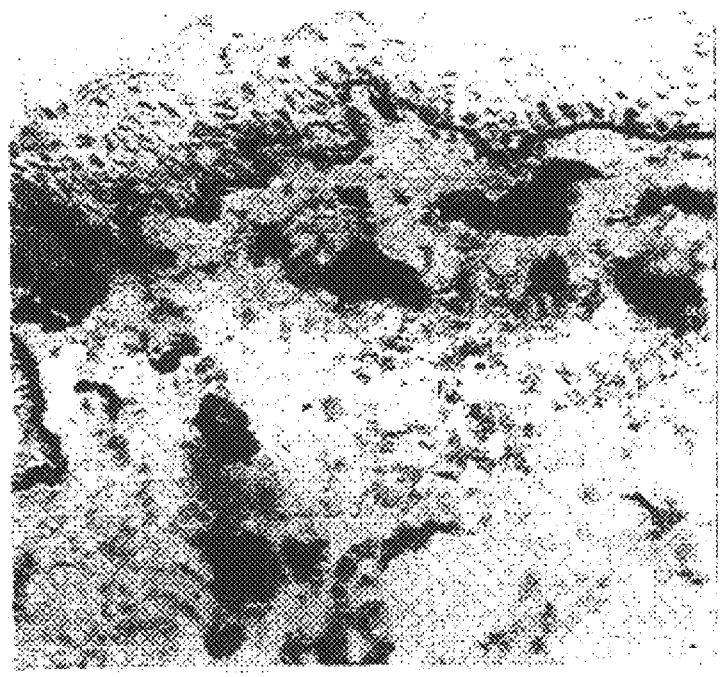
Figure 2D:
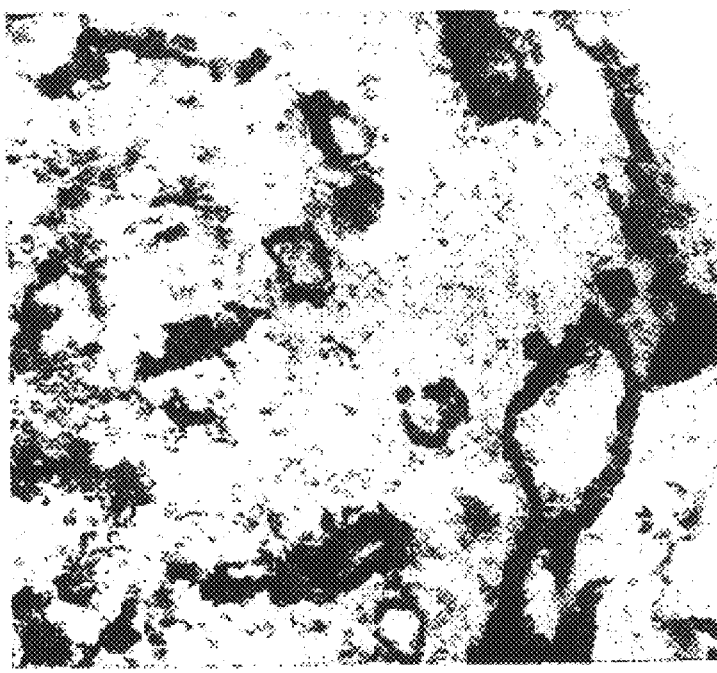
Figure 3A:
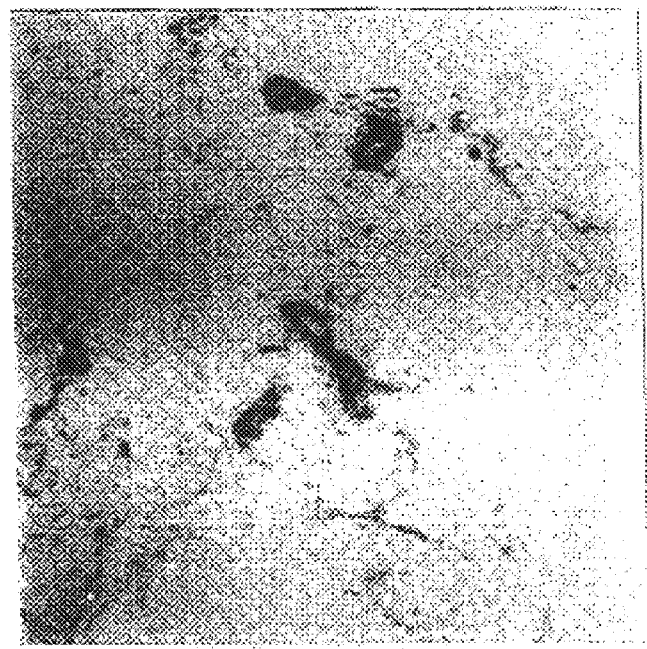
FIGS. 3A–3D illustrate the tissue distribution of the vitronectin integrin receptor, $\alpha_v\beta_3$, in tissue biopsies of bladder cancer, colon cancer, breast cancer and lung cancer, respectively. Immunohistochemistry with the LM609 antibody against $\alpha_v\beta_3$ was performed as described in Example 3C.
Figure 3B:
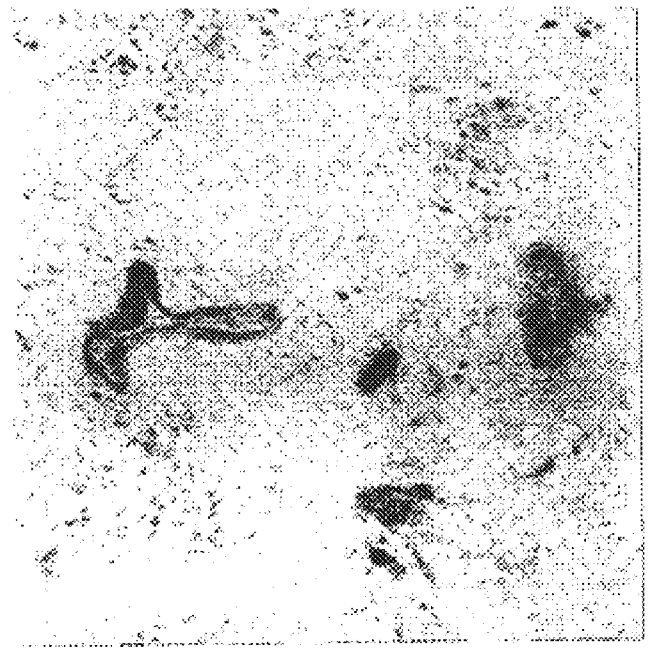
Figure 3C:
Figure 3D:
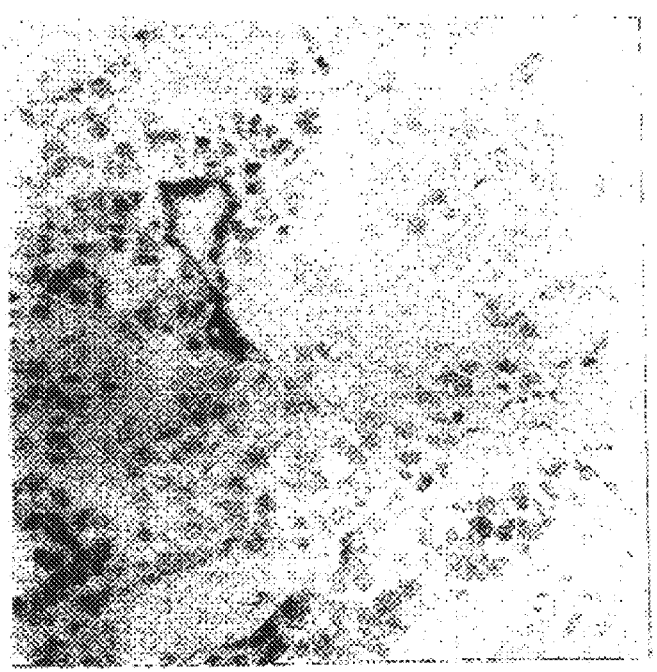

Additional sections of the human normal skin and granulation tissues prepared above were also examined for the presence of the ligands for the $\beta_3$ and $\beta_1$ integrins, von Willebrand factor and laminin, respectively. Von Willebrand factor localized to the blood vessels in normal skin (FIG. 2A) and granulation tissue (FIG. 2B), whereas laminin localized to all blood vessels as well as the epithelial basement membrane in both tissue preparations (FIGS. 2C and 2D).

C. Distribution of Anti-$\alpha_v\beta_3$ Antibodies on Cancer Tissue

In addition to the above analyses, biopsies of cancer tissue from human patients were also examined for the presence and distribution of $\alpha_v\beta_3$. The tissues were prepared as described in Example 1A with the exception that they were stained with monoclonal antibody LM609 prepared in Example 2 that is specific for the integrin receptor complex, $\alpha_v\beta_3$. In addition, tumors were also prepared for microscopic histological analysis by fixing representative examples of tumors in Bulins Fixative for 8 hours and serial sections cut and H&E stained.

The results of immunoperoxidase staining of bladder, colon breast and lung cancer tissues are shown in FIGS. 3A–3D, respectively. $\alpha_v\beta_3$ is abundantly expressed only on the blood vessels present in the four cancer biopsies analyzed and not on any other cells present in the tissue.

The results described herein thus show that the $\alpha_v\beta_3$ integrin receptor is selectively expressed in specific tissue types, namely granulated, metastatic tissues and other tissues in which angiogenesis is occurring and not normal tissue where the formation of new blood vessels has stopped. These tissues therefore provide an ideal target for therapeutic aspects of this invention.

4. Identification of $\alpha_v\beta_3$-Specific Synthetic Peptides Detected by Inhibition of Cell Attachment and by a Ligand-Receptor Binding Assay A. Inhibition of Cell Attachment As one means to determine integrin receptor specificity of the antagonists of this invention, inhibition of cell attachment assays were performed as described below.

Briefly, CS-1 hamster melanoma cells lacking expression of $\alpha_v\beta_3$ and $\alpha_v\beta_3$ were first transfected with an plasmid for expressing the $\beta_3$ subunit as previously described by Filardo et al., J. Cell Biol., 130:441–450 (1995). Specificity of potential $\alpha_v\beta_3$ antagonists was determined by the ability to block the binding of $\alpha_v\beta_3$-expressing CS-1 cells to VN or laminin coated plates. As an example of a typical assay, the wells were first coated with 10 ug/ml substrate overnight. After rinsing and blocking with 1% heat-denatured BSA in PBS at room temperature for 30 minutes, peptide 85189 (SEQ ID NO 15) over a concentration range of 0.0001 uM to 100 uM, was separately mixed with CS-1 cells for applying to wells with a cell number of 50,000 cells/well. After a 10–15 minute incubation at 37 C., the solution containing the cells and peptides was discarded. The number of attached cells was then determined following staining with 1% crystal violet. Cell associated crystal violet was eluted by the addition of 100 microliters (ul) of 10% acetic acid. Cell adhesion was quantified by measuring the optical density of the eluted crystal violet at a wave length of 600 nm.

Figure 21:
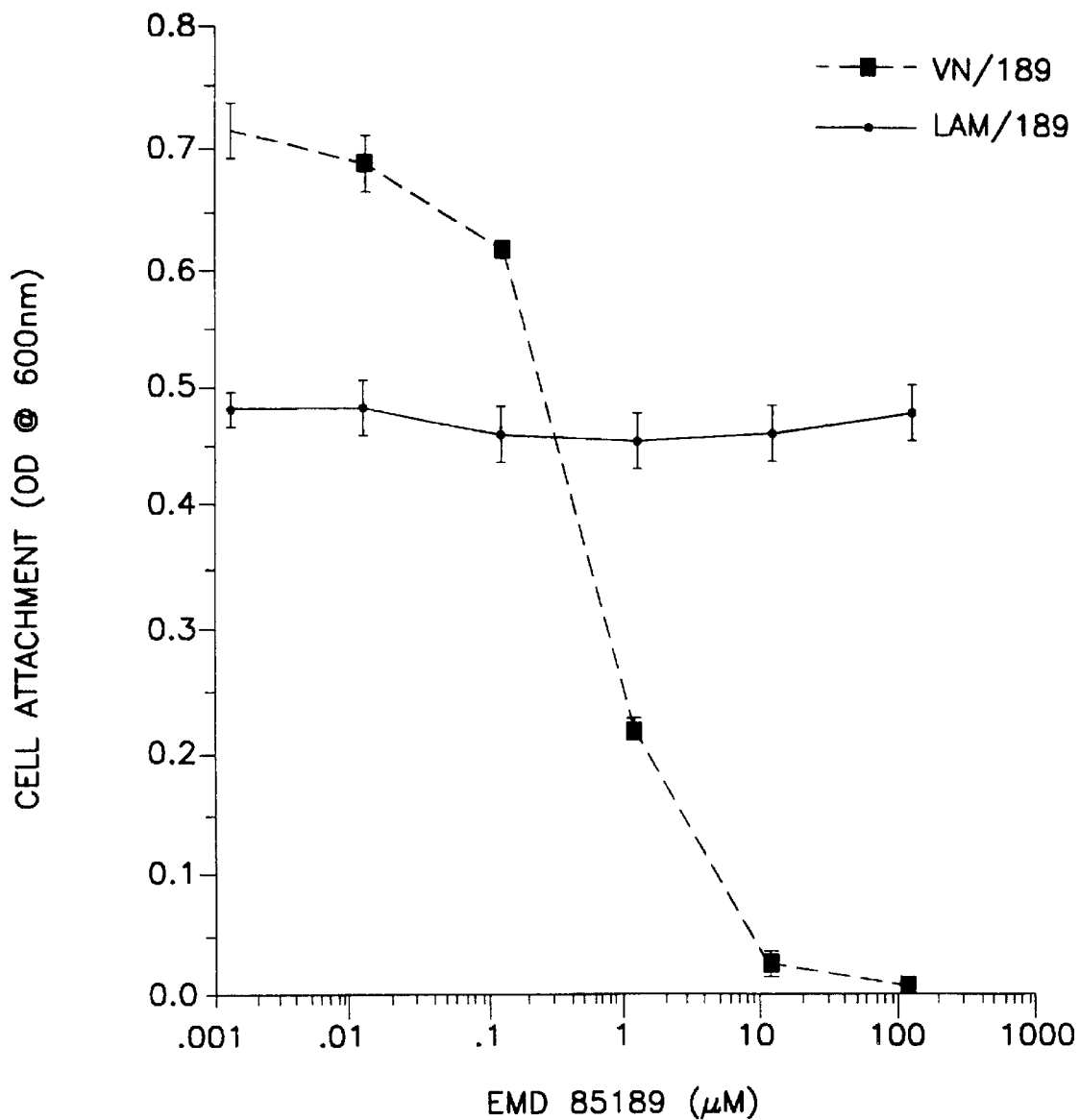
FIG. 21 shows the result of a inhibition of cell attachment assay with peptide 85189 as described in Example 4A. The effects of the peptide antagonist was assessed over a dosage range of 0.001 to 100 uM as plotted on the X-axis. Cell attachment is plotted on the Y-axis measured at an optical density (O.D.) of 600 nm. Cell attachment was measured on vitronectin- (broken lines) versus laminin- (solid lines) coated surfaces.

FIG. 21 shows the result of a typical assay with an $\alpha_v\beta_3$ antagonist, here peptide 85189. No inhibition was detected with the peptide on laminin-coated surfaces. In contrast, complete inhibition of binding was obtained on VN-coated surfaces with a peptide concentration of 10 uM or greater, as shown with the dose-response curve.

Similar assays were performed with fusion proteins containing various regions of the MMP-2 protein. The MMP-2-derived polypeptides include regions of the C-terminus of MMP-2 active in the binding interaction with $\alpha_v\beta_3$ and thereby capable of inhibiting MMP-2 activation and associated activities. These polypeptides are prepared either as synthetic polypeptides having a sequence derived from the C-terminal domain of MMP-2 as described in Example 1 or as fusion proteins including all or a portion of the C-terminal domain of MMP-2, prepared as described below. MMP-2 C-terminal molecules are presented for both chicken and human specific sequences.

Figure 22A:
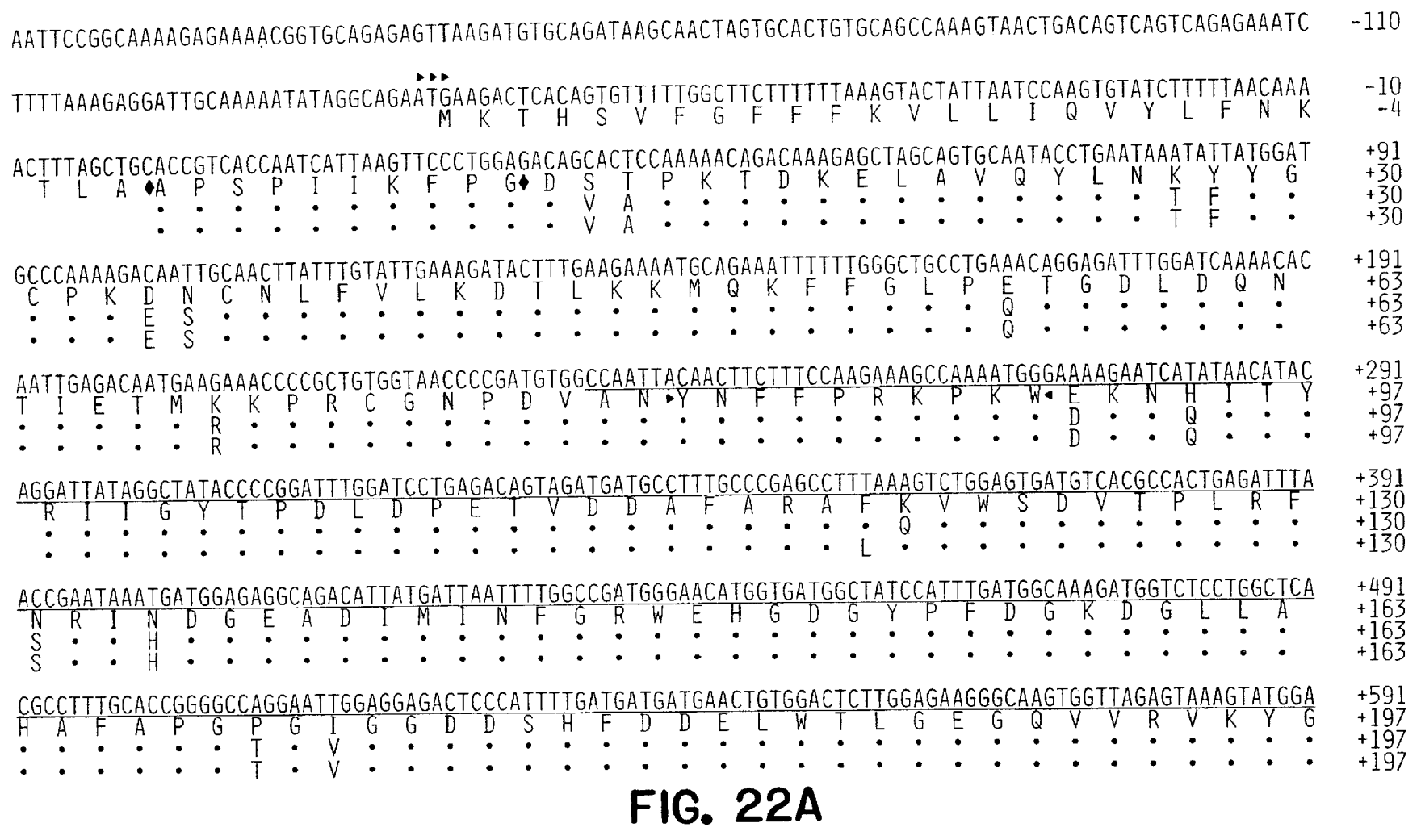
Figure 22B:
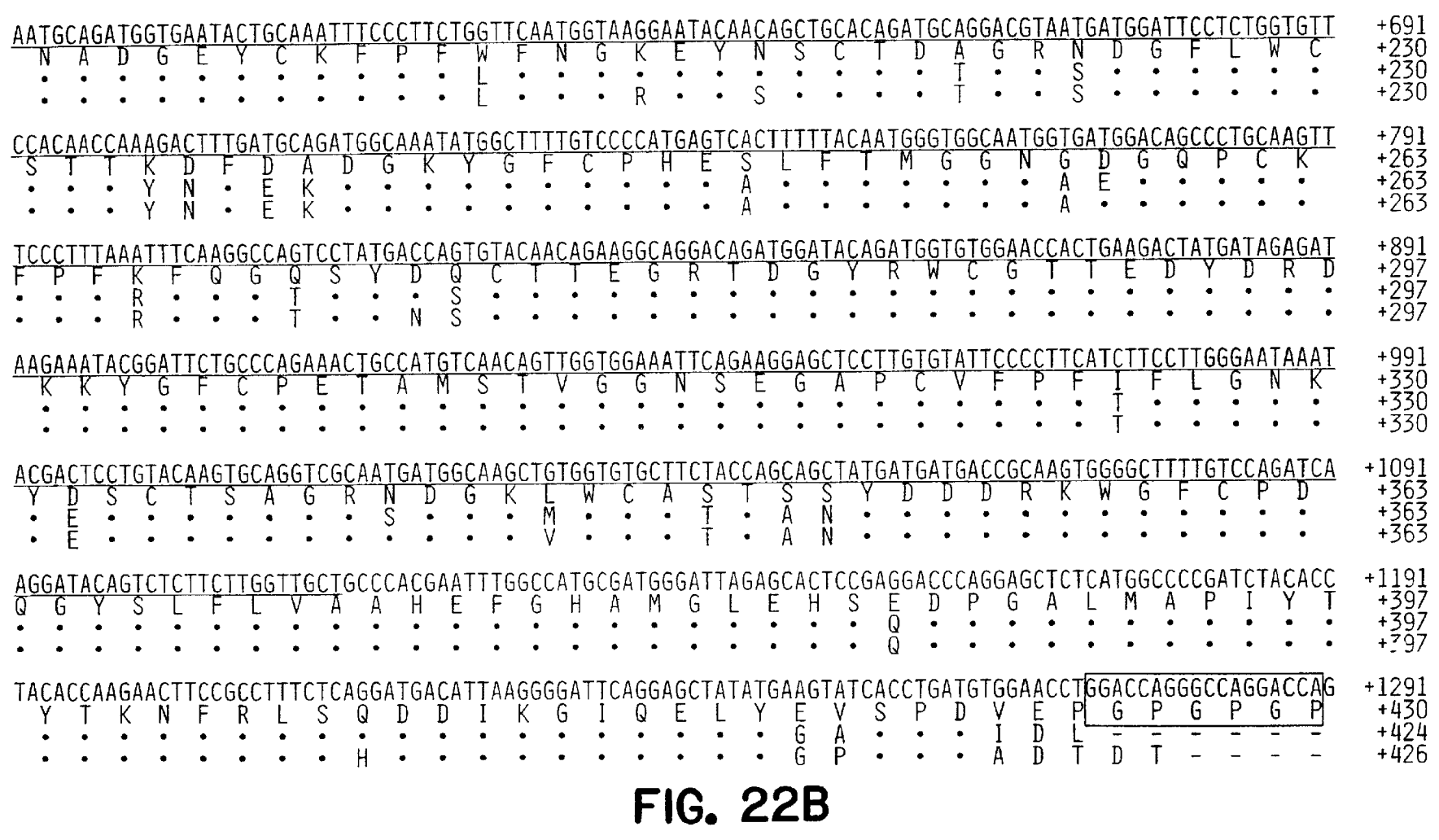
Figure 22C:
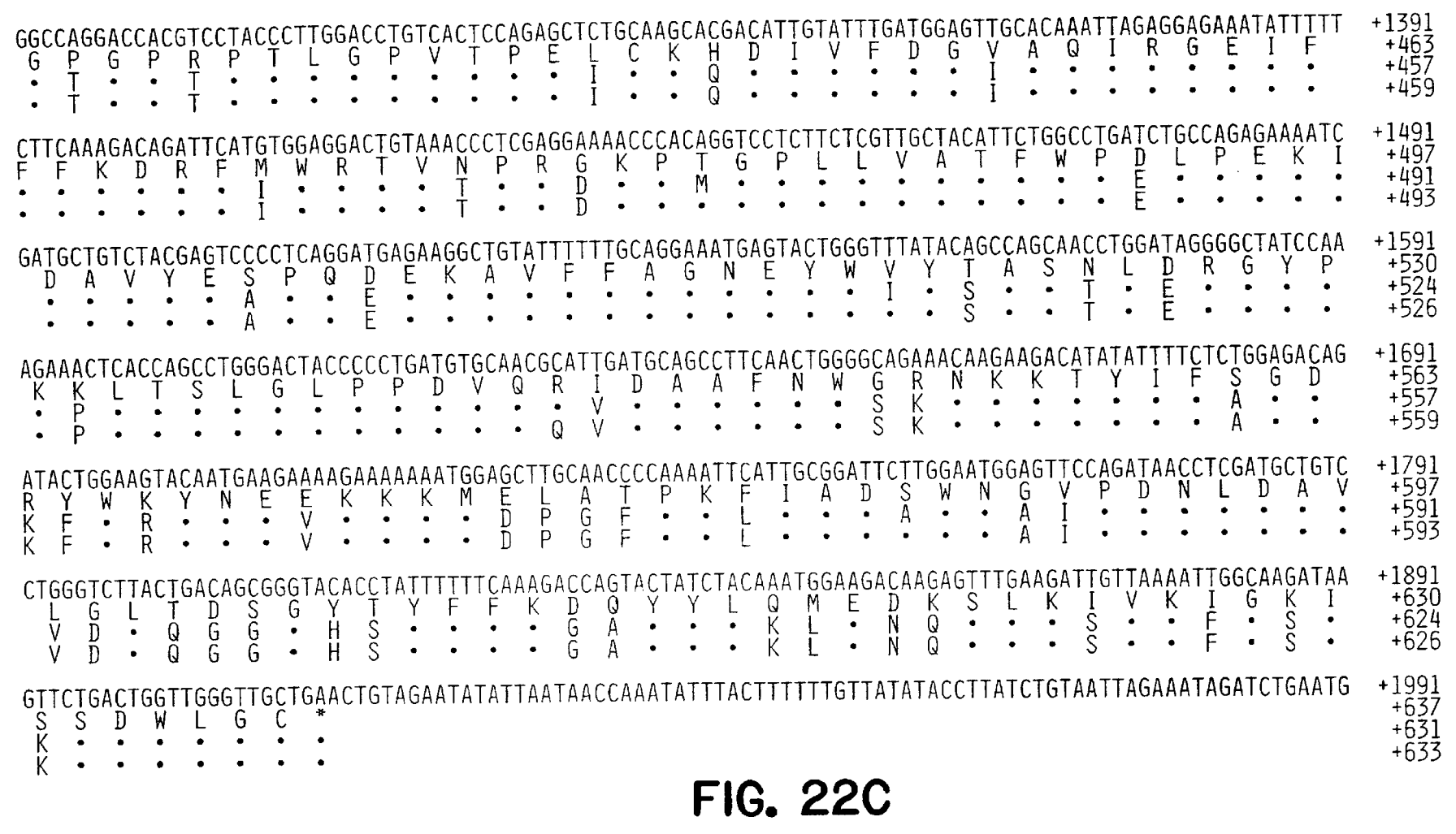

The chicken-derived MMP-2 C-terminal domain, also referred to as the hemopexin domain immediately contiguous with the hinge region, comprises the amino acid residues 445–637 of MMP-2. The complete nucleotide and encoded amino acid sequence of chicken MMP-2 is described below. The human MMP-2 nucleotide and encoded amino acid sequence is also described below. The C-terminal domain in the human MMP-2 that corresponds to the chicken region of 445–637 begin at amino acid residue 439 and ends with 631 due to six missing residues from the human sequence as shown in FIGS. 22A and 22B. Both human- and chicken-derived C-terminal MMP-2 synthetic peptides for use in practicing the methods of this invention are listed in Table 1. The amino acid residue sequences of the synthetic peptides are the same as those generated by the recombinant fusion protein counterparts but without the GST fusion component. The C-terminal MMP-2 fusion proteins derived from both chicken and human are prepared as described below.

A MMP-2 fusion protein is a chimeric polypeptide having a sequence of MMP-2 C-terminal domain or a portion thereof fused (operatively linked by covalent peptide bond) to a carrier (fusion) protein, such as glutathione sulfhydryl transferase (GST).

To amplify various regions of chicken and human MMP-2, primer sequences were designed based on the known respective cDNA sequences of chicken and human MMP-2. The complete top strand of the cDNA nucleotide sequence of unprocessed chicken MMP-2, also referred to as progelatinase, is shown in FIGS. 22A and 22B along with the deduced amino acid sequence shown on the second line (Aimes et al., Biochem. J., 300:729–736, 1994). The third and fourth lines of the figure respectively show the deduced amino acid sequence of human (Collier et al., J. Biol. Chem., 263:6579–6587 (1988)) and mouse MMP-2 (Reponen et al., J. Biol. Chem., 267:7856–7862 (1992)). Identical residues are indicated by dots while the differing residues are given by their one letter IUPAC lettering. Missing residues are indicated by a dash. The numbering of the amino acid residues starts from the first residue of the proenzyme, with the residues of the signal peptide being given negative numbers. The nucleotide sequence is numbered accordingly. The putative initation of translation (ATG) is marked with three forward arrowheads and the translation termination signal (TGA) is indicated by an asterisk. The amino terminal sequences for the chicken proenzyme and active enzyme are contained with diamonds and single arrowheads. The chicken progelatinase nucleotide and amino acid residue sequences are listed together as SEQ ID NO 29 while the encoded amino acid residue sequence is listed separately as SEQ ID NO 30.

Templates for generating amplified regions of chicken MMP-2 were either a cDNA encoding the full-length mature chicken MMP-2 polypeptide provided by Dr. J. P. Quigley of the State University of New York at Stoney Brook, N.Y. or a cDNA generated from a total cellular RNA template derived by standard techniques from an excised sample of chicken chorioallantoic membrane tissue. For the latter, the cDNA was obtained with MuLV reverse transcriptase and a downstream primer specific for the 3'-terminal nucleotides, 5'ATTGAATTCTTCTACAGTTCA3' (SEQ ID NO 31), the 5' and 3' ends of which was respectively complementary to nucleotides 1932–1912 of the published chick MMP-2 sequence. Reverse transcriptase polymerase chain reaction (RT-PCR) was performed according to the specifications of the manufacturer for the GeneAmp RNA PCR Kit (Perkin Elmer). The primer was also engineered to contain an internal EcoRI restriction site.

From either of the above-described cDNA templates, a number of C-terminal regions of chicken MMP-2, each having the natural cysteine residue at position 637 at the carboxy terminus, were obtained by PCR with the 3' primer listed above (SEQ ID NO 31) paired with one of a number of 5' primers listed below. The amplified regions encoded the following MMP-2 fusion proteins, having sequences corresponding to the amino acid residue positions as shown in FIGS. 22A and 22B and also listed in SEQ ID NO 30: 1) 203–637; 2) 274–637; 3) 292–637; 4) 410–637; 5) 445–637. Upstream or 5' primers for amplifying each of the nucleotide regions for encoding the above-listed MMP-2 fusion proteins were designed to encode the polypeptide start sites 3' to an engineered, i.e., PCR-introduced, internal BamHI restriction site to allow for directional ligation into either pGEX-1λT or pGEX-3X expression vectors. The 5' primers included the following sequences, the 5' and 3' ends of which correspond to the indicated 5' and 3' nucleotide positions of the chicken MMP-2 sequence as shown in FIGS. 22A and 22B (the amino acid residue position start sites are also indicated for each primer): 1) Nucleotides 599–619, encoding a 203 start site 5'ATGGGATCCACTGCAAATTTC3' (SEQ ID NO 32); 2) Nucleotides 809–830, encoding a 274 start site 5'GCCGGATCCATGACCAGTGTA3' (SEQ ID NO 33); 3) Nucleotides 863–883, encoding a 292 start site 5'GTGGGATCCCTGAAGACTATG3' (SEQ ID NO 34); 4) Nucleotides 1217–1237, encoding a 410 start 5'AGGGGATCCTTAAGGGGATTC3' (SEQ ID NO 35); and 5) Nucleotides 1325–1345, encoding a 445 start site 5'CTCGGATCCTCTGCAAGCACG3' (SEQ ID NO 36).

The indicated nucleotide regions of the template cDNA were subsequently amplified for 35 cycles (annealing temperature 55 C.) according to the manufacturer's instructions for the Expand High Fidelity PCR System (Boehringer Mannheim). The resulting PCR products were gel-purified, digested with BamHI and EcoRI restriction enzymes, and repurified before ligation into either pGEX-1λT or pGEX-3X vector (Pharmacia Biotech, Uppsala, Sweden) which had been similarly digested as well as dephosphorylated prior to the ligation reaction. The choice of plasmid was based upon the required reading frame of the amplification product. Competent E. coli strain BSJ72 or BL21 cells were transformed with the separate constructs by heat shock. The resulting colonies were screened for incorporation of the respective MMP-2 fusion protein-encoding plasmid by PCR prior to dideoxy sequencing of positive clones to verify the integrity of the introduced coding sequence. In addition, verification of incorporation of plasmid was confirmed by expression of the appropriately-sized GST-MMP-2 fusion protein.

Purification of each of the recombinant GST-MMP-2 fusion proteins was performed using IPTG-induced log-phase cultures essentially as described by the manufacturer for the GST Gene Fusion System (Pharmacia Biotech). Briefly, recovered bacteria were lysed by sonication and incubated with detergent prior to clarification and immobilization of the recombinant protein on sepharose 4B-coupled glutathione (Pharmacia Biotech). After extensive washing, the immobilized fusion proteins were separately eluted from the affinity matrix with 10 mM reduced glutathione in 50 mM Tris-HCl, pH 8.0, and dialyzed extensively against PBS to remove residual glutathione prior to use.

Prior attempts to produce fusion proteins between chicken MMP-2 residues 445 and 637 that only had one encoded cysteine residue resulted in insoluble products. Therefore, in order to generate additional soluble MMP-2 fusion proteins derived from the C-terminal region that did not include an endogenous terminal cysteine residue as present in the previously-described fusion protein, nucleotide sequences were introduced into amplified MMP-2 regions to encode a cysteine residue if necessary depending on the particular fusion protein. A cysteine residue is naturally present in the chicken MMP-2 sequence at position 446 and at position 637. In the human sequence, these positions correspond respectively to 440 and 631. Therefore, fusion proteins were designed to contain engineered terminal cysteine residues at the amino- or carboxy-terminus of the chicken MMP-2 sequences of interest so as to provide for disulfide-bonding with the naturally occurring cysteine at the other terminus, as required by the construct.

Oligonucleotide primers were accordingly designed to allow for amplification of chicken MMP-2 C-terminal regions for expression of soluble MMP-2/GST fusion proteins. Amplified chicken MMP-2 C-terminal regions included those for encoding amino acid residue positions 445–518, 445–552, 516–637 and 549–637. For fusion proteins containing residue 517, the naturally encoded tyrosine residue was substituted for a cysteine to allow for disulfide bonding with either cysteine at residue position 446 or 637. For fusion proteins containing residue 551, the naturally encoded tryptophan residue was substituted for a cysteine to allow for disulfide bonding with either naturally encoded cysteine at residue position 446 or 637.

Briefly, the pGEX-3X plasmid construct encoding the recombinant GST/MMP-2(410–637) fusion protein prepared above was used as a template for amplification according to the manufacturer's protocol for the Expand High Fidelity PCR Kit (Boehringer Mannheim) utilizing a set of oligonucleotide primers whose design was based on the published chicken MMP-2 sequence (also shown in FIGS. 22A and 22B. One upstream primer, designed to encode a chicken MMP-2 protein start site at position 445 after an engineered internal BamHI endonuclease restriction site for insertion into the pGEX-3X GST vector, had the nucleotide sequence (5'CTCGGATCCTCTGCAAGCACG3' (SEQ ID NO 37)). The 5' and 3' ends of the primer respectively corresponded to positions 1325–1345 of the chicken MMP-2 sequence in the figure. Another upstream primer, designed to encode a chicken MMP-2 protein start site at position 516 after an engineered internal BamHI restriction site for insertion into the pGEX-1λT GST vector and to encode a cysteine residue at position 517, had the nucleotide sequence (5'GCAGGATCCGAGTGCTGGGTTTATAC3' (SEQ ID NO 38)). The 5' and 3' ends of the primer respectively corresponded to positions 1537–1562 of the chicken MMP-2 sequence. A third upstream primer, designed to encode a chicken MMP-2 protein start site at position 549 following an engineered internal EcoRI endonuclease restriction site for insertion into the pGEX-1λT GST vector and to encode a cysteine residue at position 551, had the nucleotide sequence (5'GCAGAATTCAACTGTGGCAGAAACAAG3' (SEQ ID NO 39)). The 5' and 3' ends of the primer respectively corresponded to positions 1639–1665 of the chicken MMP-2 sequence.

These upstream primers were separately used with one of the following downstream primers listed below to produce the above-described regions from the C-terminal domain of chicken MMP-2. A first downstream primer (antisense), designed to encode a chicken MMP-2 protein termination site at position 518, to encode a cysteine residue at position 517, and to contain an internal EcoRI endonuclease restriction site for insertion into a GST vector, had the nucleotide sequence (5'GTAGAATTCCAGCACTCATTTCCTGC3' (SEQ ID NO 40)). The 5' and 3' ends of the primer, written in the 5'-3' direction, were respectively complementary in part to positions 1562–1537 of the chicken MMP-2 sequence. A second downstream primer, designed to encode a chicken MMP-2 protein termination site at position 552, to encode a cysteine residue at position 551, and to contain an internal EcoRI endonuclease restriction site for insertion into a GST vector, had the nucleotide sequence (5'TCTGAATTCTGCCACAGTTGAAGG3' (SEQ ID NO 41)). The 5' and 3' ends of the primer, written in the 5' -3' direction, were respectively complementary in part to positions 1666–1643 of the chicken MMP-2 sequence. A third downstream primer, designed to encode a chicken MMP-2 protein termination site at position 637 and to contain an internal EcoRI endonuclease restriction site for insertion into a GST vector, had the nucleotide sequence (5'ATTGAATTCTTCTACAGTTCA3' (SEQ ID NO 42)). The 5' and 3' ends of the primer, written in the 5'-3' direction, were respectively complementary in part to positions 1932–1912 of the chicken MMP-2 sequence.

The regions of the chicken MMP-2 carboxy terminus bounded by the above upstream and downstream primers, used in particular combinations to produce the fusion proteins containing at least one engineered cysteine residue as described above, were separately amplified for 30 cycles with an annealing temperature of 55 C. according to the manufacturer's instructions for the Expand High Fidelity PCR System (Boehringer Mannheim). The resulting amplification products were separately purified, digested with BamHI and or EcoRI restriction enzymes as necessary, and repurified before ligation into the appropriate GST fusion protein vector, either pGEX-3X or pGEX-1λT, as indicated above by the reading frame of the upstream oligonucleotide primer. For ligating the amplified MMP-2 products, the vectors were similarly digested as well as dephosphorylated prior to the ligation reaction. Competent *E. coli* strain BL21 cells were then separately transformed with the resultant MMP-2-containing vector constructs by heat shock. Resulting colonies were then screened for incorporation of the appropriate fusion protein-encoding plasmid by PCR and production of the appropriate sized GST-fusion protein prior to dideoxy sequencing of positive clones to verify the integrity of the introduced coding sequence. Purification of recombinant GST fusion proteins were then performed using IPTG-induced log-phase cultures essentially as described above for producing the other GST-MMP-2 fusion proteins.

The results of inhibition of cell attachment assays with various chicken MMP-2 proteins as well as with other peptides indicate that intact MMP-2, the fusion protein CTMMP-2(2-4) from residues 445–637 and peptide 66203 (SEQ ID NO 5) but not MMP-2 (1–445) and control peptide 69601 inhibited $\beta_3$-expressing CS-1 cell adhesion to vitronectin but not laminin, and thereby inhibited vitronectin receptor $\alpha_v\beta_3$ binding to vitronectin by interfering with normal $\alpha_v\beta_3$ binding activity. Other tested CTMMP-2 fusion proteins 7-1 from residues 274–637, 10-1 from residues 292–637 and 4-3 from residues 274–400 had less affect on cell adhesion compared to 2-4.

In addition to the chicken MMP-2 GST-fusion proteins described above, two human MMP-2 GST fusion proteins were produced for expressing amino acid regions 203–631 and 439–631 of the mature human MMP-2 proenzyme polypeptide. The indicated regions correspond respectively to chicken MMP-2 regions 20637 and 445–637. Human MMP-2-GST fusion proteins were produced by PCR as described above for the chicken MMP-2-GST fusion proteins utilizing a cDNA template that encoded the entire human MMP-2 open reading frame provided by Dr. W. G. Stetler-Stevenson at the National Cancer Institute, Bethesda, Md. Upstream 5' primer sequences were designed based upon the previously published sequence of human MMP-2 (Collier et al., *J. Biol. Chem.*, 263:6579–6587 (1988) and to encode an introduced internal EcoRI restriction site to allow for insertion of the amplified products into the appropriate expression vector.

One upstream primer, designed to encode a human MMP-2 protein start site at position 203 after an engineered internal EcoRI endonuclease restriction site for insertion into the pGEX-1λT GST vector, had the nucleotide sequence (5'GATGAATTCTACTGCAAGTT3' (SEQ ID NO 43)). The 5' and 3' ends of the primer respectively corresponded to positions 685–704 of the human MMP-2 open reading frame sequence. Another upstream primer, designed to encode a human MMP-2 protein start site at position 439 after an engineered internal EcoRI restriction site for insertion into the pGEX-IXT GST vector, had the nucleotide sequence (5'CACTGAATTCATCTGCAAACA3' (SEQ ID NO 44)). The 5' and 3' ends of the primer respectively corresponded to positions 1392 and 1412 of the human MMP-2 open reading frame sequence.

Each of the above primers were used separately with a downstream primer, having 5' and 3' ends respectively complementary to bases 1998 and 1978 of the human MMP-2 sequence that ends distal to the MMP-2 open reading frame and directs protein termination after amino acid residue 631. The amplified products produced expressed fusion proteins containing human MMP-2 amino acid residues 203–631 (SEQ ID NO 45) and 439–631 (SEQ ID NO 18).

The resulting PCR products were purified, digested with EcoRI and repurified for ligation into a pGEX-1λT plasmid that was similarly digested and dephosphorylated prior to the ligation reaction. Cells were transformed as described above.

Other human MMP-2 fusion proteins containing amino acid residues 410–631 (SEQ ID NO 17), 439–512 (SEQ ID NO 19), 439–546 (SEQ ID NO 20), 510–631 (SEQ ID NO 21) and 543–631 (SEQ ID NO 22) are also prepared as described above for use in the methods of this invention.

B. Ligand-Receptor Binding Assay

The synthetic peptides prepared in Example 1 along with the MMP-2 fusion proteins described above were further screened by measuring their ability to antagonize $\alpha_v\beta_3$ and $\alpha_{IIb}\beta_3$ receptor binding activity in purified ligand-receptor binding assays. The method for these binding studies has been described by Barbas et al., *Proc. Natl. Acad. Sci. USA.* 90:10003–10007 (1993), Smith et al., *J. Biol. Chem.,* 265:11008–11013 (1990), and Pfaff et al., *J. Biol. Chem.,* 269:20233–20238 (1994), the disclosures of which are hereby incorporated by reference.

Herein described is a method of identifying antagonists in a ligand-receptor binding assay in which the receptor is immobilized to a solid support and the ligand and antagonist are soluble. Also described is a ligand-receptor binding assay in which the ligand is immobilized to a solid support and the receptor and antagonists are soluble.

Briefly, selected purified integrins were separately immobilized in Titertek microtiter wells at a coating concentration of 50 nanograms (ng) per well. The purification of the receptors used in the ligand-receptor binding assays are well known in the art and are readily obtainable with methods familiar to one of ordinary skill in the art. After incubation for 18 hours at 4 C., nonspecific binding sites on the plate were blocked with 10 milligrams/milliliter (mg/ml) of bovine serum albumin (BSA) in Tris-buffered saline. For inhibition studies, various concentrations of selected peptides from Table 1 were tested for the ability to block the binding of $^{125}$I-vitronectin or $^{125}$I-fibrinogen to the integrin receptors, $\alpha_v\beta_3$ and $\alpha_{IIb}\beta_3$. Although these ligands exhibit optimal binding for a particular integrin, vitronectin for $\alpha_v\beta_3$ and fibrinogen for $\alpha_{IIb}\beta_3$, inhibition of binding studies using peptides to block the binding of fibrinogen to either receptor allowed for the accurate determination of the amount in micromoles (uM) of peptide necessary to half-maximally inhibit binding of receptor to ligand. Radiolabeled ligands were used at concentrations of 1 nM and binding was challenged separately with unlabeled synthetic peptides.

Following a three hour incubation, free ligand was removed by washing and bound ligand was detected by gamma counting. The data from the assays where selected cyclic peptides listed in Table 1 were used to inhibit the binding of receptors and radiolabeled fibrinogen to separately immobilized $\alpha_v\beta_3$ and $\alpha_{IIb}\beta_3$ receptors were highly reproducible with the error between data points typically below 11%. The $IC_{50}$ data in micromoles ($IC_{50}$ uM) are expressed as the average of duplicate data points±the standard deviation as shown in Table 2.

TABLE 2

| Peptide No. | $\alpha_V\beta_3$ (IC$_{50}$ uM) | $\alpha_{IIb}\beta_3$ (IC$_{50}$ uM) |
|---|---|---|
| 62181 | 1.96 ± 0.62 | 14.95 ± 7.84 |
| 62184 | 0.05 ± 0.001 | 0.525 ± 0.10 |
| 62185 | 0.885 ± 0.16 | 100 ± 0.001 |
| 62187 | 0.05 ± 0.001 | 0.26 ± 0.056 |
| 62186 | 57.45 ± 7.84 | 100 ± 0.001 |
| 62175 | 1.05 ± 0.07 | 0.63 ± 0.18 |
| 62179 | 0.395 ± .21 | 0.055 ± 0.007 |

Thus, the RGD-containing or RGD-derivatized cyclic peptides 62181, 62184, 62185 and 62187, each having one D-amino acid residue, exhibited preferential inhibition of fibrinogen binding to the $\alpha_v\beta_3$ receptor as measured by the lower concentration of peptide required for half-maximal inhibition as compared to that for the $\alpha_{IIb}\beta_3$ receptor. In contrast, the other RGD-containing or RGD-derivatized cyclic peptides, 62186, 62175 and 62179, were either not as effective in blocking fibrinogen binding to $\alpha_v\beta_3$ or exhibited preferential inhibition of fibrinogen binding to $\alpha_{IIb}\beta_3$ as compared to $\alpha_v\beta_3$. These results are consistent with those recently published by Pfaff, et al., *J. Biol. Chem.,* 269:20233–20238 (1994) in which the cyclic peptide RGD FV (wherein F indicates a D-amino acid residue) specifically inhibited binding of fibrinogen to the $\alpha_v\beta_3$ integrin and not to the $\alpha_{IIb}\beta_3$ or $\alpha_5\beta_1$ integrins. Similar inhibition of binding assays were performed with linearized peptides having or lacking an RGD motif, the sequences of which were derived from the $\alpha_v$ receptor subunit, $\alpha_{IIb}$ receptor subunit or vitronectin ligand amino acid residue sequences. The sequences of the linear peptides, 62880 (VN-derived amino acid residues 35–49), 62411 ($\alpha_v$-derived amino acid residues 676–687); 62503 ($\alpha_v$-derived amino acid residues 655–667) and 62502 ($\alpha_{IIb}$-derived amino acid residues 296–306), are listed in Table 1. Each of these peptides were used in separate assays to inhibit the binding of either vitronectin (VN) or fibrinogen (FG) to either $\alpha_{IIb}\beta_3$ or $\alpha_v\beta_3$. The IC$_{50}$ data in micromoles (IC$_{50}$ uM) of an individual assay for each experiment is shown in Table 3.

TABLE 3

| | $\alpha_{IIb}\beta_3$ IC$_{50}$ (uM) | | $\alpha_V\beta_3$ IC$_{50}$ (uM) | |
|---|---|---|---|---|
| Peptide No. | FG | VN | FG | VN |
| 62880 | 4.2 | 0.98 | <0.1 | 0.5 |
| 62411 | >100 | >100 | >100 | >100 |
| 62503 | >100 | >100 | >100 | >100 |
| 62502 | 90 | 5 | >100 | >100 |

The results of inhibition of ligand binding assays to selected integrin receptors with linearized peptides show that only peptide 62880 was effective at inhibiting the half-maximal binding of either FG or VN to $\alpha_v\beta_3$ as measured by the lower concentration of peptide required for half-maximal inhibition as compared to $\alpha_{IIb}\beta_3$ receptor. None of the other linearized peptides were effective at blocking ligand binding to $\alpha_v\beta_3$ although peptide 62502 was effective at blocking VN binding to $\alpha_{IIb}\beta_3$.

In other ligand receptor binding assays performed as described above with the exception that detection of binding or inhibition thereof was with ELISA and peroxidase-conjugated goat anti-rabbit IgG, the ligands VN, MMP-2 and fibronectin at a range of 5–50 ng/well and listed in the order of effectiveness were shown to bind to immobilized $\alpha_v\beta_3$ receptor while collagen did not. In addition, the ability of peptides to inhibit the binding of either MMP-2 or VN to immobilized $\alpha_v\beta_3$ was assessed with peptides 69601 (SEQ ID NO 6) and 66203 (SEQ ID NO 5). Only peptide 66203 was effective at inhibiting the binding of either substrate to the $\alpha_v\beta_3$ receptor while the control peptide 69601 failed to have an effect with either ligand.

Figure 23:
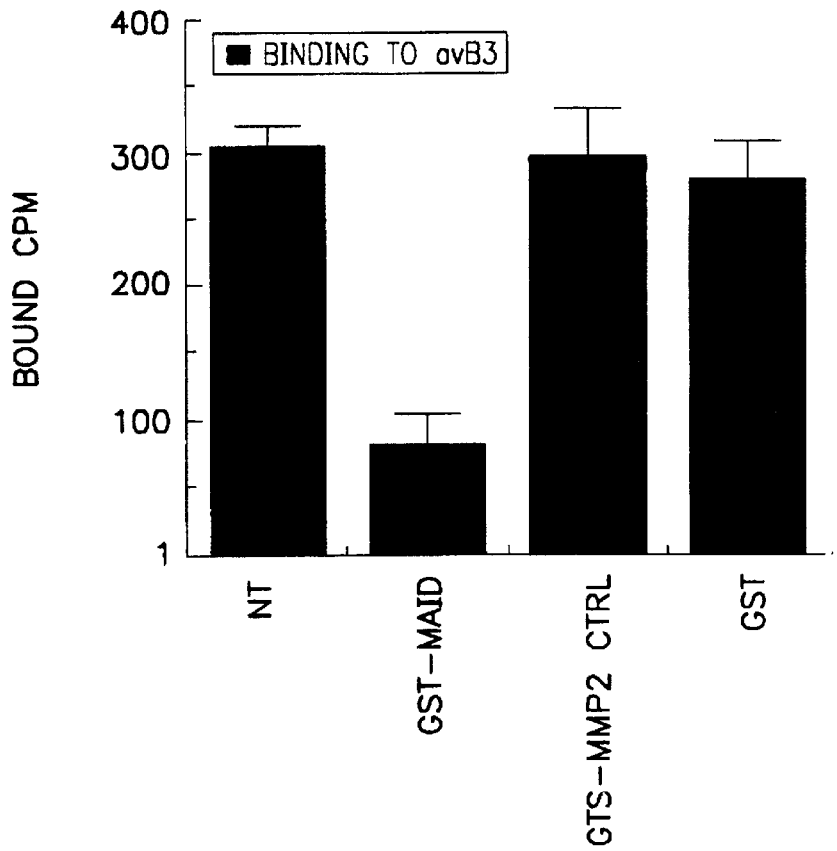
FIG. 23 shows the results in bar-graph form of a solid-phase receptor binding assay of iodinated MMP-2 to bind to $\alpha_v\beta_3$ with and without the presence of inhibitors as further described in Example 4B. The data is plotted as bound CPM on the Y-axis against the various potential inhibitors and controls.

Specificity of MMP-2 binding to integrin receptors was confirmed with a solid phase receptor binding assay in which iodinated MMP-2 was shown to bind to $\alpha_v\beta_3$ and not to $\alpha_{IIb}\beta_3$ that had been immobilized on a solid phase (300 bound cpm versus approximately 10 bound CPM). The ability of an MMP-2 derived peptide or fusion protein to inhibit the specific binding of MMP-2 to $\alpha_v\beta_3$ was demonstrated in a comparable assay, the results of which are shown in FIG. 23. The GST-CTMMP-2(445–637) (also referred as CTMMP-2(2-4)) fusion protein prepared as described above, labeled GST-MAID, inhibited the binding of iodinated MMP-2 to $\alpha_v\beta_3$ while GST alone had no effect with levels of bound CPM comparable to wells receiving no inhibitor at all (labeled NT). The MMP-2 fusion protein referred to as CTMMP-2(274–637), also referred to as CTMMP-2(10-1), failed to inhibit the binding of labeled MMP-2 to $\alpha_v\beta_3$.

Figure 24:
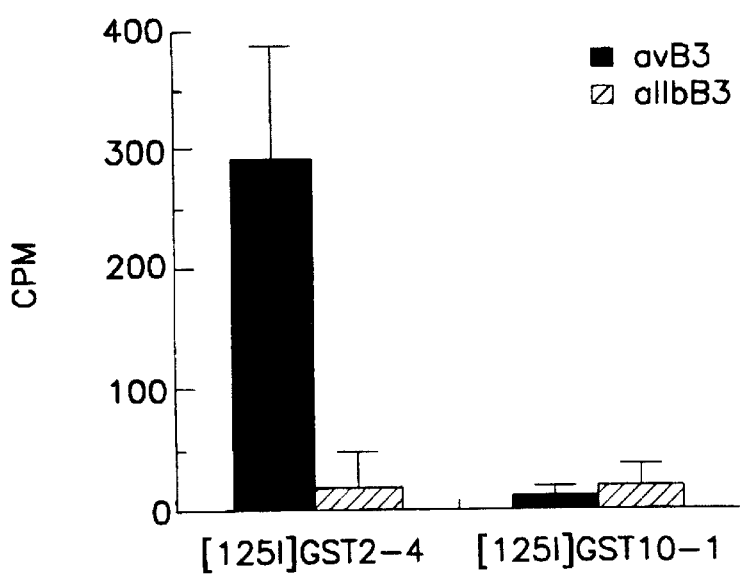
FIG. 24 shows the specificity of chicken-derived MMP-2 compositions for either the integrin receptors $\alpha_v\beta_3$ and $\alpha_{IIb}\beta_3$ in the presence of MMP-2 inhibitors as further described in Example 4B. The data is presented as described in the legend in FIG. 23.

Specificity of receptor interaction with MMP-2-derived antagonists was confirmed with binding and inhibition of binding solid phase assays. CTMMP-2(2-4), labeled in FIG. 24 as [125I]GST2-4, bound to $\alpha_v\beta_3$ and not to $\alpha_{IIb}\beta_3$ while CTMMP-2(10-1), labeled in FIG. 24 as [125I]GST10-1, did not bind to either receptor in the in vitro solid phase assay. In addition, the binding of labeled GST2-4 was competed by unlabeled GST2-4.

Thus, the ligand-receptor assay described herein can be used to screen for both circular or linearized synthetic peptides that exhibit selective specificity for a particular integrin receptor, specifically $\alpha_v\beta_3$, as used as vitronectin receptor ($\alpha_v\beta_3$) antagonists in practicing this invention.

5. Characterization of the Untreated Chick Chorioallantoic Membrane (CAM)

A. Preparation of the CAM

Angiogenesis can be induced on the chick chorioallantoic membrane (CAM) after normal embryonic angiogenesis has resulted in the formation of mature blood vessels. Angiogenesis has been shown to be induced in response to specific cytokines or tumor fragments as described by Leibovich et al., *Nature,* 329:630 (1987) and Ausprunk et al., *Am. J. Pathol.,* 79:597 (1975). CAMs were prepared from chick embryos for subsequent induction of angiogenesis and inhibition thereof as described in Examples 6 and 7, respectively. Ten day old chick embryos were obtained from McIntyre Poultry (Lakeside, Calif.) and incubated at 37 C. with 60% humidity. A small hole was made through the shell at the end of the egg directly over the air sac with the use of a small crafts drill (Dremel, Division of Emerson Electric Co. Racine Wis.). A second hole was drilled on the broad side of the egg in a region devoid of embryonic blood vessels determined previously by candling the egg. Negative pressure was applied to the original hole, which resulted in the CAM (chorioallantoic membrane) pulling away from the shell membrane and creating a false air sac over the CAM. A 1.0 centimeter (cm)×1.0 cm square window was cut through the shell over the dropped CAM with the use of a small model grinding wheel (Dremel). The small window allowed direct access to the underlying CAM.

The resultant CAM preparation was then either used at 6 days of embryogenesis, a stage marked by active neovascularization, without additional treatment to the CAM reflecting the model used for evaluating effects on embryonic neovascularization or used at 10 days of embryogenesis where angiogenesis has subsided. The latter preparation was thus used in this invention for inducing renewed angiogenesis in response to cytokine treatment or tumor contact as described in Example 6.

B. Histology of the CAM

To analyze the microscopic structure of the chick embryo CAMs and/or human tumors that were resected from the chick embryos as described in Example 8, the CAMs and tumors were prepared for frozen sectioning as described in Example 3A. Six micron (um) thick sections were cut from the frozen blocks on a cryostat microtome for immunofluorescence analysis.

Figure 4:
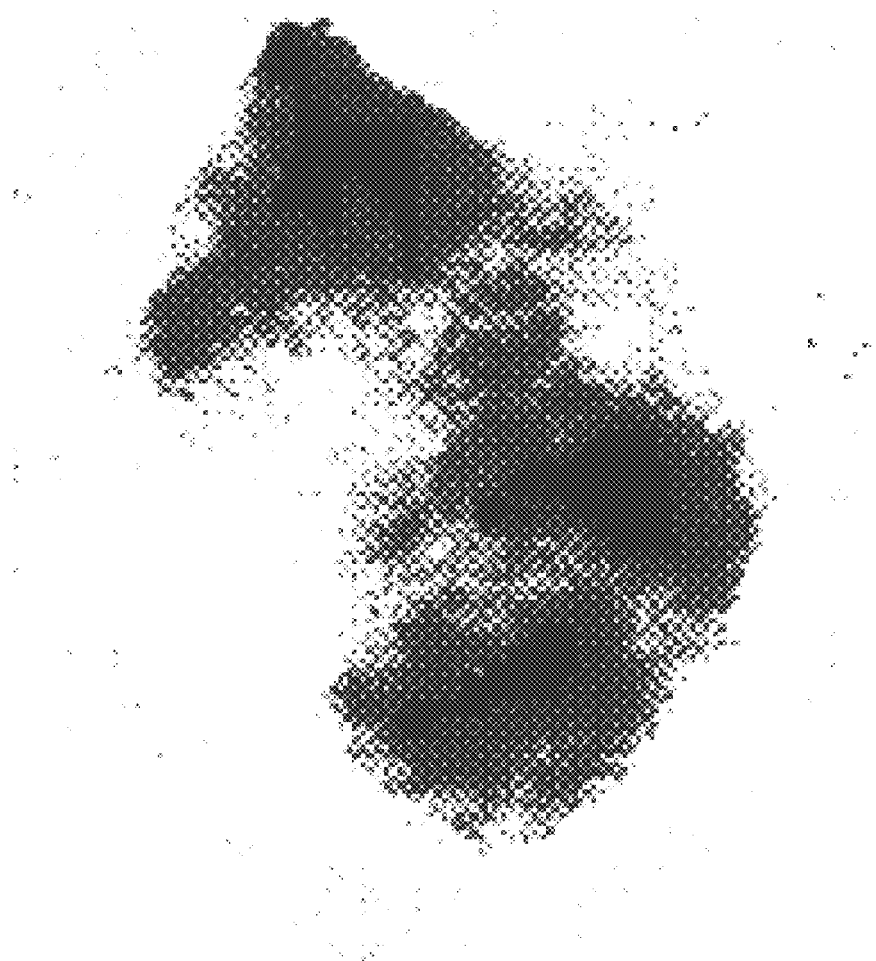
FIG. 4 illustrates a typical photomicrograph of a CAM of this invention devoid of blood vessels in an untreated 10 day old chick embryo. The preparation is described in Example 5B.

FIG. 4 shows a typical photomicrograph of an area devoid of blood vessels in an untreated 10 day old CAM. As angiogenesis in the CAM system is subsiding by this stage of embryogenesis, the system is useful in this invention for stimulating the production of new vasculature from existing vessels from adjacent areas into areas of the CAM currently lacking any vessels.

C. Integrin Profiles in the CAM Detected by Immunofluorescence

To view the tissue distribution of integrin receptors present in CAM tissues, 6 um frozen sections of both tumor tissue and chick embryo CAM tissues were fixed in acetone for 30 seconds and stained by immunofluorescence with 10 micrograms/milliliter (ug/ml) mAb CSAT, a monoclonal antibody specific for the , integrin subunit as described by Buck et al., *J. Cell Biol.,* 107:2351 (1988) and thus used for controls, or LM609 as prepared in Example 2. Primary staining was followed by staining with a 1:250 dilution of goat anti-mouse rhodamine labeled secondary antibody (Tago) to allow for the detection of the primary immunoreaction product. The sections were then analyzed with a Zeiss immunofluorescence compound microscope.

Figure 5A:
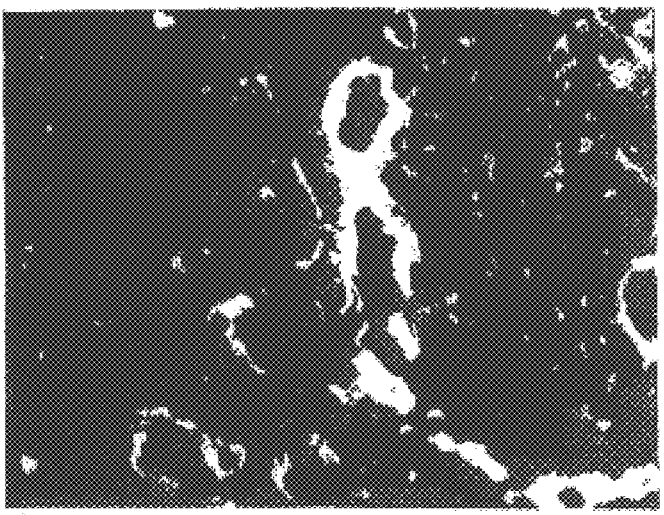
FIGS. 5A–5C illustrate the tissue distribution of the integrins $\beta_1$ and $\alpha_v\beta_3$ in the CAM preparation of this invention.
Figure 5B:
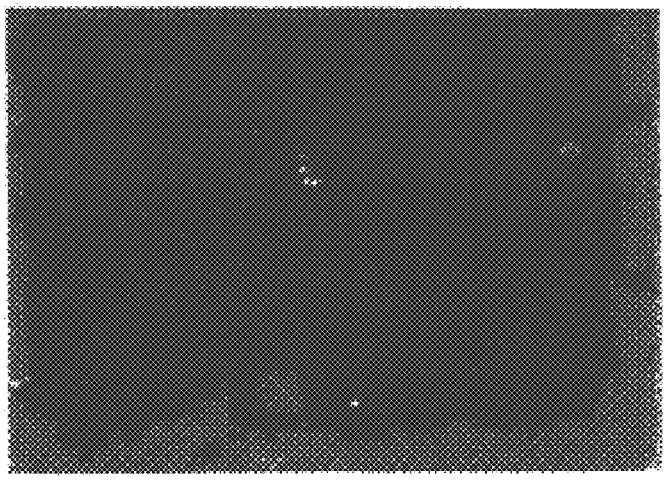

The results of the immunofluorescence analysis show that the mature blood vessels present in an untreated 10 day chick embryo expressed the integrin $\beta_1$ subunit (FIG. 5A). In contrast, in a serial section of the tissue shown in FIG. 5A, no immunoreactivity with LM609 was revealed (FIG. 5B). Thus, the integrin $\alpha_v\beta_3$ detected by the LM609 antibody was not actively being expressed by the mature blood vessels present in a 10 day old untreated chick embryo. As shown in the CAM model and in the following Examples, while the blood vessels are undergoing new growth in normal embryogenesis or induced by either cytokines or tumors, the blood vessels are expressing $\alpha_v\beta_3$. However, following active neovascularization, once the vessels have stopped developing, the expression of $\alpha_v\beta_3$ diminishes to levels not detectable by immunofluorescence analysis. This regulation of $\alpha_v\beta_3$ expression in blood vessels undergoing angiogenesis as contrasted to the lack of expression in mature vessels provides for the unique ability of this invention to control and inhibit angiogenesis as shown in the following Examples using the CAM angiogenesis assay system.

In other profiles, the metalloproteinase MMP-2 and $\alpha_v\beta_3$ colocalized on endothelial cells undergoing angiogenesis three days following bFGF induction in the 10 day old CAM model. MMP-2 was only minimally expressed on vessels that lacked the $\alpha_v\beta_3$ receptor. In addition, MMP-2 colocalized with $\alpha_v\beta_3$ on angiogenic M21-L tumor-associated blood vessels in vivo (tumors resulting from injection of M21-L human melanoma cells into the dermis of human skin grafts grown on SCID mice as described in Example 11) but not with preexisting non-tumor associated blood vessels. Similar results of the selective association of MMP-2 and $\alpha_v\beta_3$ were also obtained with $\alpha_v\beta_3$ bearing CS-1 melanoma tumors in the CAM model but not with CS-1 cells lacking $\alpha_v\beta_3$.

6. CAM Anciogenesis Assay

A. Angiogenesis Induced by Growth Factors

Angiogenesis has been shown to be induced by cytokines or growth factors as referenced in Example 5A. In the experiments described herein, angiogenesis in the CAM preparation described in Example 5 was induced by growth factors that were topically applied onto the CAM blood vessels as described herein.

Angiogenesis was induced by placing a 5 millimeter (mm)×5 mm Whatman filter disk (Whatman Filter paper No.1) saturated with Hanks Balanced Salt Solution (HBSS, GIBCO, Grand Island, N.Y.) or HBSS containing 150 nanograms/milliliter (ng/ml) recombinant basic fibroblast growth factor (bFGF) (Genzyme, Cambridge, Mass.) on the CAM of a 10-day chick embryo in a region devoid of blood vessels and the windows were latter sealed with tape. In other assays, 125 ng/ml bFGF was also effective at inducing blood vessel growth. For assays where inhibition of angiogenesis ws evaluated with intravenous injections of antagonists, angiogenesis was first induced with 1–2 ug/ml bFGF in fibroblast growth medium. Angiogenesis was monitored by photomicroscopy after 72 hours. CAMs were snap frozen, and 6 um cryostat sections were fixed with acetone and stained by immunofluorescence as described in Example 5C with 10 ug/ml of either anti-$D_1$ monoclonal antibody CSAT or LM609.

Figure 5C:
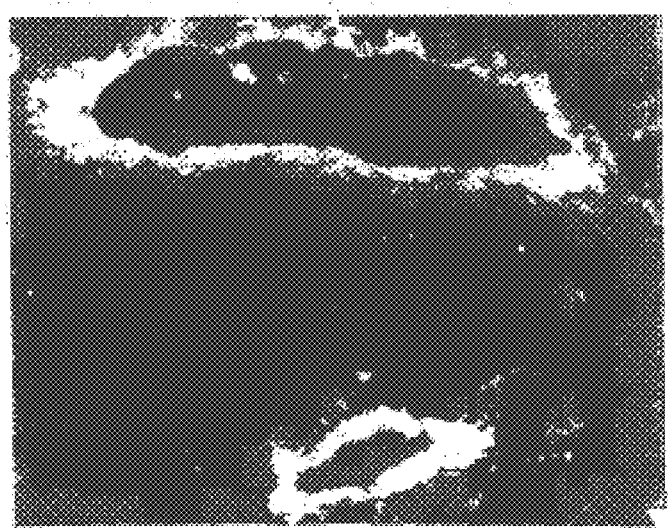

The immunofluorescence photomicrograph in FIG. 5C shows enhanced expression of $\alpha_v\beta_3$ during bFGF-induced angiogenesis on the chick CAM in contrast with the absence of $\alpha_v\beta_3$ expression in an untreated chick CAM as shown in FIG. 5B. $\alpha_v\beta_3$ was readily detectable on many (75% to 80%) of the vessels on the bFGF-treated CAMs. In addition, the expression of integrin $\beta_1$ did not change from that seen in an untreated CAM as $\beta_1$ was also readily detectable on stimulated blood vessels.

The relative expression of $\alpha_v\beta_3$ and $\beta_1$ integrins was then quantified during bFGF-induced angiogenesis by laser confocal image analysis of the CAM cryostat sections. The stained sections were then analyzed with a Zeiss laser confocal microscope. Twenty-five vessels stained with LM609 and 15 stained with CSAT (average size ~1200 sq mm$^2$, range 350 to 3,500 mm$^2$) were selected from random fields and the average rhodamine fluorescence for each vessel per unit area was measured in arbitrary units by laser confocal image analysis. Data are expressed as the mean fluorescence intensity in arbitrary units of vessels±standard error (SE).

Figure 6:
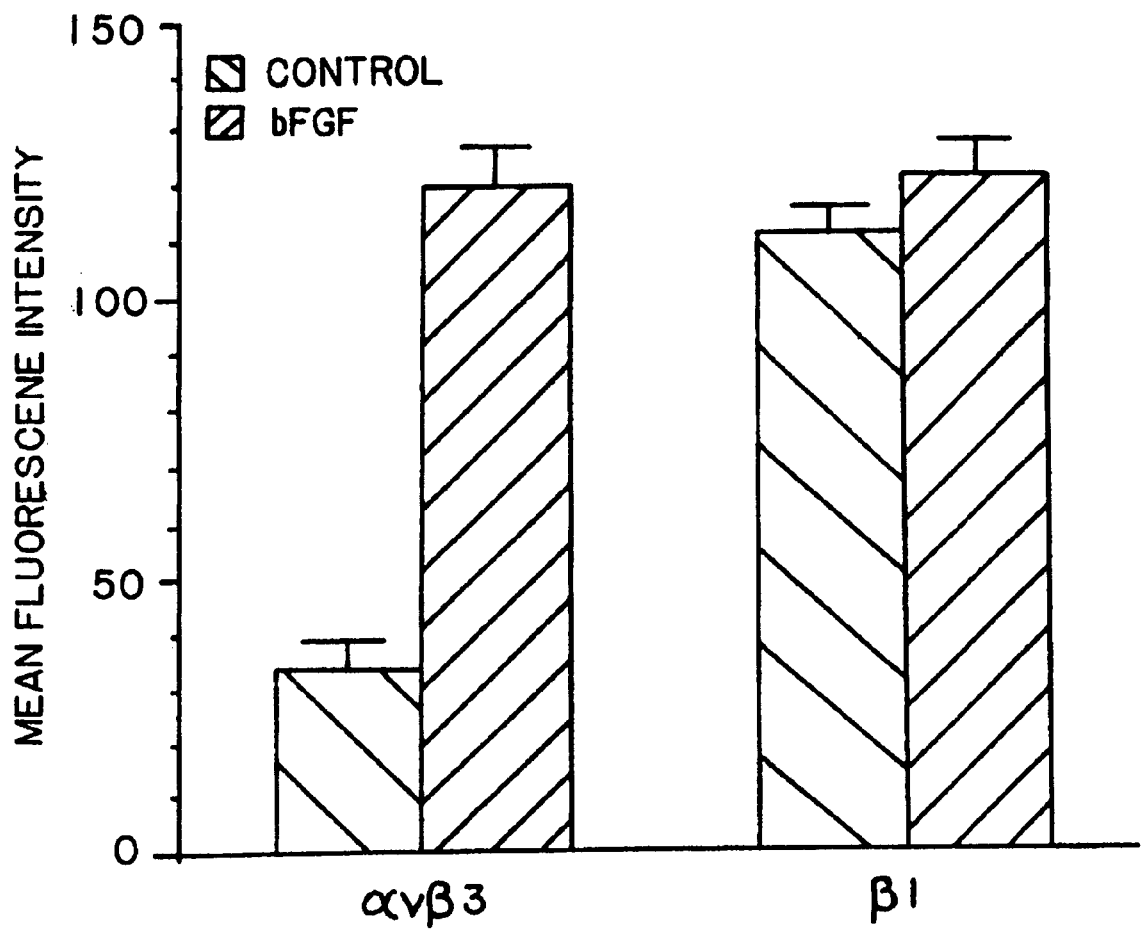
FIG. 6 illustrates the quantification in a bar graph of the relative expression of $\alpha_v\beta_3$ and $\beta_1$ in untreated and bFGF treated 10 day old CAMs as described in Example 6A. The mean fluorescence intensity is plotted on the Y-axis with the integrin profiles plotted on the X-axis.

The results plotted in FIG. 6 show that staining of $\alpha_v\beta_3$ was significantly enhanced (four times higher) on CAMs treated with bFGF as determined by the Wilcoxon Rank Sum Test (P<0.0001) whereas $\beta_1$ staining was not significantly different with bFGF treatment.

The CAM assay was further used to examine the effect of another potent angiogenesis inducer, tumor necrosis factor-alpha (TNFA), on the expression of $\beta_1$ and $\beta_3$ integrins. Filter disks impregnated with either bFGF or TNF$\alpha$ and placed on CAMs from 10 day embryos were found to promote local angiogenesis after 72 hours.

Figures 7A, 7B, 7C:
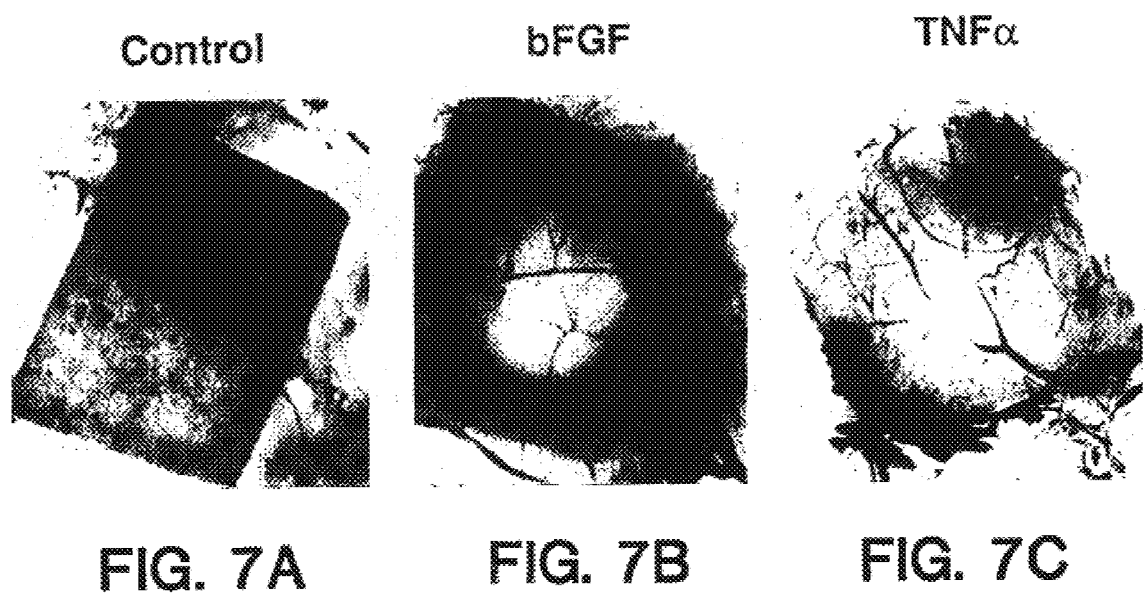
FIGS. 7A–7C illustrates the appearance of an untreated 10 day old CAM, a bFGF treated CAM, and a TNFα treated CAM, respectively, the procedures and results of which are described in Example 6A.

The results are shown in the photomicrographs of CAMs either untreated (FIG. 7A), treated with bFGF (FIG. 7B) or treated with TNF$\alpha$ (FIG. 7C). Blood vessels are readily apparent in both the bFGF and TNF$\alpha$ treated preparations but are not present in the untreated CAM. Thus, the topical application of a growth factor/cytokine resulted in the induction of angiogenesis from mature vessels in an adjacent area into the area originally devoid of blood vessels. In view of the bFGF-induced blood vessels and concomitant expression of $\alpha_v\beta_3$ as shown in FIG. 5C, treatment of TNF$\alpha$ results in comparable activities.

These findings indicate that in both human and chick, blood vessels involved in angiogenesis show enhanced expression of $\alpha_v\beta_3$. Consistent with this, expression of $\alpha_v\beta_3$ on cultured endothelial cells can be induced by various cytokines in vitro as described by Janat et al., *J. Cell Physiol.*, 151:588 (1992); Enenstein et al., *Exp. Cell Res.*, 203:499 (1992) and Swerlick et al., *J. Invest. Derm.*, 99:715 (1993).

The effect on growth-factor induced angiogenesis by antibody and peptide inhibitors is presented in Examples 7A and 7B.

B. Embryonic Angiogenesis

The CAM preparation for evaluating the effect of angiogenesis inhibitors on the natural formation of embryonic neovasculature was the 6 day embryonic chick embryo as previously described. At this stage in development, the blood vessels are undergoing de novo growth and thus provides a useful system for determining if $\alpha_v\beta_3$ participates in embryonic angiogenesis. The CAM system was prepared as described above with the exception that the assay was performed at embryonic day 6 rather than at day 10. The effect on embryonic angiogenesis by treatment with antibodies and peptides of this invention are presented in Example 7C.

C. Angiogenesis Induced by Tumors

To investigate the role of $\alpha_v\beta_3$ in tumor-induced angiogenesis, various $\alpha_v\beta_3$-negative human melanoma and carcinoma fragments were used in the CAM assay that were previously grown and isolated from the CAM of 17-day chick embryo as described by Brooks et al., *J. Cell Biol.*, 122:1351 (1993) and as described herein. The fragments induced extensive neovascularization in the presence of buffer alone.

Angiogenesis was induced in the CAM assay system by direct apposition of a tumor fragment on the CAM. Preparation of the chick embryo CAM was identical to the procedure described above. Instead of a filter paper disk, a 50 milligram (mg) to 55 mg in weight fragment of one of human melanoma tumor M21-L, human lung carcinoma tumor UCLAP-3, human pancreatic carcinoma cell line FG (Cheresh et al., I Cell 58:945–953, 1989), or human laryngeal carcinoma cell line HEp3, all of which are $\alpha_v\beta_3$ negative tumors, was placed on the CAM in an area originally devoid of blood vessels.

The M21-L human melanoma cell line, UCLAP-3 human lung carcinoma cell line, FG pancreatic carcinoma cell line, or HEp3 human laryngeal carcinoma cell line, all $\alpha_v\beta_3$ negative, were used to grow the solid human tumors on the CAMs of chick embryos. A single cell suspension of 8×10$^6$ M21-L, UCLAP-3, and FB or 5×10$^5$ HEp3 cells was first applied to the CAMs in a total volume of 30 ul of sterile HBSS. The windows were sealed with tape and the embryos were incubated for 7 days to allow growth of human tumor lesions. At the end of 7 days, now a 17-day embryo, the tumors were resected from the CAMs and trimmed free of surrounding CAM tissue. The tumors were sliced into 50 mg to 55 mg tumor fragments for use in either angiogenesis or tumor growth assays. The tumor fragments were placed on a new set of 10 day chick embryo CAMs as described in Example 6A in an area devoid of blood vessels.

Tumors grown in vivo on the chick embryo CAMs were stained for $\alpha_v\beta_3$ expression with mAb LM609 as described in Example 3A. No specific staining of tumor cells was observed indicating a lack of $\alpha_v\beta_3$ expression.

These CAM tumor preparations were then subsequently treated as described in Examples 7D and 7E for measuring the effects of antibodies and peptides on tumor-induced angiogenesis. The CAM tumor preparations were also treated as described in Examples 8, 9, and 12 for measuring the effects of antibodies and peptides on regression of tumors and apoptosis of angiogenic blood vessels and vascular cells.

7. Inhibition of Angiogenesis as Measured in the CAM Assay

A. Inhibition of Growth Factor-Induced Angiogenesis by Topical Application of Inhibitors 1) Treatment with Monoclonal Antibodies To determine whether $\alpha_v\beta_3$ plays an active role in angiogenesis, filter disks saturated with bFGF or TNF$\alpha$ were placed on CAMs then the monoclonal antibodies (also referred to as mAb), LM609 (specific for $\alpha_v\beta_3$) CSAT (specific for $\beta_1$), or P3G2 or also P1F6 (both specific for $\alpha_v\beta_5$) were added to the preparation.

Angiogenesis was induced on CAMs from 10 day chick embryos by filter disks saturated with bFGF. Disks were then treated with 50 ml HBSS containing 25 mg of mAb in a total volume of 25 ul of sterile HBSS at 0, 24, and 48 hours. At 72 hours, CAMs were harvested and placed in a 35 mm petri dish and washed once with 1 ml of phosphate buffered saline. The bottom side of the filter paper and CAM tissue was then analyzed under an Olympus stereo microscope, with two observers in a double-blind fashion. Angiogenesis inhibition was considered significant when CAMs exhibited >50% reduction in blood vessel infiltration of the CAM directly under the disk. Experiments were repeated four times per antibody, with 6 to 7 embryos per condition.

The results of the effects of mAb treatment on bFGF-induced angiogenesis is shown in FIGS. 8A–8B. An untreated CAM preparation devoid of blood vessels is shown in FIG. 8A to provide a comparison with the bFGF-blood vessel induction shown in FIG. 8B and effects thereon by the mAbs in FIGS. 8C–8E. About 75% of these CAMs treated with mAb LM609 exhibited >50% inhibition of angiogenesis as shown in FIG. 8E, and many of these appeared devoid of vessel infiltration. In contrast, the buffer control (FIG. 8A) and disks treated with mAbs CSAT (FIG. 8C) and P3G2 (FIG. 8D) consistently showed extensive vascularization.

Identical results were obtained when angiogenesis was induced with TNFα. To examine the effects of these same antibodies on preexisting mature blood vessels present from normal vessel development adjacent to the areas devoid of vessels, filter disks saturated with mAbs were placed on vascularized regions of CAMs from 10 day embryos that did not receive topical application of cytokine. None of the three mAbs affected preexisting vessels, as assessed by visualization under a stereo microscope. Thus, mAb LM609 selectively inhibited only new blood vessel growth and did not effect mature blood vessels present in adjacent areas. This same effect was seen with the application of synthetic peptides either applied topically or intravenously as described in Examples 7A2) and 7E2), respectively.

2) Treatment with Synthetic Peptides

CAM assays were also performed with the synthetic peptides of this invention to determine the effect of cyclic and linearized peptides on growth factor induced angiogenesis. The peptides were prepared as described in Example 1 and 80 ug of peptide were presented in a total volume of 25 ul of sterile HBSS. The peptide solution was applied to the CAM preparation immediately and then again at 24 and 48 hrs. At 72 hours the filter paper and surrounding CAM tissue was dissected and viewed as described above.

Results from this assay revealed were similar to those shown in FIGS. 9A–9C as described in Example 7E2) where synthetic peptides were intravenously injected into tumor induced blood vessels. Here, with the control peptide, 62186, the bFGF-induced blood vessels remained undisturbed as shown in FIG. 9A. In contrast when the cyclic RGD peptide, 62814, was applied to the filter, the formation of blood vessels was inhibited leaving the area devoid of new vasculature. This effect was similar in appearance to that shown in FIG. 9B as described in Example 7E2) below. In addition, also as shown in FIG. 9C for intravenously injected peptides, in areas in which mature blood vessels were present yet distant from the placement of the growth-factor saturated filter, no effect was seen with the topical treatment of synthetic peptides on these outlying vessels. The inhibitory activity of the peptides on angiogenesis thus is limited to the areas of angiogenesis induced by growth factors and does not effect adjacent preexisting mature vessels or result in any deleterious cytotoxicity to the surrounding area.

Similar assays are performed with the other synthetic peptides prepared in Example 1 and listed in Table 1.

3) Treatment with MMP-2 Peptide Fragments

To demonstrate the biological effects of MMP-2 peptide fragments on angiogenesis, CAM assays were performed as described above with the exception that angiogenesis was induced with filter discs saturated for 10 minutes with bFGF at a concentration of 1.0 ug/ml in HBS. The discs were then positioned on the CAM in an area that was reduced in the number of preexisting vessels. The C-terminal CTMMP-2 (410–637) fusion protein, prepared as described above, or control GST receptor associated fusion protein (RAP) (1.5 ug in 30 ul of HBSS) was applied then topically to the filter disc once per day for a total of three days. At the end of the incubation period, the embryos were sacrificed and the filter disc and underlying CAM tissue was resected and analyzed for angiogenesis withya stereo microscope. Angiogenesis was quantified by counting the number of blood vessels branch points that occur within the confines of the filter discs. The branched blood vessels are considered to correspond primarily to new angiogenic sprouting blood vessels.

Quantification was performed in a double blind manner by at least two independent observers. The results are expressed as the Angiogenic Index where the angiogenic index is the number of branch points (bFGF stimulated) minus the number of branch points (control unstimulated) per filter disc. Experiments routinely had 6–10 embryos per condition.

Figure 25A:
FIGS. 25A–B and 25C–D respectively shown control (a non-MMP-2 fragment containing fusion protein) and MMP-2 fragment GST fusion protein effects.
Figure 25B:
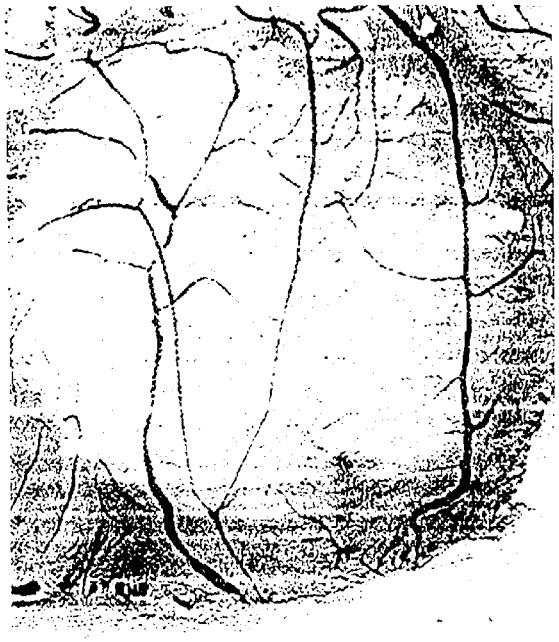
Figure 25C:
Figure 25D:
Figure 26:
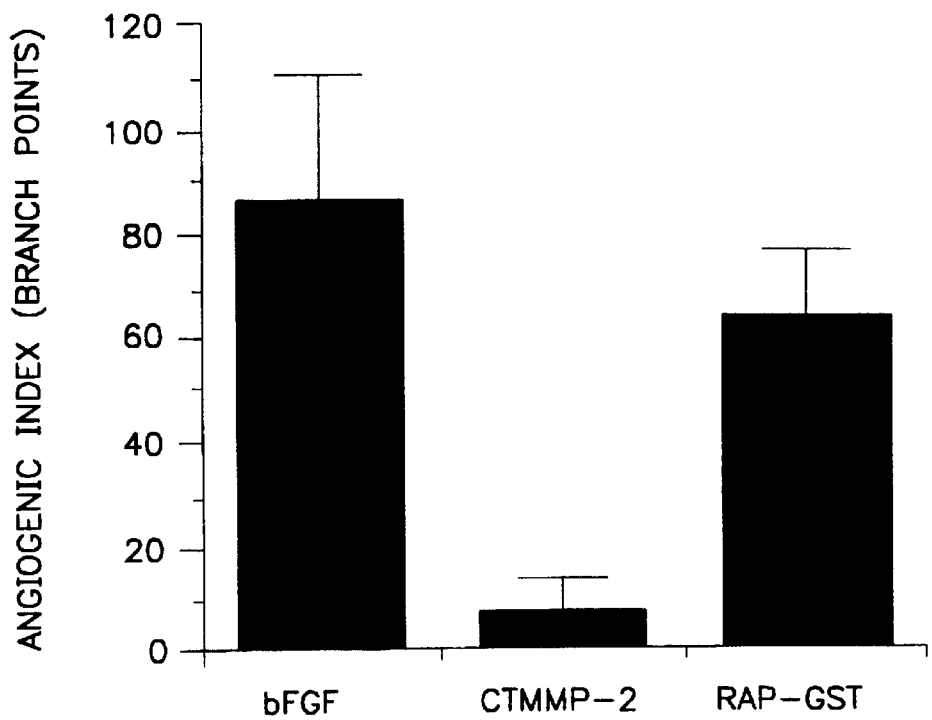
FIGS. 26 and 27 both illustrate in bar graph form the angiogenesis index (a measurement of branch points) of the effects of chicken MMP-2(410–637) GST fusion protein (labeled CTMMP-2) versus control (RAP-GST or GST-RAP) on bFGF-treated CAMs as described in Example 7A3). Angiogenic index is plotted on the Y-axis against the separate treatments on the X-axis.
Figure 27:
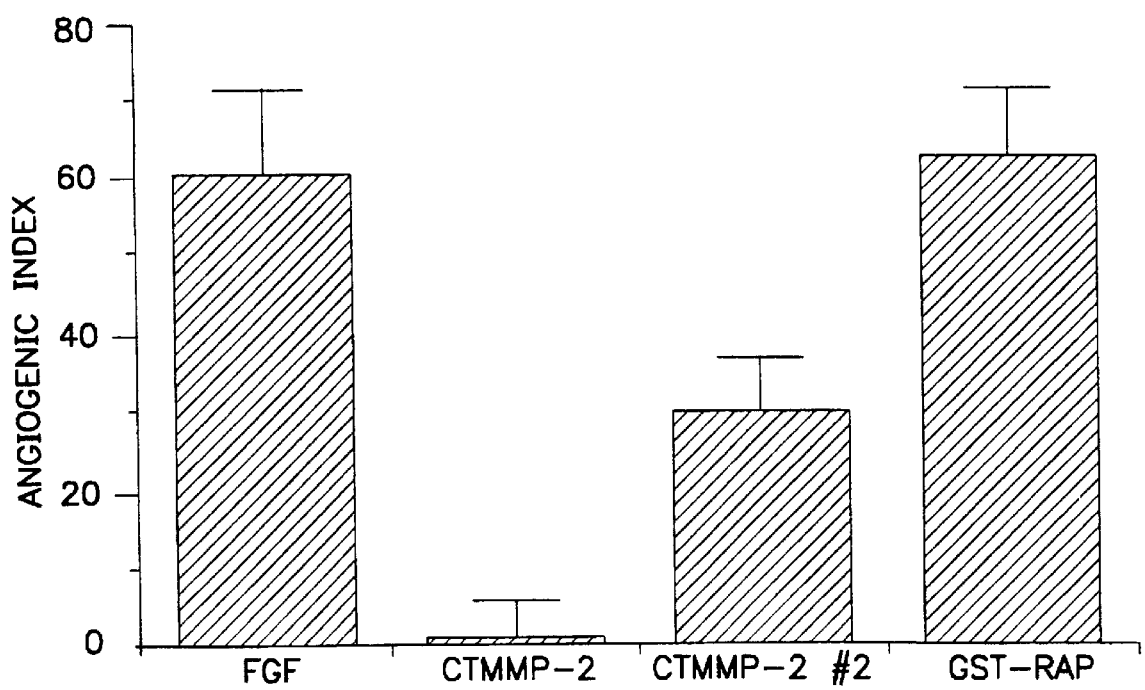

The results of the CAM angiogenesis assay are shown in FIGS. 25A–D, 26 and 27. In FIG. 25, a series of photographs divided into four figures, FIGS. 25A–D, illustrate the comparison of angiogenesis inhibited in the presence of the CTMMP-2 fusion protein (CTMMP-2(410–637)) (FIGS. 25C–D) and not inhibited in the presence of control GST fusion protein (FIGS. 25A–B). FIGS. 26 and 27 are bar graphs illustrating the angiogenesis index of CAM angiogenesis assays with CTMMP-2, the same fusion protein as above, compared to controls (bFGF only or GST-RAP fusion protein). In FIG. 27, the results of two separate experiments (#1 & #2) using CTMMP-2(410–637) fusion protein are shown.

These results demonstrated in all three figures indicate that a CTMMP-2 fusion protein or polypeptide containing a C-terminal domain of MMP-2 is a useful composition for inhibition of bFGF-mediated angiogenesis by inhibiting $\alpha_v\beta_3$.

B. Inhibition of Growth Factor-Induced Angiogenesis by Intravenous Application of Inhibitors 1) Treatment with Monoclonal Antibodies The effect on growth factor-induced angiogenesis with monoclonal antibodies intravenously injected into the CAM preparation was also evaluated for use in this invention.

The preparation of the chick embryo CAMs for intravenous injections were essentially as described in Example 7A with some modifications. During the candling procedures prominent blood vessels were selected and marks were made on the egg shell to indicate their positions. The holes were drilled in the shell and the CAMs were dropped and bFGF saturated filter papers were placed on the CAMs as described above. The windows were sealed with sterile tape and the embryos were replaced in the incubator. Twenty four hours later, a second small window was carefully cut on the lateral side of the egg shell directly over prominent blood vessels selected previously. The outer egg shell was carefully removed leaving the embryonic membranes intact. The shell membrane was made transparent with a small drop of mineral oil (Perkin-Elmer Corp, Norwalk, Conn.) which allowed the blood vessels to be visualized easily. Purified sterile mAbs, or synthetic peptides, the latter of which are described below, were inoculated directly into the blood vessels once with a 30 gauge needle at a dose of 200 ug of IgG per embryo in a total volume of 100 ul of sterile PBS. The windows were sealed with tape and the embryos were allowed to incubate until 72 hours. The filter disks and surrounding CAM tissues were analyzed as described before.

To determine the localization of LM609 mAb in CAM tissues or in tumor tissues, as shown herein and in the following Examples, that were previously inoculated intravenously with LM609, the fixed sections were blocked with 2.5% BSA in HBSS for 1 hour at room temperature followed by staining with a 1:250 dilution of goat anti-mouse rhodamine labeled secondary antibody (Tago). The sections were then analyzed with a Zeiss immunofluorescence compound microscope.

Figure 10A:
FIGS. 10A–10C illustrate the effect of intravenous application of monoclonal antibodies to growth factor induced angiogenesis as described in Example 7B1).
Figure 10B:
Figure 10C:

The results of intravenous antibody treatment to the bFGF induced blood vessel CAM preparation are shown in FIGS. 10A–10C. In FIG. 10A, angiogenesis induced as a result of bFGF treatment is shown. No change to the presence of bFGF induced vasculature was seen with intravenous exposure to mAb P3G2, an anti-$\alpha_v\beta_5$ antibody, as shown in FIG. 10B, In contrast, treatment of the bFGF induced angiogenesis CAM preparation with LM609, an anti-$\alpha_v\beta_3$ antibody, resulted in the complete inhibition of growth of new vessels into the filter area as shown in FIG. 10C. The inhibitory effect on angiogenesis is thus resulting from the inhibition of $\alpha_v\beta_3$ receptor activity by the LM609 anti-$\alpha_v\beta_3$-specific antibody. Since the blocking of the $\alpha_v\beta_5$ does not inhibit the formation of neovasculature into the CAMs filter site, $\alpha_v\beta_5$ thus is not essential as compared to $\alpha_v\beta_3$ for growth of new vessels.

2) Treatment with Synthetic Peptides

For CAM preparations in which angiogenesis was induced with 1–2 ug/ml bFGF as previously described, synthetic peptides 69601 (control) and 66203 (SEQ ID NO 5) were separately intravenously injected into CAM preparations 18 hours after bFGF induction of angiogenesis. The preparations were maintained for an additional 36–40 hours after which time the number of branch points were determined as previously described.

Figure 28:
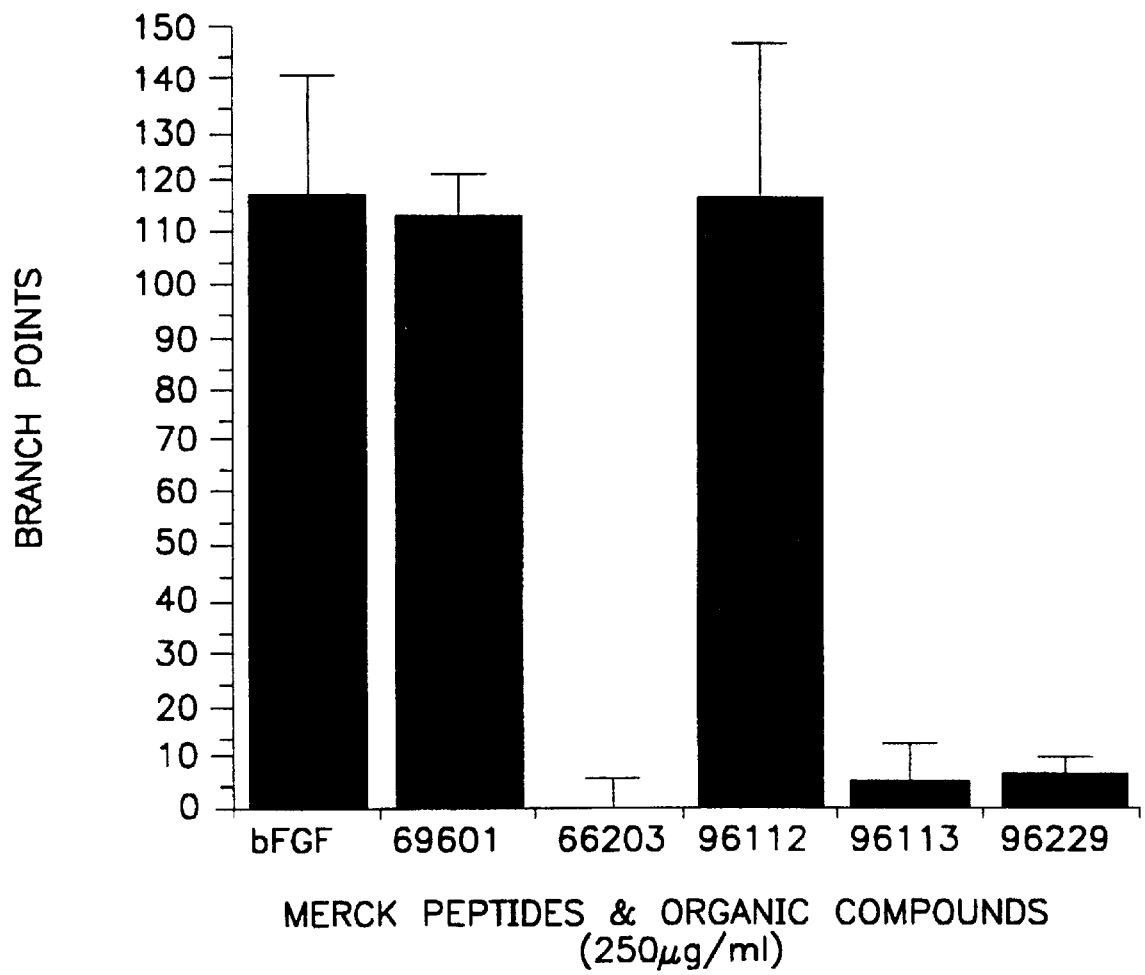
FIG. 28 shows the effects of peptides and organic compounds on bFGF-induced angiogenesis as measured by the effect on branch points plotted on the Y-axis against the various treatments on the X-axis, including bFGF alone, and bFGF-treated CAMs with peptides 69601 or 66203 and organic compounds 96112, 96113 and 96229, as described in Examples 7B and 14.

The results are shown in FIG. 28 where peptide 66203 completely inhibited bFGF-induced angiogenesis in contrast to the absence of inhibition with the control peptide.

Figure 29:
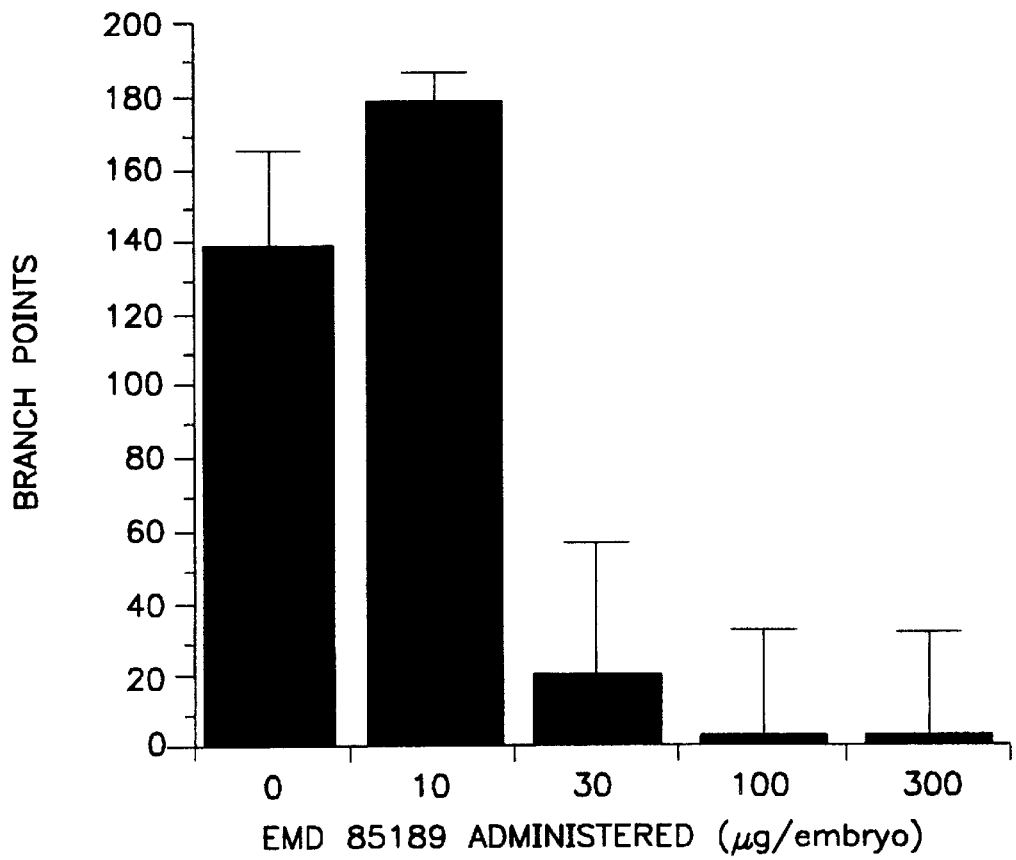
FIG. 29 graphically shows the dose response of peptide 85189 on inhibiting bFGF-induced angiogenesis as further described in Example 7B2) where the number of branch points are plotted on the Y-axis against the amount of peptide administered to the embryo on the X-axis.

In other assays, peptide 85189 (SEQ ID NO 15) was evaluated for inhibiting bFGF-induced angiogenesis in the CAM assay over a dosage range of 10 ug/embryo to 300 ug/embryo. The assay was performed as previously described. The results are shown in FIG. 29 where the lowest effective dose was 30 ug with 100 and 300 ug nearly completely inhibiting angiogenesis.

Figure 30:
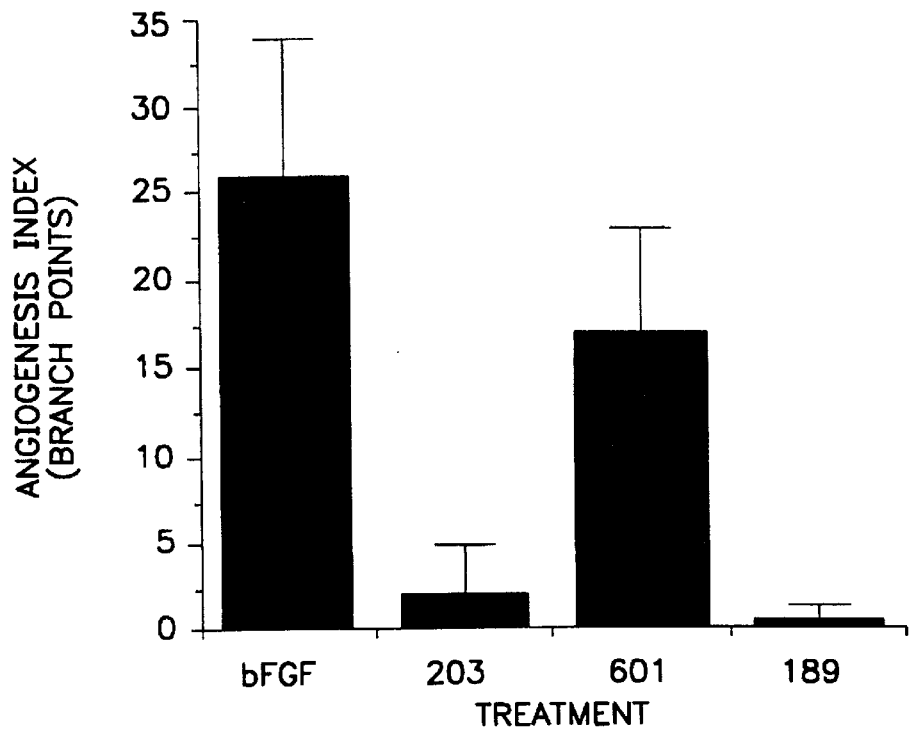
FIG. 30 shows the inhibitory activity of peptides 66203 (labeled 203) and 85189 (labeled 189) in bFGF-induced angiogenesis in the CAM assay as described in Example 7B2). Controls included no peptide in bFGF-treated CAMS and peptide 69601 (labeled 601). The data is plotted as described in the legend for FIG. 27.
Figure 3I:
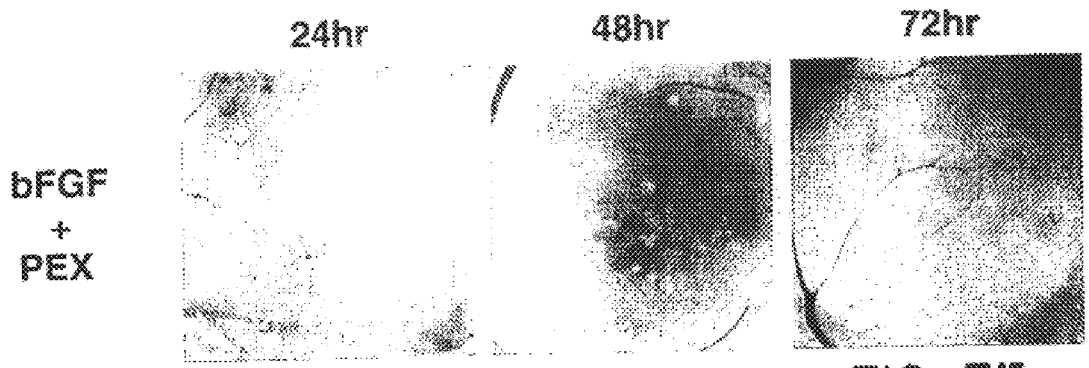
Figure 3I:
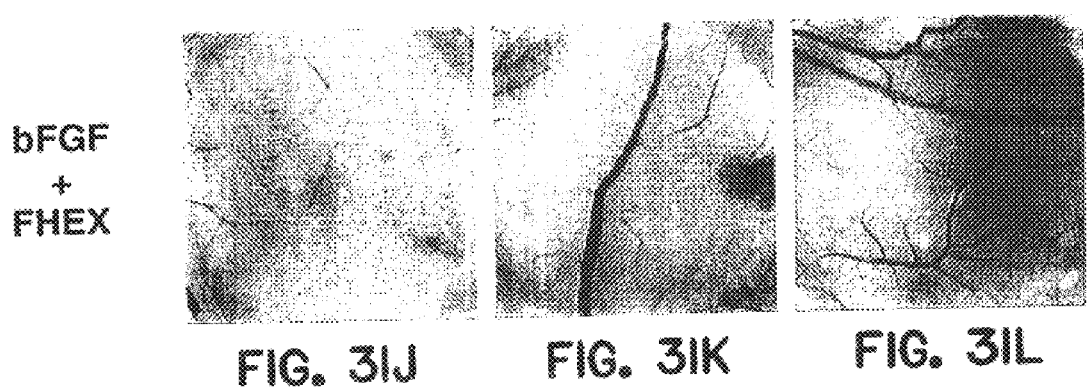

In still further assays, peptide 85189 was compared to peptides 69601 and 66203 for anti-angiogenesis activity. The assay was performed as described above with the exception that 50 ug peptide were used. The results, plotted in FIG. 30, showed that peptides 66203 (labeled 203) and 85189 (labeled 189) were effective inhibitors of bFGF-mediated angiogenesis compared to bFGF-treated (labeled bFGF) and 69601-treated (labeled 601) controls.

The effectiveness of the different salt formulations of peptide 85189 was also evaluated in similar bFGF-induced CAM assays. The peptides were used at 100 ug/embryo. The same peptide sequence in HCl (peptide 85189) and in TFA (peptide 121974) inhibited bFGF-induced angiogenesis with the HCl formulated peptide being slightly more effective than that in TFA (the respective number of branch points for peptide 85189 versus 121974 is 30 versus 60). Untreated CAMs, labeled as "no cytokine" had approximately half as many branch points as that seen with bFGF treatment, respectively 70 versus 190. Treatment with control peptide 69601 had no effect on inhibiting angiogenesis (230 branch points).

The other synthetic peptides prepared in Example 1 are separately intravenously injected into the growth factor induced blood vessels in the CAM preparation as described above. The effect of the peptides on the viability of the vessels is similarly assessed.

3) Treatment with MMP-2 Fragments

With the above-described protocol, the effect of MMP-2 fusion proteins, CTMMP-2(2-4), also referred to as CTMMP-2(445–637) and CTMMP-2(10-1), also referred to as CTMMP-2(274–637) was also evaluated. The assay was performed as previously described with the exception that 50 ug of fusion protein was administered to the bFGF-treated embryos. The effect of fusion protein treatment was assessed at 24 hours, 48 hours and 72 hours.

The results are shown for these selected time periods in FIGS. 31A–L where angiogenesis was photographically assessed under assay conditions of no treatment, bFGF treatment, bFGF treatment followed by CTMMP-2(2-4), labeled as bFGF+MAID (MAID=MMP-2 angiogenesis inhibiting domain), and bFGF treatment followed by CTMMP-2(10-1), labeled as bFGF+Control. The significant induction of angiogenesis after 48 and 72 hours following bFGF treatment was almost completely inhibited only with exposure to CTMMP-2(2-4). The extent of inhibition with CTMMP-2(2-4) was greater than that seen with CTMMP-2(10-1) which exhibited some in vivo anti-angiogenesis activity.

The other MMP-2 compositions, whole MMP-2, fragments and fusion proteins, prepared as previously described are also separately intravenously injected into the growth factor induced blood vessels in the CAM preparation as described above. The effect of the peptides on the viability of the vessels is similarly assessed.

C. Inhibition of Embryonic Angiogenesis by Topical Application

1) Treatment with Monoclonal Antibodies

To determine whether $\alpha_v\beta_3$ participates in embryonic angiogenesis, the effect of LM609 on de novo growth of blood vessels on CAMs was examined in 6 day embryos, a stage marked by active neovascularization as described in Example 5A. The CAM assay was prepared as described in Example 6C with the subsequent topical application of disks saturated with mAbs placed on CAMs of 6 day old embryos in the absence of cytokines. After 3 days, CAMS were resected and photographed. Each experiment included 6 embryos per group and was repeated 2 times.

Figures 11A, 11B, 11C:
FIGS. 11A–11C illustrate the effect on embryonic angiogenesis following topical application of anti-integrin antibodies as described in Example 7C. Angiogenesis was not inhibited by treatment of a 6 day CAM with anti-$\beta_1$ and anti-$\alpha_v\beta_5$ antibodies respectively shown in FIGS. 11A and 11B. In contrast, treatment with the anti-$\alpha_v\beta_3$ antibody LM609 resulted in the inhibition of blood vessel formation as shown in FIG. 11C.

Antibody LM609 (FIG. 11C), but not CSAT (FIG. 11A) or P3G2 (FIG. 11B), prevented vascular growth under these conditions; this indicates that $\alpha_v\beta_3$ plays a substantial role in embryonic neovascularization that was independent of added growth factors for induction of angiogenesis.

2) Treatment with Synthetic Peptides

The synthetic peptides prepared in Example 1 are separately added to the embryonic CAM preparation prepared above and as described in Example 5A2) by either topical application to the CAM or intravenous application to blood vessels. The effect of the peptides on the viability of the vessels is similarly assessed.

D. Inhibition of Tumor-Induced Angiogenesis by Topical Application

1) Treatment with Monoclonal Antibodies

In addition to the angiogenesis assays described above where the effects of anti-$\alpha_v\beta_3$ antagonists, LM609 and various peptides, on embryonic angiogenesis were evaluated, the role of $\alpha_v\beta_3$ in tumor-induced angiogenesis was also investigated. As an inducer, $\alpha_v\beta_3$-negative human M21-L melanoma fragments previously grown and isolated from the CAM of a 17-day chick embryo were used. The fragments were prepared as described in Example 6C.

As described above in Example 7A1), mabs were separately topically applied to the tumor fragments at a concentration of 25 ug in 25 ul of HBSS and the windows were then sealed with tape. The mAbs were added again in the same fashion at 24 hours and 48 hours. At 72 hours, the tumors and surrounding CAM tissues were analyzed as described above in Example 7A1).

As described in Example 6C, tumors were initially derived by transplanting cultured M21-L cells, which do not to express integrin $\alpha_v\beta_3$ as described by Felding-Habermann et al., *J. Clin. Invest.*, 89:2018 (1992) onto the CAMs of 10-day old chick embryos. These $\alpha_v\beta_3$-negative fragments induced extensive neovascularization in the presence of buffer alone, or mAbs CSAT (anti-$\beta_1$) or P3G2 (anti-$\alpha_v\beta_5$). In contrast, mAb LM609 (anti-$\alpha_v\beta_3$) abolished the infiltration of most vessels into the tumor mass and surrounding CAM.

Figure 12:
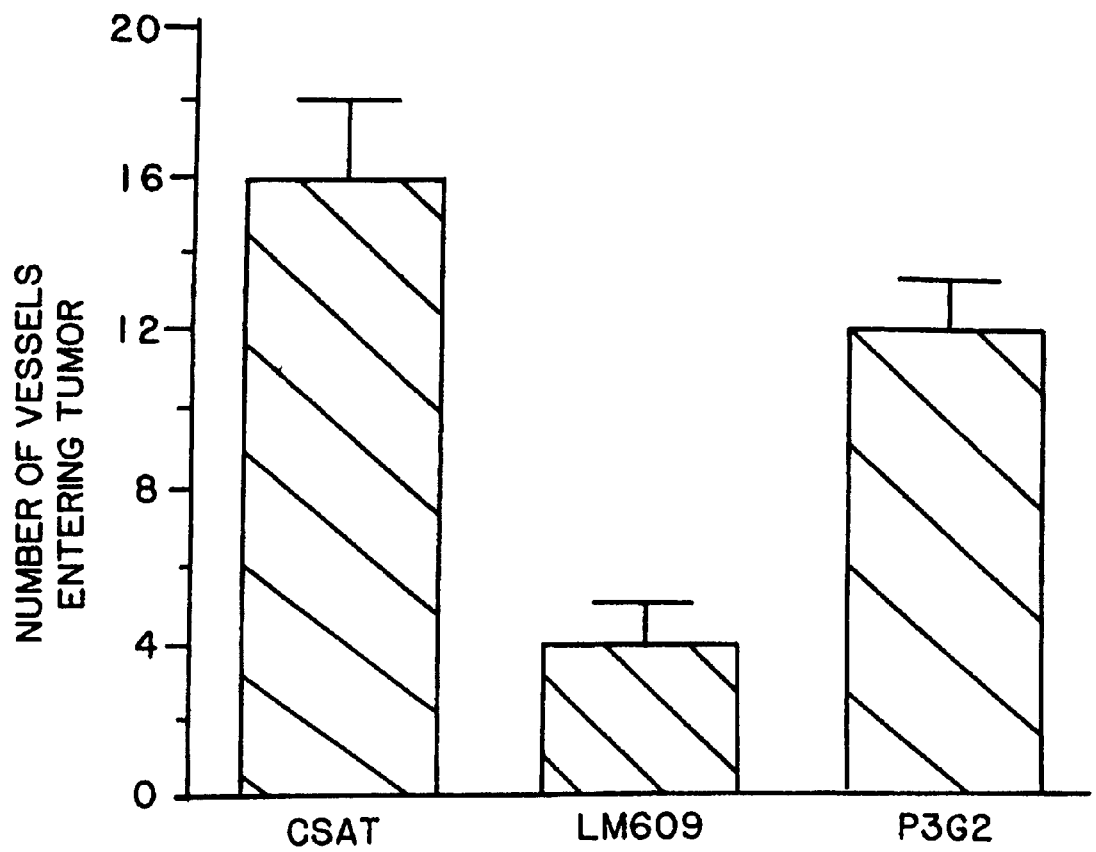
FIG. 12 illustrates the quantification of the number of vessels entering a tumor in a CAM preparation as described in Example 7D1). The graph shows the number of vessels as plotted on the Y-axis resulting from topical application of either CSAT (anti-$\alpha_1$), LM609 (anti-$\alpha_v\beta_3$) or P3G2 (anti-$\alpha_v\beta_3$).
Figure 13B:
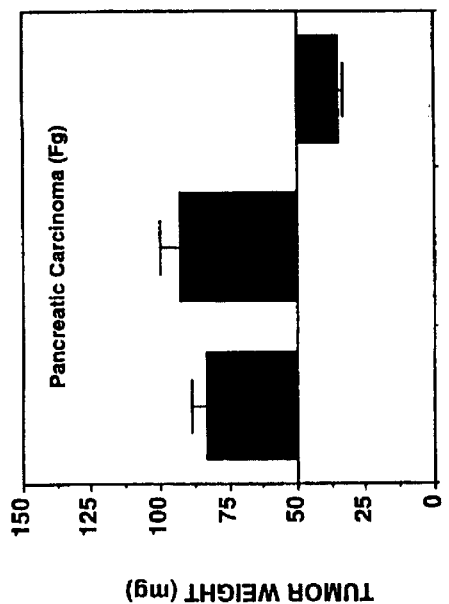
FIGS. 13A–13D illustrate a comparison between wet tumor weights 7 days following treatment and initial tumor weights as described in Example 9A1)a. Each bar represents the mean ±S.E. of 5–10 tumors per group. Tumors were derived from human melanoma (M21-L) (FIG. 13A), pancreatic carcinoma (Fg) (FIG. 13B), lung carcinoma (UCLAP-3) (FIG. 13C), and laryngeal carcinoma (HEp3) (FIG. 13D) CAM preparations and treated intravenously with PBS, CSAT (anti-$\beta_1$), or LM609 (anti-$\alpha_v\beta_3$). The graphs show the tumor weight as plotted on the Y-axis resulting from intravenous application of either CSAT (anti-$\beta_1$), LM609 (anti-$\alpha_v\beta_3$) or PBS as indicated on the X-axis.
Figure 13D:
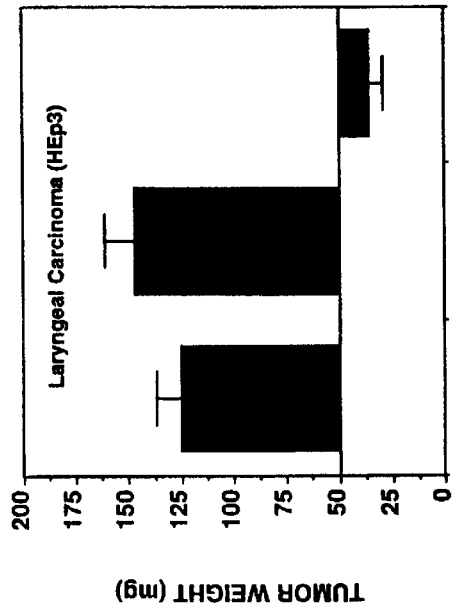
Figure 13A:
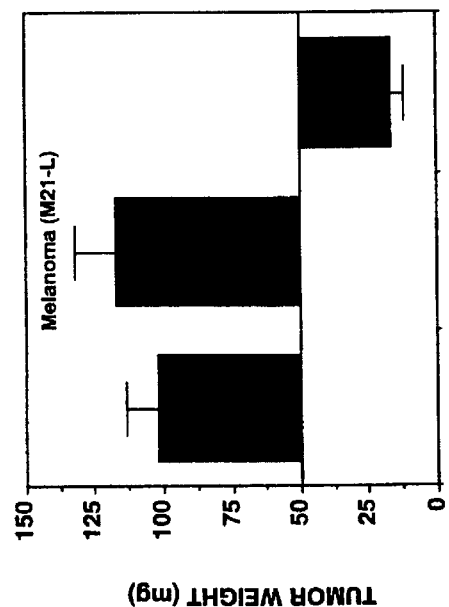
Figure 13C:
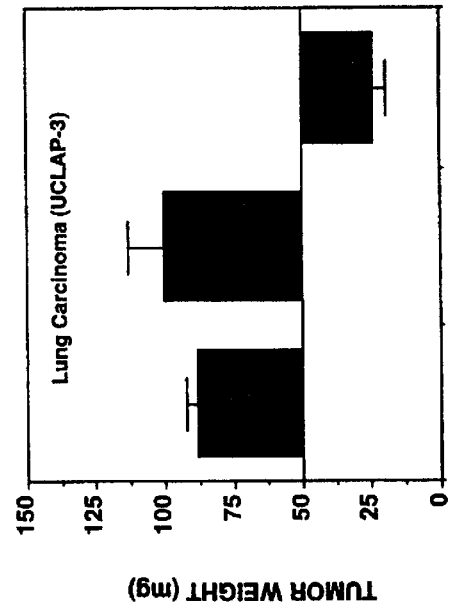

In order to quantitate the effect of the mAbs on the tumor-induced angiogenesis, blood vessels entering the tumor within the focal plane of the CAM were counted under a stereo microscope by two observers in a double-blind fashion. Each data bar presented in FIG. 12 represents the mean number of vessels±SE from 12 CAMs in each group representing duplicate experiments.

This quantitative analysis revealed a three-fold reduction in the number of vessels entering tumors treated with mAb LM609 compared to tumors treated with buffer or the other mAbs, P3G2 or CSAT (P<0.0001) as determined by Wilcoxon Rank Sum Test. The fact that M21-L tumors do not express $\alpha_v\beta_3$ indicates that mAb LM609 inhibits angiogenesis by directly affecting blood vessels rather than the tumor cells. These results correspond with the histological distribution of $\alpha_v\beta_3$ in cancer tissue biopsies shown in FIGS. 3A–3D where the distribution of $\alpha_v\beta_3$ was limited to the blood vessels in the tumor and not to the tumor cells themselves.

2) Treatment with Synthetic Peptides

The synthetic peptides prepared in Example 1, including MMP-2-derived peptides and fusion proteins are topically applied to the tumor-induced angiogenic CAM assay system as described above. The effect of the peptides on the viability of the vessels is similarly assessed.

E. Inhibition of Tumor-Induced Anaiogenesis by Intravenous Application

1) Treatment with Monoclonal Antibodies

Tumor-induced blood vessels prepared as described in Example 7E1) were also treated with mAbs applied by intravenous injection. Tumors were placed on the CAMs as described in Example 7D1) and the windows sealed with tape and 24 hours latter, 200 ug of purified mAbs were inoculated once intravenously in chick embryo blood vessels as described previously. The chick embryos were then allowed to incubate for 7 days. The extent of angiogenesis was then observed as described in above. As described in Example 8 below, after this time period, the tumors were resected and analyzed by their weight to determine the effect of antibody exposure on tumor growth or suppression.

2) Treatment with Synthetic Peptides

The effects of peptide exposure to tumor-induced vasculature in the CAM assay system was also assessed. The tumor-CAM preparation was used as described above with the exception that instead of intravenous injection of a mAb, synthetic peptides prepared as described in Example 1 and Example 7A2) were separately intravenously injected into visible blood vessels.

The results of CAM assays with the cyclic peptide, 66203 containing the HCl salt, and control peptide, 62186, are shown in FIGS. 9A–9C. In FIG. 9A, the treatment with the control peptide did not effect the abundant large blood vessels that were induced by the tumor treatment to grow into an area originally devoid of blood vessels of the CAM. In contrast when the cyclic RGD peptide, 66203, an antagonist to $\alpha_v\beta_3$, was applied to the filter, the formation of blood vessels was inhibited leaving the area devoid of new vasculature as shown in FIG. 9B. The inhibitory effect of the RGD-containing peptide was specific and localized as evidenced by an absence of any deleterious effects to vessels located adjacent to the tumor placement. Thus, in FIG. 9C, when inhibitory peptides are intravenously injected into the CAM assay system, no effect was seen on the preexisting mature vessels present in the CAM in areas adjacent yet distant from the placement of the tumor. The preexisting vessels in this location were not affected by the inhibitory peptide that flowed within those vessels although the generation of new vessels from these preexisting vessels into the tumor mass was inhibited. Thus, synthetic peptides including 66203 and 62184, previously shown in ligand-receptor assays in Example 4 to be antagonists of $\alpha_v\beta_3$, have now been demonstrated to inhibit angiogenesis that is limited to vessels undergoing development and not to mature preexisting vessels. In addition, the intravenous infusion of peptides does not result in any deleterious cytotoxicity to the surrounding area as evidence by the intact vasculature in FIG. 9C.

Similar assays are performed with the other synthetic peptides prepared in Example 1 and listed in Table 1 along with the MMP-2 compositions of this invention.

3) Treatment with MMP-2 Fragments

A CS-1 tumor ($\beta_3$-negative) was prepared in a CAM as described above. After 24 hours of tumor growth, a composition of MMP-2 fragment, designated CTMMP-2(2-4) and prepared as described in Example 4A, was administered intraveneously at 50 ug fragment in 100 ul of PBS. After 6 days, the tumor was evaluated for mass. Tumors treated with CTMMP-2(2-4) were reduced in growth rate by about 50% when compared to the growth rate of control tumors treated with CTMMP-2(10-1) or with PBS control. Thus, the $\alpha_v\beta_3$ antagonist inhibited tumor growth.

8. Inhibition of Tumor Tissue Growth with $\alpha_v\beta_3$ Antagonists as Measured in the CAM Assay As described in Example 7E1), in addition to visually assessing the effect of anti-$\alpha_v\beta_3$ antagonists on growth factor or tumor induced angiogenesis, the effect of the antagonists was also assessed by measuring any changes to the tumor mass following exposure. For this analysis, the tumor-induced angiogenesis CAM assay system was prepared as described in Example 6C and 7D. At the end of the 7 day incubation period, the resulting tumors were resected from the CAMs and trimmed free of any residual CAM tissue, washed with 1 ml of phosphate buffer saline and wet weights were determined for each tumor.

In addition, preparation of the tumor for microscopic histological analysis included fixing representative examples of tumors in Bulins Fixative for 8 hours and embedding in paraffin. Serial sections were cut and stained with hematoxylin and eosin (H&E) for microscopic analysis. Gladson, et al., *J. Clin. Invest.*, 88:1924 (1991). Sections were photographed with an Olympus compound microscope at 250×.

A. Topical Application

The results of typical human melanoma tumor (M21L) weights resulting from topical application of control buffer (HBSS), P3G2 (anti-$\alpha_v\beta_5$) or LM609 (anti-$\alpha_v\beta_3$) are listed in Table 4. A number of embryos were evaluated for each treatment with the average tumor weight in milligrams (mg) from each being calculated along with the SE of the mean as shown at the bottom of the table.

TABLE 4

| Embryo No. | mAb Treatment | Tumor Weight (mg) |
|---|---|---|
| 1 | HBSS | 108 |
| 2 | | 152 |
| 3 | | 216 |
| 4 | | 270 |
| 5 | | 109 |
| 6 | | 174 |
| 1 | P3G2 | 134 |
| 2 | | 144 |
| 3 | | 408 |
| 4 | | 157 |
| 5 | | 198 |
| 6 | | 102 |
| 7 | | 124 |
| 8 | | 99 |
| 1 | LM609 | 24 |
| 2 | | 135 |
| 3 | | 17 |
| 4 | | 27 |
| 5 | | 35 |
| 6 | | 68 |
| 7 | | 48 |
| 8 | | 59 |

| mAb Treatment | Average Tumor Weight (mg) |
|---|---|
| HBSS control | 172 ± 26 |
| P3G2 | 171 ± 36 |
| LM609 | 52 ± 13 |

Exposure of a $\alpha_v\beta_3$-negative human melanoma tumor mass in the CAM assay system to LM609 caused the decrease of the untreated average tumor weight of 172 mg±26 to 52 mg±13. The P3G2 antibody had no effect on the tumor mass. Thus, the blocking of the $\alpha_v\beta_3$ receptor by the topical application of $\alpha_v\beta_3$-specific LM609 antibody resulted in a regression of tumor mass along with an inhibition of angiogenesis as shown in the preceding Examples. The measured diameter of the tumor mass resulting from exposure to P3G2 was approximately 8 millimeters to 1 centimeter on average. In contrast, the LM609-treated tumors were on average 2 to 3 millimeters in diameter.

Frozen sections of these tumors revealed an intact tumor cytoarchitecture for the tumor exposed to P3G2 in contrast to a lack or organized cellular structure in the tumor exposed to LM609. $\alpha_v\beta_3$ receptor activity is therefore essential for an $\alpha_v\beta_3$ negative tumor to maintain its mass nourished by development of $\alpha_v\beta_3$-expressing neovasculature. The blocking of $\alpha_v\beta_3$ with the $\alpha_v\beta_3$ antagonists of this invention results in the inhibition of angiogenesis into the tumor ultimately resulting in the diminution of tumor mass.

B. Intravenous Application

The results of typical carcinoma tumor (UCLAP-3) weights resulting from intravenous application of control buffer (PBS, phosphate buffered saline), CSAT (anti-$\beta_1$) or LM609 (anti-$\alpha_v\beta_3$) are listed in Table 5. A number of embryos were evaluated for each treatment with the average tumor weight from each being calculated along with the SE of the mean as shown at the bottom of the table.

TABLE 5

| Embryo No. | mAb Treatment | Tumor Weight (mg) |
|---|---|---|
| 1 | PBS | 101 |
| 2 | | 80 |
| 3 | | 67 |
| 4 | | 90 |
| 1 | CSAT | 151 |
| 2 | | 92 |
| 3 | | 168 |
| 4 | | 61 |
| 5 | | 70 |
| 1 | LM609 | 16 |
| 2 | | 54 |
| 3 | | 30 |
| 4 | | 20 |
| 5 | | 37 |
| 6 | | 39 |
| 7 | | 12 |

| mAb Treatment | Average Tumor Weight (mg) |
|---|---|
| PBS control | 85 ± 7 |
| CSAT | 108 ± 22 |
| LM609 | 30 ± 6 |

Exposure of a $\alpha_v\beta_3$-negative human carcinoma tumor mass in the CAM assay system to LM609 caused the decrease of the untreated average tumor weight of 85 mg±7 to 30 mg±6. The CSAT antibody did not significantly effect the weight of the tumor mass. Thus, the blocking of the $\alpha_v\beta_3$ receptor by the intravenous application of $\alpha_v\beta_3$-specific LM609 antibody resulted in a regression of a carcinoma as it did for the melanoma tumor mass above along with an inhibition of angiogenesis as shown in the preceding Examples. In addition, human melanoma tumor growth was similarly inhibited by intravenous injection of LM609.

9. Regression of Tumor Tissue Growth with $\alpha_v\beta_3$ Antaaonists as Measured in the CAM Assay To further assess the effects of $\alpha_v\beta_3$ antagonists on tumor growth and survival, fragments of human melanoma and fragments of carcinomas of the lung, pancreas, and larynx were placed on CAMS of 10-day old embryos as described in Example 5A.

A. Intravenous Application

1) Treatment with Monoclonal Antibodies a. Treatment with LM609 (Anti-$\alpha_v\beta_3$) and CSAT (Anti-$B_1$)

Twenty four hours after implantation of CAM with carcinoma fragments of $\alpha_v\beta_3$-negative human melanoma M21-L, pancreatic carcinoma FG, human lung carcinoma UCLAP-3, or human laryngeal carcinoma HEp3, embryos were injected intravenously with PBS alone or a single dose (300 ug/100 ul) of either mAb LM609 (anti-$\alpha_v\beta_3$) or CSAT (anti-$\beta_1$). Tumors were allowed to propagate for six additional days. At the end of the incubation period the tumors were carefully resected and trimmed free of surrounding CAM tissue. Tumor resections were performed by two independent investigators removing only the easily definable solid tumor mass. The tumors had well defined margins, thus the thin semi-transparent membrane (CAM) which is readily distinguishable from the solid tumor mass was removed without disturbing the tumor mass itself. The resected tumors were weighed and examined morphologically and histologically.

As shown in FIG. 13, wet tumor weights at the end of 7 days were determined and compared to initial tumor weights before treatments. Each bar represents the mean±S.E. of 5–10 tumors per group. mAb LM609 inhibited tumor growth significantly (p<0.001) as compared to controls in all tumors tested. Tumors treated with PBS or CSAT proliferated in all cases. In contrast, mAb LM609 not only prevented the growth of these tumors but induced extensive regression in most cases. Importantly, these tumor cells do not express integrin $\alpha_v\beta_3$ demonstrating that the inhibition of growth was due to the anti-angiogenic effects of this antibody on neovasculature rather than upon the tumor cells directly.

b. Treatment with LM609 (Anti-$\alpha_v\beta_3$) and P3G2 (Anti-$\alpha_v\beta_5$)

Human M21-L melanoma tumor fragments (50 mg) were implanted on the CAMs of 10 day old embryos as described in Example 5A. Twenty four hours later, embryos were injected intravenously with PBS alone or a single dose (300 ug/100 ul) of either mAb LM609 (anti-$\alpha_v\beta_3$) or P3G2 (anti-$\alpha_v\beta_5$). Tumors were allowed to propagate as described in Example 9A1) a above and were examined morphologically and histologically as herein described.

Representative examples of M21-L tumors treated with mabs P3G2 (anti-$\alpha_v\beta_5$) or LM609 (anti-$\alpha_v\beta_3$) were examined morphologically. The P3G2-treated tumors were large (8 mm in diameter) and well vascularized whereas those treated with mAb LM609 were much smaller (3 mm in diameter) and lacked detectable blood vessels.

Figure 14A:
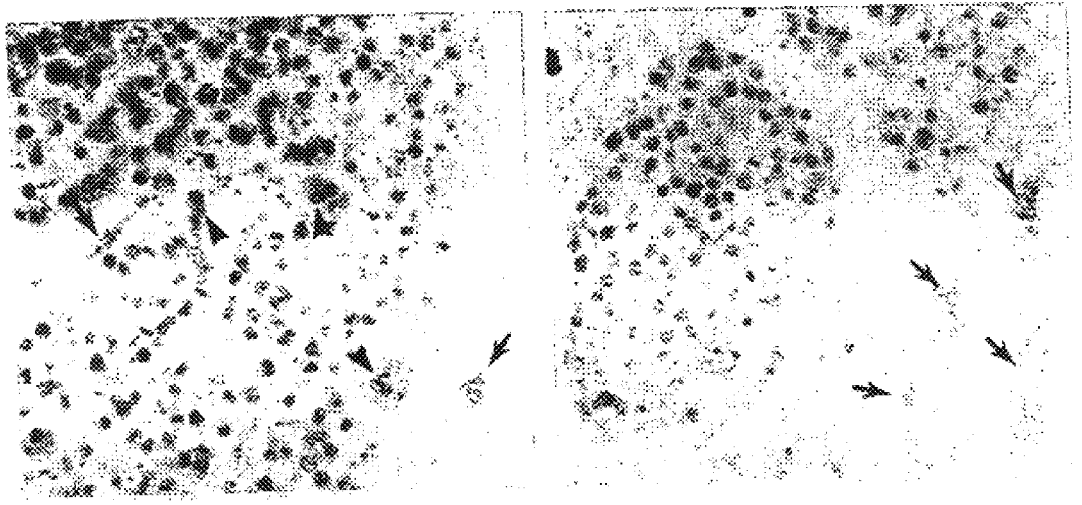
FIGS. 14A and 14B illustrate histological sections of tumors treated with the P3G2 (anti-$\alpha_v\beta_5$) (FIG. 14A) and LM609 (anti-$\alpha_v\beta_3$) (FIG. 14B), and stained with hematoxylin and eosin as described in Example 9A1)b.
Figure 14B:
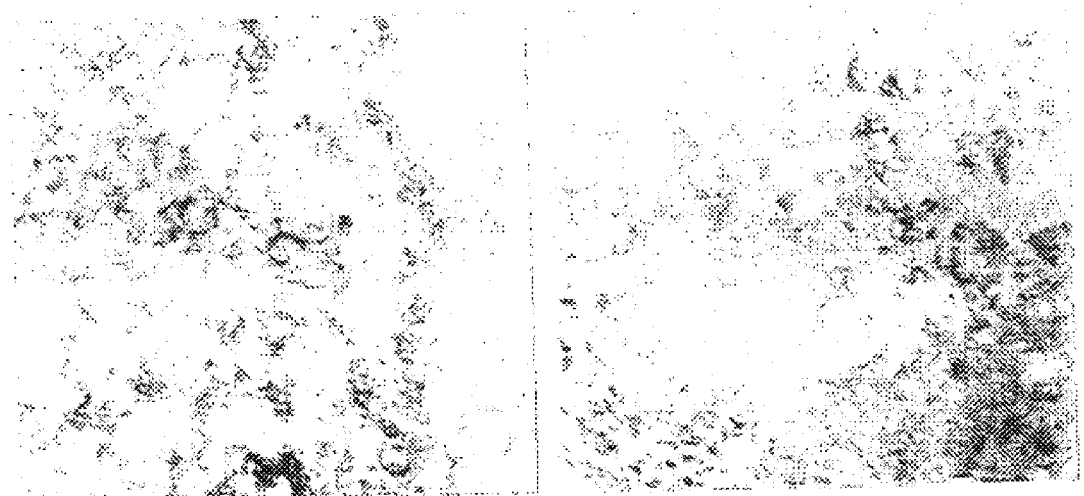
Figure 16A:
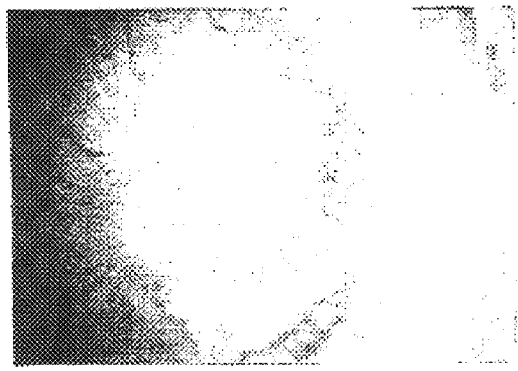
FIGS. 16A–16E represent inhibition of angiogenesis by antagonists of angiogenesis in the in vivo rabbit eye model assay as described in Example 10.
Figure 16C:
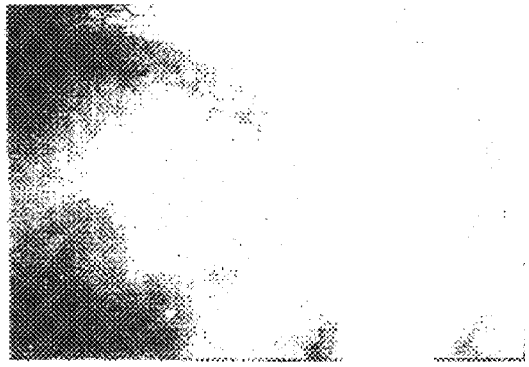
Figure 16D:
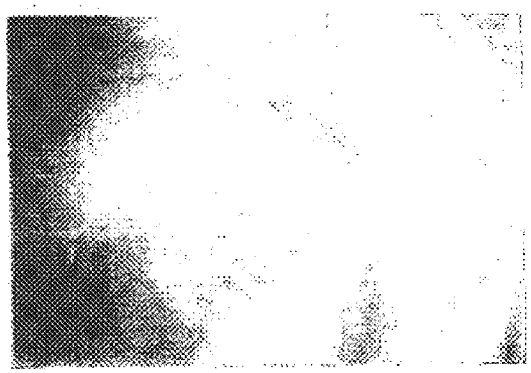
Figure 16B:
Figure 16E:

The tumors were further examined by the preparation of histological sections and staining with hematoxylin and eosin as described in Example 9A1)a. As shown in FIG. 14 (upper panel), tumors treated with mAb P3G2 (anti-$\alpha_v\beta_5$) showed numerous viable and actively dividing tumor cells as indicated by mitotic figures (arrowheads) as well as by multiple blood vessels (arrows) throughout the tumor stroma. In contrast, few if any viable tumor cells or blood vessels were detected in tumors treated with mAb LM609 (anti-$\alpha_v\beta_3$) (FIG. 14, lower panel). These results demonstrate that antagonists of integrin $\alpha_v\beta_3$ inhibit tumor-induced angiogenesis leading to the growth arrest and regression of a variety of human tumors in vivo. It is important to point out that embryos examined after seven days of tumor growth (embryonic day 17) appeared normal upon gross examination whether or not they were treated with an $\alpha_v\beta_3$ antagonist. These findings indicate that antagonists of this integrin appear non-toxic to the developing embryos.

2) Treatment with Synthetic Peptides

Human M21-L melanoma tumor fragments (50 mg) were implanted on the CAMs of 10 day oldembryos as described in Example 5A. Twenty four hours later, embryos received a single intravenous injection of 300 ug/100 ul of either the cyclo-RADfV (69601) and or cyclo-RGDfV (66203). After a total of 72 hours, tumors were removed, examined morphologically, and photographed with a stereo microscope as described in Example 9A1).

The panels shown in FIGS. 15A through 15E correspond as follows: FIG. 15A, duplicate samples treated with cyclo-RADfV peptide (69601); FIG. 15B, duplicate samples treated with cyclo-RGDfV peptide (66203); FIG. 15C, adjacent CAM tissue taken from the same embryos treated with cyclo-RGDfV peptide (66203) and FIGS. 15D and 15E, high magnification (13x) of peptide treated tumors. FIG. 15D depicts normal blood vessels from control peptide (69601) treated tumor. FIG. 15E depicts examples of disrupted blood vessels from cyclo-RGDfV peptide (66203) treated tumors (arrows).

The results illustrate that only peptide 66203 in contrast to control peptide 69601 inhibited vessel formation, and further that vessels in the CAM tissue adjacent to the tumor were not affected.

Additional tumor regression assays were performed with the $\alpha_v\beta_3$-reactive peptide 85189 (SEQ ID NO 15) against 69601 as a control. The assays were performed as described above with the exception that 100 ug of peptide was intravenously injected into the CAM at 18 hourst postimplantation. After 48 hours more, the tumors were then resected and wet weights were obtained.

Figure 32:
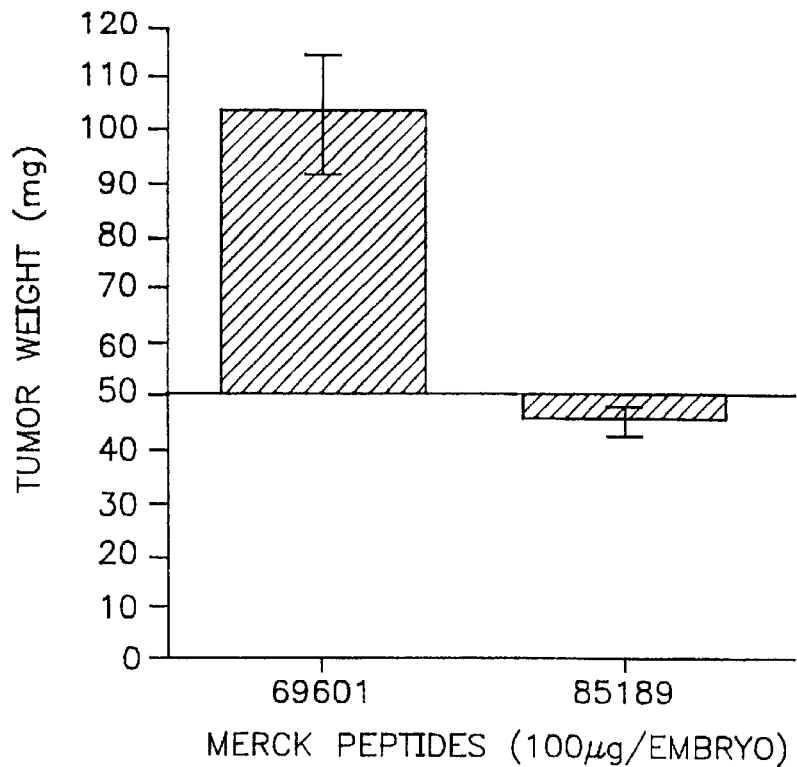
FIGS. 32, 33 and 34 respectively show the reduction in tumor weight for UCLAP-3, M21-L and FgM tumors following intravenous exposure to control peptide 69601 and antagonist 85189 as further described in Example 9A. The data is plotted with tumor weight on the Y-axis against the peptide treatments on the X-axis.
Figure 33:
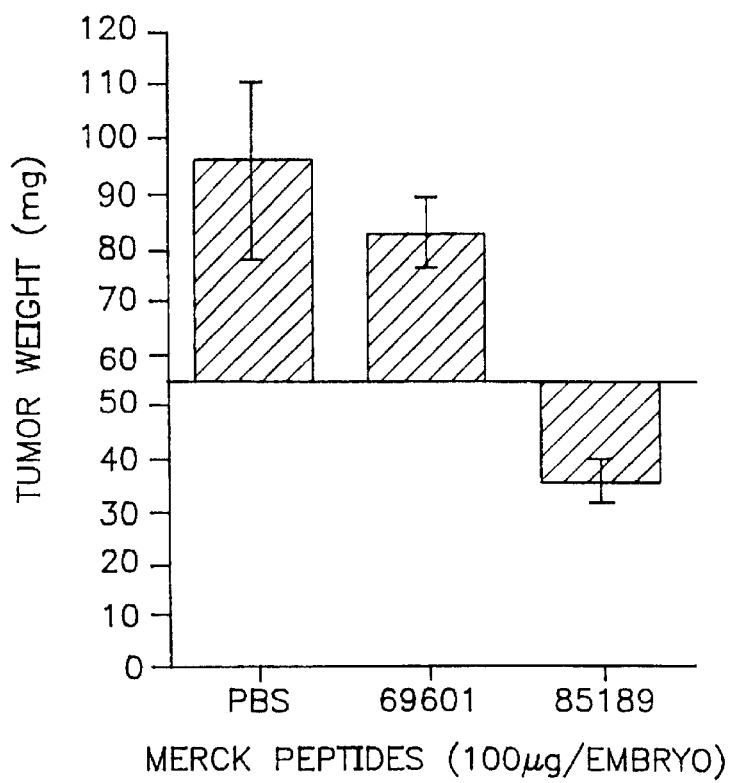
Figure 34:
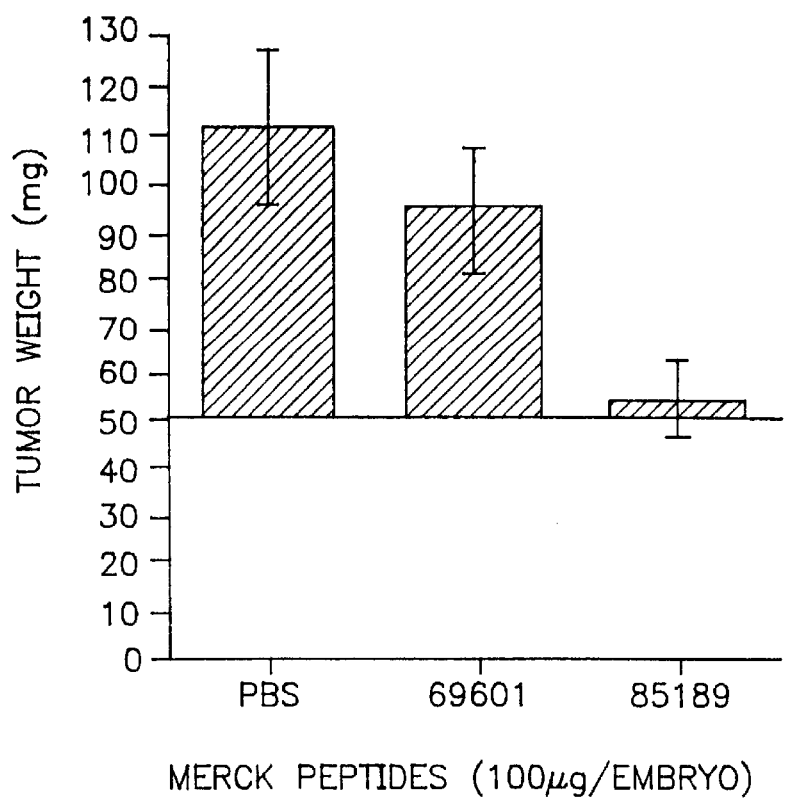

FIGS. 32, 33 and 34 respectively show the reduction in tumor weight for UCLAP-3, M21-L and FgM tumors following intravenous exposure to peptide 85189 in contrast to the lack of effect with either PBS or peptide 69601.

10. Regression of Tumor Tissue Growth with $\alpha_v\beta_3$ Antagonists as Measured by in Vivo Rabbit Eye Model Assay The effect of anti-$\alpha_v\beta_3$ antagonists on growth factor-induced angiogenesis can be observed in naturally transparent structures as exemplified by the cornea of the eye. New blood vessels grow from the rim of the cornea, which has a rich blood supply, toward the center of the cornea, which normally does not have a blood supply. Stimulators of angiogenesis, such as bFGF, when applied to the cornea induce the growth of new blood vessels from the rim of the cornea. Antagonists of angiogenesis, applied to the cornea, inhibit the growth of new blood vessels from the rim of the cornea. Thus, the cornea undergoes angiogenesis through an invasion of endothelial cells from the rim of the cornea into the tough collagen-packed corneal tissue which is easily visible. The rabbit eye model assay therefore provides an in vivo model for the direct observation of stimulation and inhibition of angiogenesis following the implantation of compounds directly into the cornea of the eye.

A. In Vivo Rabbit Eye Model Assay

1) Angiogenesis Induced by Growth Factors

Angiogenesis was induced in the in vivo rabbit eye model assay with the growth factor bFGF and is described in the following sections.

a. Preparation of Hydron Pellets Containing Growth Factor and Monoclonal Antibodies Hydron polymer pellets containing growth factor and mAbs were prepared as described by D'Amato, et al., Proc. Natl. Acad. Sci.. USA, 91:4082–4085 (1994). The individual pellets contained 650 ng of the growth factor bFGF bound to sucralfate (Carafet, Marion Merrell Dow Corporation) to stabilize the bFGF and ensure its slow release into the surrounding tissue. In addition, hydron pellets were prepared which contained either 40 ug of the mAb LM609 (anti-$\alpha_v\beta_3$) or mAb P1F6 (anti-$\alpha_v\beta_5$) in PBS. The pellets were cast in specially prepared Teflon pegs that have a 2.5 mm core drilled into their surfaces. Approximately 12 ul of casting material was placed into each peg and polymerized overnight in a sterile hood. Pellets were then sterilized by ultraviolet irradiation.

b. Treatment with Monoclonal Antibodies

Each experiment consisted of three rabbits in which one eye received a pellet comprising bFGF and LM609 and the other eye received a pellet comprising bFGF and a mouse mAb P1F6 (anti-$\alpha_v\beta_5$). The use of paired eye testing to compare LM609 (anti-$\alpha_v\beta_3$) to other mAb and PBS controls provides a means for rigorous testing to demonstrate significant differences between the mAbs tested.

The P1F6 mAb immunoreacts with the integrin $\alpha_v\beta_5$ which is found on the surface of vascular endothelial cells but is presumably not involved in angiogenesis. To determine whether the mAb P1F6 was involved in angiogenesis, pellets containing only this mAb were prepared and assayed as described below to confirm that the mAb did not induce angiogenesis.

All of the mAbs tested were purified from ascites fluid using Protein-A Sepharose CL-4B affinity column chromatography according to well-known methods. The eluted immunoglobulin was then dialyzed against PBS and treated with Detoxi-gel (Pierce Chemicals) to remove endotoxin. Endotoxin has been shown to be a potent angiogenic and inflammatory stimulant. mAbs were therefore tested for the presence of endotoxin with the Chromogenic Limulus Amebocyte Lysate Assay (Bio-Whittaker) and only those mAbs without detectable endotoxin were used in the rabbit eye model assay.

A hydron pellet comprising bFGF and mAb LM609 (anti-$\alpha_v\beta_3$) or P1F6 (anti-$\alpha_v\beta_5$) was inserted into a corneal pocket formed in the eye of rabbits. The hydron pellet also contained sucralfate to stabilize the bFGF during the assay. Individual pellets were implanted into surgically created "pockets" formed in the mid-stroma of the cornea of rabbits. The surgical procedure was done under sterile technique using a Wild model M691 operating microscope equipped with a beamsplitter to which was mounted a camera for photographically recording individual corneas. A 3 mm by 5 mm "pocket" was created in the corneal stroma by making a 3 mm incision to half the corneal thickness with a 69 Beaver blade. The stroma was dissected peripherally using an iris spatula and the pellet was implanted with its peripheral margin 2 mm from the limbus.

During the following 14 days, bFGF and mAb diffused from the implanted pellet into the surrounding tissue and thereby effected angiogenesis from the rim of the cornea.

Representative results of each treatment are depicted in FIGS. 16A through 16E. The amount of vessels present are quantitated and described in terms of clock hours which are defined as follows. The eye is divided into 12 equal sections in the same manner as a clock is divided into hours. "One clock hour of vessels" refers to that amount of vessels which fills an area of the eye equivalent to one hour on a clock. The five rabbits which received only bFGF exhibited florid angiogenesis in which new blood vessels had grown from the rim of the cornea toward the center of the cornea, which normally does not have blood vessels. One of these rabbits had only 1 clock hour of vessels to the pellet. Two of the rabbits which received both bFGF and mAb LM609 had absolutely no detectable angiogenesis up to 14 days following surgery. One of these rabbits had 3 foci of hemorrhagic and budding vessels by day 14. Two of the rabbits which received bFGF and mAb P3G2 (anti-$\alpha_v\beta_5$) showed extensive vascularization in which new blood vessels had grown from the rim of the cornea into the cornea. One of these rabbits had only 1 to 2 hours of vessels to the pellet.

As evidenced in the rabbit eye model assay, no angiogenic effect was observed on normal paralimbal vessels in the presence of the growth factor bFGF in rabbits which received mAb LM609 (anti-$\alpha_v\beta_3$). In contrast, angiogenesis was observed on paralimbal vessels in the presence of the growth factor bFGF in rabbits which received the mAb P3G2 (anti-$\alpha_v\beta_5$). The complete inhibition of corneal angiogenesis by mAb LM609 is substantially greater than any previously reported anti-angiogenic reagent.

c. Treatment with Polypeptides

Each experiment consisted of eight rabbits in which one eye received a pellet comprising 100 nanograms (ng) bFGF and the other eye received a pellet comprising 1 microgram (ug) VEGF. The pellets were inserted into the corneal pocket as described above, and the cytokines subsequently stimulated the growth of new blood vessels into the cornea. Peptides were administered subcutaneously (s.q.) in 1 ml PBS at an initial dosage of 50 ug per kg rabbit the day of pellet insertion, and daily s.q. dosages were given at 20 ug/kg thereafter. After 7 days, the cornea were evaluated as described above.

Rabbits receiving control peptide 69601 showed substantial corneal blood vessel growth at 7 days, in both vFGF and VEGF stimulated eyes. Rabbits receiving peptide 85189 showed less than 50% of the amount of corneal blood vessel growth compared to controls in vFGF-stimulated eyes and nearly 100% inhibition in VEGF-stimulated eyes.

Figure 17:
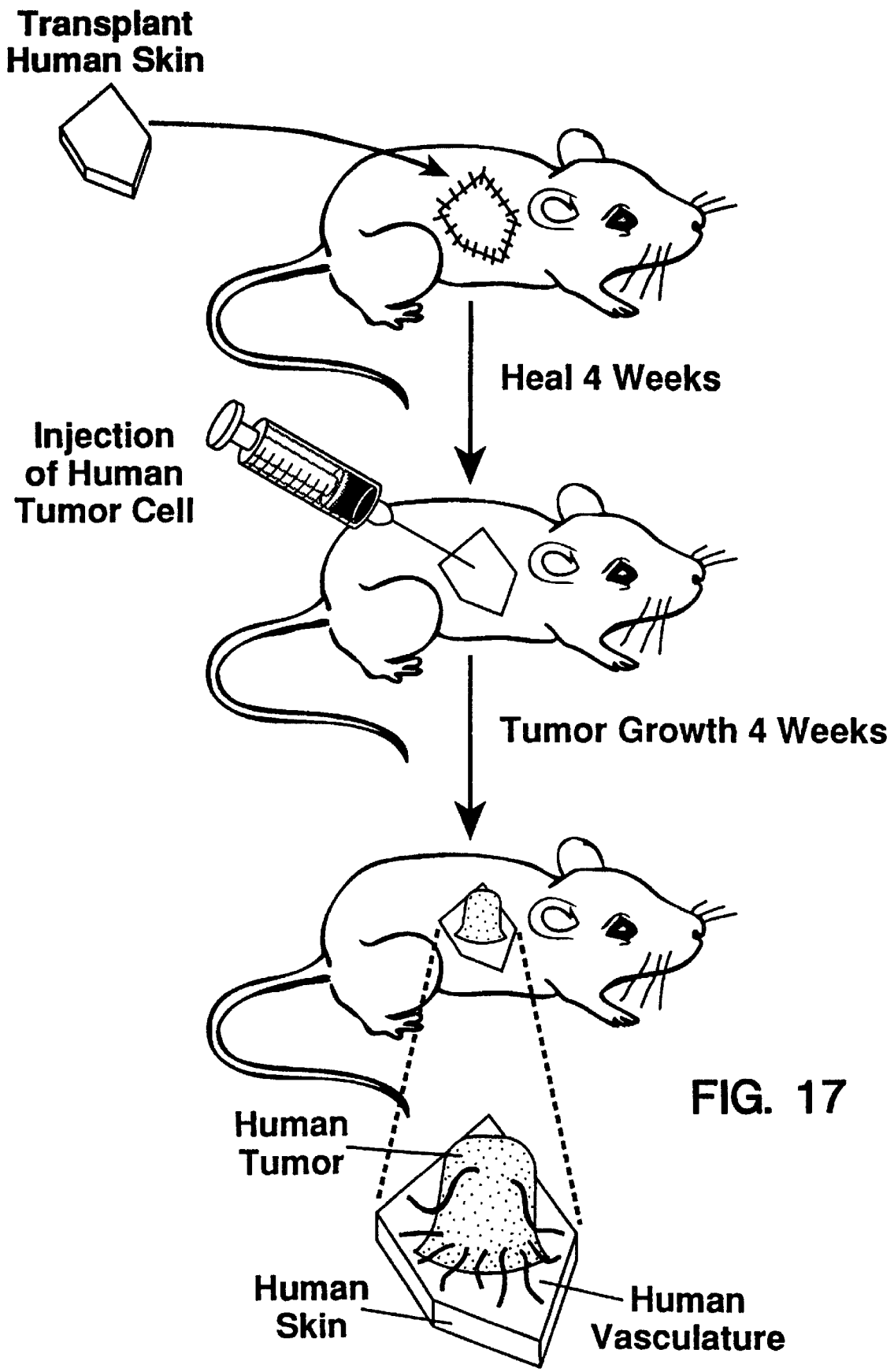
FIG. 17 represents a flow chart of how the in vivo mouse:human chimeric mouse model was generated as described in Example 11. A portion of skin from a SCID mouse was replaced with human neonatal foreskin and allowed to heal for 4 weeks. After the graft had healed, the human foreskin was inoculated with human tumor cells. During the following 4 week period, a measurable tumor was established which comprised a human tumor with human vasculature growing from the human skin into the human tumor.

11. In Vivo Regression of Tumor Tissue Growth with $\alpha_v\beta_3$ Antagonists as Measured by Chimeric Mouse:Human Assay An in vivo chimeric mouse:human model was generated by replacing a portion of skin from a SCID mouse with human neonatal foreskin (FIG. 17). After the skin graft was established, the human foreskin was inoculated with carcinoma cells. After a measurable tumor was established, either mAb LM609 (anti-$\alpha_v\beta_3$) or PBS was injected into the mouse tail vein. Following a 2–3 week period, the tumor was excised and analyzed by weight and histology.

A. In Vivo Chimeric Mouse:Human Assay

The in vivo chimeric mouse:human model is prepared essentially as described in Yan, et al., *J. Clin. Invest.*, 91:986–996 (1993). Briefly, a 2 cm$^2$ square area of skin was surgically removed from a SCID mouse (6–8 weeks of age) and replaced with a human foreskin. The mouse was anesthetized and the hair removed from a 5 cm$^2$ area on each side of the lateral abdominal region by shaving. Two circular graft beds of 2 cm$^2$ were prepared by removing the full thickness of skin down to the fascia. Full thickness human skin grafts of the same size derived from human neonatal foreskin were placed onto the wound beds and sutured into place. The graft was covered with a Band-Aid which was sutured to the skin. Micropore cloth tape was also applied to cover the wound.

The M21-L human melanoma cell line or MDA 23.1 breast carcinoma cell line (ATCC HTB 26; $\alpha_v\beta_3$ negative by immunoreactivity of tissue sections with mAb LM609), were used to form the solid human tumors on the human skin grafts on the SCID mice. A single cell suspension of 5×10$^6$ M21-L or MDA 23.1 cells was injected intradermally into the human skin graft. The mice were then observed for 2 to 4 weeks to allow growth of measurable human tumors.

B. Intravenous Application

1) Treatment With Monoclonal Antibodies

Following the growth of measurable tumors, SCID mice, which had been injected with M21L tumor cells, were injected intravenously into the tail vein with 250 $\mu$g of either the mAb LM609 (anti-$\alpha_v\beta_3$) or PBS twice a week for 2 to 3 weeks. After this time, the tumors were resected from the skin and trimmed free of surrounding tissue. Several mice were evaluated for each treatment with the average tumor weight from each treatment being calculated and shown at the bottom of Table 6.

TABLE 6

| M21L Tumor Number | Treatment | Tumor Weight (mg) |
| --- | --- | --- |
| 1 | PBS | 158 |
| 2 | | 192 |
| 3 | | 216 |
| 4 | | 227 |

TABLE 6-continued

| | | |
|---|---|---|
| 5 | LM609 | 195 |
| 6 | | 42 |
| 7 | | 82 |
| 8 | | 48 |
| 9 | | 37 |
| 10 | | 100 |
| 11 | | 172 |
| Treatment | Average Tumor Weight (mg) | |
| PBS | 198 | |
| LM609 | 113 | |

Exposure of the M21L $\alpha_v\beta_3$-negative human carcinoma tumor mass in the mouse:human chimeric assay system to LM609 (anti-$\alpha_v\beta_3$) caused the decrease from the PBS treated average tumor weight of 198 mg to 113 mg.

Representative examples of M21L tumors treated with the mAb LM609 (anti-$\alpha_v\beta_3$) and PBS were examined morphologically. The PBS-treated tumors were large (8 to 10 mm in diameter) and well vascularized whereas those treated with mAb LM609 (anti-$\alpha_v\beta_3$) were much smaller (3 to 4 mm in diameter) and lacked detectable blood vessels.

Figure 35:
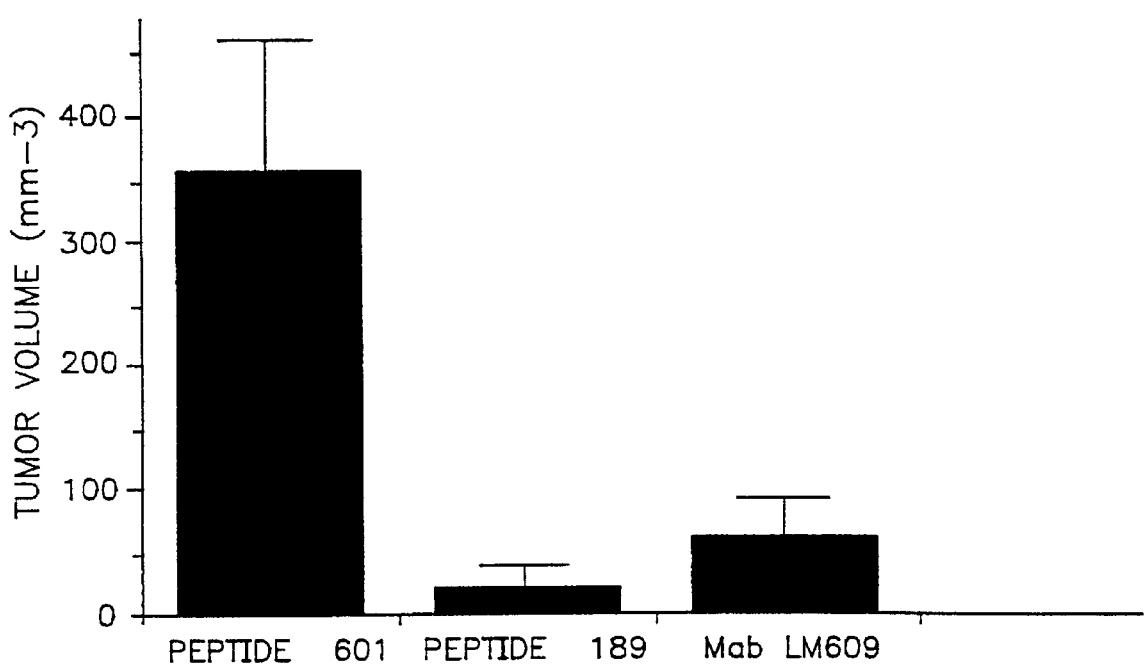
FIG. 35 illustrates the effect of peptides and antibodies on melanoma tumor growth in the chimeric mouse:human model as further described in Example 11B. The peptides assessed included control 69601 (labeled 601) and antagonist 85189 (labeled 189). The antibody tested was LM609. Tumor volume in $mm^3$ is plotted on the Y-axis against the various treatments on the X-axis.

In other experiments with M21-L melanoma tumor cells in the mouse:human chimeric assay system, the response with mAB LM609 was compared with the response obtained with the synthetic peptide 85189 (SEQ ID NO 15) as compared to control synthetic peptide 69601 (SEQ ID NO 6). The assays were performed as described above. The results, shown in FIG. 35, demonstrate that the synthetic peptide 85189 reduced tumor volume to below 25 mm³ as compared to control peptide where the tumor volume was approximately 360 mm³. The mAB LM609 also significantly reduced tumor volume to approximately 60 mm³.

Tumors formed in skin grafts which had been injected with MDA 23.1 cells were detectable and measurable. Morphological examination of the established tumors revealed that neovascularization from the grafted human tissue into the MDA 23.1 tumor cells had occurred.

Thus, blocking of the $\alpha_v\beta_3$ receptor by the intravenous application of $\alpha_v\beta_3$-specific LM609 antibody and peptides resulted in a regression of a carcinoma in this model system in the same manner as the CAM and rabbit eye model systems as described in Examples 9 and 10, respectively.

2) Treatment with Synthetic Peptides

Figure 36A:
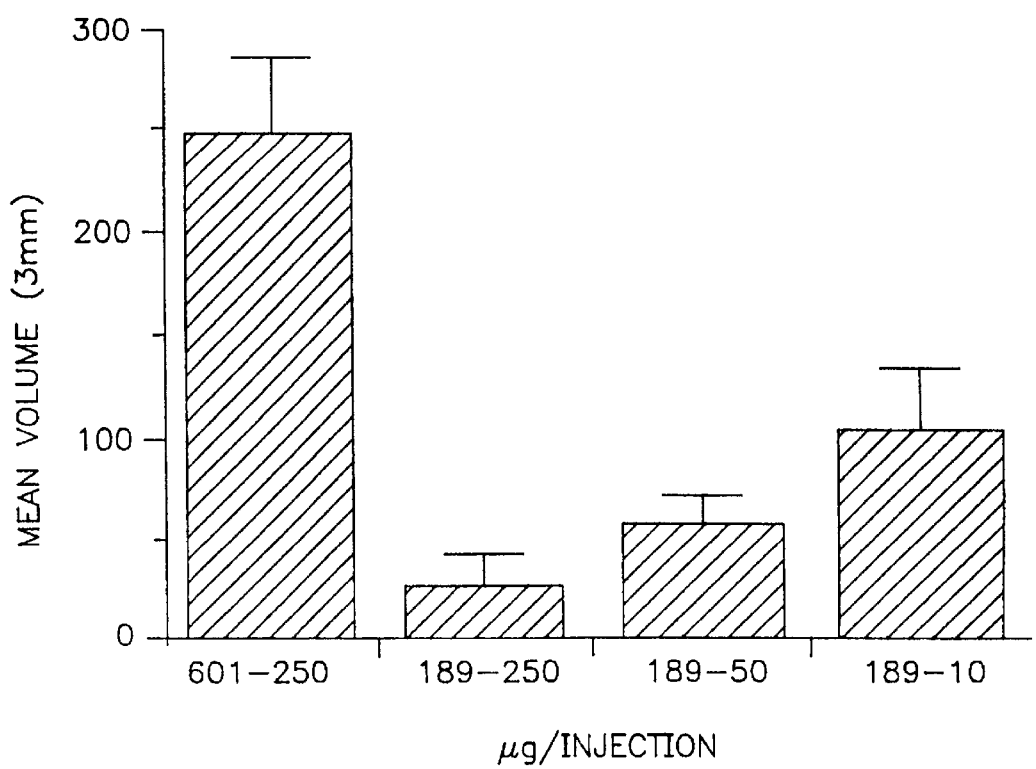
FIGS. 36A and B respectively show the effect of antagonist 85189 (labeled 189) compared to control peptide 69601 (labeled 601) in reducing the volume and wet weight of M21L tumors over a dosage range of 10, 50 and 250 ug/injection as further described in Example 11C.
Figure 36B:
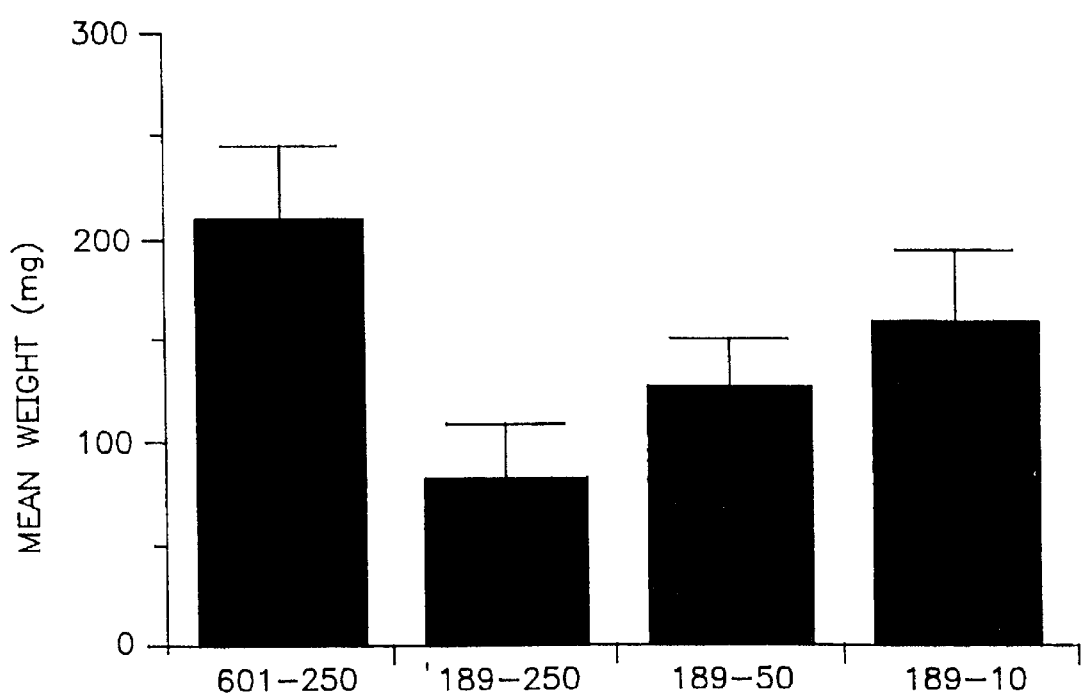

In a procedure similar to that described above for monoclonal antibodies, peptide antagonists of $\alpha_v\beta_3$ were injected intravenously into the tail vein of SCID mice having measurable M21-L tumors. In a preliminary analysis, a dose response curve was performed for peptides 69601 (control) and 85189 (test) injected over a concentration range of 10 to 250 ug/ml. The mean volume and weight of resected tumors following treatment were determined with the results respectively shown in FIGS. 36A and 36B. Peptide 85189 was effective at inhibiting M21-L tumor growth over the concentration range tested compared to treatment with control peptide with the most effective dosage being 250 ug/ml.

For analyzing peptide 85189 treatment effectiveness over a time course, two treatment regimens were evaluated in the same SCID tumor model. In one assay, treatment with either peptide 85189 or 69601 was initiated on day 6, with day 0 being the day of M21-L tumor injection of 3×10⁶ cells subcutaneously into mouse skin, with intraperitoneal injections of 250 ug/ml peptide 85189 or control 69601 every other day until day 29. The other assay was identically performed with the exception that treatment was initiated on day 20. At the end of the assays, the tumors were resected and the mean tumor volume in mm³ was determined. The data was plotted as this value +/- the standard error of the mean.

Figure 37A:
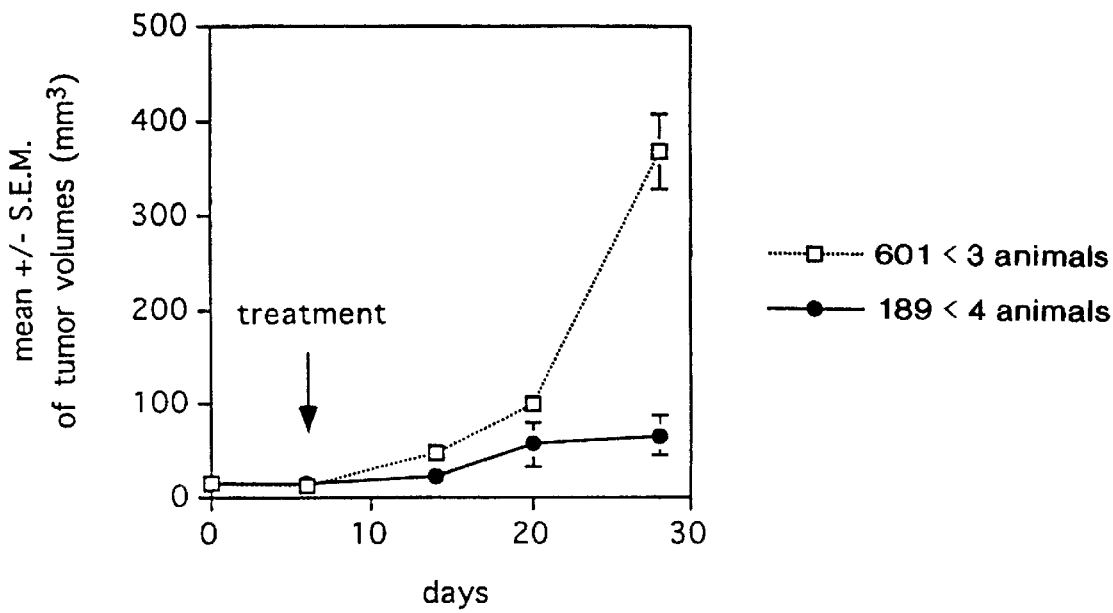
FIGS. 37A and 37B show the effectiveness of antagonist peptide 85189 (labeled 189 with a solid line and filled circles) against control peptide 69601 (labeled 601 on a dotted line and open squares) at inhibiting M21L tumor volume in the mouse:human model with two different treatment regimens as further described in Example 11C. Tumor volume in $mm^3$ is plotted on the Y-axis against days on the X-axis.
Figure 37B:
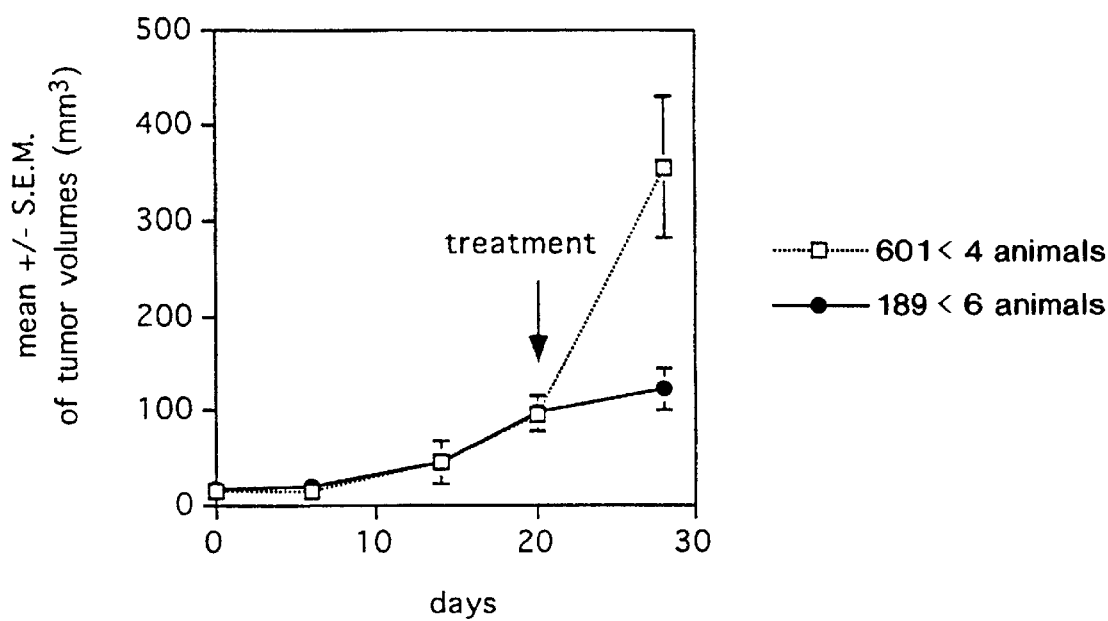

The results of these assays, respectively shown in FIGS. 37A and 37B, indicate that peptide 85189 but not 69601 inhibited tumor growth at various days after treatment was initiated, depending on the particular treatment regimen. Thus, peptide 85189 is an effective $\alpha_v\beta_3$ antagonist of both angiogenesis and thus tumor growth.

12. Stimulation of Vascular Cells to Enter the Cell Cycle and Undergo Apoptosis in the Presence of Antagonists of Intearin $\alpha_v\beta_3$ as Measured in the CAM Assay The angiogenic process clearly depends on the capacity of cytokines such as bFGF and VEGF to stimulate vascular cell proliferation. Mignatti et al., *J. Cell. Biochem.*, 471:201 (1991); Takeshita et al., *J. Clin. Invest.*, 93:662 (1994); and Koyama et al., *J. Cell. Physiol.*, 158:1 (1994). However, it is also apparent that signaling events may regulate the differentiation of these vascular cells into mature blood vessels. Thus, it is conceivable that interfering with signals related to either growth or differentiation of vascular cells undergoing new growth or angiogenesis may result in the perturbation of angiogenesis.

Integrin ligation events have been shown to participate in both cell proliferation as well as apoptosis or programmed cell death in vitro. Schwartz, *Cancer Res.*, 51:1503 (1993); Meredith et al., *Mol. Biol. Cell.*, 4:953 (1993); Frisch et al., *J. Cell Biol.*, 124:619 (1994); and Ruoslahti et al., *Cell*, 77:477 (1994). Close examination of the effects of $\alpha_v\beta_3$ antagonists on angiogenesis reveals the presence of discontinuous and disrupted tumor-associated blood vessels. Therefore, it is possible that the loss of blood vessel continuity may be due to selective necrosis or apoptosis of vascular cells.

To explore this possibility, CAMs were examined after induction of angiogenesis with the growth factor bFGF and treatment with the mAb and cyclic peptides of this invention.

A. Treatment with Monoclonal Antibodies

Apoptosis can be detected by a variety of methods which include direct examination of DNA isolated from tissue to detect fragmentation of the DNA and the detection of 3'OH in intact tissue with an antibody that specifically detects free 3'OH groups of fragmented DNA.

1) Analysis of DNA Fragmentation

Angiogenesis was induced by placing filter disks saturated with bFGF on the CAMs of 10-day old embryos as described in Examples 6A. Immunohistological analysis of CAMs with LM609 (anti-$\alpha_v\beta_3$) revealed peak expression of $\alpha_v\beta_3$ on blood vessels 12 to 24 hours after initiation of angiogenesis with bFGF. Thus, 24 hours after stimulation with bFGF, embryos were inoculated intravenously with 100 μl of PBS alone or PBS containing 300 μg of either mAb CSAT (anti-$\beta_1$) or LM609 (anti-$\alpha_v\beta_3$).

DNA fragmentation was detected by resecting the CAM tissue directly below bFGF saturated filter disks 24 or 48 hours after intravenous inoculations with mAb LM609 (anti-$\alpha_v\beta_3$), CSAT (anti-$\beta_1$), or PBS. Resected CAM tissues were washed three times with sterile PBS and finely minced, resuspended in 0.25% bacterial collagenase (Worthington Biochemical; Freehold, N.J.) and incubated for 90 minutes at 37 C. with occasional vortexing. DNA was extracted from equal numbers of CAM cells from single cell suspension as previously described. Bissonette, et al., *Nature*, 359:552 (1992). Briefly, equal numbers of CAM cells were lysed in 10 mM Tris-HCl, pH 8.0, 10 mM EDTA in 0.5% (v/v) Triton X-100 (Sigma, St. Louis, Mo.). Cell lysates were centrifuged at 16,000×g for 15 minutes at 4 C. to separate soluble fragmented DNA from the intact chromatin pellet. Fragmented DNA was washed, precipitated, and analyzed on a 1.2% (w/v) agarose gel.

Soluble fragmented DNA was isolated from an equal number of CAM cells from each treatment, separated electrophoretically on an agarose gel, and visualized by staining with ethidium bromide. No difference was detected in the relative amount of DNA fragmentation resulting from the three different treatments 24 hours after treatment. However, by 48 hours following treatment with mAb LM609 (anti-$\alpha_v\beta_3$), a significant increase in DNA fragmentation was observed when compared to embryos treated with either mAb CSAT (anti-$\beta_1$) or PBS alone.

2) Stimulation of Vascular Cells to Enter the Cell Cycle

To experimentally examine the role of $\alpha_v\beta_3$ in these processes, cells derived from CAMs treated with or without bFGF were stained with propidium iodide and immunoreacted with mAb LM609 (anti-$\alpha_v\beta_3$).

CAMs isolated from embryos 24 and 48 hours after treatment with mAb LM609 (anti-$\alpha_v\beta_3$), CSAT (anti-$\beta_1$), or PBS were dissociated into single cell suspensions by incubation with bacterial collagenase as described above. Single cells were then permeabilized and stained with Apop Tag Insitu Detection Kit according to the manufacturer's instructions (Oncor, Gaithersburg, Md.). Apop Tag is an antibody that specifically detects free 3'OH groups of fragmented DNA. Detection of such free 3'OH groups is an established method for the detection of apoptotic cells. Gavrieli et al., *J. Cell Biol.*, 119:493 (1992).

Apop Tag stained cells were then rinsed in 0.1% (v/v) Triton X-100 in PBS and resuspended in FACS buffer containing 0.5% (w/v) BSA, 0.02% (w/v) sodium azide and 200 ug/ml RNase A in PBS. Cells were incubated for 1.5 hrs, washed, and analyzed by fluorescence activated cell sorting. Cell fluorescence was measured using a FACScan flow cytometer and data analyzed as described below.

Cell fluorescence was measured with a FACScan flow cytometer (Becton Dickinson, Mountain View, Calif.). Side scatter (SSC) and forward scatter (FSC) were determined simultaneously and all data were collected with a Hewlet Packard (HP9000) computer equipped with FACScan research software (Becton Dickinson, Mountain View, Calif.). The data were analyzed with P.C Lysis version I software (Becton Dickinson, Mountain View, Calif.). Negative control gates were set by using cell suspensions without the addition of primary antibodies from the Apop Tag kit. Identical gating was applied to both cell populations resulting in the analysis of approximately 8,000 cells per different cell treatment.

Figure 18:
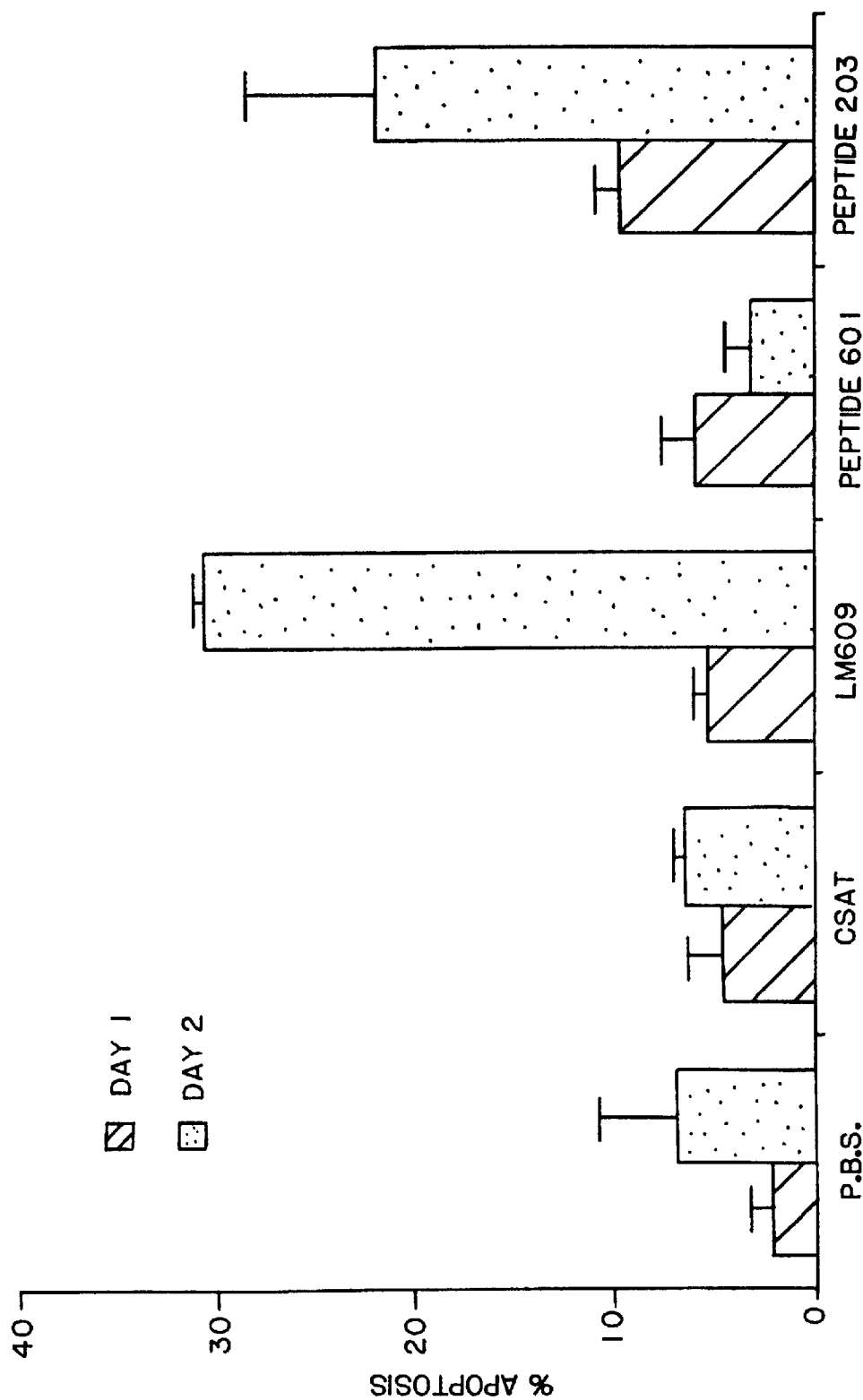
FIG. 18 illustrates the percent of single cells derived from mAb-treated and peptide-treated CAMs and stained with Apop Tag as determined by FACS analysis and described in Example 12. The black and stippled bars represent cells from embryos treated 24 hours and 48 hours prior to the assay, respectively. Each bar represents the mean±S.E. of three replicates. CAMs were treated mAb LM609 (anti-$\alpha_v\beta_3$), or CSAT (anti-$\alpha_1$), or PBS. CAMs were also treated with cyclic peptide 66203 (cyclo-RGDfV, indicated as Peptide 203) or control cyclic peptide 69601 (cyclo-RADfV, indicated as Peptide 601).

The percent of single cells derived from mAb treated CAMs and stained with Apop Tag as determined by FACS analysis is shown in FIG. 18. The black bar represents cells from embryos treated 24 hours prior to analysis. The stippled bar represents cells from embryos treated 48 hours prior to analysis. Each bar represents the mean±S.E. of three replicates.

As shown in FIG. 18, CAMs treated two days prior with mAb LM609 (anti-$\alpha_v\beta_3$) showed a 3 to 4-fold increase in Apop Tag staining as compared to CAMs treated with either PBS alone or CSAT (anti-$\beta_1$).

B. Treatment with Synthetic Peptides

CAM assays with growth factor-induced angiogenesis, as described in Example 6A, were also performed with the synthetic peptides of this invention to determine the effect of cyclic peptides on apoptosis. The peptides cyclo-RGDfV (66203) and cyclo-RADfV (69601) were prepared as described in Example 1. The peptide solutions or PBS were injected into the CAM preparation at a concentration of 300 ug/ml. At 24 and 48 hours, the filter paper and surrounding CAM tissue was dissected and stained with the Apop Tag to detect apoptosis as described above in Example 12A2).

As shown in FIG. 18, CAMs treated two days prior with peptide 69203 (cyclo-RGDfV) showed a 3 to 4-fold increase in Apop Tag staining as compared to CAMs treated with either PBS alone or control cyclic peptide 69601 (cyclo-RADfV).

C. Effect of Treatment with Monoclonal Antibodies on Apoptosis and Cell Cycle

Single cell suspensions were also examined for the number of copies of chromosomal DNA by staining with propidium iodide to determine the effect of treatment with monoclonal antibodies on the cell cycle and for apoptosis by staining with the Apop Tag.

Single cell suspensions of CAMS treated 24 or 48 hours prior with mAb LM609 (anti-$\alpha_v\beta_3$) or CSAT (anti-$\beta_1$) or PBS were prepared as described in Example 12A1).

For staining of cells with the Apop Tag, cell suspensions were washed three times with buffer containing 2.5% (w/v) BSA and 0.25% (w/v) sodium azide in PBS. Cells were then fixed in 1% (w/v) paraformaldehyde in PBS for 15 minutes followed by three washes as described above. To prevent nonspecific binding, single cell suspensions were blocked with 5 (w/v) BSA in PBS overnight at 4 C. Cells were then washed as before, stained with Apop Tag, and cell fluorescence measured with a FACScan as described above in Example 12A.

Cells from each experimental condition were stained with propidium iodide (Sigma, St. Louis, Mo.) at 10 ug/ml in PBS for 1 hour, washed two times with PES, and analyzed for nuclear characteristics typical of apoptosis, including chromatin condensation and segmentation. The percentage of apoptotic cells were estimated by morphological analysis of cells from at least 10 to 15 randomly selected microscopic fields.

Figure 19:
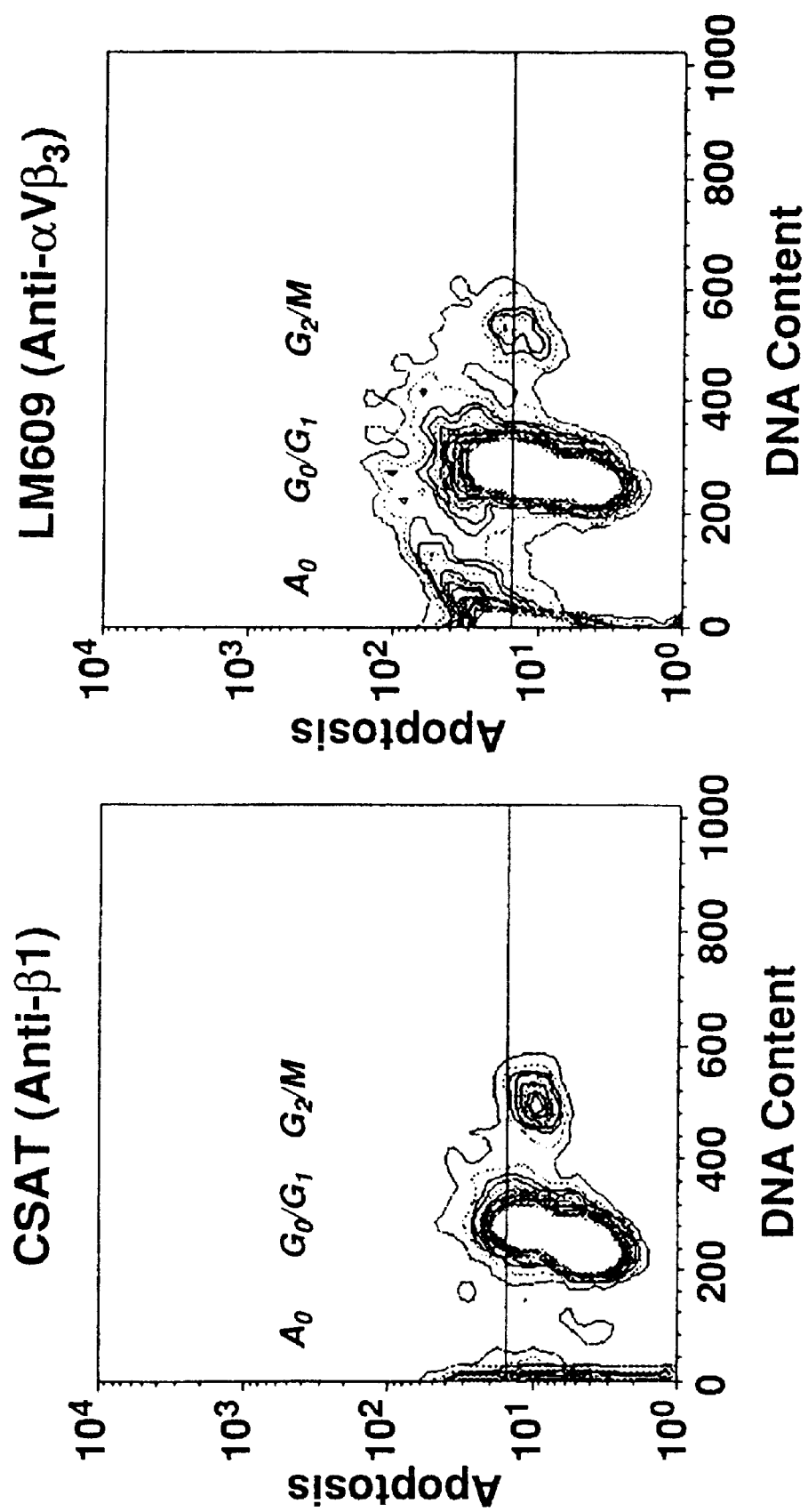
FIGS. 19A and 19B illustrate the combined results of single cell suspensions of CAMs from embryos treated with either CSAT (anti-$\beta_1$) (FIG. 19A) or LM609 (ant-$\alpha_v\beta_3$) (FIG. 19B), stained with Apop Tag and propidium iodide, and analyzed by FACS as described in Example 12C. The Y axis represents Apop Tag staining in numbers of cells (Apoptosis), the X axis represents propidium iodide staining (DNA content). The horizontal line represents the negative gate for Apop Tag staining. The left and right panels indicates CAM cells from CSAT (anti-$\beta_1$) (FIG. 19A) and LM609 (anti-$\alpha_v\beta_3$) (FIG. 19B) treated embryos, respectively. Cell cycle analysis was performed by analysis of approximately 8,000 events per condition.
Figure 20A:
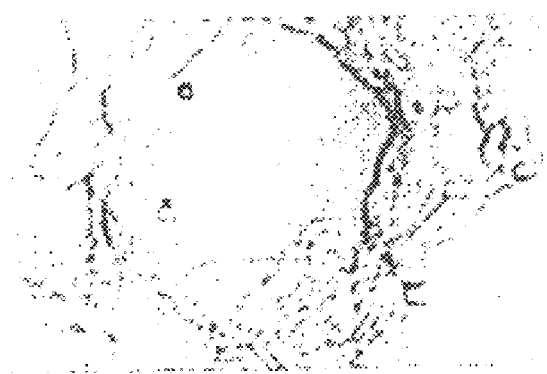
FIGS. 20A–20C represent CAM tissue from CSAT (anti-$\beta_1$) treated embryos and FIGS. 20D–20F represent CAM tissue from LM609 (anti-$\alpha_v\beta_3$) treated embryos prepared as described in Example 12C.
Figure 20B:
Figure 20C:
Figure 20D:
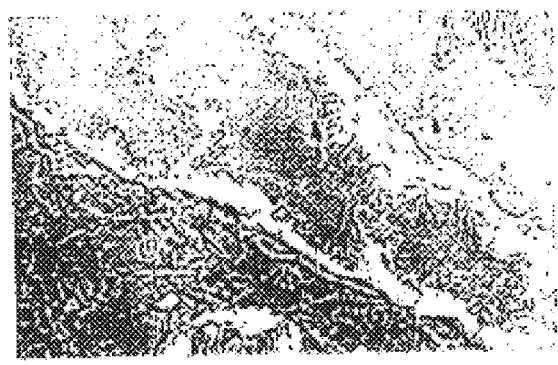
Figure 20E:
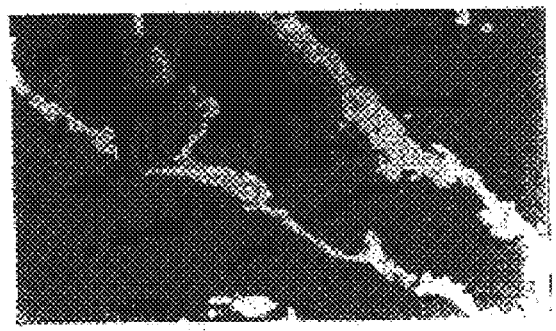
Figure 20F:
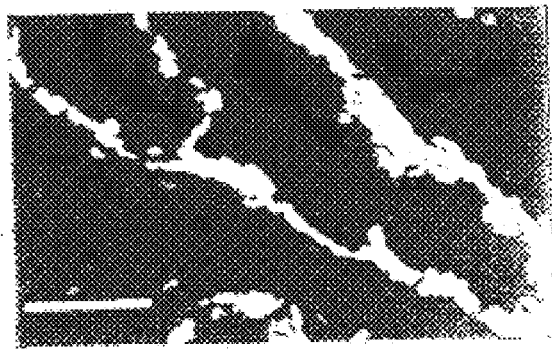

The combined results of single cell suspensions of CAMs from embryos treated with either CSAT (anti-$\beta_1$) or LM609 (anti-$\alpha_v\beta_3$), stained with Apop Tag and propidium iodide, and analyzed by FACS are given in FIG. 19. The Y axis represents Apop Tag staining (apoptosis), the X axis represents propidium iodide staining (DNA content). The horizontal line represents the negative gate for Apop Tag staining. The left and right panels indicate CAM cells from CSAT and LM609 treated embryos, respectively. Cell cycle analysis was performed by analysis of approximately 8,000 events per condition and data represented in a contour plot.

Samples of single cells stained with the DNA dye propidium iodide revealed that 25–30%i of the LM609 (anti-$\alpha_v\beta_3$) treated CAM cells 48 hours after treatment showed evidence of nuclear condensation and/or segmentation. These processes are characteristic of cells undergoing apoptosis. This is in contrast to CAMs treated with CSAT (anti-$\beta_1$) where 90–95w of the cells showed normal nuclear staining.

As shown in FIG. 19, consistent with the induction of apoptosis by LM609, a significant number of cells in a peak containing less than one copy of DNA was observed (AO). This peak has been previously shown to represent fragmented DNA in late stage apoptotic cells. Telford et al., *Cytometry*, 13:137 (1992). Furthermore, these AO cells readily stain with Apop Tag confirming the ability of this reagent to detect apoptotic cells. However, in addition to the staining of cells in AO, a significant number of cells containing greater than one copy of DNA also stained with Apop Tag (FIG. 19). These results demonstrate the LM609 has the ability to promote apoptosis among vascular cells that had already entered the cell cycle. In contrast, cells derived from control CAMs which had entered the cell cycle showed minimal Apop Tag staining consistent with the few apoptotic cells detected in control treated CAMs.

Among those cells in the bFGF stimulated CAMs that had entered the cell cycle (S and G2/M phase), 70% showed positive staining with LM609 (anti-$\alpha_v\beta_3$). This is compared to 10% LM609 staining observed among cycling cells from non-bFGF treated CAMs. These findings indicate that after bFGF stimulation, the majority of the $\alpha_v\beta_3$-bearing cells show active proliferation.

Taken together these findings indicate that intravenous injection of mAb LM609 or cyclic peptide antagonist of $\alpha_v\beta_3$ promote apoptosis within the chick CAM following induction of angiogenesis.

CAMs were also examined histologically for expression of $\alpha_v\beta_3$ by immunoreactivity with LM609 and for cells which were undergoing apoptosis by immunoreactivity with Apop Tag. CAM sections resected from embryos treated 48 hours prior with LM609 (anti-$\alpha_v\beta_3$), CSAT (anti-$\beta_1$), or PBS prepared in Example 5A were washed, embedded in OTC (Baxter) and snap frozen in liquid nitrogen. Six micron sections of CAM tissues were cut, fixed in acetone for 30 seconds, and stored at −70 C. until use. Tissue sections were prepared for staining by a brief rinse in 70% (v/v) ethanol (ETOH) followed by washing three times in PBS. Next, sections were blocked with 5% (w/v) BSA in PBS for 2 hours, followed by incubation with 10 ug/ml of mAb LM609 for 2 hours. The sections were then washed and incubated with a 1:50 dilution of rhodamine conjugated goat anti-mouse IgG (Fisher Scientific, Pittsburg, Pa.) for 2 hours. Finally, the same sections were washed and stained with the Apop Tag as described in Example 12A2). The stained tissue sections were mounted and analyzed by confocal immunofluorescent microscopy.

In FIG. 20, panels A through C represent CAM tissue from CSAT (anti-$\beta_1$) treated embryos and panels D through F represent CAM tissue from LM609 (anti-$\alpha_v\beta_3$) treated embryos. Panels A and D depict tissues stained with Apop Tag and visualized by fluorescence (FITC) superimposed on a D.I.C. image. Panels B and E depict the same tissues stained with mAb LM609 (anti-$\alpha_v\beta_3$) and visualized by fluorescence (rhodamine). Panels C and F represent merged images of the same tissues stained with both Apop Tag and LM609 where yellow staining represents colocalization. The bar represents 15 and 50 $\mu$m in the left and right panels, respectively.

As shown in FIGS. 20(A–C), after intravenous injection of CSAT or PBS control, staining with Apop Tag appeared minimal and random, indicating a minimal level of apoptosis within the tissue. In contrast, CAMs from embryos previously treated with LM609 or cyclic peptide 203 showed a majority of the vessels staining intensely with Apop Tag while minimal reactivity was observed among surrounding nonvascular cells (FIGS. 20D–F). Furthermore, when both Apop Tag and LM609 were used to stain these tissues (19C and 19F) significant co-localization was only observed between these markers in CAMs derived from embryos treated with $\alpha_v\beta_3$ antagonists (FIG. 20F). These findings demonstrate that after induction of angiogenesis in vivo, inhibitors of integrin $\alpha_v\beta_3$ selectively promote apoptosis of $\alpha_v\beta_3$-bearing blood vessels.

While angiogenesis is a complex process involving many molecular and cell biological events, several lines of evidence suggest that vascular cell integrin $\alpha_v\beta_3$ plays a relatively late role in this process. First, immunohistological analysis reveals that expression of $\alpha_v\beta_3$ on vascular cells reached a maximum 12–24 hours after the induction of angiogenesis with bFGF. Secondly, antagonists of $\alpha_v\beta_3$ perturb angiogenesis induced by multiple activators suggesting that this receptor is involved in common pathway downstream from perhaps all primary signaling events leading to angiogenesis. Thirdly, mAb LM609 or cyclic peptide treated CAMs did not show a significant increase in apoptosis as measured by DNA laddering until 48 hours post treatment with these antagonists. Finally, antagonists of $\alpha_v\beta_3$ promote apoptosis of vascular cells that have already been induced to enter the cell cycle.

The results presented herein provide the first direct evidence that integrin ligation events can regulate cell survival in vivo. It is therefore hypothesized that once angiogenesis begins, individual vascular cells divide and begin to move toward the angiogenic source, after which, $\alpha_v\beta_3$ ligation provides a signal allowing continued cell survival which leads to differentiation and the formation of mature blood vessels. However, if $\alpha_v\beta_3$ ligation is prevented then the cells fail to receive this molecular cue and the cells go into apoptosis by default. This hypothesis would also predict that after differentiation has occurred mature blood vessels no longer require $\alpha_v\beta_3$ signaling for survival and thus are refractory to antagonists of this integrin.

Finally, the results presented herein provide evidence that antagonists of integrin $\alpha_v\beta_3$ may provide a powerful therapeutic approach for the treatment of neoplasia or other diseases characterized by angiogenesis. First, antagonists of $\alpha_v\beta_3$ disrupt newly forming blood vessels without affecting the pre-existing vasculature. Second, these antagonists had no significant effect on chick embryo viability, suggesting they are non-toxic. Third, angiogenesis was significantly blocked regardless of the angiogenic stimuli. Finally, systemic administration of $\alpha_v\beta_3$ antagonists causes dramatic regression of various histologically distinct human tumors.

13. Preparation of Organic Molecule 3 Antagonists

The synthesis of organic $\alpha_v\beta_3$ antagonist Compounds 7 (96112), 9 (99799), 10 (96229), 12 (112854), 14 (96113), 15 (79959), 16 (81218), 17 (87292) and 18 (87293) is described below and is also shown in the noted figures. Organic antagonists are also referred to by the numbers in parentheses. The resultant organic molecules, referred to as organic mimetics of this invention as previously defined, are then used in the methods for inhibiting $\alpha_v\beta_3$-mediated angiogenesis as described in Example 11.

For each of the syntheses described below, optical rotations were measured on Perkin-Elmer 241 spectrophotometer UV and visible spectra were recorded on a Beckmann DU-70 spectrometer. $^1$H and $^{13}$C NMR spectra were recorded at 400 and 500 MHz on Bruker AMX-400 and AMX-500 spectrometer. High-resolution mass spectra (HRMS) were recorded on a VG ZAB-ZSE mass spectrometer under fast atom bombardment (FAB) conditions. Column chromatography was carried out with silica gel of 70–230 mesh. Preparative TLC was carried out on Merck Art. 5744 (0.5 mm). Melting points were taken on a Thomas Hoover apparatus.

Figure 38:
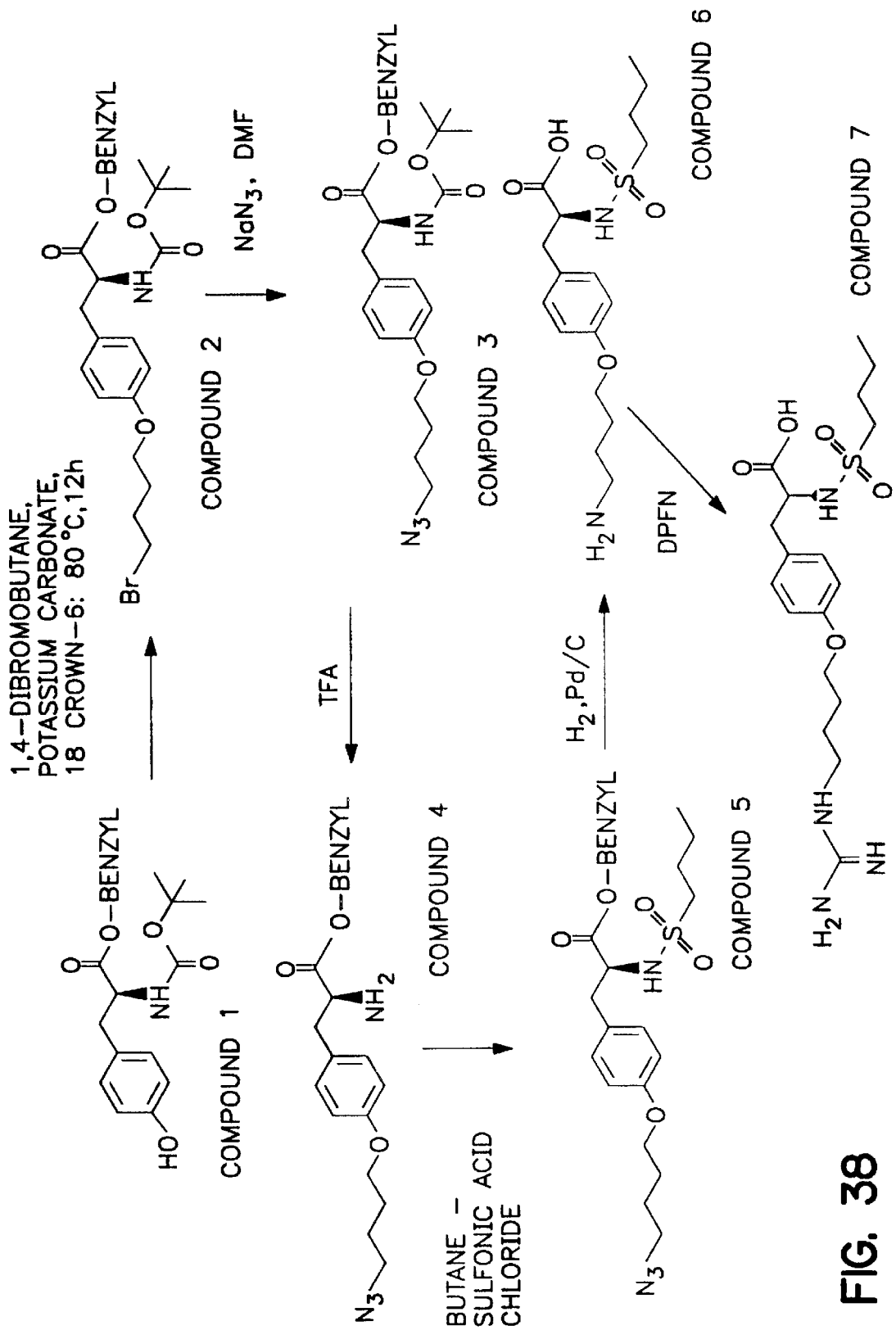

A. Compound 1: t-Boc-L-tyrosine benzyl ester as Illustrated in FIG. 38

COMPOUND 1

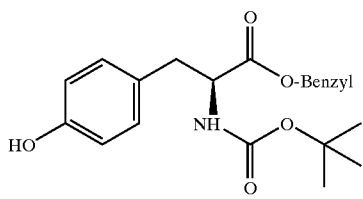

To a solution of N-(tert-butoxycarbonyl)-L-tyrosine(t-Boc-L-tyrosine) (1.0 equivalents; Aldrich) in 0.10 M (M) methylene chloride was added dicyclohexylcarbodiimide (DCC) (1.5 equivalents) at 25 C. and allowed to stir for 1 hour. Next, 1.5 equivalents benzyl alcohol was added and the mixture was stirred for an additional 12 hours at 25 C. The reaction mixture was then diluted with ethyl acetate (0.10 M) and washed twice (2x) with water, once (1x) with brine and dried over magnesium sulfate. The solvent was then removed in vacuo and the crude product was then purified by silica gel column chromatography. Compound 1, t-Boc-L-tyrosine benzyl ester can also be commercially purchased from Sigma.

B. Compound 2: (S)-3-(4-(4-Bromobutyloxy)phenyl-2-N-tert-butyloxycarbonyl-propionic Acid Benzyl Ester as Illustrated in FIG. 38 Step i

COMPOUND 2

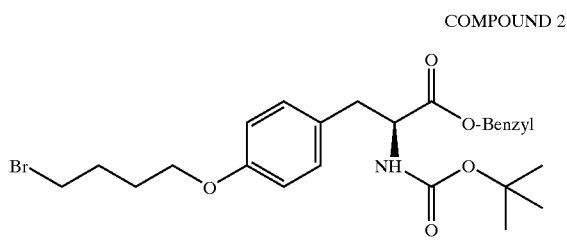

A mixture of t-Boc-L-tyrosine benzyl ester (2 grams, 5.38 mmol; synthesized as described above), 1,4-dibromobutane (1.9 ml, 16.2 mmol; Aldrich), potassium carbonate (5 g) and 18-crown-6 (0.1 g; Aldrich), was heated at 80 C. for 12 hours. After cooling, the precipate was filtered off and the reaction mixture was evaporated to dryness in vacuo. The crude product was then purified by crystallization using 100% hexane to yield 2.5 g (92%) of Compound 2.

C. Compound 3: (S)-3-(4-(4-Azidobutyloxy)phenyl-2-N-tert-butyloxycarbonyl-propionic Acid Benzyl Ester as Illustrated in FIG. 38 Step ii

COMPOUND 3

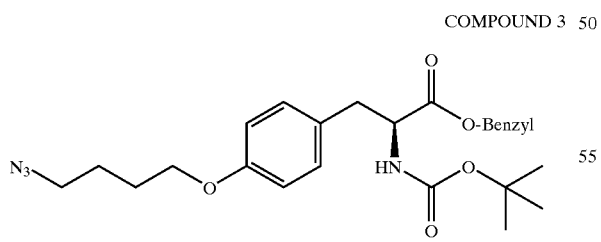

Compound 2 (2.5 g, 4.9 mmol) was stirred with sodium azide (1.6 g, 25 mmol) in dimethylformamide (DMF) (20 ml) at 25 C. for 12 hours. The solvent was then evaporated and the residue was treated with water (approx 10 ml) and extracted twice with ethyl acetate. The organic layers were combined, dried via magnesium sulfate and evaporated to yield 2.0 grams (90%) of Compound 3 as a colorless syrup (FAB-MS: 469 (M+H$^+$).

D. Compound 4: (S)-3-(4-(4-Azidobutyloxy)phenyl-2-amino-propionic acid benzyl ester as illustrated in FIG. 38 step iii

COMPOUND 4

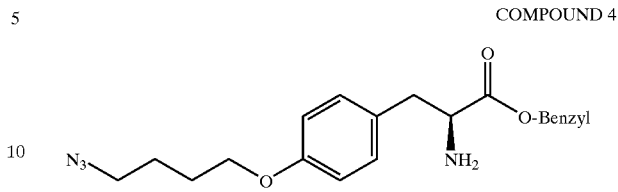

Compound 3 (2.0 g (4.4 mmol)) was dissolved in trifluoroacetic acid (TFA; 2 ml) and stirred for 3 hours at room temperature. Evaporation in vacuo yielded 1.6 grams (quantitative) of Compound 4 as a colorless syrup that was used without further purification for the next step. FAB-MS: 369 (M+H$^+$).

E. Compound 5: (S)-3-(4-(4-Azidobutyloxy)phenyl-2-butylsulfonamido-propionic acid benzyl ester as illustrated in FIG. 38 step iv

COMPOUND 5

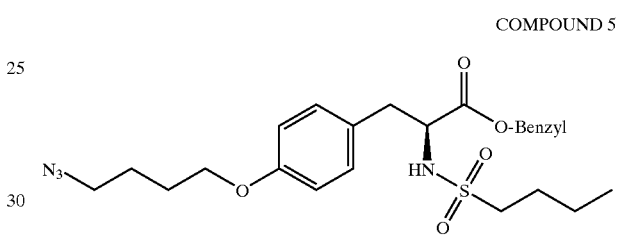

A mixture of Compound 4 (1.6 g; 4.3 mmol), butane sulfonic acid chloride (0.84 ml; 6.6 mmol) and triethyl amine (1.5 equivalents) were stirred in methylene chloride (20 ml) for 12 hours at room temperature. The reaction mixture was then evaporated and the residue was dissolved in ethylacetate, washed with dilute HCl, aqueous sodium bicarbonate and water. After evaporation to dryness the crude product was purified by flash chromatography (silica gel, toluene/ethylacetate 15:1) to yield 1.4 grams (67%) of Compound 5 as an amorphous solid.

F. Compound 6: (S)-3-(4-(4-Aminobutyloxy)phenyl-2-butylsulfonamido-propionic Acid as Illustrated in FIG. 38 Step v

COMPOUND 6

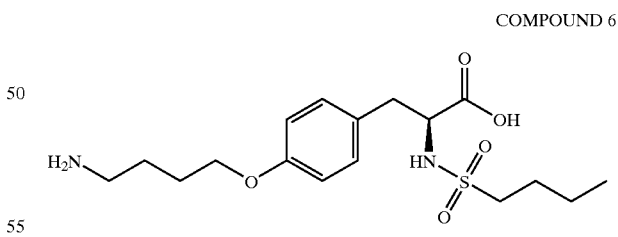

Compound 5 (1.3 g (2.6 mmol) was dissolved in 20 ml of ethyl acetate/methanol/water 5/3/1 and 0.2 ml trifluoroacetic acid (TFA) and hydrogenated under hydrogen (1 atmosphere; Parr Shaker apparatus) at 25 C. in the presence of 100 mg palladium (10% on charcoal). After 3 hours, the catalyst was filtered off and the solvent was evaporated to yield Compound 6 as an oily residue. After lyophilization from water 1.0 gram (quantitative) of Compound 6 was obtained as a white powder. FAB-MS: 373 (M$^+$H$^+$).

G. Compound 7: (S)-3-(4-(4-Guanidinobutyloxy)phenyl-2-butylsulfonamido-propionic Acid as Illustrated in FIG. 38

Step vi

COMPOUND 7

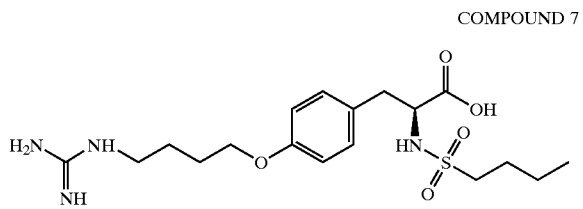

Compound 6 (200 mg; 0.5 mmol), 3,5-dimethylpyrazol-1-carboxamidine nitrate (DPFN) (170 mg; 0.8 mmol; Aldrich Chemical Company) and triethylamine (0.15 ml, 1.0 mmol) in dimethylformamide (DMF; 5 ml) were heated at 60 C. for 12 hours. After cooling, the solvent was evaporated in vacuo, and the residue was purified by HPLC (Lichrocart RP-18, gradient acetonitrile/ water+0.3% TFA 99:1 to 1:99) to yield 50 mg (25%) of Compound 7 as a white, amorphous powder, after lyophilization. FAB-MS: 415 ($M^+H^+$), m.p.: 70 C.

Figure 39:
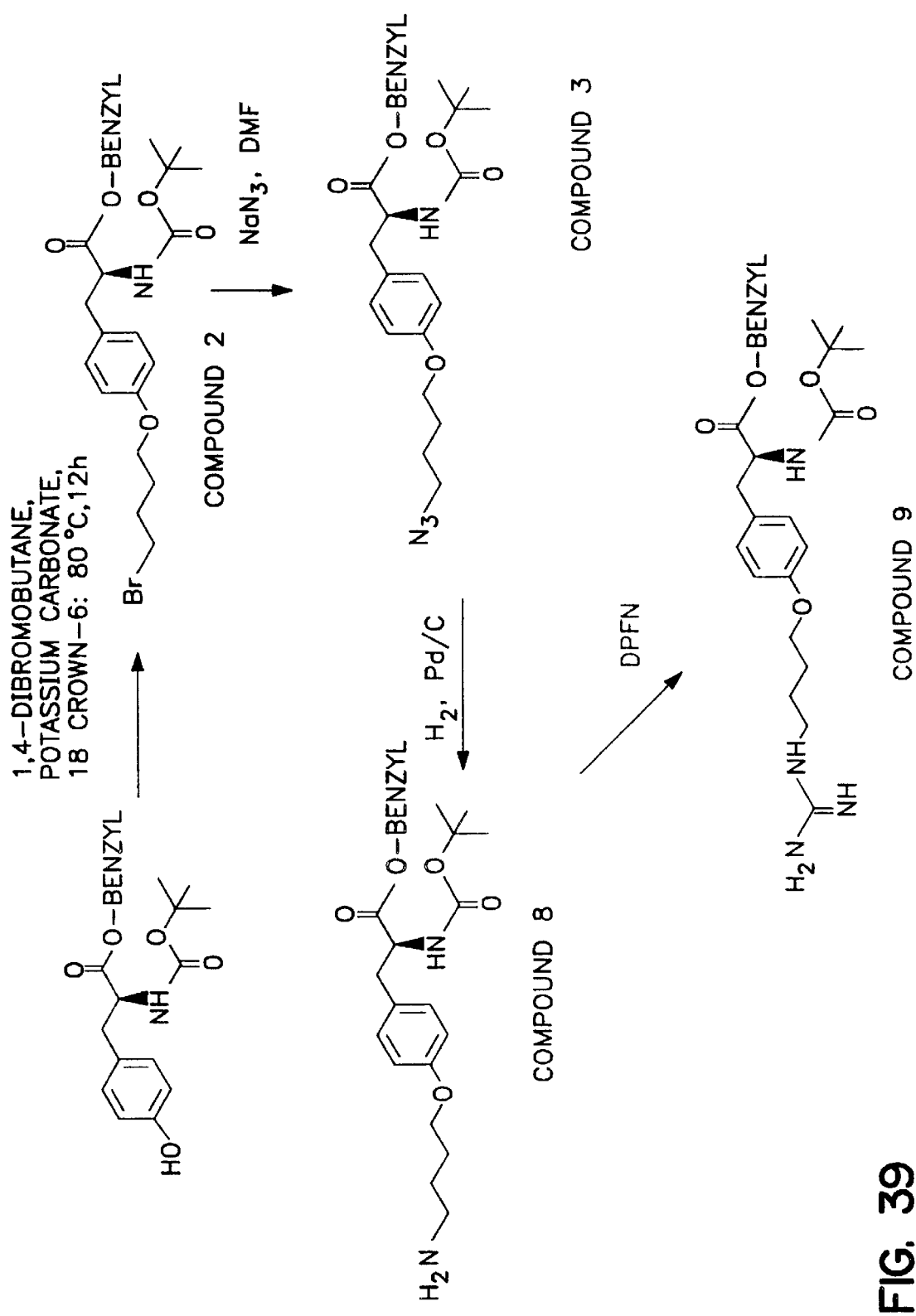

H. Compound 8: (S)-3-(4-(4-Aminobutyloxy)phenyl-2-N-tert.butyloxycarbonyl-propionic Acid as Illustrated in FIG. 39 Step iii

COMPOUND 8

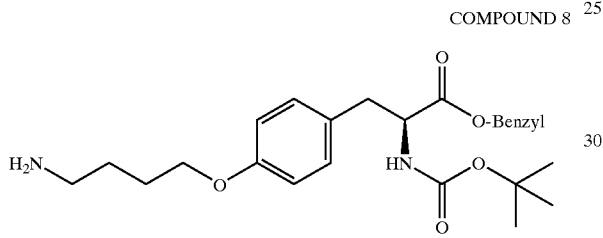

Compound 3 (0.5 g (1.07 mmol) was dissolved in 10 ml of ethyl acetate/ methanol/ water 5/3/1 and 0.1 ml trifluoroacetic acid (TFA) and hydrogenated under hydrogen (1 atmosphere; Parr Shaker apparatus) at 25 C. in the presence of 30 mg palladium (10% on charcoal). After 3 hours, the catalyst was filtered off and the solvent was evaporated to yield Compound 8 as an oily residue. After lyophilization from water 370 milligram (quantitative) of Compound 8 was obtained as a white powder. FAB-MS: 353 ($M^+H^+$).

I. Compound 9: (S)-3-(4-(4-Guanidinobutyloxy)phenyl-2-N-tert.butyloxycarbonyl-propionic Acid as Illustrated in FIG. 39 Step iv

COMPOUND 9

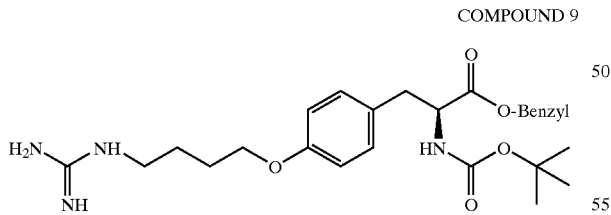

Compound 8 (200 mg; 0.5 mmol), 3,5-dimethylpyrazol-1-carboxamidine nitrate (DPFN) (170 mg; 0.8 mmol; Aldrich Chemical Company) and triethylamine (0.15 ml, 1.0 mmol) in dimethylformamide (DMF; 5 ml) were heated at 60 C. for 12 hours. After cooling, the solvent was evaporated in vacuo, and the residue was purified by HPLC (Lichrocart RP-18, gradient acetonitrile/water+0.3% TFA 99:1 to 1:99) to yield 160 mg (90%) of Compound 9 as a white, amorphous powder, after lyophilization. FAB-MS: 395 ($M^+H^+$).

Figure 40:
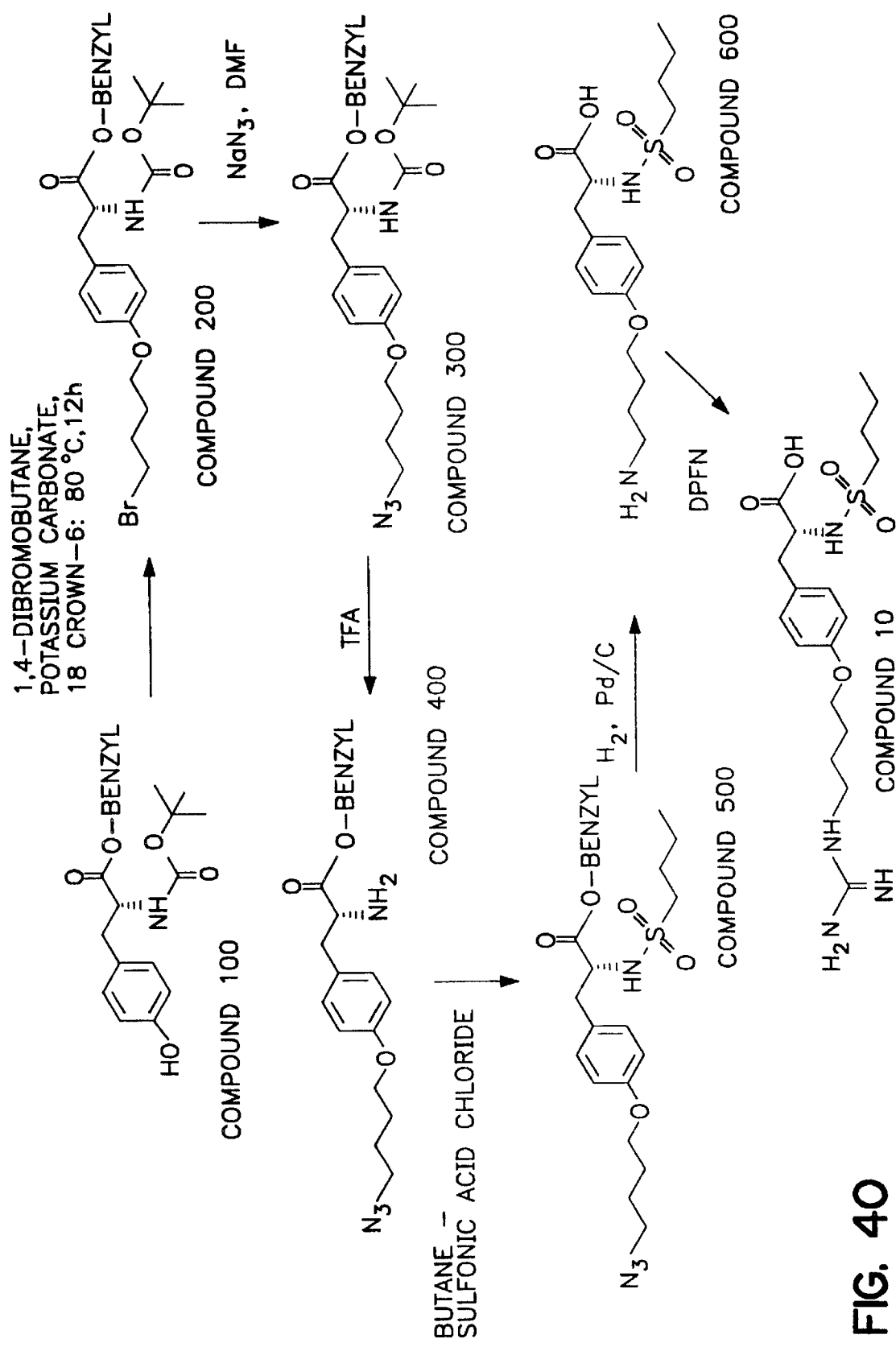

J. Compound 10: (R)-3-(4-(4-Guanidinobutyloxy)phenyl-2-butylsulfonamido-propionic Acid as Illustrated in FIG. 40

Steps i–vi

COMPOUND 10

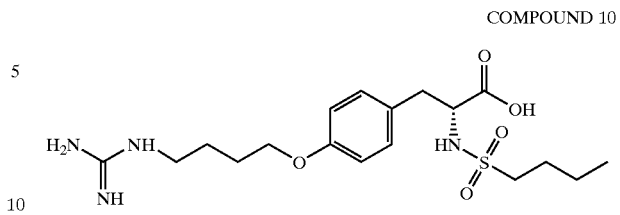

The identical reaction sequence to synthesize Compound 7 was used to prepare the D-tyrosine analog 10 of which 205 mg were obtained as a white amorphous material FAB-MS: 415 ($M^+H^+$) as follows using intermediate Compounds 100–600 to form Compound 10.

1) Compound 100: t-Boc-D-tyrosine benzyl ester as Illustrated in FIG. 40

COMPOUND 100

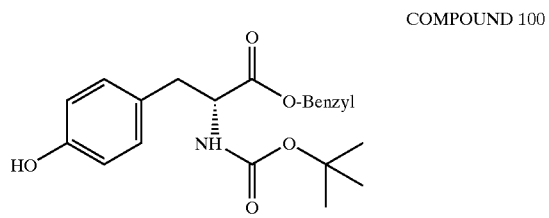

To a solution of N-(tert-butoxycarbonyl)D-tyrosine(t-Boc-L-tyrosine) (1.0 equivalents; Aldrich) in 0.10 M methylene chloride was added dicyclohexylcarbodiimide (DCC) (1.5 equivalents) at 25 C. and allowed to stir for 1 hour. Next, 1.5 equivalents benzyl alcohol was added and the mixture was stirred for an additional 12 hours at 25 C. The reaction mixture was then diluted with ethyl acetate (0.10 M) and washed 2× with water, 1× with brine and dried over magnesium sulfate. The solvent was then removed in vacuo and the crude product was then purified by silica gel column chromatography.

2) Compound 200: (R)-3-(4-(4-Bromobutyloxy)phenyl-2-N-tert-butyloxycarbonyl-propionic acid benzyl ester as illustrated in FIG. 40 Step i

COMPOUND 200

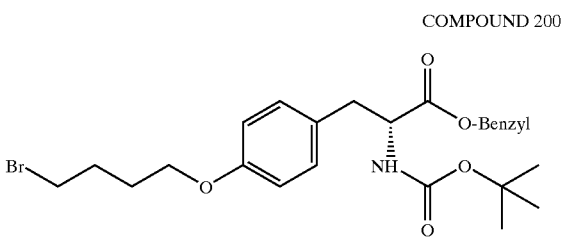

A mixture of t-Boc-D-tyrosine benzyl ester (2 grams, 5.38 mmol; synthesized as described above), 1,4-dibromobutane (1.9 ml, 16.2 mmol; Aldrich), potassium carbonate (5 g) and 18-crown-6 (0.1 g; Aldrich), was heated at 80 C. for 12 hours. After cooling, the precipate was filtered off and the reaction mixture was evaporated to dryness in vacuo. The crude product was then purified by crystallization using 100% hexane to yield 2.5 g (92%) of Compound 200.

3) Compound 300: (R)-3-(4-(4-Azidobutyloxy)phenyl-2-N-tert-butyloxycarbonyl-propionic acid benzyl ester as illustrated in FIG. 40 Step ii

COMPOUND 300

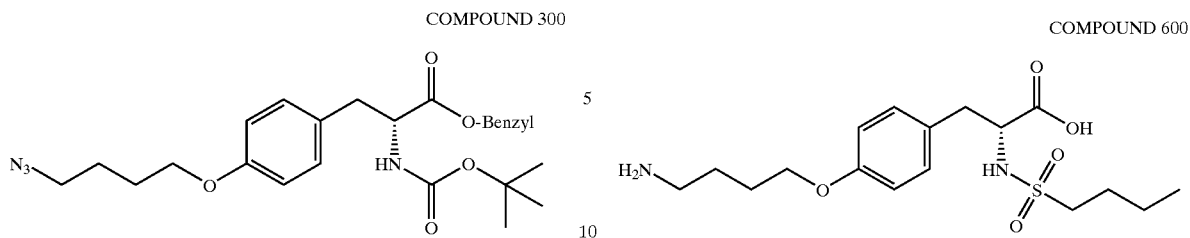

COMPOUND 600

Compound 200 (2.5 g, 4.9 mmol) was stirred with sodium azide (1.6 g, 25 mmol) in dimethylformamide (DMF) (20 ml) at 25 C. for 12 hours. The solvent was then evaporated and the residue was treated with water (approx 10 ml) and extracted twice with ethyl acetate. The organic layers were combined, dried via magnesium sulfate and evaporated to yield 2.0 grams (90%) of Compound 300 as a colorless syrup (FAB-MS: 469 ($M^+H^+$)).

4) Compound 400: (R)-3-(4-(4-Azidobutyloxy)phenyl-2-amino-propionic Acid Benzyl Ester as Illustrated in FIG. 40 Step iii

COMPOUND 400

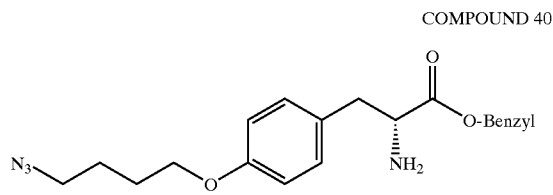

Compound 300 (2.0 g (4.4 mmol)) was dissolved in trifluoroacetic acid (TFA; 2 ml) and stirred for 3 hours at room temperature. Evaporation in vacuo yielded 1.6 grams (quantitative) of Compound 400 as a colorless syrup that was used without further purification for the next step. FAB-MS: 369 ($M^+H^+$).

5) Compound 500: (R)-3-(4-(4-Azidobutyloxy)phenyl-2-butylsulfonamido-propionic Acid Benzyl Ester as Illustrated in FIG. 40 Step iv

COMPOUND 500

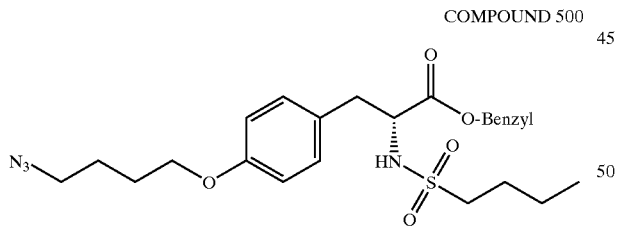

A mixture of Compound 400 (1.6 g; 4.3 mmol), butane sulfonic acid chloride (0.84 ml; 6.6 mmol) and triethyl amine (1.5 equivalents) were stirred in methylene chloride (20 ml) for 12 hours at room temperature. The reaction mixture was then evaporated and the residue was dissolved in ethylacetate, washed with dilute HCl, aqueous sodium bicarbonate and water. After evaporation to dryness the crude product was purified by flash chromatography (silica gel, toluene/ethylacetate 15:1) to yield 1.4 grams (67%) of Compound 500 as an amorphous solid.

6) Compound 600: (R)-3-(4-(4-Aminobutyloxy)phenyl-2-butylsulfonamido-propionic Acid as Illustrated in FIG. 40 Step v Compound 500 (1.3 g (2.6 mmol) was dissolved in 20 ml of ethyl acetate/methanol/water 5/3/1 and 0.2 ml trifluoroacetic acid (TFA) and hydrogenated under hydrogen (1 atmosphere; Parr Shaker apparatus) at 25 C. in the presence of 100 mg palladium (10% on charcoal). After 3 hours, the catalyst was filtered off and the solvent was evaporated to yield Compound 600 as an oily residue. After lyophilization from water 1.0 gram (quantitative) of Compound 600 was obtained as a white powder. FAB-MS: 373 ($M^+H^+$).

7) Compound 10: (R)-3-(4-(4-Guanidinobutyloxy)phenyl-2-butylsulfonamido-propionic Acid as Illustrated in FIG. 40 Step vi Compound 600 (200 mg; 0.5 mmol), 3,5-dimethylpyrazol-1-carboxamidine nitrate (DPFN) (170 mg; 0.8 mmol; Aldrich Chemical Company) and triethylamine (0.15 ml, 1.0 mmol) in dimethylformamide (DMF; 5 ml) were heated at 60 C. for 12 hours. After cooling, the solvent was evaporated in vacuo, and the residue was purified by HPLC (Lichrocart RP-18, gradient acetonitrile/water+0.3% TFA 99:1 to 1:99) to yield 50 mg (25%) of Compound 10 as a white, amorphous powder, after lyophilization. FAB-MS: 415 ($M^+H^+$), m.p.: 70 C.

K. Compound 11: (S)-3-(4-(4-Azidobutyloxy)phenyl-2-(10-camphorsulfonamido)-propionic Acid Benzyl Ester as Illustrated in FIG. 4

COMPOUND 11

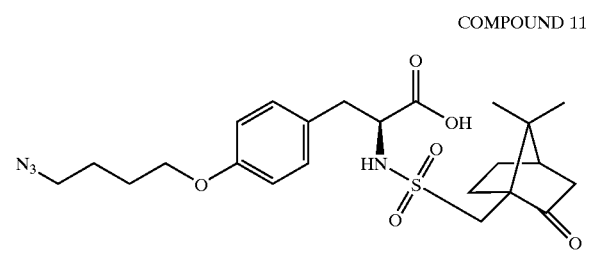

A mixture of compound 4 (1.0 g; 2.7 mmol), 10-camphorsulfonic acid chloride (6.6 mmol; Aldrich Chemical Company) and triethyl amine (1.5 equivalents) were stirred in methylene chloride (20 mL) for 12 hours at room temperature. The reaction mixture was then evaporated and the residue was dissolved in ethylacetate, washed with dilute HCl, aqueous sodium bicarbonate and water. After evaporation to dryness the crude product was purified by flash chromatography (silica gel, toluene/ethylacetate 15:1) to yield 1.4 grams (67%) of compound 11 as an amorphous solid.

Figure 41:
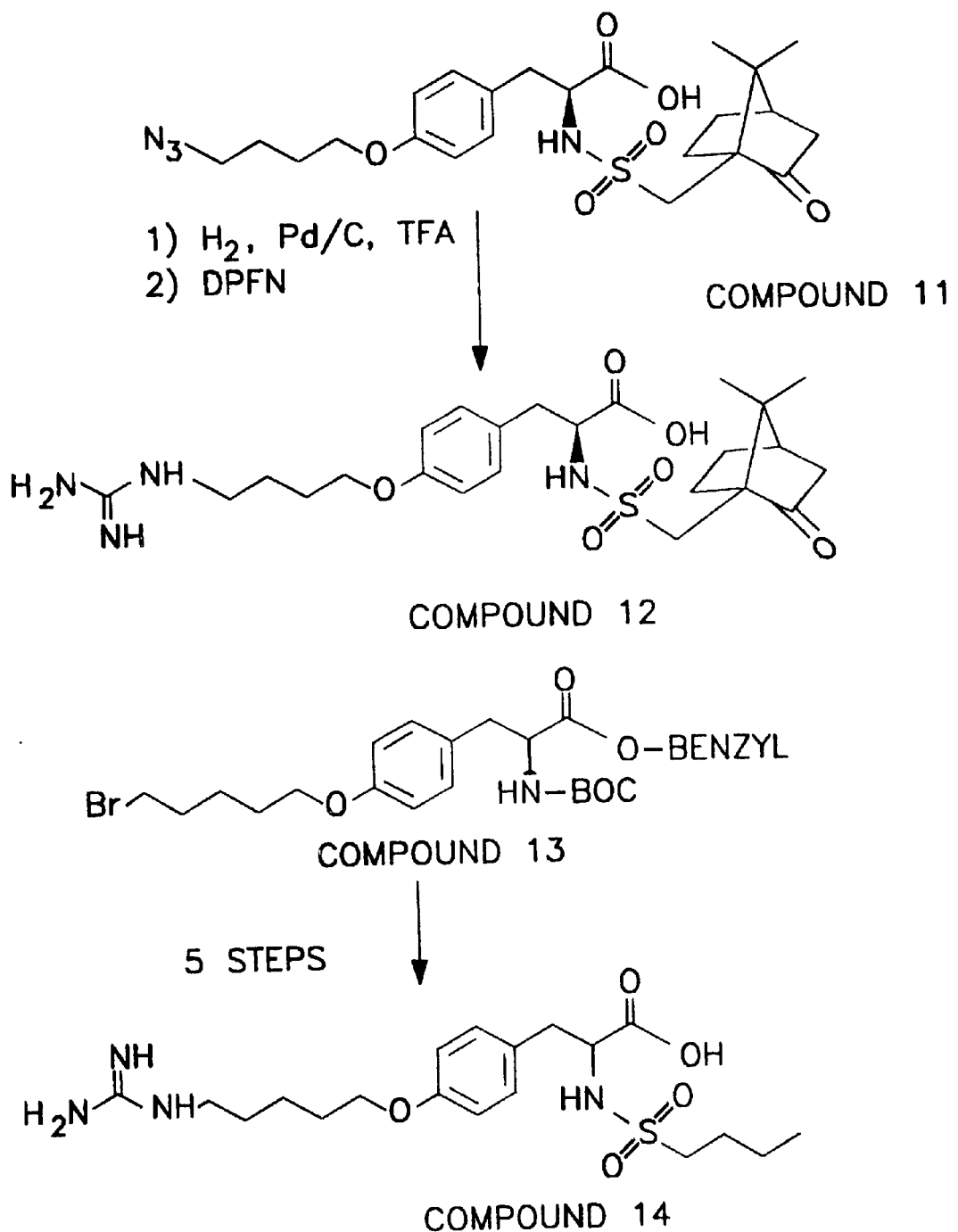

L. Compound 12: (S)-3-(4-(4-Guanidinobutyloxy)phenyl-2-(10-camphorsulfonamido)-propionic Acid as Illustrated in FIG. 41 steps i–ii

COMPOUND 12

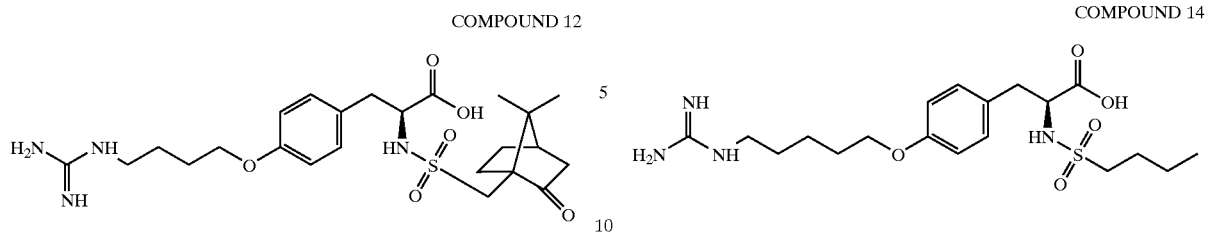

Compound 12 was obtained after hydrogenation and guanylation of Compound 11 according to the following conditions:

Step i: Compound 11 (1.3 g (2.6 mmol) was dissolved in 20 ml of ethyl acetate/methanol/water 5/3/1 and 0.2 ml trifluoroacetic acid (TFA) and hydrogenated under hydrogen (1 atmosphere; Parr Shaker apparatus) at 25 C. in the presence of 100 mg palladium (10% on charcoal). After 3 hours, the catalyst was filtered off and the solvent was evaporated to yield the intermediate amine as an oily residue. After lyophilization from water 1.0 gram (quantitative) of the intermediate amine was obtained as a white powder, which was carried on as follows:

Step ii: The above formed intermediate amine compound (200 mg; 0.5 mmol), 3,5-dimethylpyrazol-1-carboxamidine nitrate (DPFN) (170 mg; 0.8 mmol; Aldrich Chemical Company) and triethylamine (0.15 ml, 1.0 mmol) in dimethylformamide (DMF; 5 ml) were heated at 60 C. for 12 hours. After cooling, the solvent was evaporated in vacuo, and the residue was purified by HPLC (Lichrocart RP-18, gradient acetonitrile/water+0.3% TFA 99:1 to 1:99) to yield 50 mg (25%) of Compound 12 as a white, amorphous powder, after lyophilization. FAB-MS: 509.6 (M$^+$H$^+$).

M. Compound 13: (S)-3-(4-(5-Bromopentyloxy)phenyl-2-N-tert.butyloxycarbonyl-propionic Acid Benzyl Ester as Illustrated in FIG. 41

COMPOUND 13

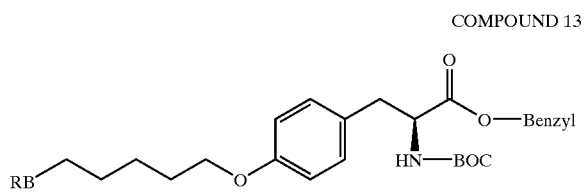

A mixture of t-Boc-L-tyrosine benzyl ester (4.5 grams, 12.1 mmol; Compound 1 synthesized as described above), 1,5-dibromopentane (5 ml, 36.7 mmol; Aldrich), potassium carbonate (10 g) and 18-crown-6 (0.25 g; Aldrich), was heated at 80 C. for 12 hours. After cooling, the precipitate was filtered off and the reaction mixture was evaporated to dryness in vacuo. The crude product was then purified by crystallization using 100% hexane to yield 5.35 g (85%) of Compound 13.

N. Compound 14: (S)-3-(4-(5-Guanidinopentyloxy)phenyl-2-butylsulfonamido-propionic Acid as Illustrated in FIG. 41 steps i–v

COMPOUND 14

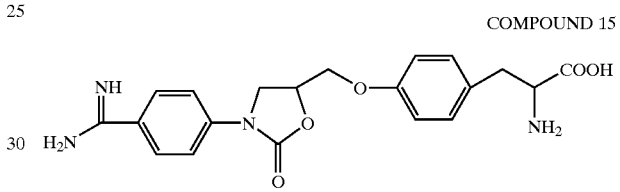

The 5 step reaction sequence of bromine-azide-exchange, Boc-cleavage, sulfonylation with butane sulfonic acid chloride, hydrogenation and guanylation with DPFN was carried out identically to the above procedures using intermediate Compounds 1–6 to form Compound 7 or the procedures using Compounds 100–600 to form Compound 10, as disclosed above. Compound 14 was obtained as a white powder FAB-MS: 429 (M$^+$H$^+$).

O. Compound 15: 3-(4-amidinophenyl)-5-(4-(2-carboxy-2-amino-ethyl)phenoxy)methyl-2-oxazolidinone, dihydrochloride as Shown in FIG. 42

1) Synthesis of Starting Material 2-N-BOC-amino-3-(4-hydroxy-phenyl)propionate for Compound 15

COMPOUND 15

The starting material 2-N-BOC-amino-3-(4-hydroxy-phenyl)propionate was obtained via esterification of (D or L), N-(tert-butoxycarbonyl)-L(D)-tyrosine (t-Boc-L(D)-tyrosine) (1.0 equivalents; Sigma) in 0.10 M methanol and dilute 1% HCl. The reaction mixture was stirred at 25 C. for 12 hours and then neutralized via potassium carbonate and then diluted with ethyl acetate (0.10 M) and washed 2× with water, 1× with brine and dried over magnesium sulfate. The solvent was then removed in vacuo and the crude product was then purified by silica gel column chromatography to obtain 2-N-BOC-amino-3-(4-hydroxy-phenyl)propionate.

2) Synthesis of starting material 3-D-N-BOC-amidino-phenyl-5-methanesulfonyloxy-methyl-2-oxazolidinone for Compound 15: 3-step procedure as follows:

p-amino-benzonitrile (1.0 equivalents; Aldrich) in methylene chloride (0.10 M) was stirred with 2,3-epoxypropanol (1.0 equivalents; Aldrich) for 12 hours at 25 C. The solvent was next removed in vacuo and the crude 4-(2,3-dihydroxypropylamino)benzonitrile was carried onto the next step as follows:

4-(2,3-dihydroxypropylamino)benzonitrile (1.0 equivalents; as described above), in dimethylformamide (0.10 M), at 25 C., was stirred with diethyl carbonate (1.1 equivalents; Aldrich) and potassium tert-butylate (1.1 equivalents; Aldrich) at 110 C. for 6 hours. Next, the reaction mixture was diluted with ethyl acetate (0.10 M) and washed 2× with water, 1× with brine and dried over magnesium sulfate. The solvent was then removed in vacuo and the crude product was then purified by silica gel column chromatography to obtain 3-(4-cyanophenyl)-5-hydroxymethyl-2-oxazolidine and carried onto the next step as follows:

3-(4-cyanophenyl)-5-hydroxymethyl-2-oxazolidine (1.0 equivalents; as described above), in methylene chloride (0.10 M) at 25 C. was stirred with 1.1 equivalents hydrogen sulfide, 1.1 equivalents methyl iodide, and 1.1 equivalents ammonium acetate. The reaction mixture was stirred for 6 hours and then diluted with ethyl acetate (0.10 M) and washed 2× with water, 1× with brine and dried over magnesium sulfate. The solvent was then removed in vacuo and the crude product was then purified by silica gel column chromatography to obtain the amidine which was carried onto the next step as follows:

1.0 equivalents of the amidine, synthesized as described above, was protected with 1.1 equivalents of BOC-ON (2-(BOC-oxyimino)-2-phenylacetonitrile; Aldrich) in methylene chloride (0.10 M) at 25 C. and stirred for 6 hours. Next, the reaction mixture was diluted with ethyl acetate (0.10 M) and washed 2× with water, 1× with brine and dried over magnesium sulfate. The solvent was then removed in vacuo and the crude product was then esterified in 0.10 M methylene chloride and 1.1 lents; synthesized as described above), with 4 ml 2N NaOH for 4 hours at room temperature. The mixture was then followed with 40 ml 2N HCl-solution in dioxane added dropwise at 0 C. to 25 C. for 3 hours. The reaction mixture was then quenched with sodium bicarbonate (5 equivalents) and then diluted with ethyl acetate (0.10 M) and washed 2× with water, 1× with brine and dried over magnesium sulfate. The solvent was then removed in vacuo and the crude product was then purified by silica gel column chromatography to obtain Compound 15: 3-(4-amidinophenyl)-5-(4-(2-carboxy-2-amino-ethyl)phenoxy)methyl-2-oxazolidinone, dihydrochloride; m.p. 165C(d).

P. Compound 16: 3-(4-amidinophenyl)-5-(4-(2-carboxy-2-N-butylsulfonylaminoethyl)phenoxy)methyl-2-oxazolidinone as Shown in FIG. X (Old 14)

1) Synthesis of starting material 2-N-butylsulfonylamino-3-(4-hydroxy-phenyl)propionate for Compound 16

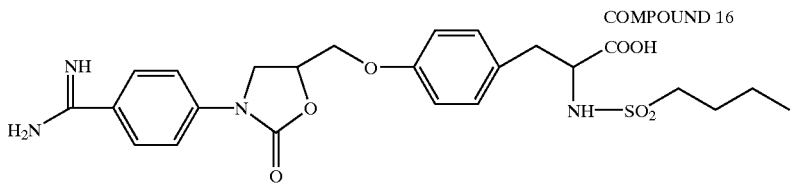

COMPOUND 16 equivalents methanesulfonyl chloride. The reaction mixture was stirred at 0 C. for 6 hours and then quenched with water (5 equivalents) and then diluted with ethyl acetate (0.10 M) and washed 2× with water, 1× with brine and dried over magnesium sulfate. The solvent was then removed in vacuo and the crude product was then purified by silica gel column chromatography to obtain 3-p-N-BOC-amidino-phenyl-5-methanesulfonyloxy-methyl-2-oxazolidinone.

3) Coupling of intermediates 2-N-BOC-amino-3-(4-hydroxy-phenyl)propionate with 3-p-N-BOC-amidino-phenyl-5-methanesulfonyloxy-methyl-2-oxazolidinone to form protected form of Compound 15, 3-(4-BOC-amidinophenyl)-5-(4-(2-methoxy-carbonyl-2N-BOC-aminoethyl)phenoxylmethyl-2-oxazolidinone A mixture of 1.9 grams 2-N-BOC-amino-3-(4-hydroxy-phenyl)propionate (as described above), 20 ml dimethylformamide (DMF) and NaH (1.0 equivalent), was stirred for 30 minutes at room temperature. After stirring, 1.8 grams 3-p-N-BOC-amidino-phenyl-5-methanesulfonyloxy-methyl-2-oxazolidinone (as described above) in 10 ml dimethylformamide (DMF) was added and stirred again for 15 minutes at room temperature. The reaction mixture was then diluted with ethyl acetate (0.10 M) and washed 2× with water, 1× with brine and dried over magnesium sulfate. The solvent was then removed in vacuo and the crude product was then purified by silica gel column chromatography to obtain protected form of Compound 15, 3-(4-BOC-amidinophenyl)-5-(4-(2-methoxy-carbonyl-2N-BOC-aminoethyl)phenoxylmethyl-2-oxazolidinone which was carried onto the next step.

4) Deprotection of protected form of compound 15 to form Compound 15: 3-(4-amidinophenyl)-5-(4-(2-carboxy-2-amino-ethyl)phenoxy)methyl-2-oxazolidinone, dihydrochloride, FIG. 42

Treatment of the protected form of Compound 15, 3-(4-BOC-amidinophenyl)-5-(4-(2-methoxy-carbonyl-2N-BOC-aminoethyl)phenoxylmethyl-2-oxazolidinone (1.0 equiva- The starting material 2-N-butylsulfonylamino-3-(4-hydroxy-phenyl)propionate was obtained via esterification of ((D or L) tyrosine) (1.0 equivalents; Sigma) in 0.10 M methanol and dilute 1% HCl. The reaction mixture was stirred at 25 C. for 12 hours and then neutralized via potassium carbonate and then diluted with ethyl acetate (0.10 M) and washed 2× with water, 1× with brine and dried over magnesium sulfate. The solvent was then removed in vacuo and the crude product was then carried on as follows:

A mixture of the above compound (4.3 mmol), butane sulfonic acid chloride (6.6 mmol) and triethyl amine (1.5 equivalents) were stirred in methylene chloride (20 ml) for 12 hours at room temperature. The reaction mixture was then evaporated and the residue was dissolved in ethylacetate, washed with dilute HCl, aqueous sodium bicarbonate and water. After evaporation to dryness the crude product was purified by flash chromatography (silica gel, toluene/ethylacetate 15:1) to yield the title compound.

2) Synthesis of starting material 3-p-N-BOC-amidino-phenyl-5-methanesulfonyloxy-methyl-2-oxazolidinone for Compound 16: 3-step procedure as follows:

p-amino-benzonitrile (1.0 equivalents; Aldrich) in methylene chloride (0.10 M) was stirred with 2,3-epoxypropanol (1.0 equivalents; Aldrich) for 12 hours at 25 C. The solvent was next removed in vacuo and the crude 4-(2,3-dihydroxypropylamino)benzonitrile was carried onto the next step as follows:

4-(2,3-dihydroxypropylamino)benzonitrile (1.0 equivalents; as described above), in dimethylformamide (0.10 M), at 25 C., was stirred with diethyl carbonate (1.1 equivalents; Aldrich) and potassium tert-butylate (1.1 equivalents; Aldrich) at 110 C. for 6 hours. Next, the reaction mixture was diluted with ethyl acetate (0.10 M) and washed 2× with water, 1× with brine and dried over magnesium sulfate. The solvent was then removed in vacuo and the crude product was then purified by silica gel column chromatography to obtain 3-(4- cyanophenyl)-5-hydroxymethyl-2-oxazolidine and carried onto the next step as follows:

3-(4-cyanophenyl)-5-hydroxymethyl-2-oxazolidine (1.0 equivalents; as described above), in methylene chloride (0.10 M) at 25 C. was stirred with 1.1 equivalents hydrogen sulfide, 1.1 equivalents methyl iodide, and 1.1 equivalents ammonium acetate. The reaction mixture was stirred for 6 hours and then diluted with ethyl acetate (0.10 M) and washed 2× with water, 1× with brine and dried over magnesium sulfate. The solvent was then removed in vacuo and the crude product was then purified by silica gel column chromatography to obtain the amidine which was carried onto the next step as follows:

1.0 equivalents of the amidine, synthesized as described above, was protected with 1.1 equivalents of BOC-ON (2-(BOC-oxyimino)-2-phenylacetonitrile; Aldrich) in methylene chloride (0.10 M) at 25 C. and stirred for 6 hours. Next, the reaction mixture was diluted with ethyl acetate (0.10 M) and washed 2× with water, 1× with brine and dried over magnesium sulfate. The solvent was then removed in vacuo and the crude product was then esterified in 0.10 M methylene chloride and 1.1 equivalents methanesulfonyl chloride. The reaction mixture was stirred at 0 C. for 6 hours and then quenched with water (5 equivalents) and then diluted with ethyl acetate (0.10 M) and washed 2× with water, 1× with brine and dried over magnesium sulfate. The solvent was then removed in vacuo and the crude product was then purified by silica gel column chromatography to obtain 3-p-N-BOC-amidino-phenyl-5-methanesulfonyloxy-methyl-2-oxazolidinone.

3) Coupling of intermediates 2-N-butylsulfonylamino-3-(4-hydroxy-phenyl)propionate with 3-p-N-BOC-amidino-phenyl-5-methanesulfonyloxy-methyl-2-oxazolidinone to form Protected form of Compound 16, 3-(4-BOC-amidinophenyl)-5-(4-(2-methoxy-carbonyl-2-N-butylsulfonylaminoethyl)rphenyoxylmethyl-2-oxazolidinone A mixture of 1.9 grams 2-N-butylsulfonylamino-3-(4-hydroxy-phenyl)propionate (as described above), 20 ml dimethylformamide (DMF) and NaH (1.0 equivalent), was stirred for 30 minutes at room temperature. After stirring, 1.8 grams 3-p-N-BOC-amidino-phenyl-5-methanesulfonyloxy-methyl-2-oxazolidinone (as described above) in 10 ml dimethylformamide (DMF) was added and stirred again for 15 minutes at room temperature. The reaction mixture was then diluted with ethyl acetate (0.10 M) and washed 2× with water, 1× with brine and dried over magnesium sulfate. The solvent was then removed in vacuo and the crude product was then purified by silica gel column chromatography to obtain protected form of Compound 16, 3-(4-BOC-amidinophenyl)-5-(4-(2-methoxy-carbonyl-2-N-butylsulfonylaminoethyl)-phenyoxylmethyl-2-oxazolidinone which was carried onto the next step.

4) Deprotection of protected form of Compound 16 to Form Compound 16: 3-(4-amidinophenyl)-5-(4-(2-carboxy-2-N-butylsulfonylaminoethyl)phenoxy)methyl-2-oxazolidinone. FIG. 42

Treatment of the protected form of Compound 16, 3-(4-BOC-amidinophenyl) -5(4-(2-methoxy-carbonyl-2-N-butylsulfonylaminoethyl)phenyoxylmethyl-2-oxazolidinone (1.0 equivalents; synthesized as described above), with 4 ml 2N NaOH for 4 hours at room temperature. The mixture was then followed with 40 ml 2N HCl-solution in dioxane added dropwise at 0 C. to 25 C. for 3 hours. The reaction mixture was then quenched with sodium bicarbonate (5 equivalents) and then diluted with ethyl acetate (0.10 M) and washed 2× with water, 1× with brine and dried over magnesium sulfate. The solvent was then removed in vacuo and the crude product was then purified by silica gel column chromatography to obtain Compound 16: 3-(4-amidinophenyl)-5-(4-(2-carboxy-2-N-butylsulfonylaminoethyl)phenoxy)methyl-2-oxazolidinone; m.p. 236–237 C.

Q. Compound 17: 3-(4-amidinophenyl)-5-(4-(2-carboxy-2-N-propyl-sulfonylaminoethyl)phenoxy)methyl-2-oxazolidinone as shown in FIG. 42

1) Synthesis of starting material 2-N-propyl-sulfonylamino-3-(4-hydroxy-phenyl)propionate for Compound 17;

COMPOUND 17

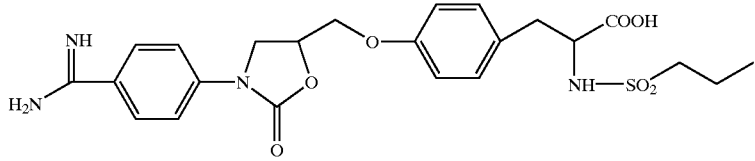

The starting material 2-N-propyl-sulfonylamino-3-(4-hydroxy-phenyl)propionate was obtained via esterification of ((D or L) tyrosine) (1.0 equivalents; Sigma) in 0.10 M methanol and dilute 1% HCl. The reaction mixture was stirred at 25 C. for 12 hours and then neutralized via potassium carbonate and then diluted with ethyl acetate (0.10 M) and washed 2× with water, 1× brine and dried over magnesium sulfate. The solvent was then removed in vacuo and the crude product was then carried on as follows:

A mixture of the above compound (4.3 mmol), propyl sulfonic acid chloride (6.6 mmol; Aldrich) and triethyl amine (1.5 equivalents) were stirred in methylene chloride (20 ml) for 12 hours at room temperature. The reaction mixture was then evaporated and the residue was dissolved in ethylacetate, washed with dilute HCl, aqueous sodium bicarbonate and water. After evaporation to dryness the crude product was purified by flash chromatography (silica gel, toluene/ethylacetate 15:1) to yield the title compound.

2) Synthesis of starting material 3-p-N-BOC-amidino-phenyl-5-methanesulfonyloxy-methyl-2-oxazolidinone for Compound 17: 3-step Procedure as Follows:

p-amino-benzonitrile (1.0 equivalents; Aldrich) in methylene chloride (0.10 M) was stirred with 2,3-epoxypropanol (1.0 equivalents; Aldrich) for 12 hours at 25 C. The solvent was next removed in vacuo and the crude 4-(2,3-dihydroxypropylamino)benzonitrile was carried onto the next step as follows:

4-(2,3-dihydroxypropylamino)benzonitrile (1.0 equivalents; as described above), in dimethylformamide (0.10 M), at 25 C., was stirred with diethyl carbonate (1.1 equivalents; Aldrich) and potassium tert-butylate (1.1 equivalents; Aldrich) at 110 C. for 6 hours. Next, the reaction mixture was diluted with ethyl acetate (0.10 M) and washed 2x with water, 1x with brine and dried over magnesium sulfate. The solvent was then removed in vacuo and the crude product was then purified by silica gel column chromatography to obtain 3-(4-cyanophenyl)-5-hydroxymethyl-2-oxazolidine and carried onto the next step as follows:

3-(4-cyanophenyl)-5-hydroxymethyl-2-oxazolidine (1.0 equivalents; as described above), in methylene chloride (0.10 M) at 25 C. was stirred with 1.1 equivalents hydrogen sulfide, 1.1 equivalents methyl iodide, and 1.1 equivalents ammonium acetate. The reaction mixture was stirred for 6 hours and then diluted with ethyl acetate (0.10 M) and washed 2x with water, 1x with brine and dried over magnesium sulfate. The solvent was then removed in vacuo and the crude product was then purified by silica gel column chromatography to obtain the amidine which was carried onto the next step as follows:

1.0 equivalents of the amidine, synthesized as described above, was protected with 1.1 equivalents of BOC-ON (2-(BOC-oxyimino)-2-phenylacetonitrile; Aldrich) in methylene chloride (0.10 M) at 25 C. and stirred for 6 hours. Next, the reaction mixture was diluted with ethyl acetate (0.10 M) and washed 2x with water, 1x with brine and dried over magnesium sulfate. The solvent was then removed in vacuo and the crude product was then esterified in 0.10 M methylene chloride and 1.1 equivalents methanesulfonyl chloride. The reaction mixture was stirred at 0 C. for 6 hours and then quenched with water (5 equivalents) and then diluted with ethyl acetate (0.10 M) and washed 2x with water, 1x with brine and dried over magnesium sulfate. The solvent was then removed in vacuo and the crude product was then purified by silica gel column chromatography to obtain 3-p-N-BOC-amidino-phenyl-5-methanesulfonyloxy-methyl-2-oxazolidinone.

3) Coupling of intermediates 2-N-propyl-sulfonylamino-3-(4-hydroxy-phenyl)propionate with 3-p-N-BOC-amidino-phenyl-5-methanesulfonyloxy-methyl-2-oxazolidinone to form protected form of Compound 17, 3-(4-BOC-amidinophenyl)-5-(4-(2-methoxy-carbonyl-2-N-propyl-sulfonylaminoethyl)-phenyoxylmethyl-2-oxazolidinone A mixture of 1.9 grams 2-N-propyl-sulfonylamino-3-(4-hydroxy-phenyl)propionate (as described above), 20 ml dimethylformamide (DMF) and NaH (1.0 equivalent), was stirred for 30 minutes at room temperature. After stirring, 1.8 grams 3-p-N-BOC-amidino-phenyl-5-methanesulfonyloxy-methyl-2-oxazolidinone (as described above) in 10 ml dimethylformamide (DMF) was added and stirred again for 15 minutes at room temperature. The reaction mixture was then diluted with ethyl acetate (0.10 M) and washed 2x with water, 1x with brine and dried over magnesium sulfate. The solvent was then removed in vacuo and the crude product was then purified by silica gel column chromatography to obtain protected form of Compound 17, 3-(4-BOC-amidinophenyl)-5-(4-(2-methoxy-carbonyl-2-N-propyl-sulfonylaminoethyl)-phenyoxylmethyl-2-oxazolidinone which was carried onto the next step.

4) Deprotection of protected form of compound 17 to Form Compound 17: 3-(4-amidinophenyl)-5-(4-(2-carboxy-2-N-propylsulfonylaminoethyl)phenoxy)methyl-2-oxazolidinone. FIG. 42

Treatment of the protected form of Compound 17, 3-(4-BOC-amidinophenyl)-5-(4-(2-methoxy-carbonyl-2-N-propylsulfonylaminoethyl)phenyoxylmethyl-2-oxazolidinone (1.0 equivalents; synthesized as described above), with 4 ml 2N NaOH for 4 hours at room temperature. The mixture was then followed with 40 ml 2N HCl-solution in dioxane added dropwise at 0 C. to 25 C. for 3 hours. The reaction mixture was then quenched with sodium bicarbonate (5 equivalents) and then diluted with ethyl acetate (0.10 M) and washed 2x with water, 1x with brine and dried over magnesium sulfate. The solvent was then removed in vacuo and the crude product was then purified by silica gel column chromatography to obtain Compound 17: 3-(4-amidinophenyl)-5-(4-(2-carboxy-2-N-propylsulfonylaminoethyl)phenoxy)methyl-2-oxazolidinone; m.p. 200 C. (d).

R. Compound 18: 3-(4-amidinophenyl)-5-(4-(2-carboxy-2-N-ethyl-sulfonylaminoethyl)phenoxy)methyl-2-oxazolidinone as Shown in FIG. 42

1) Synthesis of starting material 2-N-ethyl-sulfonylamino-3-(4-hydroxy-phenyl)propionate for Compound 18

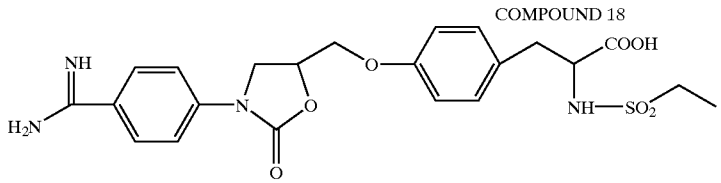

COMPOUND 18

The starting material 2-N-ethyl-sulfonylamino-3-(4-hydroxy-phenyl)propionate was obtained via esterification of ((D or L) tyrosine) (1.0 equivalents; Sigma) in 0.10 M methanol and dilute 1% HCl. The reaction mixture was stirred at 25 C. for 12 hours and then neutralized via potassium carbonate and then diluted with ethyl acetate (0.10 M) and washed 2x with water, 1x with brine and dried over magnesium sulfate. The solvent was then removed in vacuo and the crude product was then carried on as follows:

A mixture of the above compound (4.3 mmol), ethyl sulfonic acid chloride (6.6 mmol; Aldrich) and triethyl amine (1.5 equivalents) were stirred in methylene chloride (20 ml) for 12 hours at room temperature. The reaction mixture was then evaporated and the residue was dissolved in ethylacetate, washed with dilute HCl, aqueous sodium bicarbonate and water. After evaporation to dryness the crude product was purified by flash chromatography (silica gel, toluene/ethylacetate 15:1) to yield the title compound.

2) Synthesis of starting material 3-D-N-BOC-amidino-phenyl-5-methanesulfonyloxy-methyl-2-oxazolidinone for Compound 18: 3-step Procedure as Follows:

p-amino-benzonitrile (1.0 equivalents; Aldrich) in methylene chloride (0.10 M) was stirred with 2,3-epoxypropanol (1.0 equivalents; Aldrich) for 12 hours at 25 C. The solvent was next removed in vacuo and the crude 4-(2,3-dihydroxypropylamino)benzonitrile was carried onto the next step as follows:

4-(2,3-dihydroxypropylamino)benzonitrile (1.0 equivalents; as described above), in dimethylformamide (0.10 M), at 25 C., was stirred with diethyl carbonate (1.1 equivalents; Aldrich) and potassium tert-butylate (1.1 equivalents; Aldrich) at 110 C. for 6 hours. Next, the reaction mixture was diluted with ethyl acetate (0.10 M) and washed 2× with water, 1× with brine and dried over magnesium sulfate. The solvent was then removed in vacuo and the crude product was then purified by silica gel column chromatography to obtain 3-(4-cyanophenyl)-5-hydroxymethyl-2-oxazolidine and carried onto the next step as follows:

3-(4-cyanophenyl)-5-hydroxymethyl-2-oxazolidine (1.0 equivalents; as described above), in methylene chloride (0.10 M) at 25 C. was stirred with 1.1 equivalents hydrogen sulfide, 1.1 equivalents methyl iodide, and 1.1 equivalents ammonium acetate. The reaction mixture was stirred for 6 hours and then diluted with ethyl acetate (0.10 M) and washed 2× with water, 1× with brine and dried over magnesium sulfate. The solvent was then removed in vacuo and the crude product was then purified by silica gel column chromatography to obtain the amidine which was carried onto the next step as follows:

1.0 equivalents of the amidine, synthesized as described above, was protected with 1.1 equivalents of BOC-ON (2-(BOC-oxyimino)-2-phenylacetonitrile; Aldrich) in methylene chloride (0.10 M) at 25 C. and stirred for 6 hours. Next, the reaction mixture was diluted with ethyl acetate (0.10 M) and washed 2× with water, 1× with brine and dried over magnesium sulfate. The solvent was then removed in vacuo and the crude product was then esterified in 0.10 M methylene chloride and 1.1 equivalents methanesulfonyl chloride. The reaction mixture was stirred at 0 C. for 6 hours and then quenched with water (5 equivalents) and then diluted with ethyl acetate (0.10 M) and washed 2× with water, 1× with brine and dried over magnesium sulfate. The solvent was then removed in vacuo and the crude product was then purified by silica gel column chromatography to obtain 3-p-N-BOC-amidino-phenyl-5-methanesulfonyloxy-methyl-2-oxazolidinone.

3) Coupling of intermediates 2-N-ethyl-sulfonylamino-3-(4-hydroxy-phenyl)propionate with 3-n-N-BOC-amidino-phenyl-5-methanesulfonyloxy-methyl-2-oxazolidinone to form protected form of Compound 18, 3-(4-BOC-amidinophenyl)-5-(4-(2-methoxy-carbonyl-2-N-ethyl-sulfonylaminoethyl)-phenyoxylmethyl-2-oxazolidinone A mixture of 1.9 grams 2-N-ethyl-sulfonylamino-3-(4-hydroxy-phenyl)propionate (as described above), 20 ml dimethylformamide (DMF) and NaH (1.0 equivalent), was stirred for 30 minutes at room temperature. After stirring, 1.8 grams 3-p-N-BOC-amidino-phenyl-5-methanesulfonyloxy-methyl-2-oxazolidinone (as described above) in 10 ml dimethylformamide (DMF) was added and stirred again for 15 minutes at room temperature. The reaction mixture was then diluted with ethyl acetate (0.10 M) and washed 2× with water, 1× with brine and dried over magnesium sulfate. The solvent was then removed in vacuo and the crude product was then purified by silica gel column chromatography to obtain protected form of Compound 18, 3-(4-BOC-amidinophenyl)-5-(4-(2-methoxy-carbonyl-2-N-ethyl-sulfonylaminoethyl)-phenyoxylmethyl-2-oxazolidinone which was carried onto the next step.

4) Deprotection of protected form of Compound 18 to form Compound 18: 3-(4-amidinophenyl)-5-(4-(2-carboxy-2-N-ethylsulfonylaminoethyl)phenoxy)methyl-2-oxazolidinone. FIG. 42

Treatment of the protected form of Compound 18, 3-(4-BOC-amidinophenyl)-5-(4-(2-methoxy-carbonyl-2-N-ethylsulfonylaminoethyl)phenyoxylmethyl-2-oxazolidinone (1.0 equivalents; synthesized as described above), with 4 ml 2N NaOH for 4 hours at room temperature. The mixture was then followed with 40 ml 2N HCl-solution in dioxane added dropwise at 0 C. to 25 C. for 3 hours. The reaction mixture was then quenched with sodium bicarbonate (5 equivalents) and then diluted with ethyl acetate (0.10 M) and washed 2× with water, 1× with brine and dried over magnesium sulfate. The solvent was then removed in vacuo and the crude product was then purified by silica gel column chromatography to obtain Compound 18: 3-(4-amidinophenyl)-5-(4-(2-carboxy-2-N-ethylsulfonylaminoethyl)phenoxy)methyl-2-oxazolidinone; m.p. 212 C. (d).

14. Inhibition of Growth Factor-Induced Anaiogenesis as Measured in the CAM Assay with by Intravenous Application of $\alpha_v\beta_3$ Ligand Organic Mimetics The effect on growth factor-induced angiogenesis with organic mimetics of an $\alpha_v\beta_3$ ligand intravenously injected into the CAM preparation was also evaluated for use in this invention.

The 10 day old CAM preparation was used as previously described in Example 5A. Twenty-four hours after bFGF-induced angiogenesis was initiated, the organic mimetics referred to as compounds 16 (81218), 17 (87292) and 18 (87293) were separately intravenously injected into the CAM preparation in a volume of 100 ul at a concentration of 1 mg/ml (100 ug/embryo) in 20% tetraglycol-PBS at pH 7.0. In parallel assays, compounds 7 (96112), 9 (99799), 10 (96229), 12 (112854) and 14 (96113) were similarly evaluated. The effects of the organic mimetics were analyzed 48 hours later where quantification was performed by counting the number of blood vessel branch points in the area of the filter disc in a double blind approach.

Figure 43:
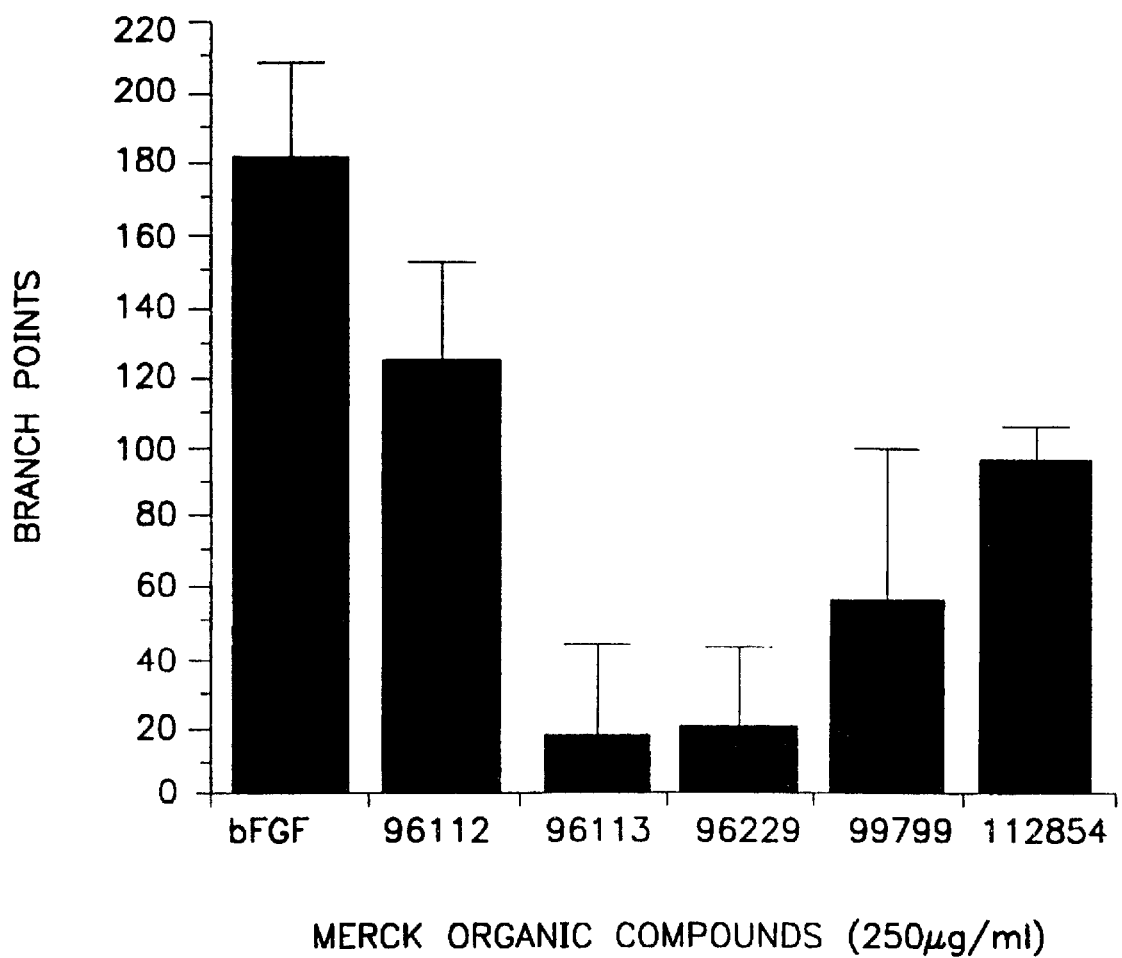
FIGS. 43 and 44 show the effects of various organic molecules on bFGF-induced angiogenesis in a CAM assay as further described in Example 14. Branch points are plotted on the Y-axis against the various compounds used at 250 ug/ml on the X-axis in FIG. 43 and 100 ug/ml in FIG. 44.
Figure 44:
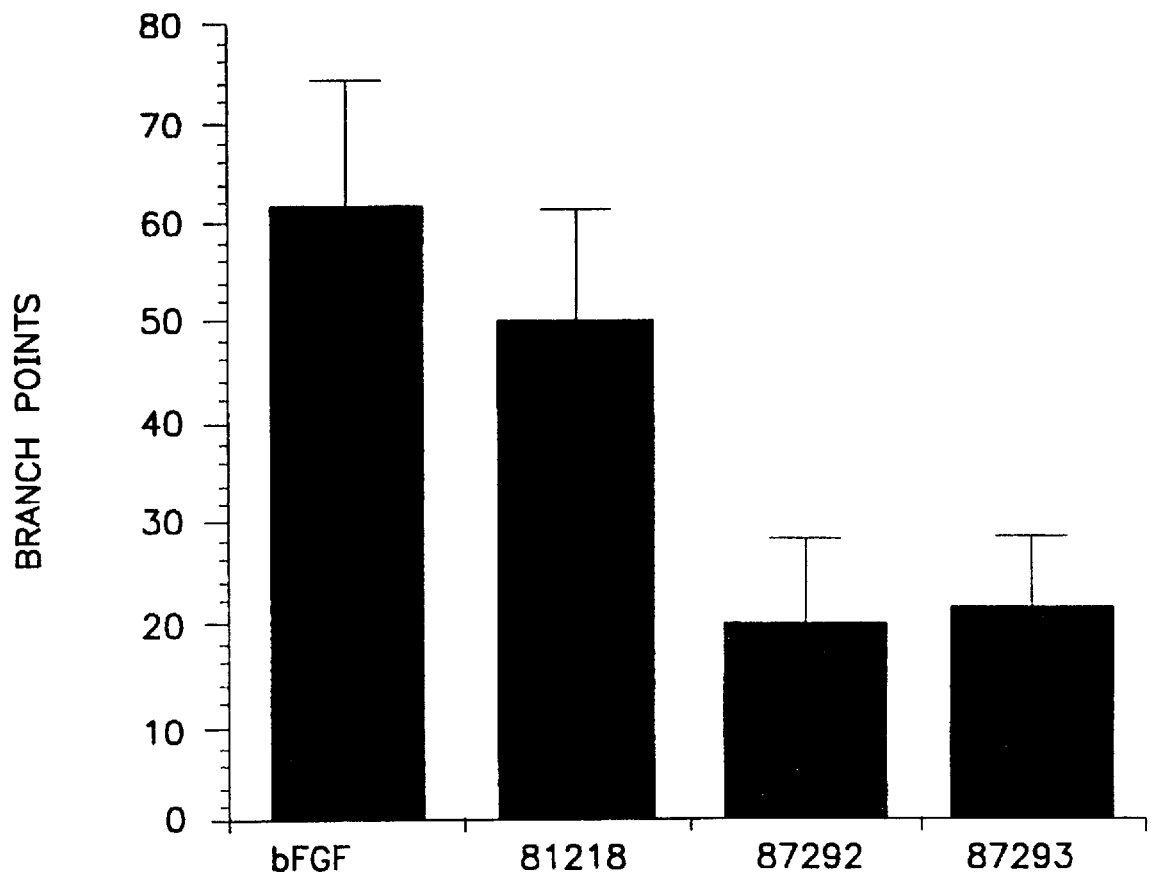

The results are respectively shown in FIGS. 43 and 44. In FIG. 43, compounds 14 (96113), 10 (96229), 9 (99799) and 12 (112854), in decreasing order of inhibition, were effective at reducing the number of branch points of new blood vessels compared to control bFGF induction and compared to compound 7 (96112). In FIG. 44, compounds 17 (87292) and 18 (87293) exhibited anti-angiogenic properties as compared to untreated bFGF control and treatment with compound 16 (81218).

In a third assay, organic compounds 7 (96112), 10 (96229) and 14 (96113) were assessed as inhibitors of bFGF-induced angiogenesis along with peptides 69601 and 66203. For this assay, 250 ug/ml of organic compounds were administered 18 hours after bFGF treatment as described in Example 7B. The results are shown in FIG. 28 where as above, compounds 14 (96113) and 10 (96229) almost completely inhibited the formation of new blood vessels induced by bFGF.

Thus, the aforementioned Examples demonstrate that integrin $\alpha_v\beta_3$ plays a key role in angiogenesis induced by a variety of stimuli and as such $\alpha_v\beta_3$ is a valuable therapeutic target with the $\alpha_v\beta_3$ antagonists of this invention for diseases characterized by neovascularization.

The foregoing written specification is considered to be sufficient to enable one skilled in the art to practice the invention. The present invention is not to be limited in scope by the cell line deposited, since the deposited embodiment is intended as a single illustration of one aspect of the invention and any cell line that is functionally equivalent is within the scope of this invention. The deposit of material does not constitute an admission that the written description herein contained is inadequate to enable the practice of any aspect of the invention, including the best mode thereof, nor is it to be construed as limiting the scope of the claims to the specific illustration that it represents. Indeed, various modifications of the invention in addition to those shown and described herein will become apparent to those skilled in the art from the foregoing description and fall within the scope of the appended claims.

What is claimed is:

1. An article of manufacture comprising packaging material and a pharmaceutical agent contained within said packaging material, wherein said pharmaceutical agent is effective for inhibiting angiogenesis in a tissue and wherein said packaging material comprises a label which indicates that said pharmaceutical agent can be used for treating conditions by inhibition of angiogenesis and wherein said pharmaceutical agent comprises an angiogenesis-inhibiting amount of an $\alpha_v\beta_3$ antagonist, wherein said antagonist is a matrix metalloproteinase polypeptide that consists of amino acid residue sequence shown in SEQ ID NO 17, 18,19, 20,21, 22, 23, 25, 26, 27 or 28, said polypeptide capable of binding to $\alpha_v\beta_3$.

2. The article of manufacture of claim 1 wherein said tissue is inflamed and said condition is arthritis or rheumatoid arthritis.

3. The article of manufacture of claim 1 wherein said tissue is a solid tumor or solid tumor metastasis.

4. The article of manufacture of claim 1 wherein said tissue is retinal tissue and said condition is retinopathy, diabetic retinopathy or macular degeneration.

5. An $\alpha_v\beta_3$ antagonist comprising a matrix metalloproteinase polypeptide that consists of an amino acid residue sequence shown in SEQ ID NO 17, 18, 19, 20, 21, 22, 23, 25, 26, 27 or 28, said polypeptide capable of binding to $\alpha_v\beta_3$.

6. A pharmaceutical agent comprising an $\alpha_v\beta_3$ antagonist according to claim 5 in a pharmaceutically acceptable carrier in an amount sufficient to inhibit angiogenesis in a tissue.

* * * * *